United States Patent
Mirosevich et al.

(10) Patent No.: US 8,747,904 B2
(45) Date of Patent: Jun. 10, 2014

(54) POLYMERIC MICELLES FOR POLYNUCLEOTIDE ENCAPSULATION

(75) Inventors: Janni Mirosevich, Tampa, FL (US); Gregoire Cardoen, Tampa, FL (US); Kevin N. Sill, Tampa, FL (US); Habib Skaff, Tampa, FL (US)

(73) Assignee: Intezyne Technologies, Inc., Tampa, FL (US)

( * ) Notice: Subject to any disclaimer, the term of this patent is extended or adjusted under 35 U.S.C. 154(b) by 109 days.

(21) Appl. No.: 13/591,122

(22) Filed: Aug. 21, 2012

(65) Prior Publication Data
US 2013/0266617 A1 Oct. 10, 2013

Related U.S. Application Data

(62) Division of application No. 12/770,331, filed on Apr. 29, 2010, now Pat. No. 8,287,910.

(60) Provisional application No. 61/174,334, filed on Apr. 30, 2009.

(51) Int. Cl.
*A61K 31/7088* (2006.01)
*A61K 9/14* (2006.01)
*A61K 9/127* (2006.01)
*A61K 48/00* (2006.01)

(52) U.S. Cl.
USPC ....... 424/497; 424/450; 424/85.1; 424/133.1; 514/44

(58) Field of Classification Search
USPC .................. 424/497, 450, 85.1, 133.1; 514/44
See application file for complete search history.

(56) References Cited

PUBLICATIONS

U.S. Appl. No. 11/396,872, filed Nov. 2006, Breitenkamp et al.*

* cited by examiner

*Primary Examiner* — Anoop Singh
*Assistant Examiner* — Anna Falkowitz
(74) *Attorney, Agent, or Firm* — Kevin N. Sill

(57) ABSTRACT

The present invention provides micelles having a polynucleotide encapsulated therein, the micelle comprising copolymers comprising hydrophobic moieties in a cationic complexing block. The invention further provides methods of preparing and using said micelles, and compositions thereof.

22 Claims, 13 Drawing Sheets

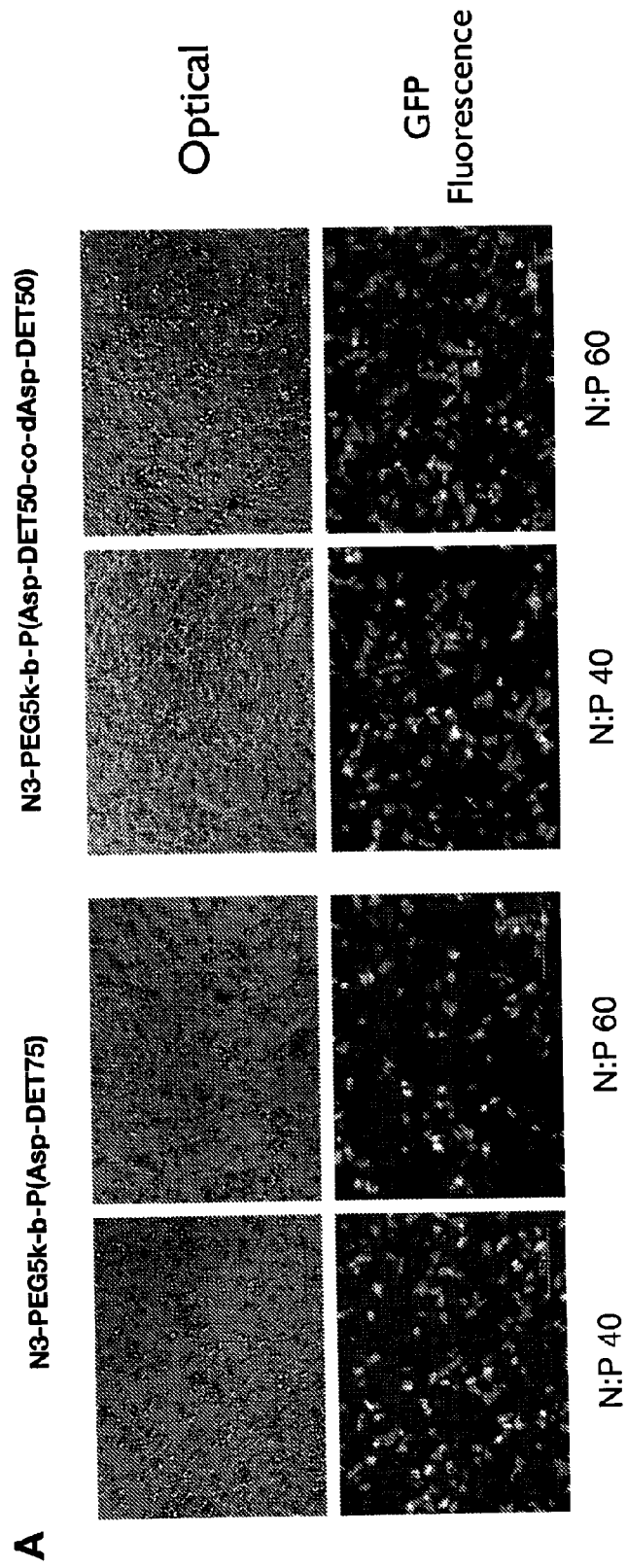
Figure 1: GFP and Luciferase Expression of HCT-116 Cells Transiently Transfected with L versus D/L Asp-DET PEG Polymers.

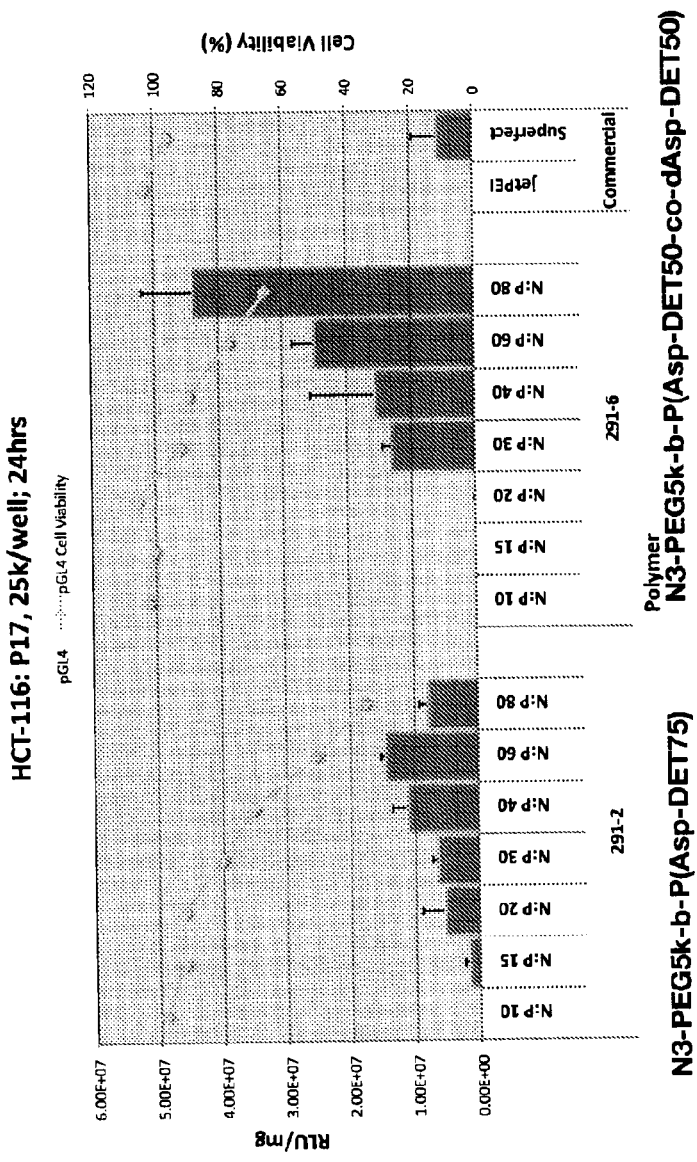
Figure 1: GFP and Luciferase Expression of HCT-116 Cells Transiently Transfected with L versus D/L Asp-DET PEG Polymers.

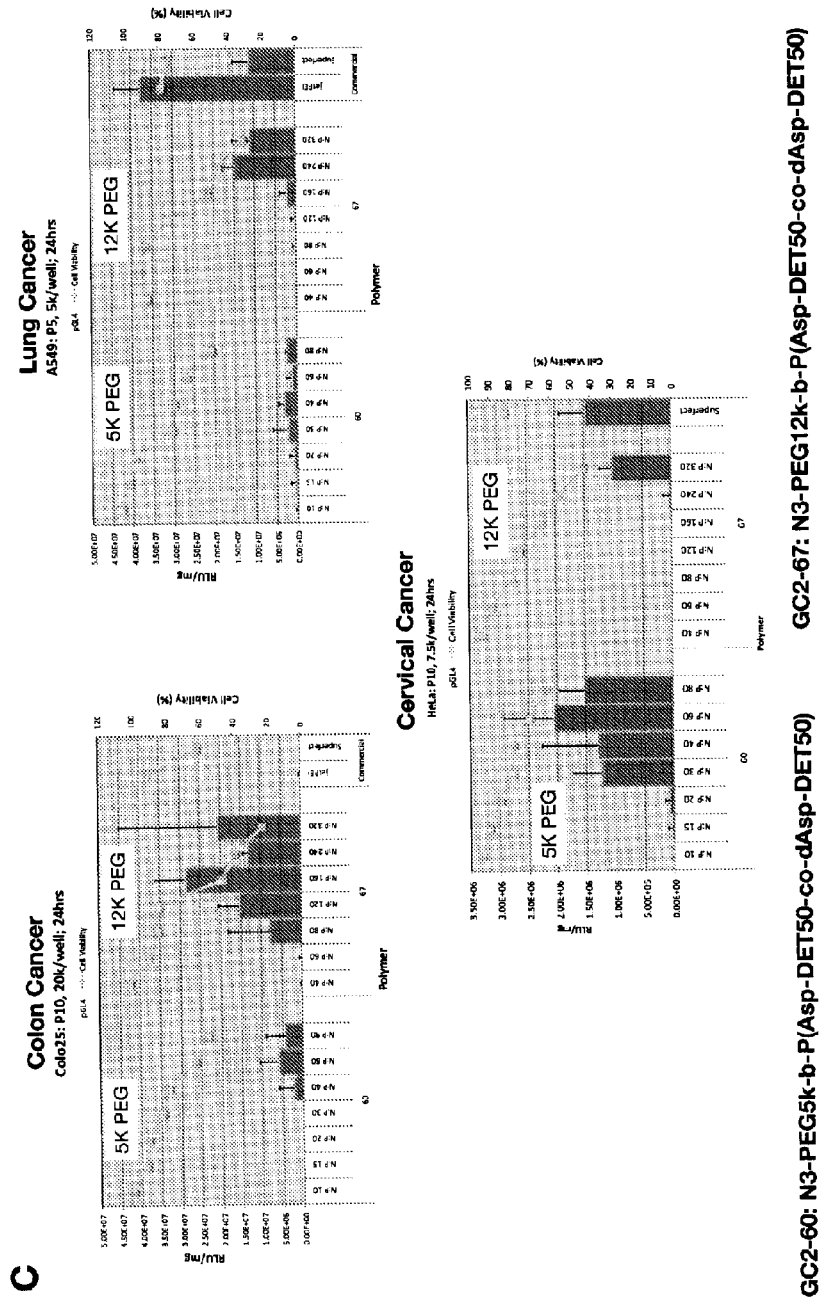
Figure 1: GFP and Luciferase Expression of HCT-116 Cells Transiently Transfected with 5 and 12k PEG D/L Asp-DET Polymers.

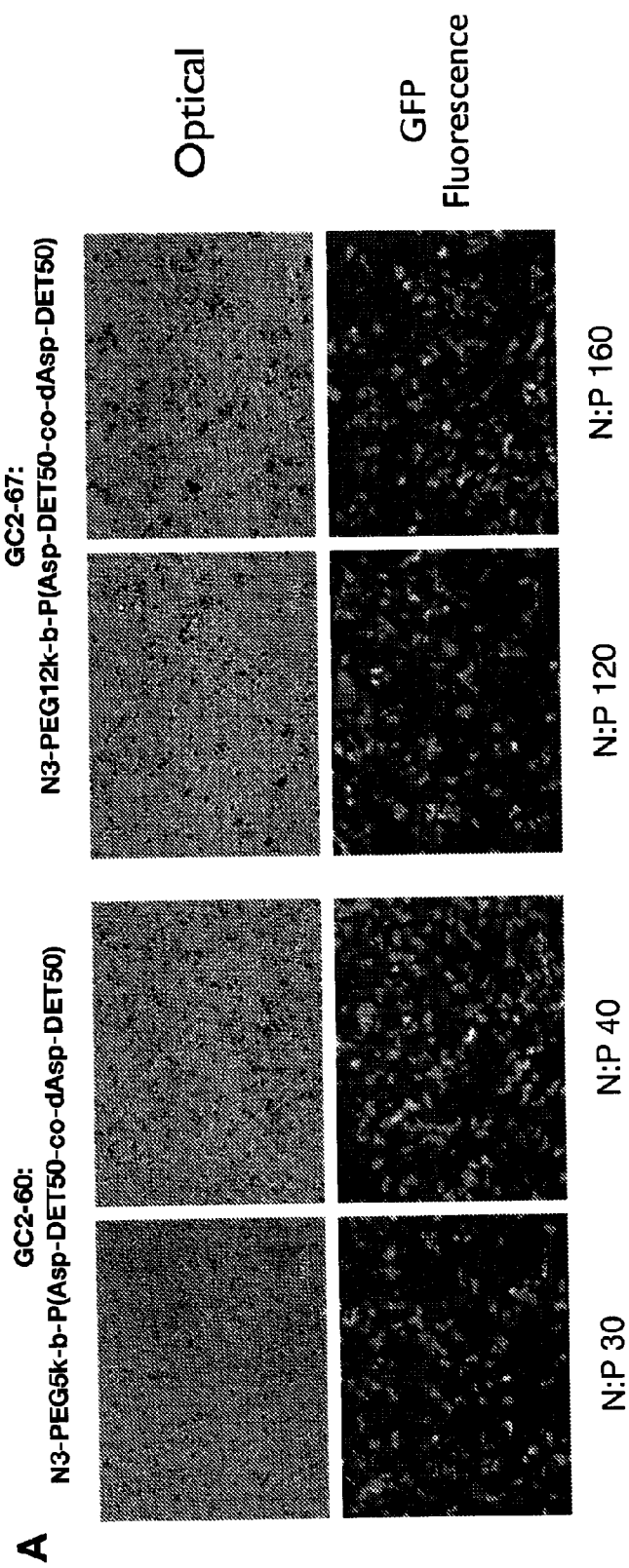
Figure 2: GFP and Luciferase Expression of HCT-116 Cells Transiently Transfected with 5 and 12k PEG D/L Asp-DET Polymers.

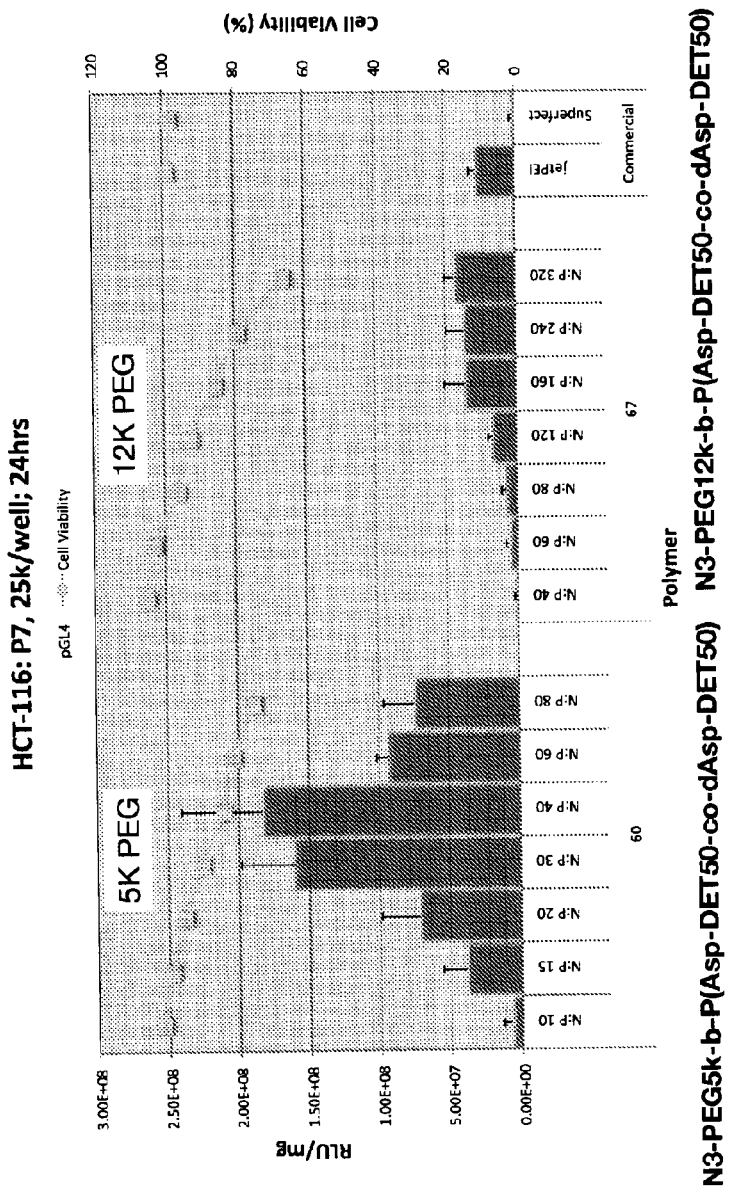
Figure 2: GFP and Luciferase Expression of HCT-116 Cells Transiently Transfected with 5 and 12k PEG D/L Asp-DET Polymers.

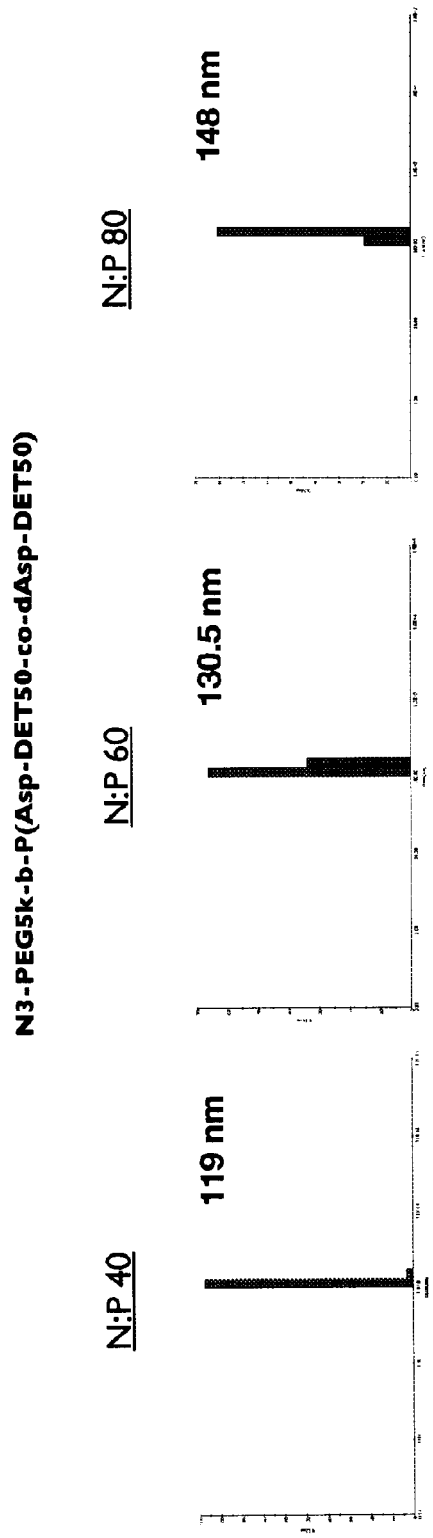

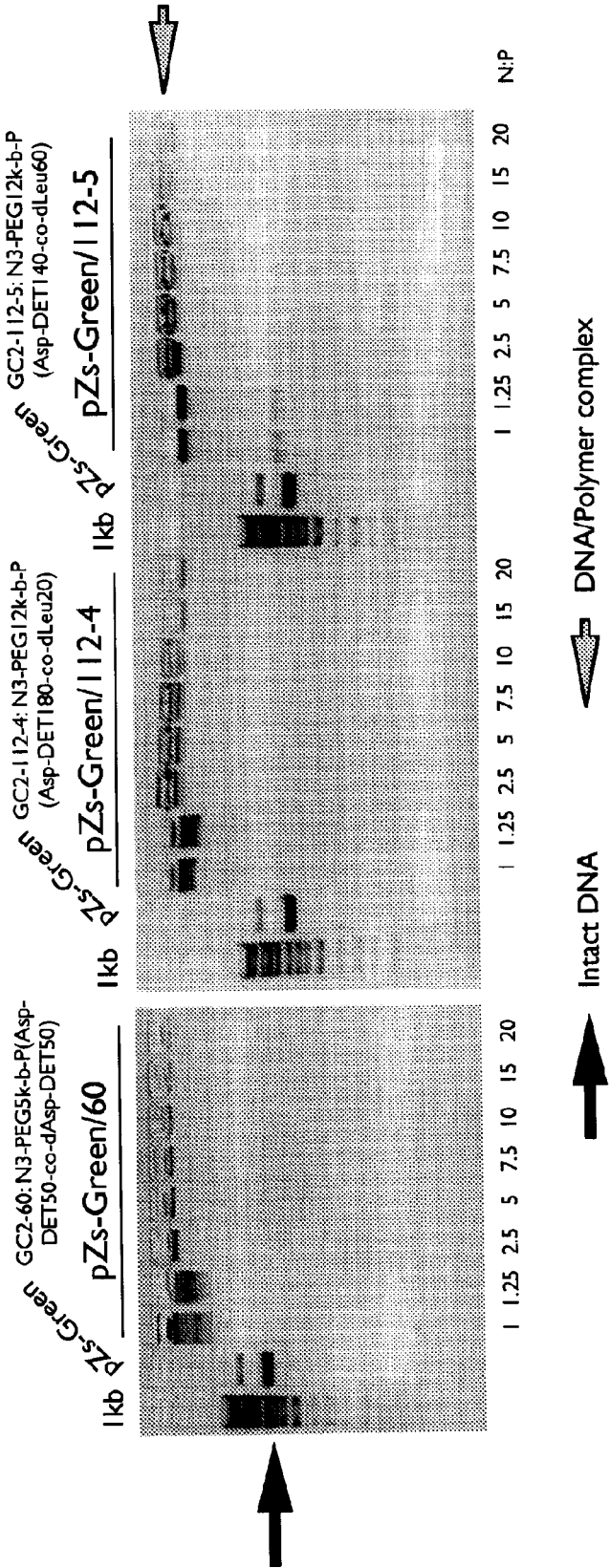
Figure 4: Gel Retardation of DNA Complexed with Polymers.

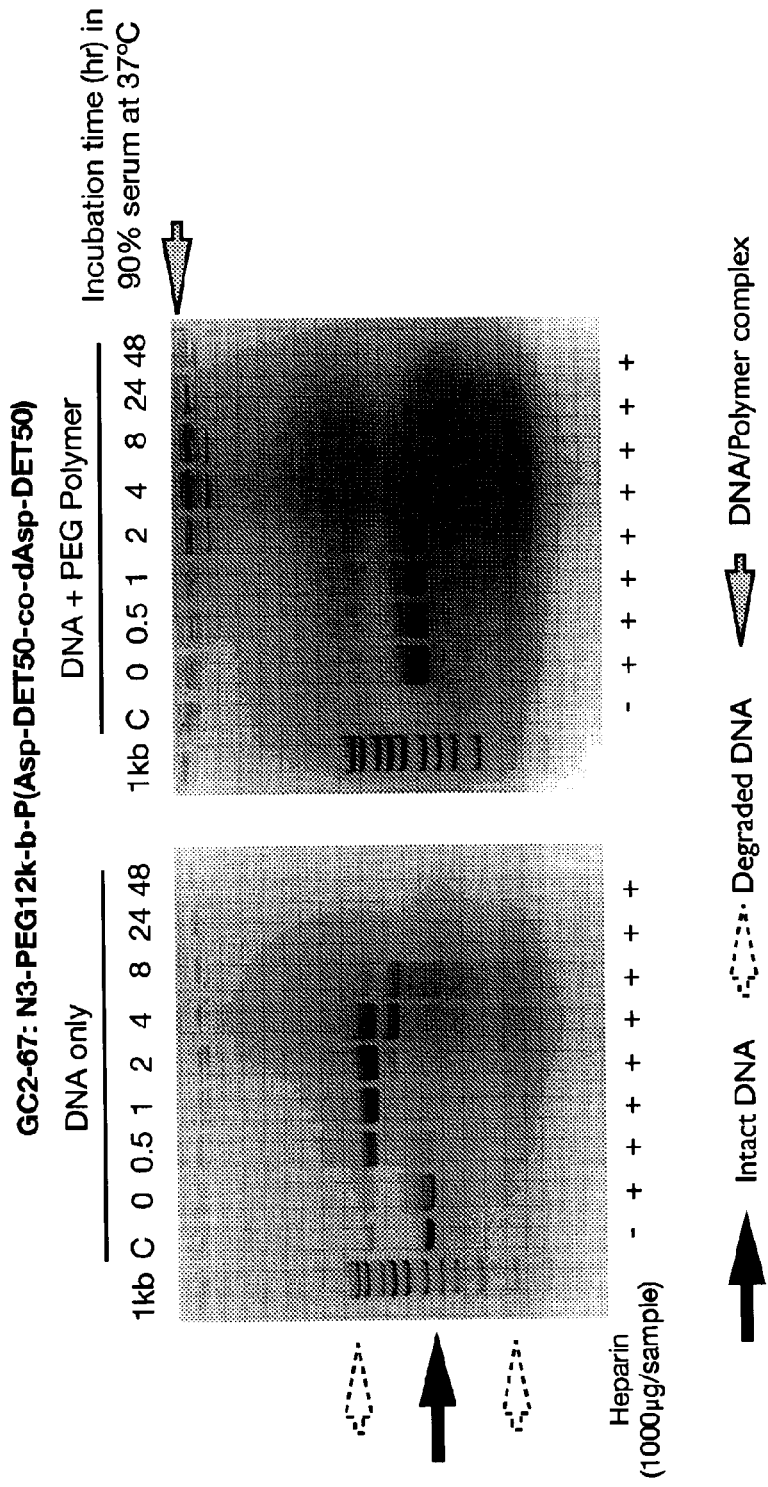
Figure 5: Polymers Protect DNA from Degradation in Serum.

Figure 6: In vivo Studies Using 5 and 12k PEG D/L Asp-DET Polymers.
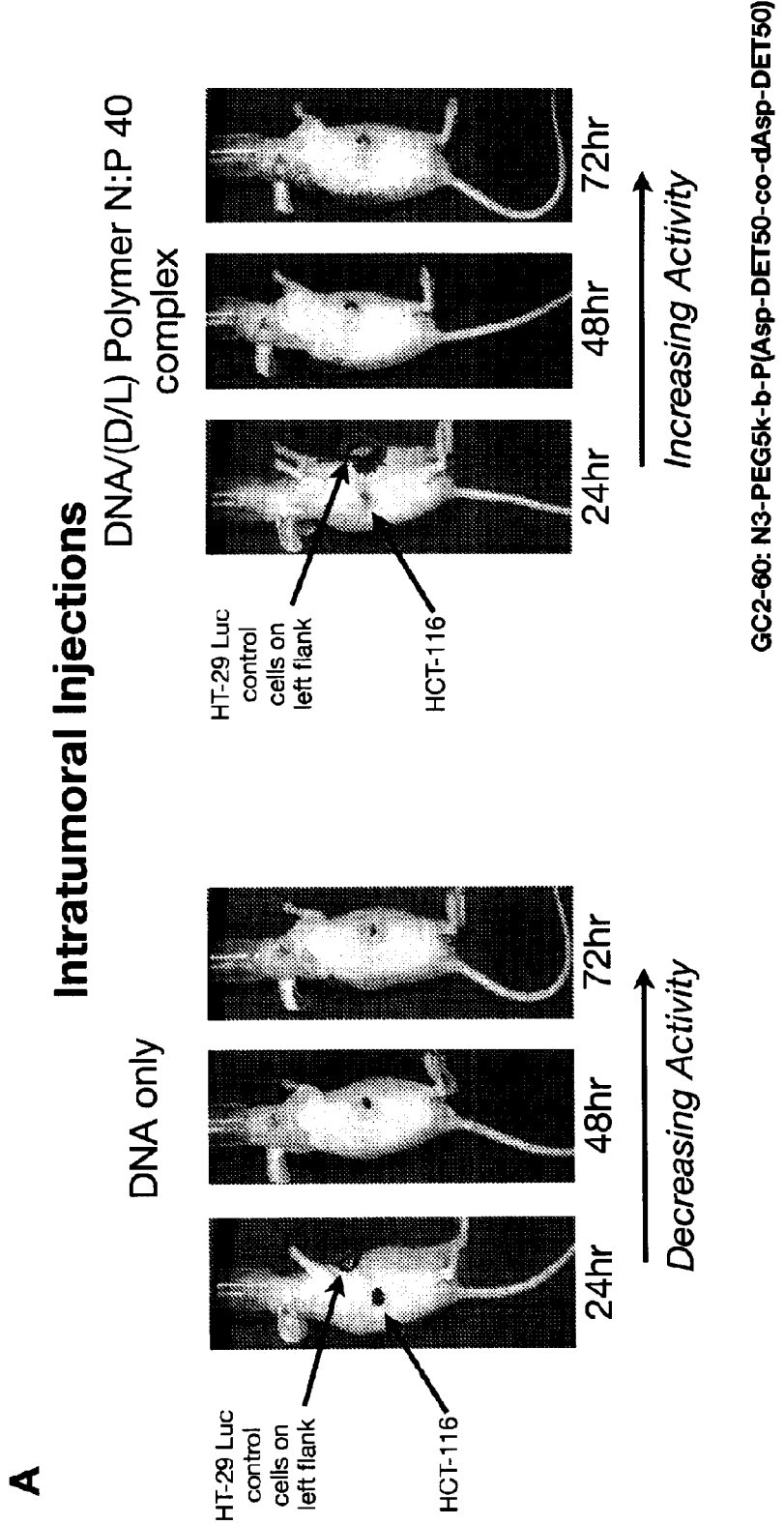

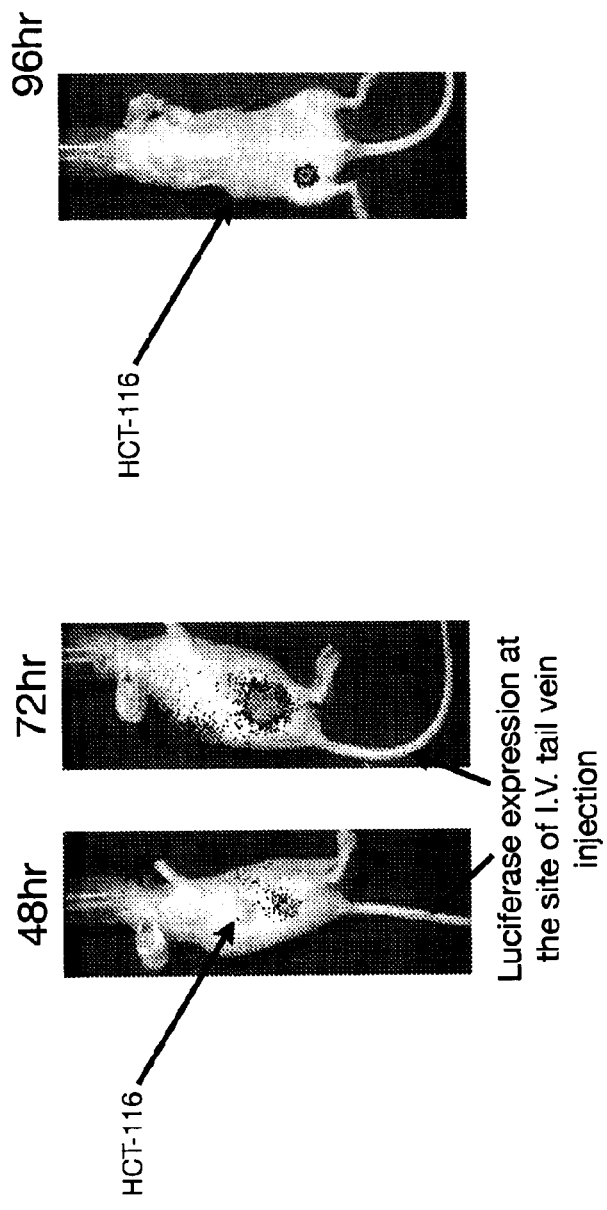
Figure 6: In vivo Studies Using 5k PEG D/L Asp-DET Polymers.
B   I.V. Injections of DNA/(D/L) Polymer N:P 40 complex

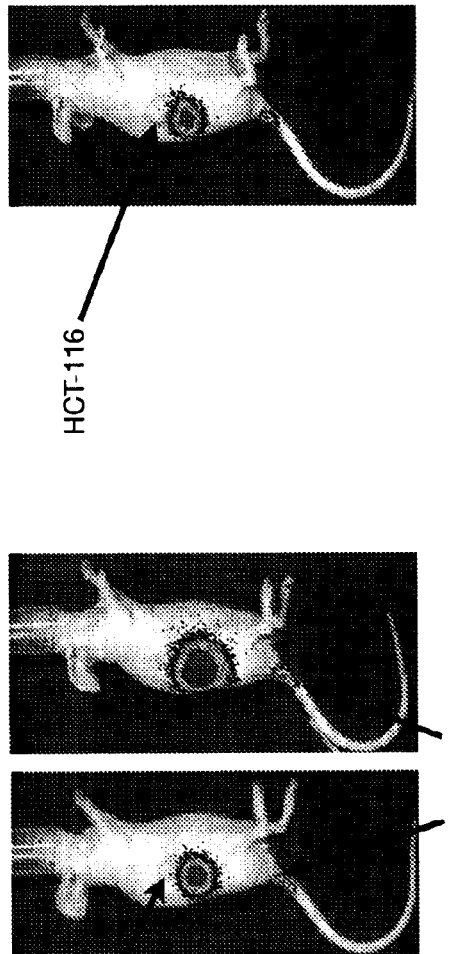
Figure 6: In vivo Studies Using 12k PEG D/L Asp-DET Polymers.

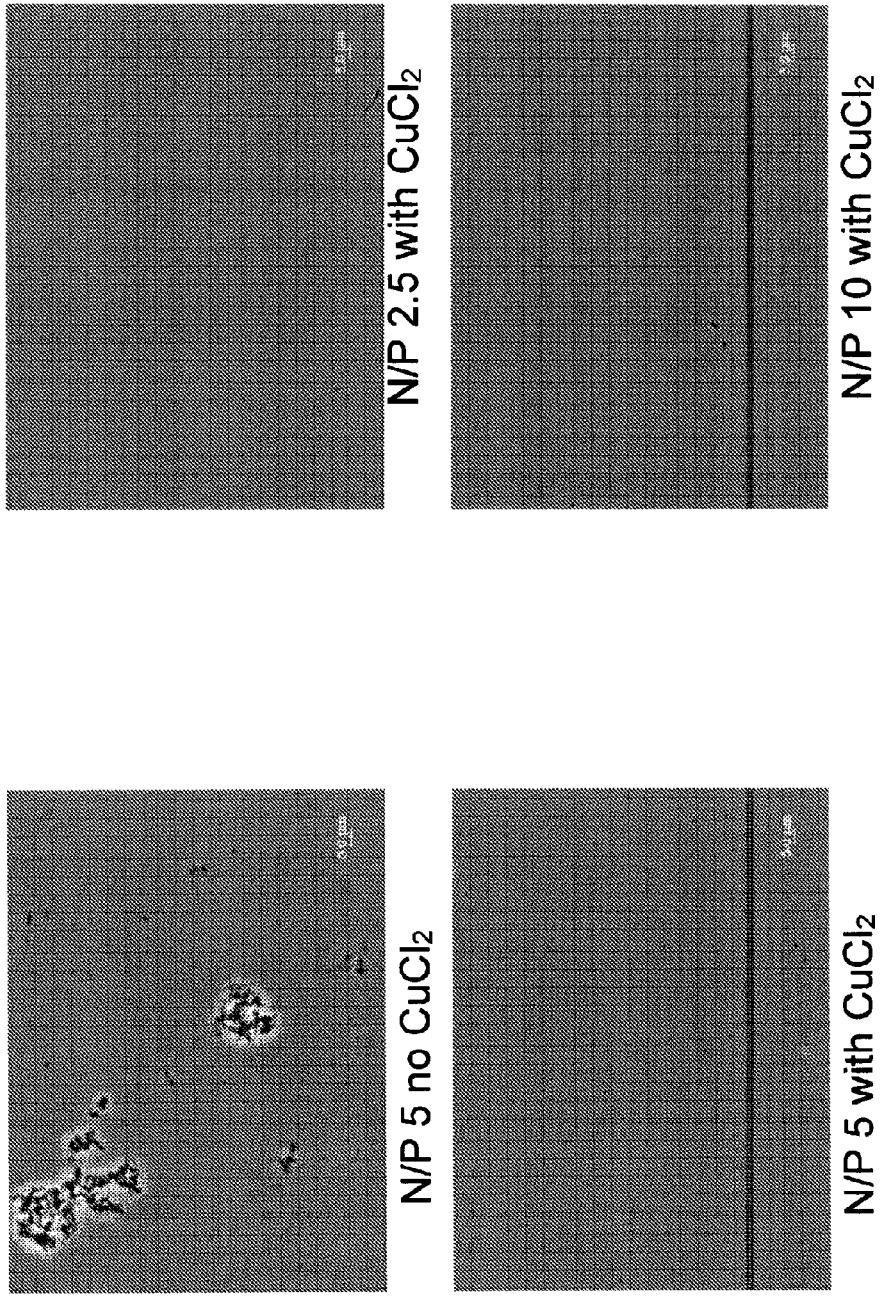
Figure 7 - Optical Microscopy of Example 88

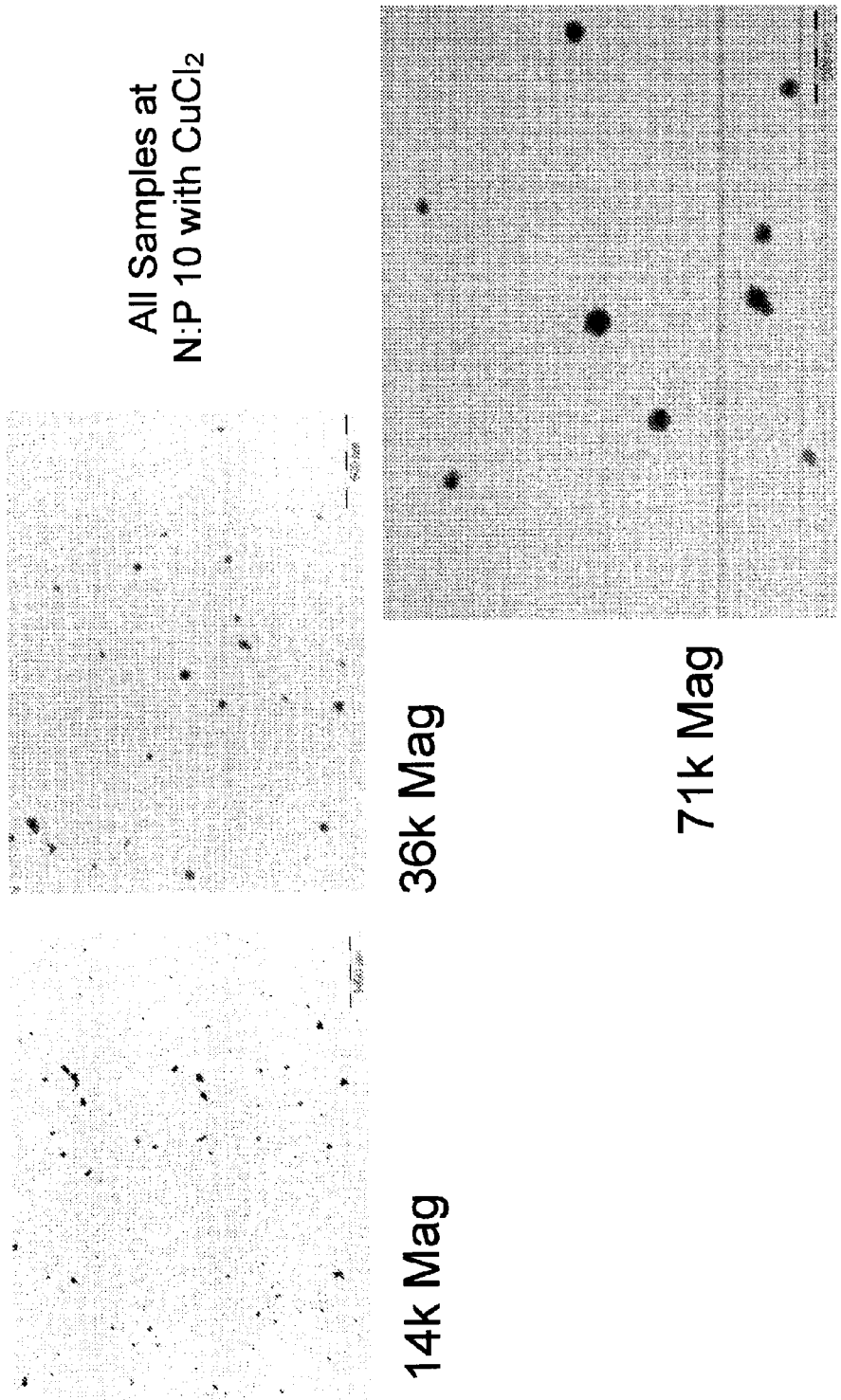

US 8,747,904 B2

POLYMERIC MICELLES FOR POLYNUCLEOTIDE ENCAPSULATION

CROSS-REFERENCE TO RELATED APPLICATIONS

The present invention claims priority to U.S. provisional application Ser. No. 61/174,334, filed Apr. 30, 2009, the entirety of which is hereby incorporated by reference.

FIELD OF THE INVENTION

The present invention relates to the field of polymer chemistry and more particularly to micelles and uses thereof.

In accordance with 37 CFR 1.52(e)(5), a Sequence Listing in the form of a text file (entitled "Intezyne 0126_ST25.txt," created on Apr. 3, 2013, and 8 kilobytes) is incorporated herein by reference in its entirety.

BACKGROUND OF THE INVENTION

The development of new therapeutic agents has dramatically improved the quality of life and survival rate of patients suffering from a variety of disorders. However, drug delivery innovations are needed to improve the success rate of these treatments. Specifically, delivery systems are still needed which effectively minimize premature excretion and/or metabolism of therapeutic agents and deliver these agents specifically to diseased cells thereby reducing their toxicity to healthy cells.

Rationally-designed, nanoscopic drug carriers, or "nanovectors," offer a promising approach to achieving these goals due to their inherent ability to overcome many biological barriers. Moreover, their multi-functionality permits the incorporation of cell-targeting groups, diagnostic agents, and a multitude of therapeutic agents in a single delivery system. Polymer micelles, formed by the molecular assembly of functional, amphiphilic block copolymers, represent one notable type of multifunctional nanovector.

Polymer micelles are particularly attractive due to their ability to deliver large payloads of a variety of drugs (e.g. small molecule, proteins, and DNA/RNA therapeutics), their improved in vivo stability as compared to other colloidal carriers (e.g. liposomes), and their nanoscopic size which allows for passive accumulation in diseased tissues, such as solid tumors, by the enhanced permeation and retention (EPR) effect. Using appropriate surface functionality, polymer micelles are further decorated with cell-targeting groups and permeation enhancers that can actively target diseased cells and aid in cellular entry, resulting in improved cell-specific delivery.

While self-assembly represents a convenient method for the bottom-up design of nanovectors, the forces that drive and sustain the assembly of polymer micelles are concentration dependent and inherently reversible. In clinical applications, where polymer micelles are rapidly diluted following administration, this reversibility, along with high concentrations of micelle-destabilizing blood components (e.g. proteins, lipids, and phospholipids), often leads to premature dissociation of the drug-loaded micelle before active or passive targeting is effectively achieved. For polymer micelles to fully reach their cell-targeting potential and exploit their envisioned multi-functionality, in vivo circulation time must be improved. Drug delivery vehicles are needed that are stable to post-administration dilution, can avoid biological barriers (e.g. reticuloendothelial system (RES) uptake), and deliver drugs in response to the physiological environment encountered in diseased tissues, such as solid tumors.

BRIEF DESCRIPTION OF THE DRAWINGS

FIGS. 1a-c. GFP and Luciferase Expression of HCT-116 Cells Transiently Transfected with 5 and 12 k PEG D/L Asp-DET Polymers.

FIG. 2a-b. GFP and Luciferase Expression of HCT-116 Cells Transiently Transfected with D/L Asp-DET or Asp-DET-D/Leu Polymers.

FIG. 3. Size Analysis of Polyplexes at Optimal N:P Ratios For DNA Transfection.

FIG. 4. Gel Retardation of DNA Complexed with Polymers.

FIG. 5. Polymers Protect DNA from Degradation in Serum.

FIG. 6a-c. In vivo Studies Using 5 and 12 k PEG D/L Asp-DET Polymers.

FIG. 7. Optical microscopy images from Example 88

FIG. 8. Transmission Electron Microscopy images from Example 88

DETAILED DESCRIPTION OF CERTAIN EMBODIMENTS OF THE INVENTION

1. General Description

There are several key factors that limit the use of lipoplexes and polyplexes for in vivo gene delivery applications, particularly when systemic delivery is desired. These include instability of these electrostatic assemblies in high salt environments, irreversible protein binding to the complex that can alter its pharmacokinetic profile, and capture by RES due to excess positive charge. The covalent attachment of poly(ethylene glycol) (PEG) to gene carriers has been shown to address many of these limitations by sterically shielding the complex from unwanted cellular and protein interactions as well as imparting the inherent, stealth properties of PEG. MacLachlan and coworkers have demonstrated that PEG-lipid conjugates, used in conjunction with traditional lipids, can improve the stability and circulation half-life of DNA-loaded lipoplexes (*J. Control. Release*, 2006, 112, 280). Similarly, Kissel and coworkers have developed PEG-modified PEI polyplexes that showed enhanced circulation lifetimes when compared to unmodified PEI polyplexes (*Pharm. Res.*, 2002, 19, 810).

PEG has become a standard choice for the hydrophilic, corona-forming segment of block copolymer micelles, and numerous studies have confirmed its ability to reduce RES uptake of micellar delivery systems. See Kwon, G.; Suwa, S.; Yokoyama, M.; Okano, T.; Sakurai, Y.; Kataoka, K. *J. Cont. Rel.* 1994, 29, 17-23; Caliceti, P.; Veronese, F. M. *Adv. Drug Del. Rev.* 2003, 55, 1261-1277; Ichikawa, K.; Hikita, T.; Maeda, N.; Takeuchi, Y.; Namba, Y.; Oku, N. *Bio. Pharm. Bull.* 2004, 27, and 443-444. The ability to tailor PEG chain lengths offers numerous advantages in drug carrier design since studies have shown that circulation times and RES uptake are influenced by the length of the PEG block. In general, longer PEG chains lead to longer circulation times and enhanced stealth properties. In a systematic study of PEG-b-poly(lactic-co-glycolic acid) (PLGA) micelles with PEG molecular weights ranging from 5,000-20,000 Da, Langer and coworkers found that micelles coated with 20,000 Da PEG chains were the least susceptible to liver uptake. After 5 hours of circulation, less than 30% of the micelles had accumulated in the liver. See Gref, R.; Minamitake, Y.; Peracchia, M. T.; Trubetskoy, V.; Torchilin, V.; Langer, R. *Science* 1994, 263, 1600-1603.

While PEGylation of nanovectors is an effective method to reduce RES uptake and extend in vivo circulation lifetime, other challenges exist which limit the ultimate effectiveness of colloidal drug carriers. One such barrier relates to their self-assembly and subsequent in vivo stability. Self-assembly represents a convenient, bottom-up approach to nanovector design. The hydrophobic forces that drive the aqueous assembly of colloidal drug carriers, such as polymer micelles and liposomes, are relatively weak, and these assembled structures dissociate below a finite concentration known as the critical micelle concentration ("CMC"). The CMC value of these systems is of great importance in clinical applications since drug-loaded colloidal carriers are diluted in the bloodstream following administration and rapidly reach concentrations below the CMC (µM or less) leading to micelle dissociation. In addition, non-specific interactions with surfactant-like components in the blood (e.g. proteins, lipids, etc.) also act to destabilize drug-loaded micelles. See Savić, R.; Azzam, T.; Eisenberg, A.; Maysinger, D. *Langmuir* 2006, 22, 3570-3578. These events often lead to premature drug release outside the targeted area, rendering the drug carrier and cell-targeting strategies ineffective.

Despite the large volume of work on micellar drug carriers, little effort has focused on improving their in vivo stability to dilution. In most cases, amphiphilic block copolymers lack the functionality necessary for post-assembly crosslinking strategies. Wooley and coworkers have addressed this issue by crosslinking the poly(acrylic acid) corona of the polymer micelles, forming shell-crosslinked nanoparticles. See Thurmond, K. B.; Huang, H. Y.; Clark, C. G.; Kowalewski, T.; Wooley, K. L. *Coll. Surf. B.* 1999, 16, 45-54. Covalent crosslinking produces nanoparticles with improved stability and offers the additional benefit of enhanced therapeutic payload since the core-forming block is chemically removed after crosslinking. See Zhang, Q.; Remsen, E. E.; Wooley, K. L. *J. Am. Chem. Soc.* 2000, 122, 3642-3651.

In a separate approach, Kataoka and coworkers have developed methods to reversibly crosslink the core of diblock polymer micelles to improve stability. For example, the chemotherapy drug cisplatin was encapsulated using PEG-b-poly(aspartic acid) copolymers, forming reversible chemical bonds in the micelle core. See Nishiyama, N.; Yokoyama, M.; Aoyagi, T.; Okano, T.; Sakurai, Y.; Kataoka, K. *Langmuir* 1999, 15, 377-383. The micelles were stable to dilution as determined by dynamic light scattering studies, and the core-crosslinking was reversible in the presence of chloride ions, resulting in dissociation of the polymer micelles and release of cisplatin. However, in vivo studies using tumor-bearing mice showed remarkably fast decay of the cisplatin-loaded micelles, which resulted in accumulation of the drug in the liver and spleen. See Nishiyama, N.; Kato, Y.; Sugiyama, Y.; Kataoka, K. *Pharm. Res.* 2001, 18, 1035-1041. Kataoka's group has also reported alternative core crosslinking strategies that utilize disulfide chemistry. In this case, cysteine units were randomly incorporated into the lysine portion of PEG-b-poly(L-lysine) copolymers and used for encapsulation of antisense RNA. See Kakizawa, Y.; Harada, A.; Kataoka, K. *J. Am. Chem. Soc.* 1999, 121, 11247-11248; and Kakizawa, Y.; Harada, A.; Kataoka, K. *Biomacromolecules* 2001, 2, 491-497. The cysteine side chains were subsequently oxidized in the core to form disulfide crosslinked, RNA-loaded micelles. These micelles were shown to selectively dissociate in the presence of glutathione (GSH), a reducing agent found in appreciable quantities in the cell cytoplasm, offering an effective method for intracellular delivery of the therapeutic. Other core crosslinking techniques have been devised that utilize polymer end-groups, such as methacrylate and olefinic functionality, which are crosslinked by free radicals. See Iijima, M.; Nagasaki, Y.; Okada, T.; Kato, M.; Kataoka, K. *Macromolecules* 1999, 32, 1140-1146; and Tian, L.; Yam, L.; Wang, J. Z.; Tat, H.; Uhrich, K. E. *J. Mat. Chem.* 2004, 14, 2317-2324. One notable disadvantage of the core crosslinking approach is the inherent reduction of free-volume in the micelle core, which ultimately limits drug loading in the micelle.

Armes and coworkers have used covalent chemistries to crosslink the outer core of micelles made from poly[(ethylene oxide)-block-2-(dimethylamino)ethyl methacrylate-block-2-(diethylamino)methacrylate] copolymers. The addition of the bifunctional crosslinker, 1,2-bis(2-iodoethoxy)ethane, was shown to effectively crosslink the 2-(dimethylamino) ethyl methacrylate block, forming irreversible quaternary ammonium crosslinks. See Liu, S.; Weaver, J. V. M.; Tang, Y.; Billingham, N. C.; Armes, S. P. *Macromolecules*, 2002, 35, 6121-6131. McCormick and coworkers have synthesized poly(ethylene oxide)-block-[(N,N-dimethylacrylamide)-stat-(N-acryloxysuccinimide)]-block-(N-isopropylacrylamide) copolymers where the N-acryloxysuccinimide units are reacted with cystamine to crosslink the outer core of the micelle through reversible disulfide bonds. See Li, Y.; Lokitz, B. S.; Armes, S. P.; McCormick, C. L. *Macromolecules* 2006, 39, 2726-2728.

Block copolymers of PEG and cationic poly(amino acid)s (e.g. PEG-b-poly(L-Lysine)) have been synthesized and utilized as reagents for DNA and RNA delivery (*J. Bioact. Compat. Pol.*, 2000, 15, 115, *Bioconjugate Chem.*, 1997, 8, 702). When block copolymers of this type are combined with nucleic acid-based agents, the cationic block condenses and encapsulates the negatively charged agent, forming a complex with a PEG corona (often referred to as polyion complexes (PICs)). Although PEG can improve the pharmacokinetic profiles of PICs and other lipo- and polyplexes (*Gene Ther.*, 2002, 9, 407), it may also reduce transfection efficiency by minimizing interactions with the cellular membrane and subsequent cell uptake. The conjugation of targeting ligands that bind to cellular receptors and promote endocytosis of DNA and RNA-loaded PICs is a promising approach to promote cell uptake while retaining the stealth properties imparted by the PEG corona (*Bioconjugate Chem.*, 2007, 18, 1415).

In addition to addressing the buffering capacity and endosomal escape, one must consider the morphology of the PIC. The non-viral delivery agents discussed above typically describe a block copolymer consisting of a hydrophilic PEG chain and a cationic block, which is inherently hydrophilic. As discussed previously, the purpose of the PEG chain is to impart a "stealth" nature to the PIC and the cationic segment is responsible for interacting with the polynucleotide to form the ion complex. Often, PICs formed with such block copolymers are described as possessing a micellar structure, with the ion complex on the interior surrounded by a PEG outer shell; however, no conclusive, experimental evidence exists to show that these PICs exist as an idealized micelle. One must consider the fact that hydrophobic interactions, the fundamental thermodynamic driving force for micelle formation, are not present in a system composed of block copolymer possessing two hydrophilic segments. Since there is no hydrophobic core to drive the micelle assembly (as found in amphiphilic block copolymers), one can envision PIC morphologies where individual ion complexes, and thus charge, are dispersed randomly throughout the complex and are not sequestered to the interior. If an excess of positive charge, as found at N:P ratios greater than one, is localized at the exterior of the complex, the stealth effect of the PEG is negated and the complex would be susceptible to opsonization and subsequent clearance by the RES system. Thus, it would be advantageous to prepare a block copolymer that is capable of both complexing a polynucleotide assembling into a micellar structure.

The present invention describes the incorporation of hydrophobic moieties into the cationic complexing block to drive the assembly of a micellar PIC. In certain aspects, the present invention provides multiblock copolymers comprising a polymeric hydrophilic block and a mixed random copolymer block consisting of hydrophobic and amine-containing amino acid residues. In some embodiments, provided copolymers further comprise a crosslinked or crosslinkable block. In certain embodiments, a provided multiblock copolymer is suitable for polynucleotide encapsulation.

Another aspect of the present invention describes the use of metal ions to compact the polynucleotide prior to polyplex formation. The interaction of metal salts and nucleic acids is described by Bennett in U.S. Pat. No. 6,372,722 and in Hackl, et. al, Journal of Molecular Structure, Vols. 408-409, pg. 229-232. Briefly, when the polynucleotide is a plasmid DNA, it is believed that a polyvalent metal center can interact with the phosphate groups of the polynucleotide, inducing compaction of the plasmid. Without wishing to be bound to any particular theory, it is believed that "pre-compacting" the polynucleotide with a polyvalent metal followed by the polyplex formation by the addition of a suitable diblock copolymer described herein will allow for polyplexes with a more narrow size distribution.

2. Definitions

Compounds of this invention include those described generally above, and are further illustrated by the embodiments, sub-embodiments, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry," Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As used herein, the term "polynucleotide" refers to DNA or RNA. In some embodiments, a polynucleotide is a short interfering RNA (siRNA), a microRNA (miRNA), a plasmid DNA (pDNA), a short hairpin RNA (shRNA), messenger RNA (mRNA), and antisense RNA (aRNA), to name a few, and encompasses both the nucleotide sequence and any structural embodiments thereof, such as double stranded, single stranded, helical, hairpin, etc.

As used herein, the term "micelle" refers to a polymer assembly comprised of a hydrophilic shell (or corona) and a hydrophobic and/or ionic interior. In addition, the term micelle may refer to any poly ion complex assembly consisting of a multiblock copolymer possessing a net positive charge and a suitable negatively charged polynucleotide.

As used herein, the term "multiblock copolymer" refers to a polymer comprising one synthetic polymer portion and two or more poly(amino acid) portions. Such multi-block copolymers include those having the format W—X'—X", wherein W is a synthetic polymer portion and X and X' are poly(amino acid) chains or "amino acid blocks." In certain embodiments, the multiblock copolymers of the present invention are triblock copolymers. As described herein, one or more of the amino acid blocks may be "mixed blocks," meaning that these blocks can contain a mixture of amino acid monomers thereby creating multiblock copolymers of the present invention. In some embodiments, the multiblock copolymers of the present invention comprise a mixed amino acid block and are tetrablock copolymers.

As used herein, the term "triblock copolymer" refers to a polymer comprising one synthetic polymer portion and two poly(amino acid) portions.

As used herein, the term "tetrablock copolymer" refers to a polymer comprising one synthetic polymer portion and three poly(amino acid) portions.

As used herein, the term "pentablock copolymer" refers to a polymer comprising two synthetic polymer portions and three poly(amino acid) portions, where one synthetic polymer portion is on each side of the poly(amino acid) portion (i.e. W—X—X'—X"—W' wherein W and W' are synthetic polymer blocks and X, X', and X" are each a poly(amino acid) block).

As used herein, the term "portion" or "block" refers to a repeating polymeric sequence of defined composition. A portion or a block may consist of a single monomer or may be comprise of on or more monomers, resulting in a "mixed block".

One skilled in the art will recognize that a monomer repeat unit is defined by parentheses depicted around the repeating monomer unit. The number (or letter representing a numerical range) on the lower right of the parentheses represents the number of monomer units that are present in the polymer chain. In the case where only one monomer represents the block (e.g. a homopolymer), the block will be denoted solely by the parentheses. In the case of a mixed block, multiple monomers comprise a single, continuous block. It will be understood that brackets will define a portion or block. For example, one block may consist of four individual monomers, each defined by their own individual set of parentheses and number of repeat units present. All four sets of parentheses will be enclosed by a set of brackets, denoting that all four of these monomers combine in random, or near random, order to comprise the mixed block. For clarity, the randomly mixed block of [BCADDCBADABCDABC] would be represented in shorthand by [(A)$_4$(B)$_4$(C)$_4$(D)$_4$].

As used herein, the term "inner core" as it applies to a micelle of the present invention refers to the center of the micelle formed by the terminal poly(amino acid) block. In accordance with the present invention, the inner core is not crosslinked. By way of illustration, in a triblock polymer of the format W—X'—X", as described above, the inner core corresponds to the X" block. It is contemplated that the X" block can be a mixed block.

As used herein, the term "outer core" as it applies to a micelle of the present invention refers to the layer formed by the first poly(amino acid) block. The outer core lies between the inner core and the hydrophilic shell. In certain embodiments, the outer core is either crosslinkable or is cross-linked. By way of illustration, in a triblock polymer of the format W—X'—X", as described above, the outer core corresponds to the X' block. It is contemplated that the X' block can be a mixed block. In some embodiments, the outer core may be comprised of a hydrophobic amino acid block that serves to stabilize the micelle through hydrophobic interactions.

As used herein, the terms "polynucleotide-loaded", "complexed", "loaded" and "encapsulated" and derivatives thereof, are used interchangeably. In accordance with the present invention, a "polynucleotide-loaded" micelle refers to a micelle having one or more polynucleotides situated within the inner core of the micelle. This is also referred to as a polynucleotide being "encapsulated" within the micelle.

As used herein, the term "polymeric hydrophilic block" refers to a polymer that is not a poly(amino acid) and is hydrophilic in nature. Such hydrophilic polymers are well known in the art and include poly(ethyleneoxide) (also referred to as PEO, polyethylene glycol or PEG), and derivatives thereof, poly(N-vinyl-2-pyrolidone), and derivatives thereof, poly(phosphocholine methacrylate) and derivatives thereof, poly(N-isopropylacrylamide), and derivatives thereof, poly(hydroxyethyl acrylate), and derivatives thereof, poly(hydroxylethyl methacrylate), and derivatives thereof, and polymers of N-(2-hydroxypropoyl)methacrylamide (HMPA) and derivatives thereof.

As used herein, the term "poly(amino acid)" or "amino acid block" refers to a covalently linked amino acid chain wherein each monomer is an amino acid unit. Such amino acid units include natural and unnatural amino acids. Such poly(amino acids) include those having suitably protected functional groups. For example, amino acid monomers may have hydroxyl or amino moieties that are optionally protected by a suitable hydroxyl protecting group or a suitable amine protecting group, as appropriate. Such suitable hydroxyl protecting groups and suitable amine protecting groups are described in more detail herein, infra. As used herein, an amino acid block comprises one or more monomers or a set of two or more monomers. In certain embodiments, an amino acid block comprises one or more monomers such that the overall block is hydrophilic. In other embodiments, an amino acid block comprises one or more monomers such that the overall block is hydrophobic. In still other embodiments, amino acid blocks of the present invention include random amino acid blocks, i.e., blocks comprising a mixture of amino acid residues.

As used herein, the phrase "natural amino acid side-chain group" refers to the side-chain group of any of the 20 amino acids naturally occurring in proteins. Such natural amino acids include the nonpolar, or hydrophobic amino acids, glycine, alanine, valine, leucine isoleucine, methionine, phenylalanine, tryptophan, and proline. Cysteine is sometimes classified as nonpolar or hydrophobic and other times as polar. Natural amino acids also include polar, or hydrophilic amino acids, such as tyrosine, serine, threonine, aspartic acid (also known as aspartate, when charged), glutamic acid (also known as glutamate, when charged), asparagine, and glutamine. Certain polar, or hydrophilic, amino acids have charged side-chains. Such charged amino acids include lysine, arginine, and histidine. One of ordinary skill in the art would recognize that protection of a polar or hydrophilic amino acid side-chain can render that amino acid nonpolar. For example, a suitably protected tyrosine hydroxyl group can render that tyroine nonpolar and hydrophobic by virtue of protecting the hydroxyl group.

As used herein, the term "D,L-mixed poly(amino acid) block" refers to a poly(amino acid) block wherein the poly (amino acid) consists of a mixture of amino acids in both the D- and L-configurations. In certain embodiments, the D,L-mixed poly(amino acid) block consists of a mixture of D-configured hydrophobic amino acids and L-configured cationic amino acid side-chain groups such that the overall poly (amino acid) block comprising is hydrophobic. In certain embodiments, the D,L-mixed poly(amino acid) block consists of a mixture of D-configured hydrophobic amino acids and L-configured hydrophilic cationic amino acid side-chain groups such that the overall poly(amino acid) block comprising is hydrophilic.

As used herein, the phrase "unnatural amino acid side-chain group" refers to the side-chain group of amino acids not included in the list of 20 amino acids naturally occurring in proteins, as described above. Such amino acids include the D-isomer of any of the 20 naturally occurring amino acids. Unnatural amino acids also include homoserine, ornithine, norleucine, and thyroxine. Other unnatural amino acids side-chains are well known to one of ordinary skill in the art and include unnatural aliphatic side chains. Other unnatural amino acids include modified amino acids, including those that are N-alkylated, cyclized, phosphorylated, acetylated, amidated, azidylated, labelled, and the like. In some embodiments, an unnatural amino acid is a D-isomer. In some embodiments, an unnatural amino acid is a L-isomer.

As used herein, the phrase "amine-containing amino acid side-chain group" refers to natural or unnatural amino acid side-chain groups, as defined above, which comprise an amine moiety. The amine moiety may be primary, secondary, tertiary, or quaternary, and may be part of an optionally substituted group aliphatic or optionally substituted aryl group.

As used herein, the phrase N to P (N/P or N:P) refers to the ratio of protonatable nitrogens (N) to negatively charged phosphate groups in the DNA or RNA backbone (P).

As used herein, the phrase "metal ion" or "polyvalent metal ion" refers to a metal ion that has a charge of +2 or greater. Examples of such ions include, but are not limited to: Ca, Cu, Ti, Cr, Fe, Mn, Co, Ni, Zn, Ru, Rh, Ag, Cd, Au, Hg, Tl, Be, Mg, Sr, and Ba.

As used herein, the phase "hydrophobic amino acid side-chain group" refers to natural or unnatural amino acid side-chain groups, as defined above, which are hydrophobic. These groups are not necessarily mutually exclusive from amine-containing amino acid side-chain groups. For example, tryptophan and histidine, which possess amine-containing side-chain groups, may be considered to be hydrophobic.

As used herein, the phrase "living polymer chain-end" refers to the terminus resulting from a polymerization reaction that maintains the ability to react further with additional monomer or with a polymerization terminator.

As used herein, the term "termination" refers to attaching a terminal group to a polymer chain-end by the reaction of a living polymer with an appropriate compound. Alternatively, the term "termination" may refer to attaching a terminal group to an amine or hydroxyl end, or derivative thereof, of the polymer chain.

As used herein, the term "polymerization terminator" is used interchangeably with the term "polymerization terminating agent" and refers to a compound that reacts with a living polymer chain-end to afford a polymer with a terminal group. Alternatively, the term "polymerization terminator" may refer to a compound that reacts with an amine or hydroxyl end, or derivative thereof, of the polymer chain, to afford a polymer with a terminal group.

As used herein, the term "polymerization initiator" refers to a compound, which reacts with, or whose anion or free base form reacts with, the desired monomer in a manner that results in polymerization of that monomer. In certain embodiments, a polymerization initiator is the compound that reacts with an alkylene oxide to afford a polyalkylene oxide block. In some embodiments, a polymerization initiator is an amine salt described herein.

The term "aliphatic" or "aliphatic group," as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-20 carbon atoms. In some embodiments, aliphatic groups contain 1-10 carbon atoms. In other embodiments, aliphatic groups contain 1-8 carbon atoms. In still other embodiments, aliphatic groups contain 1-6 carbon atoms, and in yet other embodiments aliphatic groups contain 1-4 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "heteroatom" means one or more of oxygen, sulfur, nitrogen, phosphorus, or silicon. This includes any oxidized form of nitrogen, sulfur, phosphorus, or silicon; the quaternized form of any basic nitrogen, or; a substitutable nitrogen of a heterocyclic ring including =N— as in 3,4-dihydro-2H-pyrrolyl, —NH— as in pyrrolidinyl, or =N(R$^\dagger$)— as in N— substituted pyrrolidinyl.

The term "unsaturated," as used herein, means that a moiety has one or more units of unsaturation.

The term "aryl" used alone or as part of a larger moiety as in "aralkyl," "aralkoxy," or "aryloxyalkyl," refers to monocyclic, bicyclic, and tricyclic ring systems having a total of five to fourteen ring members, wherein at least one ring in the system is aromatic and wherein each ring in the system contains three to seven ring members. The term "aryl" may be used interchangeably with the term "aryl ring."

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R$^\circ$; —(CH$_2$)$_{0-4}$OR$^\circ$; —O—(CH$_2$)$_{0-4}$C(O)OR$^\circ$; —(CH$_2$)$_{0-4}$CH(OR$^\circ$)$_2$; —(CH$_2$)$_{0-4}$SR$^\circ$; —(CH$_2$)$_{0-4}$Ph, which may be substituted with R$^\circ$; —(CH$_2$)$_{0-4}$O(CH$_2$)$_{0-1}$Ph which may be substituted with R$^\circ$; —CH=CHPh, which may be substituted with R$^\circ$; —NO$_2$; —CN; —N$_3$; —(CH$_2$)$_{0-4}$N(R$^\circ$)$_2$; —(CH$_2$)$_{0-4}$N(R$^\circ$)C(O)R$^\circ$; —N(R$^\circ$)C(S)R$^\circ$; —(CH$_2$)$_{0-4}$N(R$^\circ$)C(O)NR$^\circ$$_2$; —N(R$^\circ$)C(S)NR$^\circ$$_2$; —(CH$_2$)$_{0-4}$N(R$^\circ$)C(O)OR$^\circ$; —N(R$^\circ$)N(R$^\circ$)C(O)R$^\circ$; —N(R$^\circ$)N(R$^\circ$)C(O)NR$^\circ$$_2$; —N(R$^\circ$)N(R$^\circ$)C(O)OR$^\circ$; —(CH$_2$)$_{0-4}$C(O)R$^\circ$; —C(S)R$^\circ$; —(CH$_2$)$_{0-4}$C(O)OR$^\circ$; —(CH$_2$)$_{0-4}$C(O)SR$^\circ$; —(CH$_2$)$_{0-4}$C(O)OSiR$^\circ$$_3$; —(CH$_2$)$_{0-4}$OC(O)R$^\circ$; —OC(O)(CH$_2$)$_{0-4}$SR—, SC(S)SR$^\circ$; —(CH$_2$)$_{0-4}$SC(O)R$^\circ$; —(CH$_2$)$_{0-4}$C(O)NR$^\circ$$_2$; —C(S)NR$^\circ$$_2$; —C(S)SR$^\circ$; —SC(S)SR$^\circ$, —(CH$_2$)$_{0-4}$OC(O)NR$^\circ$$_2$; —C(O)N(OR$^\circ$)R$^\circ$; —C(O)C(O)R$^\circ$; —C(O)CH$_2$C(O)R$^\circ$; —C(NOR$^\circ$)R$^\circ$; —(CH$_2$)$_{0-4}$SSR$^\circ$; —(CH$_2$)$_{0-4}$S(O)$_2$R$^\circ$; —(CH$_2$)$_{0-4}$S(O)$_2$OR$^\circ$; —(CH$_2$)$_{0-4}$OS(O)$_2$R$^\circ$; —S(O)$_2$NR$^\circ$$_2$; —(CH$_2$)$_{0-4}$S(O)R$^\circ$; —N(R$^\circ$)S(O)$_2$NR$^\circ$$_2$; —N(R$^\circ$)S(O)$_2$R$^\circ$; —N(OR$^\circ$)R$^\circ$; —C(NH)NR$^\circ$$_2$; —P(O)$_2$R$^\circ$; —P(O)R$^\circ$$_2$; —OP(O)R$^\circ$$_2$; —OP(O)(OR$^\circ$)$_2$; SiR$^\circ$$_3$; —(C$_{1-4}$ straight or branched)alkylene)O—N(R$^\circ$)$_2$; or —(C$_{1-4}$ straight or branched)alkylene)C(O)O—N(R$^\circ$)$_2$, wherein each R$^\circ$ may be substituted as defined below and is independently hydrogen, C$_{1-6}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur, or, notwithstanding the definition above, two independent occurrences of R$^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R$^\circ$ (or the ring formed by taking two independent occurrences of R$^\circ$ together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, (CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R$^\circ$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. A suitable tetravalent substituent that is bound to vicinal substitutable methylene carbons of an "optionally substituted" group is the dicobalt hexacarbonyl cluster represented by

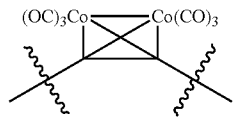

when depicted with the methylenes which bear it.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^†$, —NR$^†_2$, —C(O)R$^†$, —C(O)OR$^†$, —C(O)C(O)R$^†$, —C(O)CH$_2$C(O)R$^†$, —S(O)$_2$R$^†$, —S(O)$_2$NR$^†_2$, —C(S)NR$^†_2$, —C(NH)NR$^†_2$, or —N(R$^†$)S(O)$_2$R$^†$; wherein each R$^†$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^†$ are independently halogen, —R$^●$, -(haloR$^●$), —OH, —OR$^●$, —O(haloR$^●$), —CN, —C(O)OH, —C(O)OR$^●$, —NH$_2$, —NHR$^●$, —NR$^●_2$, or —NO$_2$, wherein each R$^●$ is unsubstituted or where preceded by "halo" is substituted only with one or more halogens, and is independently C$_1$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Protected hydroxyl groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Examples of suitably protected hydroxyl groups further include, but are not limited to, esters, carbonates, sulfonates allyl ethers, ethers, silyl ethers, alkyl ethers, arylalkyl ethers, and alkoxyalkyl ethers. Examples of suitable esters include formates, acetates, proprionates, pentanoates, crotonates, and benzoates. Specific examples of suitable esters include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetate), crotonate, 4-methoxy-crotonate, benzoate, p-benylbenzoate, 2,4,6-trimethylbenzoate. Examples of suitable carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of suitable silyl ethers include trimethylsilyl, triethylsilyl, t-butyldimethylsilyl, t-butyldiphenylsilyl, triisopropylsilyl ether, and other trialkylsilyl ethers. Examples of suitable alkyl ethers include methyl, benzyl, p-methoxybenzyl, 3,4-dimethoxybenzyl, trityl, t-butyl, and allyl ether, or derivatives thereof. Alkoxyalkyl ethers include acetals such as methoxymethyl, methylthiomethyl, (2-methoxyethoxy) methyl, benzyloxymethyl, beta-(trimethylsilyl)ethoxymethyl, and tetrahydropyran-2-yl ether. Examples of suitable arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

Protected amines are well known in the art and include those described in detail in Greene (1999). Suitable mono-protected amines further include, but are not limited to, aralkylamines, carbamates, allyl amines, amides, and the like. Examples of suitable mono-protected amino moieties include t-butyloxycarbonylamino (—NHBOC), ethyloxycarbonylamino, methyloxycarbonylamino, trichloroethyloxycarbonylamino, allyloxycarbonylamino (—NHAlloc), benzyloxocarbonylamino (—NHCBZ), allylamino, benzylamino (—NHBn), fluorenylmethylcarbonyl (—NHFmoc), formamido, acetamido, chloroacetamido, dichloroacetamido, trichloroacetamido, phenylacetamido, trifluoroacetamido, benzamido, t-butyldiphenylsilyl, and the like. Suitable di-protected amines include amines that are substituted with two substituents independently selected from those described above as mono-protected amines, and further include cyclic imides, such as phthalimide, maleimide, succinimide, and the like. Suitable di-protected amines also include pyrroles and the like, 2,2,5,5-tetramethyl-[1,2,5]azadisilolidine and the like, and azide.

Protected aldehydes are well known in the art and include those described in detail in Greene (1999). Suitable protected aldehydes further include, but are not limited to, acyclic acetals, cyclic acetals, hydrazones, imines, and the like. Examples of such groups include dimethyl acetal, diethyl acetal, diisopropyl acetal, dibenzyl acetal, bis(2-nitrobenzyl) acetal, 1,3-dioxanes, 1,3-dioxolanes, semicarbazones, and derivatives thereof.

Protected carboxylic acids are well known in the art and include those described in detail in Greene (1999). Suitable protected carboxylic acids further include, but are not limited to, optionally substituted C$_{1-6}$ aliphatic esters, optionally substituted aryl esters, silyl esters, activated esters, amides, hydrazides, and the like. Examples of such ester groups include methyl, ethyl, propyl, isopropyl, butyl, isobutyl, benzyl, and phenyl ester, wherein each group is optionally substituted. Additional suitable protected carboxylic acids include oxazolines and ortho esters.

Protected thiols are well known in the art and include those described in detail in Greene (1999). Suitable protected thiols further include, but are not limited to, disulfides, thioethers, silyl thioethers, thioesters, thiocarbonates, and thiocarbamates, and the like. Examples of such groups include, but are not limited to, alkyl thioethers, benzyl and substituted benzyl thioethers, triphenylmethyl thioethers, and trichloroethoxycarbonyl thioester, to name but a few.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, in neutron scattering experiments, as analytical tools, or probes in biological assays.

As used herein, the term "detectable moiety" is used interchangeably with the term "label" and relates to any moiety capable of being detected (e.g., primary labels and secondary labels). A "detectable moiety" or "label" is the radical of a detectable compound.

"Primary" labels include radioisotope-containing moieties (e.g., moieties that contain $^{32}$P, $^{33}$P, $^{35}$S, or $^{14}$C), mass-tags, and fluorescent labels, and are signal-generating reporter groups which can be detected without further modifications.

Other primary labels include those useful for positron emission tomography including molecules containing radioisotopes (e.g. $^{18}$F) or ligands with bound radioactive metals (e.g. $^{62}$Cu). In other embodiments, primary labels are contrast agents for magnetic resonance imaging such as gadolinium, gadolinium chelates, or iron oxide (e.g $Fe_3O_4$, $Fe_2O_3$, $MFe_2O_4$, where M is a suitable metal such as Mn, etc.) particles. Similarly, semiconducting nanoparticles (e.g. cadmium selenide, cadmium sulfide, cadmium telluride) are useful as fluorescent labels. Other metal nanoparticles (e.g colloidal gold) also serve as primary labels.

"Secondary" labels include moieties such as biotin, or protein antigens, that require the presence of a second compound to produce a detectable signal. For example, in the case of a biotin label, the second compound may include streptavidin-enzyme conjugates. In the case of an antigen label, the second compound may include an antibody-enzyme conjugate. Additionally, certain fluorescent groups can act as secondary labels by transferring energy to another compound or group in a process of nonradiative fluorescent resonance energy transfer (FRET), causing the second compound or group to then generate the signal that is detected.

Unless otherwise indicated, radioisotope-containing moieties are optionally substituted hydrocarbon groups that contain at least one radioisotope. Unless otherwise indicated, radioisotope-containing moieties contain from 1-40 carbon atoms and one radioisotope. In certain embodiments, radioisotope-containing moieties contain from 1-20 carbon atoms and one radioisotope.

The terms "fluorescent label," "fluorescent group," "fluorescent compound," "fluorescent dye," and "fluorophore," as used herein, refer to compounds or moieties that absorb light energy at a defined excitation wavelength and emit light energy at a different wavelength. Examples of fluorescent compounds include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660, Alexa Fluor 680, Alexa Fluor 700, and Alexa Fluor 750), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red, Texas Red-X.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-Methoxytetrafluorobenzyl)oxy]phenyl]-3-methylglyceronyl]isonipecotic Acid, 4'-[2,3,5,6-Tetrafluoro-4-(pentafluorophenoxyl)]methyl acetophenone, and their derivatives. The synthesis and utility of these mass-tags is described in U.S. Pat. Nos. 4,650,750, 4,709,016, 5,360,8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags.

The term "substrate," as used herein refers to any material or macromolecular complex to which a functionalized end-group of a block copolymer can be attached. Examples of commonly used substrates include, but are not limited to, glass surfaces, silica surfaces, plastic surfaces, metal surfaces, surfaces containing a metallic or chemical coating, membranes (e.g., nylon, polysulfone, silica), micro-beads (eg., latex, polystyrene, or other polymer), porous polymer matrices (e.g., polyacrylamide gel, polysaccharide, polymethacrylate), macromolecular complexes (e.g., protein, polysaccharide).

The term "fusogenic peptide" refers to a peptide sequence that promotes escape from endolysosomal compartments. Great efforts have been undertaken to further enhance endolysosomal escape and thus prevent lysosomal degradation. A key strategy has been adapted from viral elements that promote escape from the harsh endolysosomal environment and deliver their genetic information intact into the nucleus. Apart from complete virus capsids and purified capsid proteins, short amino acid sequences derived from the N-terminus of *Haemophilus Influenza* Haemagglutinin-2 have also been shown to induce pH-sensitive membrane disruption, leading to improved transfection of DNA-polycation polymer complexes in vitro. One such example is the INF7 peptide (GLFGAIAGFIENGWEGMIDGGGC). At neutral pH (pH 7.0) the INF peptide forms a random coil structure without fusogenic activity. However, this peptide undergoes a conformational change into an amphipathic α-helix at pH 5.0 and aggregates resulting in the formation of pores which destabilize endosomal membranes causing vesicle leakage. Indeed, the INF7 peptide has been used in combination with polymer based delivery systems and shown to tremendously enhance gene transfection activity without affecting cell cytotoxicity. Other synthetic fusogenic peptides include the GAL4 (WEAALAEALAEALAEHLAEALAEALEALAA) and KALA (WEAKLAKALAKALAKHLAKALAKALKACEA) peptides. These peptides have previously been used to successfully promote extensive membrane destabilization and subsequently, contribute to transfection enhancement.

As used herein, the term "targeting group" refers to any molecule, macromolecule, or biomacromolecule which selectively binds to receptors that are expressed or over-expressed on specific cell types. Targeting groups are well known in the art and include those described in International application publication number WO 2008/134731, published Nov. 6, 2008, the entirety of which is hereby incorporated by reference. In some embodiments, the targeting group is a moiety selected from folate, a Her-2 binding peptide, a urokinase-type plasminogen activator receptor (uPAR) antagonist, a CXCR4 chemokine receptor antagonist, a GRP78 peptide antagonist, an RGD peptide, an RGD cyclic peptide, a luteinizing hormone-releasing hormone (LHRH) antagonist peptide, an aminopeptidase targeting peptide, a brain homing peptide, a kidney homing peptide, a heart homing peptide, a gut homing peptide, an integrin homing peptide, an angiogencid tumor endothelium homing peptide, an ovary homing peptide, a uterus homing peptide, a sperm homing peptide, a microglia homing peptide, a synovium homing peptide, a urothelium homing peptide, a prostate homing peptide, a lung homing peptide, a skin homing peptide, a retina homing peptide, a pancreas homing peptide, a liver homing peptide, a lymph node homing peptide, an adrenal gland homing peptide, a thyroid homing peptide, a bladder homing peptide, a breast homing peptide, a neuroblastoma homing peptide, a lymphona homing peptide, a muscle homing peptide, a wound vasculature homing peptide, an adipose tissue homing peptide, a virus binding peptide, or a fusogenic peptide.

The term "oligopeptide", as used herein refers to any peptide of 2-65 amino acid residues in length. In some embodiments, oligopeptides comprise amino acids with natural amino acid side-chain groups. In some embodiments, oligopeptides comprise amino acids with unnatural amino acid side-chain groups. In certain embodiments, oligopeptides are 2-50 amino acid residues in length. In certain embodiments, oligopeptides are 2-40 amino acid residues in length. In some embodiments, oligopeptides are cyclized variations of the linear sequences.

3. Description of Exemplary Embodiments

A. Multiblock Copolymers

As described generally above, in certain embodiments the present invention provides a micelle comprising a multiblock copolymer which comprises a polymeric hydrophilic block and a one or more poly(amino acid) blocks which may or may not consist of a mixed poly(amino acid) block; characterized in that said micelle has an inner core suitable for polynucleotide encapsulation and a hydrophilic shell. In certain embodiments, a provided multiblock copolymer further comprises an optionally crosslinked or crosslinkable block.

Amphiphilic multiblock copolymers, as described herein, can self-assemble in aqueous solution to form nano- and micron-sized structures. In water, these multiblock cationic copolymers co-assemble with polynucleotides through electrostatic interactions between the cationic side chains of the polymer and the anionic phosphates of the polynucleotide. In some cases, the number of phosphates on the polynucleotides may exceed the number of cationic charges on the multiblock copolymer. It will be appreciated that multiple polymers may be used to achieve charge neutrality (i.e. N/P=1) between the polymer and encapsulated polynucleotide. It will also be appreciated that when an excess of polymer is used to encapsulate a polynucleotide, the polymer/polynucleotide complex can possess an overall positive charge (i.e. N/P>1). Without wishing to be bound by any particular theory, it is believed that the mixed random copolymer block consisting of hydrophobic and amine-containing amino acid residues collapses to form the micellar core, while the hydrophilic PEG block forms a peripheral corona and imparts water solubility. It will be appreciated that the hydrophilic PEG corona may also shield the excess charge of the polycation/polynucleotide complex in the micelle core (e.g. when N/P>1), rendering the exterior of the micelle charge neutral. In certain embodiments, the multiblock copolymers in accordance with the present invention possess distinct hydrophilic and cationic segments that form micelles. In addition, these multiblock polymers optionally comprise a poly(amino acid) block which contains functionality suitable for crosslinking. It will be appreciated that this functionality is found on the corresponding amino acid side-chain (i.e., $R^x$).

B. Polynucleotide Encapsulation

As described above, the present invention provides a polynucleotide-loaded micelle comprising multiblock copolymers which comprise a polymeric hydrophilic block and a mixed random copolymer block consisting of hydrophobic and amine-containing amino acid residues; characterized in that said micelle has a polynucleotide-loaded inner core and a hydrophilic shell. In some embodiments, the multiblock copolymers of the provided polynucleotide-loaded micelles further comprise a crosslinked or crosslinkable block.

Polyplex complex formation between the multiblock copolymers described above, and the various polynucleotide moieties described below, are typically prepared by mixing the multiblock copolymers and polynucleotides in an aqueous solution. The main mechanism of action for polyplex formation essentially involves electrostatic interactions between the positive charges of the cationic amine-containing amino acid residues, within the multiblock copolymers, and the negative charges of the phosphate polynucleotide backbone.

As described herein, micelles of the present invention can be loaded with any polynucleotide agent. In one embodiment, the encapsulated polynucleotide is a plasmid DNA (pDNA). As used herein, pDNA is defined as a circular, double-stranded DNA that contains a DNA sequence (cDNA or complementary DNA) that is to be expressed in cells either in culture or in vivo. The size of pDNA can range from 3 kilo base pairs (kb) to greater than 50 kb. The cDNA that is contained within plasmid DNA is usually between 1-5 kb in length, but may be greater if larger genes are incorporated. pDNA may also incorporate other sequences that allow it to be properly and efficiently expressed in mammalian cells, as well as replicated in bacterial cells. In certain embodiments, the encapsulated pDNA expresses a therapeutic gene in cell culture, animals, or humans that possess a defective or missing gene that is responsible for and/or correlated with disease.

In certain embodiments, an encapsulated polynucleotide is capable of silencing gene expression via RNA interference (RNAi). As defined herein, RNAi is cellular mechanism that suppresses gene expression during translation and/or hinders the transcription of genes through destruction of messenger RNA (mRNA). Without wishing to be bound by any particular theory, it is believed that endogenous double-stranded RNA located in the cell are processed into 20-25 nt short-interfering RNA (siRNA) by the enzyme Dicer. siRNA subsequently binds to the RISC complex (RNA-induced silencing nuclease complex), and the guide strand of the siRNA anneals to the target mRNA. The nuclease activity of the RISC complex then cleaves the mRNA, which is subsequently degraded (*Nat. Rev. Mol. Cell. Biol.*, 2007, 8, 23).

In some embodiments, an encapsulated polynucleotide is a siRNA. As used herein, siRNA is defined as a linear, double-stranded RNA that is 20-25 nucleotides (nt) in length and possesses a 2 nt, 3' overhang on each end which can induce gene knockdown in cell culture or in vivo via RNAi. In certain embodiments, an encapsulated siRNA suppresses disease-relevant gene expression in cell culture, animals, or humans.

In certain embodiments, an encapsulated polynucleotide is pDNA that expresses a short-hairpin RNA (shRNA). As used herein, shRNA is a linear, double-stranded RNA, possessing a tight hairpin turn, which is synthesized in cells through transfection and expression of a exogenous pDNA. Without wishing to be bound by any particular theory, it is believed that the shRNA hairpin structure is cleaved to produce siRNA, which mediates gene silencing via RNA interference. In certain embodiments, the encapsulated shRNA suppresses gene expression in cell culture, animals, or humans that are responsible for a disease via RNAi.

In certain embodiments, an encapsulated polynucleotide is a microRNA (miRNA). As used herein, miRNA is a linear, single-stranded RNA that ranges between 21-23 nt in length and regulates gene expression via RNAi (Cell, 2004, 116, 281). In certain embodiments, an encapsulated miRNA suppresses gene expression in cell culture, animals, or humans that are responsible for a disease via RNAi.

In some embodiments, an encapsulated polynucleotide is a messenger RNA (mRNA). As used herein, mRNA is defined as a linear, single stranded RNA molecule, which is responsible for translation of genes (from DNA) into proteins. In certain embodiments, an encapsulated mRNA is encoded from a plasmid cDNA to serve as the template for protein translation. In certain embodiments, an encapsulated mRNA translates therapeutic proteins, in vitro and/or in vivo, which can treat disease.

In certain embodiments, an encapsulated polynucleotide is an antisense RNA (aRNA). As used herein, aRNA is a linear, single-stranded RNA that is complementary to a targeted mRNA located in a cell. Without wishing to be bound by any particular theory, it is believed that aRNA inhibits translation of a complementary mRNA by pairing with it and obstructing the cellular translation machinery. It is believed that the mechanism of action for aRNA is different from RNAi because the paired mRNA is not destroyed. In certain embodiments, an encapsulated aRNA suppresses gene expression in cell culture, animals, or humans that are responsible for a disease by binding mRNA and physically obstructing translation.

In certain embodiments, a polynucleotide is combined with a suitable metal ion, then micelle formation performed by the introduction of a suitable multiblock copolymer. Without wishing to be bound by any particular theory, it is believed that such combination of a polynucleotide with a suitable metal ion acts to pre-compact the polynucleotide prior to micelle formation, thereby allowing for a more uniform particle size distribution. In certain embodiments, a polynucleotide first combined with a suitable metal ion is DNA. In certain embodiments, a polynucleotide first combined with a suitable metal ion is pDNA. In some embodiments, a metal ion is copper. In some embodiments, a metal ion is calcium. In some embodiments, a metal ion is selected from one or more of the following: Mg, Ca, Cu, Mn, Zn, Ni, or Fe.

In certain embodiments, the present invention provides a micelle having a polynucleotide encapsulated therein, comprising a diblock copolymer of formula I:

wherein:
n is 50-2500;
$x^1$ is 0 to 250;
$x^2$ is 0 to 250;
$y^1$ is 0 to 250, provided that $x^1$ and $y^1$ are not simultaneously zero;
$y^2$ is 0 to 250, provided that $y^1$ and $y^2$ are not simultaneously zero;
$R^x$ is a natural or unnatural amino acid side-chain group that is hydrophobic;
$R^y$ is a natural or unnatural amino acid side-chain group comprising an ester moiety;
$R^1$ is —Z(CH$_2$CH$_2$Y)$_p$(CH$_2$)$_t$R$^3$, wherein:
Z is a valence bond, a bivalent triazolyl moiety, —O—, —S—, —C≡C—, or —CH$_2$—;
each Y is independently —O— or —S—;
p is 0-10;
t is 0-10; and
$R^3$ is hydrogen, —N$_3$, —CN, a mono-protected amine, a di-protected amine, a protected aldehyde, a protected hydroxyl, a protected carboxylic acid, a protected thiol, a 9-30 membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety or a targeting group;
Q is a valence bond or a bivalent, saturated or unsaturated, straight or branched C$_{1-12}$ alkylene chain, wherein 0-6 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:
-Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;
$R^2$ is selected from an optionally substituted aliphatic group or a fusogenic peptide.

In some embodiments, the present invention provides a micelle having a polynucleotide encapsulated therein, comprising a diblock copolymer of formula I:

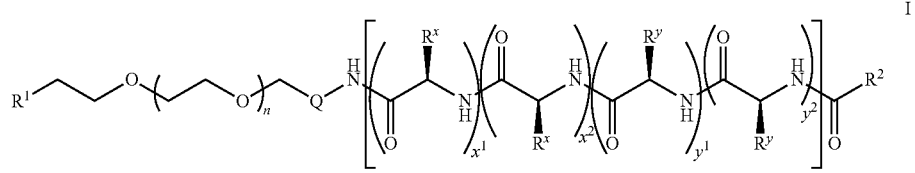

I

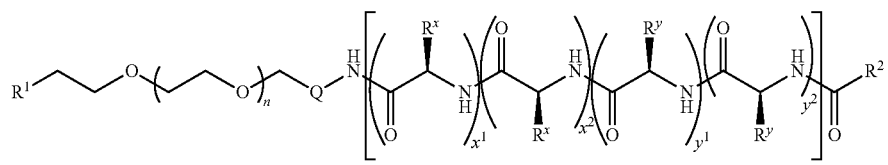

I as described above, wherein the polynucleotide is combined with a suitable metal ion. In some embodiments, the polynucleotide combined with a suitable metal ion is DNA. In some embodiments, the polynucleotide combined with a suitable metal ion is pDNA.

In certain embodiments, the present invention provides a micelle having a polynucleotide encapsulated therein, comprising a diblock copolymer of formula I-a:

As defined generally above, the Ry group of formulae I or I-a is a natural or unnatural amino acid side-chain group comprising an ester moiety capable of undergoing aminolysis. One of ordinary skill in the art would recognize that many readily available amine-containing compounds are suitable for such aminolysis reactions. Exemplary amine derivatives suitable for such aminolysis are set forth in Table 1, below.

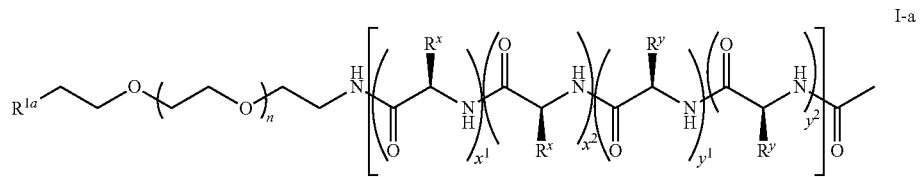

I-a wherein:
n is 50-2500;
$x^1$ is 0 to 250;
$x^2$ is 0 to 250;
$y^1$ is 0 to 250, provided that $x^1$ and $y^1$ are not simultaneously zero;
$y^2$ is 0 to 250, provided that $y^1$ and $y^2$ are not simultaneously zero;
$R^x$ is an amino acid side-chain group corresponding to that of glycine, alanine, norleucine, phenylalanine, isoleucine, norvaline, proline, leucine, methionine, or valine;
$R^y$ is an amino acid side-chain group corresponding to that of benzyl aspartate, benzyl glutamate, t-butyl aspartate, t-butyl glutamate, methyl aspartate, methyl glutamate, alkyl aspartate or alkyl glutamate;
$R^{1a}$ is —$N_3$, —$OCH_2C\equiv CH$, or —$OCH_3$.

In certain embodiments, the present invention provides a micelle having a polynucleotide encapsulated therein, comprising a diblock copolymer of formula I-a:

TABLE 1

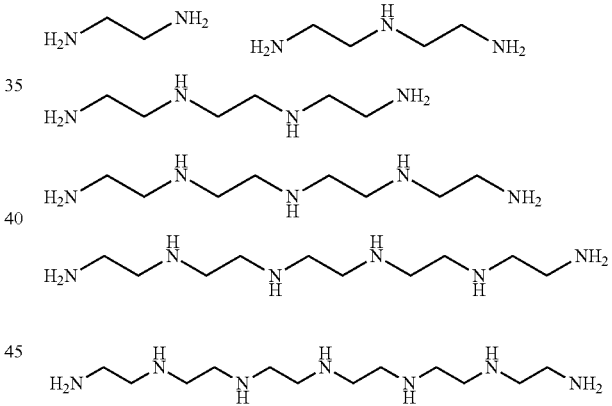

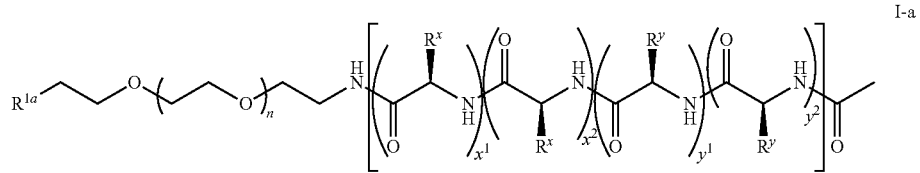

I-a as described above, wherein the polynucleotide is combined with a suitable metal ion. In some embodiments, the polynucleotide combined with a suitable metal ion is DNA. In some embodiments, the polynucleotide combined with a suitable metal ion is pDNA.

In some embodiments, the $R^{1a}$ group of formula I-a is —$N_3$. In certain embodiments, the $R^{1a}$ group of formula I-a is —$OCH_2C\equiv CH$. In some embodiments, the $R^{1a}$ group of formula I-a is —$OCH_3$.

TABLE 1-continued

TABLE 1-continued

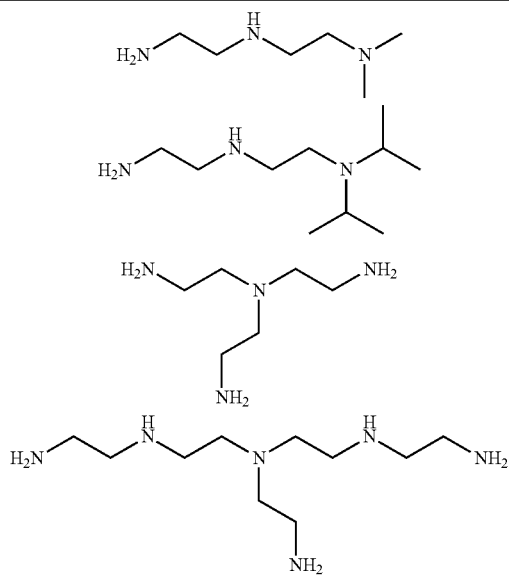

TABLE 1-continued

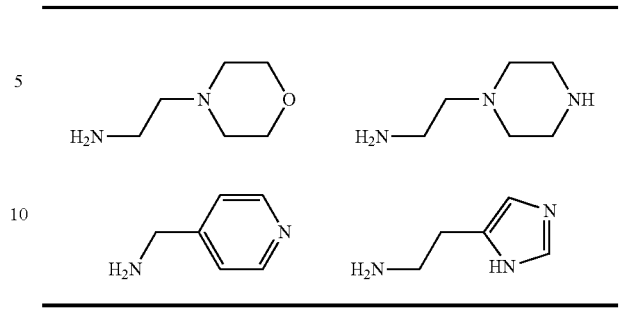

When compounds of formulae I or I-a are treated with a suitable amine under aminolysis conditions, a rearrangement to a beta-amino acid or racemization of the side chain's stereocenter is a possible side reaction. The mechanism for this rearrangement is detailed in Kataoka et. al. *Reactive and Functional Polymers,* 2007, 67, 1361-1372 and is represented in Scheme 1, below.

Scheme 1.

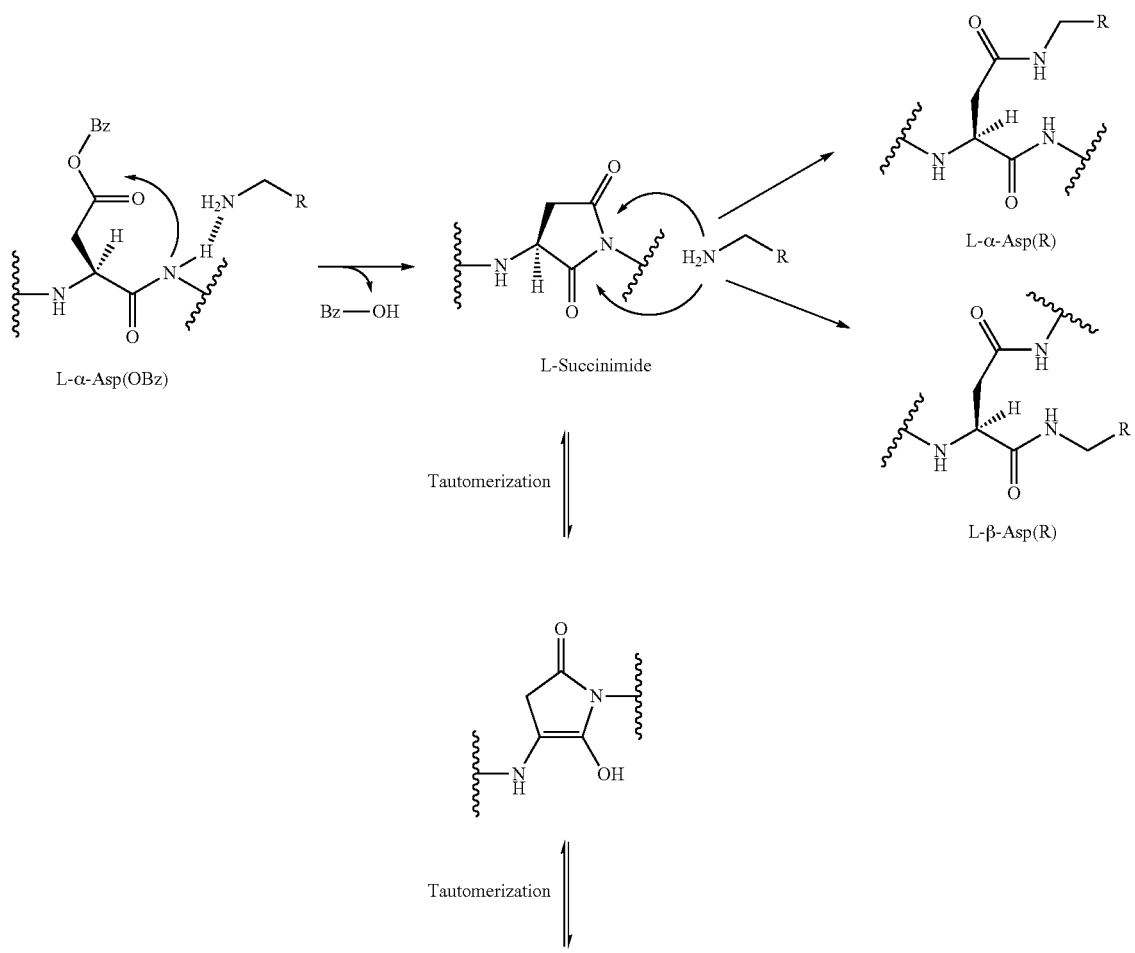

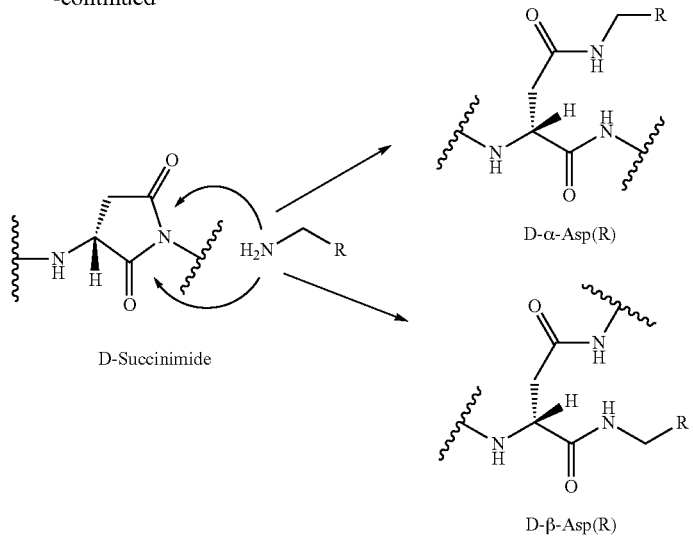

D-Succinimide

D-α-Asp(R)

D-β-Asp(R)

The exact reaction conditions (e.g. temperature, solvent polarity, equivalents of amine) all influence the nature of the side reactions that can occur. Thus, during the course of aminolysis, one can envision four classes of product compounds: a case where both racemization of the stereocenter and rearrangement to the beta amino acid occurs, a case where only racemization occurs, a case where only rearrangement to the beta amino acid occurs, and a case where neither racemization nor rearrangement occurs. Without wishing to be bound to any particular theory, it is believed that if the starting material is enriched in either L or D stereocenters, then the resulting product will retain at least a portion of, and, in some embodiments, the majority of, the original stereochemical enrichment. One of ordinary skill in the art will recognize that such partial racemization and/or rearrangement, when present, results in the formation of a mixed block.

In certain embodiments, the present invention provides a micelle having a polynucleotide encapsulated therein, comprising a diblock copolymer of formula I-b:

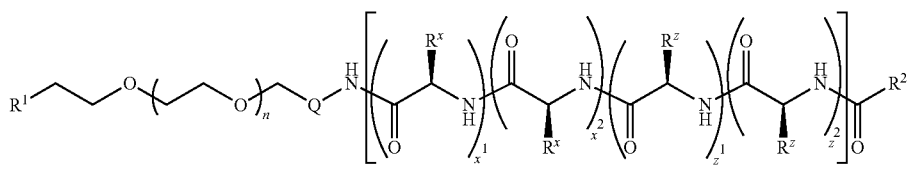

I-b wherein:
n is 50-2500;
$x^1$ is 0 to 250;
$x^2$ is 0 to 250;
$z^1$ is 0 to 250, provided that $x^1$ and $z^1$ are not simultaneously zero;
$z^2$ is 0 to 250, provided that $z^1$ and $z^2$ are not simultaneously zero;
$R^x$ is a natural or unnatural amino acid side-chain group that is hydrophobic;
$R^z$ is -L-$R^4$ wherein:
  L is a bivalent, straight or branched, $C_{4-20}$ alkylene chain wherein at least one methylene unit of -L- is replaced by —C(O)NR— and 1-10 additional methylene units are independently replaced by —N(R)— or -Het-;
  Het is a bivalent 5-6 membered saturated, partially unsaturated, or aromatic ring having at least one nitrogen and 0-3 additional heteroatoms independently selected from nitrogen, oxygen, or sulfur;

$R^4$ is R or N(R)$_2$;
each R is hydrogen or $C_{1-6}$ aliphatic, or two R on the same nitrogen are taken together with the nitrogen to form a 5-6 membered heterocyclic ring having 1-3 heteroatoms independently selected from nitrogen, oxygen, or sulfur;
$R^1$ is —Z(CH$_2$CH$_2$Y)$_p$(CH$_2$)$_t$R$^3$, wherein:
  Z is a valence bond, a bivalent triazolyl moiety, —O—, —S—, —C≡C—, or —CH$_2$—;
  each Y is independently —O— or —S—;
  p is 0-10;
  t is 0-10; and
$R^3$ is hydrogen, —N$_3$, —CN, a mono-protected amine, a di-protected amine, a protected aldehyde, a protected hydroxyl, a protected carboxylic acid, a protected thiol, a 9-30 membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety or a targeting group;
Q is a valence bond or a bivalent, saturated or unsaturated, straight or branched $C_{1-12}$ alkylene chain, wherein 0-6 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:
-Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;
R² is selected from an optionally substituted aliphatic group or a fusogenic peptide.

In certain embodiments, the present invention provides a micelle having a polynucleotide encapsulated therein, comprising a diblock copolymer of formula I-b:

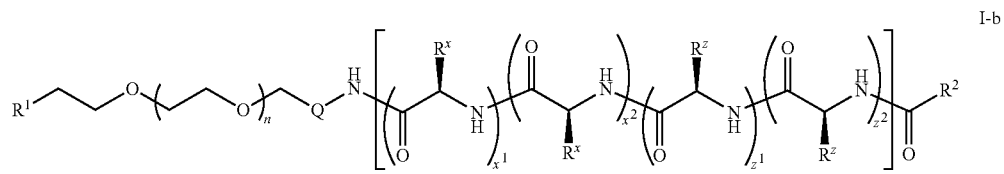

I-b as described above, wherein the polynucleotide is combined with a suitable metal ion. In some embodiments, the polynucleotide combined with a suitable metal ion is DNA. In some embodiments, the polynucleotide combined with a suitable metal ion is pDNA.

Another aspect of the present invention provides a method for preparing a multi-block copolymer of formula I-b:

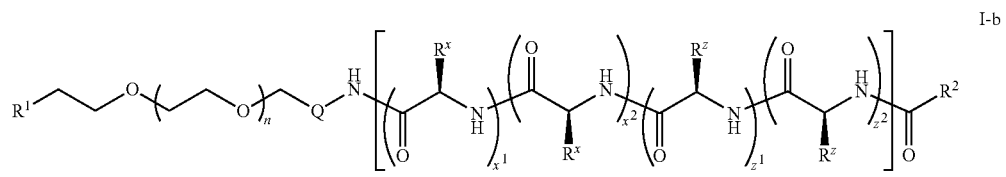

I-b wherein each of $R^1$, $R^x$, $R^z$, $R^2$, Q, n, $x^1$, $x^2$, $z^1$, and $z^2$ is as defined above and described herein, said method comprising the steps of:

a) providing a compound of formula I:

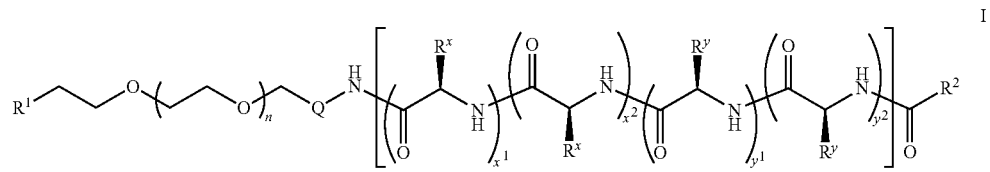

I wherein each of $R^1$, $R^x$, $R^y$, $R^2$, Q, n, $x^1$, $x^2$, $y^1$, and $y^2$ is as defined above and described herein, and b) reacting the compound of formula I with a suitable amine to form the compound of formula I-b.

In certain embodiments, the present invention provides a micelle having a polynucleotide encapsulated therein, comprising a diblock copolymer of formula I-c:

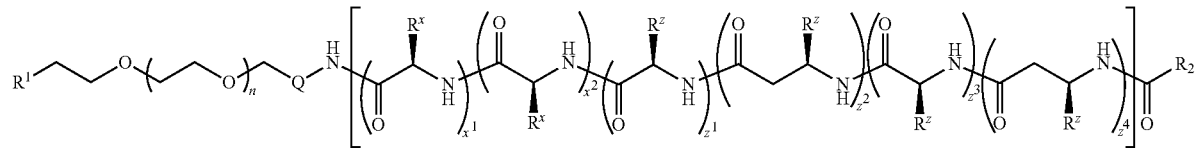

I-c wherein:

n is 50-2500;

$x^1$ is 0 to 250;

$x^2$ is 0 to 250;

$z^1$ is 0 to 250;

$z^2$ is 0 to 250;

$z^3$ is 0 to 250, provided that $z^1$ and $z^3$ are not simultaneously zero;

$z^4$ is 0 to 250;

$R^x$ is a natural or unnatural amino acid side-chain group that is hydrophobic;

each $R^z$ is independently -L-$R^4$ wherein:

L is a bivalent, straight or branched, $C_{4-20}$ alkylene chain wherein at least one methylene unit of -L- is replaced by —C(O)NR— and 1-10 additional methylene units are independently replaced by —N(R)— or -Het-;

Het is a bivalent 5-6 membered saturated, partially unsaturated, or aromatic ring having at least one nitrogen and 0-3 additional heteroatoms independently selected from nitrogen, oxygen, or sulfur;

$R^4$ is R or $N(R)_2$;

each R is hydrogen or $C_{1-6}$ aliphatic, or two R on the same nitrogen are taken together with the nitrogen to form a 5-6 membered heterocyclic ring having 1-3 heteroatoms independently selected from nitrogen, oxygen, or sulfur;

methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:

-Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;

$R^2$ is selected from an optionally substituted aliphatic group or a fusogenic peptide.

It will be appreciated that the phrase "each $R^z$ is independently -L-$R^4$" is intended to encompass a mixed block that may result from the beta-amino acid rearrangement chemistry depicted in Scheme 1, above. In certain embodiments, a $R^z$ group in a $z^2$ block is a homolog of a $R^z$ group in a $z^1$ block.

In certain embodiments, the present invention provides a micelle having a polynucleotide encapsulated therein, comprising a diblock copolymer of formula I-c:

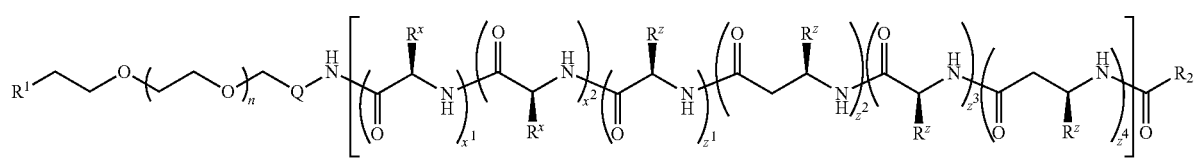

I-c $R^1$ is —Z(CH$_2$CH$_2$Y)$_p$(CH$_2$)$_t$R$^3$, wherein:

Z is a valence bond, a bivalent triazolyl moiety, —O—, —S—, —C≡C—, or —CH$_2$—;

each Y is independently —O— or —S—;

p is 0-10;

t is 0-10; and $R^3$ is hydrogen, —N$_3$, —CN, a mono-protected amine, a di-protected amine, a protected aldehyde, a protected hydroxyl, a protected carboxylic acid, a protected thiol, a 9-30 membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety or a targeting group;

Q is a valence bond or a bivalent, saturated or unsaturated, straight or branched $C_{1-12}$ alkylene chain, wherein 0-6 as described above, wherein the polynucleotide is combined with a suitable metal ion. In some embodiments, the polynucleotide combined with a suitable metal ion is DNA. In some embodiments, the polynucleotide combined with a suitable metal ion is pDNA.

In certain embodiments, the present invention provides a micelle having a polynucleotide encapsulated therein, comprising a diblock copolymer of formula I-d:

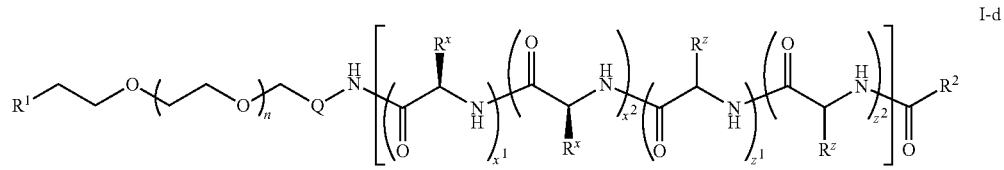

I-d wherein:

n is 50-2500;

$x^1$ is 0 to 250;

$x^2$ is 0 to 250;

$z^1$ is 0 to 250, provided that $x^1$ and $z^1$ are not simultaneously zero;

$z^2$ is 0 to 250, provided that $z^1$ and $z^2$ are not simultaneously zero;

$R^x$ is a natural or unnatural amino acid side-chain group that is hydrophobic;

$R^z$ is -L-$R^4$ wherein:

L is a bivalent, straight or branched, $C_{4-20}$ alkylene chain wherein at least one methylene unit of -L- is replaced by —C(O)NR— and 1-10 additional methylene units are independently replaced by —N(R)— or -Het-;

Het is a bivalent 5-6 membered saturated, partially unsaturated, or aromatic ring having at least one nitrogen and 0-3 additional heteroatoms independently selected from nitrogen, oxygen, or sulfur;

$R^4$ is R or $N(R)_2$;

each R is hydrogen or $C_{1-6}$ aliphatic, or two R on the same nitrogen are taken together with the nitrogen to form a 5-6 membered heterocyclic ring having 1-3 heteroatoms independently selected from nitrogen, oxygen, or sulfur;

$R^2$ is selected from an optionally substituted aliphatic group or a fusogenic peptide.

In certain embodiments, the present invention provides a micelle having a polynucleotide encapsulated therein, comprising a diblock copolymer of formula I-d:

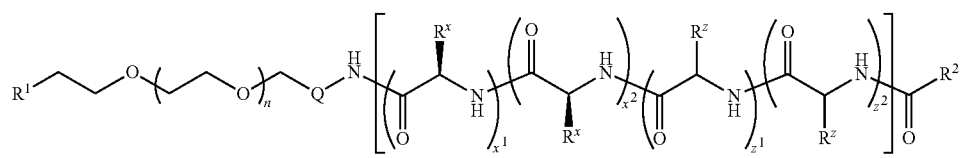

I-d as described above, wherein the polynucleotide is combined with a suitable metal ion. In some embodiments, the polynucleotide combined with a suitable metal ion is DNA. In some embodiments, the polynucleotide combined with a suitable metal ion is pDNA.

In certain embodiments, the present invention provides a micelle having a polynucleotide encapsulated therein, comprising a diblock copolymer of formula I-e:

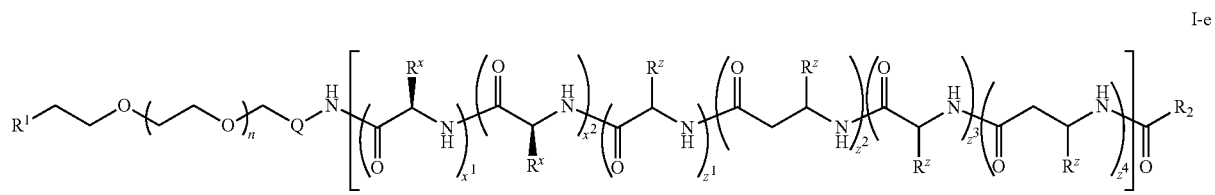

I-e $R^1$ is —$Z(CH_2CH_2Y)_p(CH_2)_tR^3$, wherein:
Z is a valence bond, a bivalent triazolyl moiety, —O—, —S—, —C≡C—, or —CH$_2$—;
each Y is independently —O— or —S—;
p is 0-10;
t is 0-10; and
$R^3$ is hydrogen, —$N_3$, —CN, a mono-protected amine, a di-protected amine, a protected aldehyde, a protected hydroxyl, a protected carboxylic acid, a protected thiol, a 9-30 membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety or a targeting group;

Q is a valence bond or a bivalent, saturated or unsaturated, straight or branched $C_{1-12}$ alkylene chain, wherein 0-6 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:

-Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;

wherein:
n is 50-2500;
$x^1$ is 0 to 250;
$x^2$ is 0 to 250;
$z^1$ is 0 to 250;
$z^2$ is 0 to 250;
$z^3$ is 0 to 250, provided that $z^1$ and $z^3$ are not simultaneously zero;
$z^4$ is 0 to 250;
$R^x$ is a natural or unnatural amino acid side-chain group that is hydrophobic;
each $R^z$ is independently -L-$R^4$ wherein:
L is a bivalent, straight or branched, $C_{4-20}$ alkylene chain wherein at least one methylene unit of -L- is replaced by —C(O)NR— and 1-10 additional methylene units are independently replaced by —N(R)— or -Het-;
Het is a bivalent 5-6 membered saturated, partially unsaturated, or aromatic ring having at least one nitrogen and 0-3 additional heteroatoms independently selected from nitrogen, oxygen, or sulfur;
$R^4$ is R or $N(R)_2$;
each R is hydrogen or $C_{1-6}$ aliphatic, or two R on the same nitrogen are taken together with the nitrogen to form a 5-6 membered heterocyclic ring having 1-3 heteroatoms independently selected from nitrogen, oxygen, or sulfur;
$R^1$ is —$Z(CH_2CH_2Y)_p(CH_2)_tR^3$, wherein:
Z is a valence bond, a bivalent triazolyl moiety, —O—, —S—, —C≡C—, or —CH$_2$—;
each Y is independently —O— or —S—;

p is 0-10;

t is 0-10; and $R^3$ is hydrogen, —$N_3$, —CN, a mono-protected amine, a di-protected amine, a protected aldehyde, a protected hydroxyl, a protected carboxylic acid, a protected thiol, a 9-30 membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety or a targeting group;

Q is a valence bond or a bivalent, saturated or unsaturated, straight or branched $C_{1-12}$ alkylene chain, wherein 0-6 methylene units of Q are independently replaced by -Cy-, —O—, —NH—, —S—, —OC(O)—, —C(O)O—, —C(O)—, —SO—, —$SO_2$—, —$NHSO_2$—, —$SO_2NH$—, —NHC(O)—, —C(O)NH—, —OC(O)NH—, or —NHC(O)O—, wherein:

-Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;

$R^2$ is selected from an optionally substituted aliphatic group or a fusogenic peptide.

In certain embodiments, the present invention provides a micelle having a polynucleotide encapsulated therein, comprising a diblock copolymer of formula I-e:

In certain embodiments, the $x^2$ group of formulae I, I-a, I-b, I-c, I-d, or I-e is about 0 to about 250. In some embodiments $x^2$ is about 0 to about 50. In certain embodiments, the $x^2$ group of formulae I, I-a, I-b, I-c, I-d, or I-e is 0. In some embodiments, $x^2$ is about 10. In some embodiments, $x^2$ is about 20. In some embodiments, $x^2$ is about 40. In some embodiments, $x^2$ is selected from 10±5, 20±5, 30±5, 40±5, or 50±5.

In certain embodiments, the $y^1$ group of formulae I or I-a is about 0 to about 250. In other embodiments, $y^1$ is about 100 to about 200. In certain embodiments, the $y^1$ group of formula I is 0. In some embodiments, $y^1$ is about 140. In some embodiments, $y^1$ is about 160. In some embodiments, $y^1$ is about 180. In some embodiments, $y^1$ is selected from 150±10, 160±10, 170±10, 180±10, or 190±10.

In certain embodiments, the $y^2$ group of formulae I or I-a is about 0 to about 250. In some embodiments, $y^2$ is about 100 to about 200. In certain embodiments, the $y^2$ group of formulae I or I-a is 0. In some embodiments, $y^2$ is about 140. In some embodiments, $y^2$ is about 160. In some embodiments, $y^2$ is about 180. In some embodiments, $y^2$ is selected from 150±10, 160±10, 170±10, 180±10, or 190±10.

In certain embodiments, the $z^1$ group of formulae I-b, I-c, I-d, or I-e is about 0 to about 250. In some embodiments, $z^1$ is about 100-200. In certain embodiments, the $z^1$ group of formulae I-b, I-c, I-d, or I-e is 0. In some embodiments, $z^1$ is about 140. In some embodiments, $z^1$ is about 160. In some embodiments, $z^1$ is about 180. In some embodiments, $z^1$ is selected from 150±10, 160±10, 170±10, 180±10, or 190±10.

In certain embodiments, the $z^2$ group of formulae I-b, I-c, I-d, or I-e is about 0 to about 250. In some embodiments, $z^2$ is about 100-200. In certain embodiments, the $z^2$ group of formulae I-b, I-c, I-d, or I-e is 0. In some embodiments, $z^2$ is about 140. In some embodiments, $z^2$ is about 160. In some

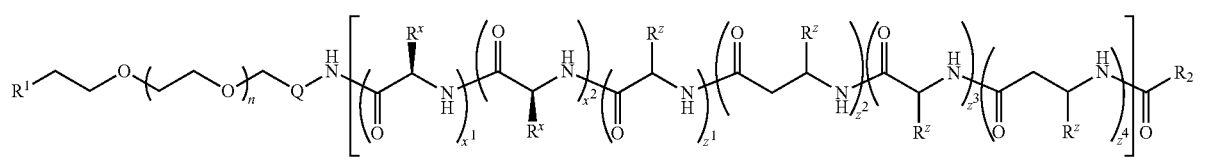

I-e as described above, wherein the polynucleotide is combined with a suitable metal ion. In some embodiments, the polynucleotide combined with a suitable metal ion is DNA. In some embodiments, the polynucleotide combined with a suitable metal ion is pDNA.

As defined generally above, the n group of formulae I, I-a, I-b, I-c, I-d, or I-e is 50-2500. In some embodiments, n is about 110 to about 460. In certain embodiments, the present invention provides compounds of formulae I, I-a, I-b, I-c, I-d, or I-e, as described above, wherein n is about 270. In some embodiments, n is about 225. In some embodiments, n is about 350. In some embodiments, n is about 110. In some embodiments, n is about 454. In some embodiments, n is selected from 110±10, 180±10, 225±10, 275±10, 315±10, or 450±10.

In certain embodiments, the $x^1$ group of formulae I, I-a, I-b, I-c, I-d, or I-e is about 0 to about 250. In certain embodiments, the $x^1$ group of formulae I, I-a, I-b, I-c, I-d, or I-e is about 10. In some embodiments $x^1$ is about 0 to about 50. In some embodiments, $x^1$ is about 20. In some embodiments, $x^1$ is about 30. In some embodiments, $x^1$ is about 40. In some embodiments, $x^1$ is selected from 10±5, 20±5, 30±5, 40±5, or 50±5.

embodiments, $z^2$ is about 180. In some embodiments, $z^2$ is selected from 150±10, 160±10, 170±10, 180±10, or 190±10.

In certain embodiments, the sum of $x^1$ and $x^2$ is about 25 and the sum of $z^1$ and $z^2$ is about 25. In certain embodiments, the sum of $x^1$ and $x^2$ is about 50 and the sum of $z^1$ and $z^2$ is about 50. In certain embodiments, the sum of $x^1$ and $x^2$ is about 100 and the sum of $z^1$ and $z^2$ is about 100.

In certain embodiments, the $z^3$ group of formulae I-c or I-e is about 0 to about 250. In some embodiments, $z^3$ is about 100-200. In certain embodiments, the $z^3$ group of formulae I-c or I-e is 0. In some embodiments, $z^3$ is about 140. In some embodiments, $z^3$ is about 160. In some embodiments, $z^3$ is about 180. In some embodiments, $z^3$ is selected from 150±10, 160±10, 170±10, 180±10, or 190±10.

In certain embodiments, the $z^4$ group of formulae I-c or I-e is about 0 to about 250. In other embodiments, $z^4$ is about 100-200. In certain embodiments, the $z^4$ group of formulae I-c or I-e is 0. In some embodiments, $z^4$ is about 140. In some embodiments, $z^4$ is about 160. In some embodiments, $z^4$ is about 180. In some embodiments, $z^4$ is selected from 150±10, 160±10, 170±10, 180±10, or 190±10.

In some embodiments, the $R^1$ group of formulae I, I-a, I-b, I-c, I-d, or I-e is —$N_3$, which is suitable for Click chemistry and therefore useful for conjugating said compound to biological systems or macromolecules such as proteins, viruses, and cells, to name but a few. The Click reaction is known to proceed quickly and selectively under physiological conditions. In contrast, most conjugation reactions are carried out using the primary amine functionality on proteins (e.g. lysine or protein end-group). Because most proteins contain a multitude of lysines and arginines, such conjugation occurs uncontrollably and/or non-specifically at multiple sites on the protein. This is particularly problematic when lysines or arginines are located around the active site of an enzyme or other biomolecule. Thus, in some embodiments the present invention provides a method of conjugating the azide end group of a compound of formula formulae I, I-a, I-b, I-c, I-d, or I-e to a macromolecule via Click chemistry. In certain embodiments, the present invention provides a macromolecule conjugated to a compound of formula I via the $R^1$ azide group.

In certain embodiments, Z is a bivalent triazolyl moiety. In some embodiments, Z is a valence bond.

In some embodiments, p is 0. In some embodiments, p is 1-10.

In some embodiments, t is 0. In some embodiments, t is 1-10.

In some embodiments, $R^3$ is —$N_3$. In some embodiments, $R^3$ is —$OCH_3$.

In some embodiments, the $R^3$ group of formulae I, I-a, I-b, I-c, I-d, or I-e is a targeting group. Targeting groups are well known in the art and include those described in International application publication number WO 2008/134731, published Nov. 6, 2008, the entirety of which is hereby incorporated by reference. In some embodiments, a T targeting group is a moiety selected from folate, a Her-2 binding peptide, a urokinase-type plasminogen activator receptor (uPAR) antagonist, a CXCR4 chemokine receptor antagonist, a GRP78 peptide antagonist, an RGD peptide, an RGD cyclic peptide, a luteinizing hormone-releasing hormone (LHRH) antagonist peptide, an aminopeptidase targeting peptide, a brain homing peptide, a kidney homing peptide, a heart homing peptide, a gut homing peptide, an integrin homing peptide, an angiogencid tumor endothelium homing peptide, an ovary homing peptide, a uterus homing peptide, a sperm homing peptide, a microglia homing peptide, a synovium homing peptide, a urothelium homing peptide, a prostate homing peptide, a lung homing peptide, a skin homing peptide, a retina homing peptide, a pancreas homing peptide, a liver homing peptide, a lymph node homing peptide, an adrenal gland homing peptide, a thyroid homing peptide, a bladder homing peptide, a breast homing peptide, a neuroblastoma homing peptide, a lymphona homing peptide, a muscle homing peptide, a wound vasculature homing peptide, an adipose tissue homing peptide, a virus binding peptide, or a fusogenic peptide. In certain embodiments, a targeting group is a peptide moiety. In some embodiments, a targeting group is a moiety selected from a tumor homing group, a prostate specific membrane antigen homing peptide, an aminopeptidate N homing peptide, a Her-2 homing peptide, a colong cancer homing peptide, a VEGFR1 homing peptide, or a CXCR4 homing peptide. In certain embodiments, a targeting group is an oliogopeptide.

As defined generally above, the Q group of formulae I, I-a, I-b, I-c, I-d, or I-e is a valence bond or a bivalent, saturated or unsaturated, straight or branched $C_{1-12}$ hydrocarbon chain, wherein 0-6 methylene units of Q are independently replaced by -Cy-, —O—, —NH—, —S—, —OC(O)—, —C(O)O—, —C(O)—, —SO—, —$SO_2$—, —$NHSO_2$—, —$SO_2NH$—, —NHC(O)—, —C(O)NH—, —OC(O)NH—, or —NHC(O)O—, wherein -Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur. In certain embodiments, Q is a valence bond. In other embodiments, Q is a bivalent, saturated $C_{1-12}$ alkylene chain, wherein 0-6 methylene units of Q are independently replaced by -Cy-, —O—, —NH—, —S—, —OC(O)—, —C(O)O—, or —C(O)—, wherein -Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur. In some embodiments, Q is —$CH_2$—.

In certain embodiments, the Q group of formulae I, I-a, I-b, I-c, I-d, or I-e is -Cy- (i.e. a $C_1$ alkylene chain wherein the methylene unit is replaced by -Cy-), wherein -Cy- is an optionally substituted 5-8 membered bivalent, saturated, partially unsaturated, or aryl ring having 0-4 heteroatoms independently selected from nitrogen, oxygen, or sulfur. According to one aspect of the present invention, -Cy- is an optionally substituted bivalent aryl group. In some embodiments, -Cy- is an optionally substituted bivalent phenyl group. In some embodiments, -Cy- is an optionally substituted 5-8 membered bivalent, saturated carbocyclic ring. In some embodiments, -Cy- is an optionally substituted 5-8 membered bivalent, saturated heterocyclic ring having 1-2 heteroatoms independently selected from nitrogen, oxygen, or sulfur. Exemplary -Cy- groups include optionally substituted bivalent rings selected from phenyl, pyridyl, pyrimidinyl, cyclohexyl, cyclopentyl, or cyclopropyl.

As defined above, the $R^x$ group of formulae I, I-a, I-b, I-c, I-d, or I-e is a natural or unnatural hydrophobic amino acid side-chain group. In certain embodiments, hydrophobic amino acid side-chain groups correspond to that of glycine, alanine, valine, leucine, isoleucine, norleucine, phenylalanine, methionine, norvaline, or proline. In certain embodiments, $R^x$ is an amino acid side-chain group corresponding to that of leucine. In certain embodiments, $R^x$ is an amino acid side-chain group corresponding to that of norleucine. In certain embodiments, $R^x$ is an amino acid side-chain group corresponding to that of phenylalanine.

As defined above, the $R^y$ group of formulae I or I-a forms a natural or unnatural amino acid side-chain group that contains an ester capable of undergoing aminolysis. In certain embodiments, ester containing amino acid side-chain groups correspond to that of benzyl aspartate, benzyl glutamate, t-butyl aspartate, t-butyl glutamate, methyl aspartate, methyl glutamate, alkyl aspartate or alkyl glutamate. In some embodiments, the ester containing amino acid side-chain group corresponds to that of benzyl aspartate. In some embodiments, the ester containing amino acid side-chain group corresponds to that of benzyl glutamate.

As defined generally above, the $R^z$ group of formulae I-b, I-c, I-d, or I-e contains an amide and one or more primary, secondary, tertiary amines, aryl amine or imidazole derivative or mixture thereof. In certain embodiments, the $R^z$ group is selected from a group found in Table 1.

TABLE 1

Representative R^z groups (i–xx: chemical structures of representative R^z groups)

TABLE 1-continued

Representative $R^z$ groups

xxi

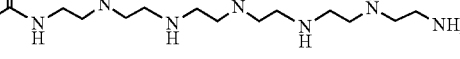

xxii

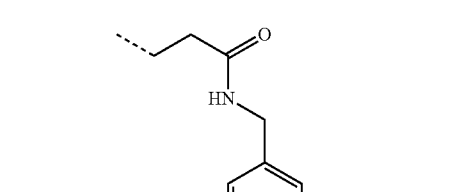

xxiii

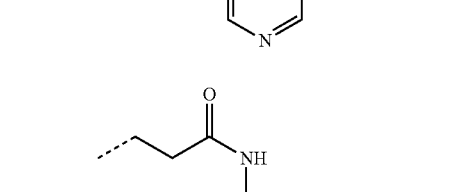

xxiv

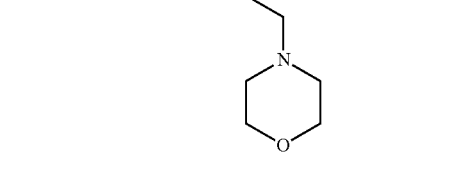

xxv

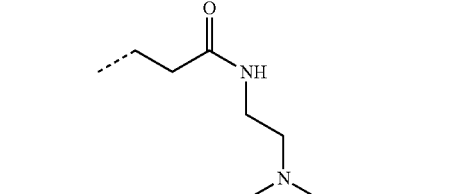

xxvi

TABLE 1-continued

Representative $R^z$ groups

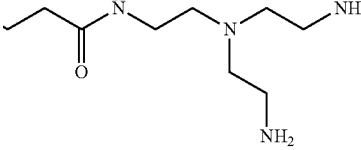

xxvii

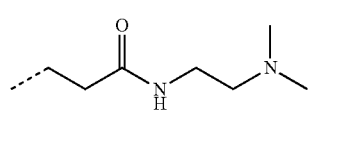

xxviii

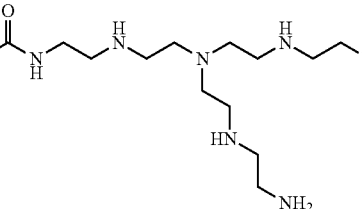

xxix

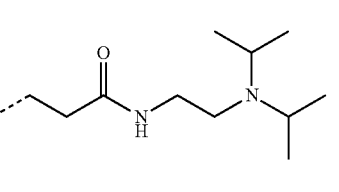

xxx

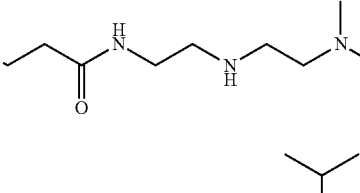

xxxi

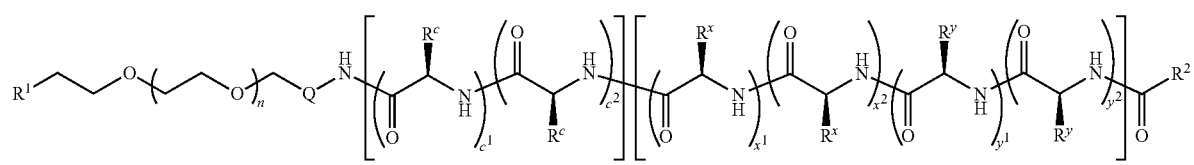

xxxii

In some embodiments, the $R^2$ group of formulae I, I-b, I-c, I-d, or I-e is optionally substituted aliphatic. In some embodiments, $R^2$ is $C_{1-4}$ optionally substituted aliphatic. In certain embodiments, $R^2$ is methyl.

In certain embodiments, the present invention provides a micelle having a polynucleotide encapsulated therein, comprising a triblock copolymer of formula II:

II

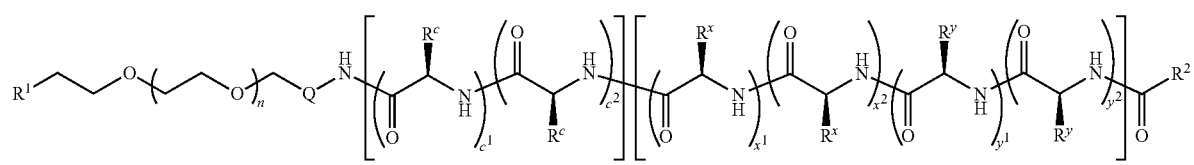

wherein:

n is 50-2500;

$c^1$ is 0 to 100;

$c^2$ is 0 to 100, provided that $c^1$ and $c^2$ are not simultaneously zero;

$x^1$ is 0 to 250;

$x^2$ is 0 to 250;

$y^1$ is 0 to 250, provided that $x^1$ and $y^1$ are not simultaneously zero;

$y^2$ is 0 to 250, provided that $y^1$ and $y^2$ are not simultaneously zero;

$R^c$ is a natural or unnatural amino acid side-chain group that is capable of crosslinking;

$R^x$ is a natural or unnatural amino acid side-chain group that is hydrophobic;

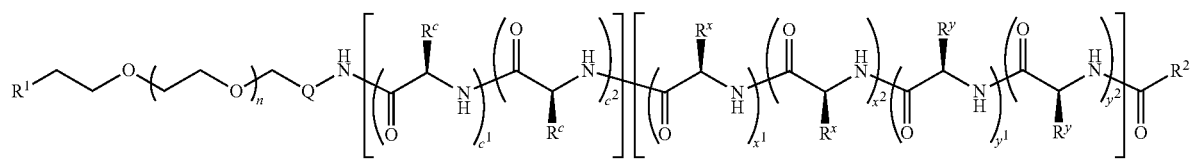

$R^y$ is a natural or unnatural amino acid side-chain group that contains an ester;

$R^1$ is —$Z(CH_2CH_2Y)_p(CH_2)_tR^3$, wherein:
  Z is a valence bond, a bivalent triazolyl moiety, —O—, —S—, —C≡C—, or —CH$_2$—;
  each Y is independently —O— or —S—;
  p is 0-10;
  t is 0-10; and $R^3$ is —$N_3$, —CN, a mono-protected amine, a di-protected amine, a protected aldehyde, a protected hydroxyl, a protected carboxylic acid, a protected thiol, a 9-30 membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety or a targeting group;

Q is a valence bond or a bivalent, saturated or unsaturated, straight or branched $C_{1-12}$ alkylene chain, wherein 0-6 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:

-Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;

$R^2$ is selected from an optionally substituted aliphatic group or a fusogenic peptide.

In certain embodiments, the present invention provides a micelle having a polynucleotide encapsulated therein, comprising a triblock copolymer of formula II:

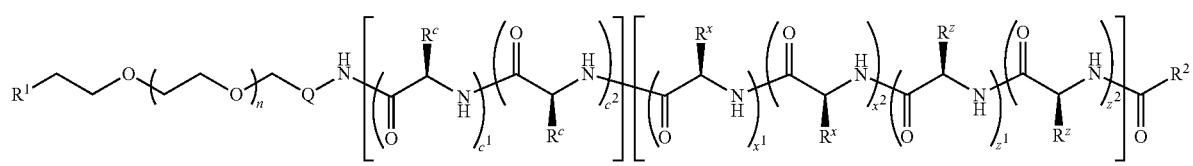

as described above, wherein the polynucleotide is combined with a suitable metal ion. In some embodiments, the polynucleotide combined with a suitable metal ion is DNA. In some embodiments, the polynucleotide combined with a suitable metal ion is pDNA.

In certain embodiments, the present invention provides a micelle having a polynucleotide encapsulated therein, comprising a triblock copolymer of formula II-a:

wherein:

n is 50-2500;

$c^1$ is 0 to 100;

$c^2$ is 0 to 100, provided that $c^1$ and $c^2$ are not simultaneously zero;

$x^1$ is 0 to 250;

$x^2$ is 0 to 250;

$z^1$ is 0 to 250, provided that $x^1$ and $z^1$ are not simultaneously zero;

$z^2$ is 0 to 250, provided that $z^1$ and $z^2$ are not simultaneously zero;

$R^c$ is a natural or unnatural amino acid side-chain group that is capable of crosslinking;

$R^x$ is a natural or unnatural amino acid side-chain group that is hydrophobic;

$R^z$ is -L-$R^4$ wherein:

L is a bivalent, straight or branched, $C_{4-20}$ alkylene chain wherein at least one methylene unit of -L- is replaced by —C(O)NR— and 1-10 additional methylene units are independently replaced by —N(R)— or -Het-;

Het is a bivalent 5-6 membered saturated, partially unsaturated, or aromatic ring having at least one nitrogen and 0-3 additional heteroatoms independently selected from nitrogen, oxygen, or sulfur;

$R^4$ is R or $N(R)_2$;

each R is hydrogen or $C_{1-6}$ aliphatic, or two R on the same nitrogen are taken together with the nitrogen to form a 5-6 membered heterocyclic ring having 1-3 heteroatoms independently selected from nitrogen, oxygen, or sulfur;

$R^1$ is —Z(CH$_2$CH$_2$Y)$_p$(CH$_2$)$_t$R$^3$, wherein:

Z is a valence bond, a bivalent triazolyl moiety, —O—, —S—, —C≡C—, or —CH$_2$—;

each Y is independently —O— or —S—;

p is 0-10;

t is 0-10; and $R^3$ is —$N_3$, —CN, a mono-protected amine, a di-protected amine, a protected aldehyde, a protected hydroxyl, a protected carboxylic acid, a protected thiol, a 9-30 membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety or a targeting group;

Q is a valence bond or a bivalent, saturated or unsaturated, straight or branched $C_{1-12}$ alkylene chain, wherein 0-6 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:

-Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;

$R^2$ is selected from an optionally substituted aliphatic group or a fusogenic peptide.

In certain embodiments, the present invention provides a micelle having a polynucleotide encapsulated therein, comprising a triblock copolymer of formula II-a:

II-a as described above, wherein the polynucleotide is combined with a suitable metal ion. In some embodiments, the polynucleotide combined with a suitable metal ion is DNA. In some embodiments, the polynucleotide combined with a suitable metal ion is pDNA.

Another aspect of the present invention provides a method for preparing a multi-block copolymer of formula II-a:

II-a wherein each of $R^1$, $R^c$, $R^x$, $R^z$, $R^2$, Q, n, $c^1$, $c^2$, $x^1$, $x^2$, $z^1$, and $z^2$ is as defined above and described herein, said method comprising the steps of:

a) providing a compound of formula II:

II wherein each of $R^1$, $R^c$, $R^x$, $R^y$, $R^2$, Q, n, $c^1$, $c^2$, $x^1$, $x^2$, $y^1$, and $y^2$ is as defined above and described herein, and b) reacting the compound of formula II with a suitable amine to form the compound of formula II-a.

In certain embodiments, the present invention provides a micelle having a polynucleotide encapsulated therein, comprising a triblock copolymer of formula II-b:

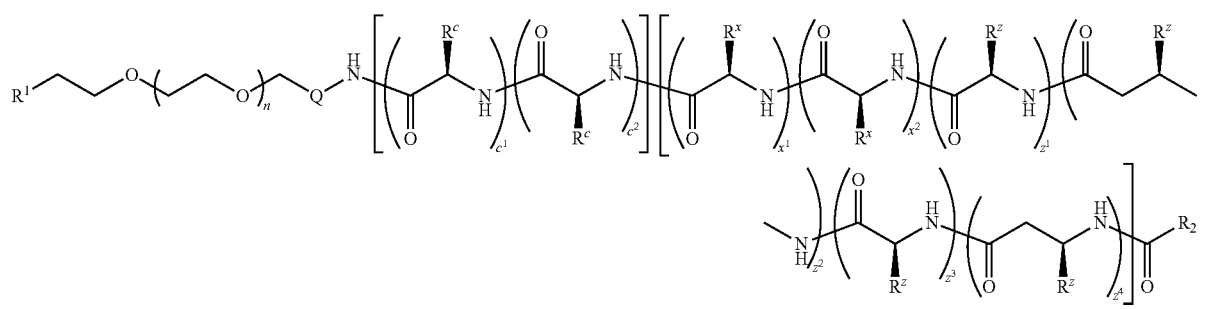

wherein:

n is 50-2500;

$c^1$ is 0 to 100;

$C^2$ is 0 to 100, provided that $c^1$ and $c^2$ are not simultaneously zero;

$x^1$ is 0 to 250;

$x^2$ is 0 to 250;

$z^1$ is 0 to 250;

$z^2$ is 0 to 250;

$z^3$ is 0 to 250, provided that $z^1$ and $z^3$ are not simultaneously zero;

$z^4$ is 0 to 250;

$R^c$ is a natural or unnatural amino acid side-chain group that is capable of crosslinking;

$R^x$ is a natural or unnatural amino acid side-chain group that is hydrophobic;

each $R^z$ is independently -L-$R^4$ wherein:

L is a bivalent, straight or branched, $C_{4-20}$ alkylene chain wherein at least one methylene unit of -L- is replaced by —C(O)NR— and 1-10 additional methylene units are independently replaced by —N(R)— or -Het-;

Het is a bivalent 5-6 membered saturated, partially unsaturated, or aromatic ring having at least one nitrogen and 0-3 additional heteroatoms independently selected from nitrogen, oxygen, or sulfur;

$R^4$ is R or $N(R)_2$;

each R is hydrogen or $C_{1-6}$ aliphatic, or two R on the same nitrogen are taken together with the nitrogen to form a 5-6 membered heterocyclic ring having 1-3 heteroatoms independently selected from nitrogen, oxygen, or sulfur;

$R^1$ is —Z(CH$_2$CH$_2$Y)$_p$(CH$_2$)$_t$R$^3$, wherein:

Z is a valence bond, a bivalent triazolyl moiety, —O—, —S—, —C≡C—, or —CH$_2$—;

each Y is independently —O— or —S—;

p is 0-10;

t is 0-10; and $R^3$ is —$N_3$, —CN, a mono-protected amine, a di-protected amine, a protected aldehyde, a protected hydroxyl, a protected carboxylic acid, a protected thiol, a 9-30 membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety or a targeting group;

Q is a valence bond or a bivalent, saturated or unsaturated, straight or branched $C_{1-12}$ alkylene chain, wherein 0-6 methylene units of Q are independently replaced by -Cy-, —O—, —NH—, —S—, —OC(O)—, —C(O) O—, —C(O)—, —SO—, —SO$_2$—, —NHSO$_2$—, —SO$_2$NH—, —NHC(O)—, —C(O)NH—, —OC(O) NH—, or —NHC(O)O—, wherein:

-Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;

$R^2$ is selected from an optionally substituted aliphatic group or a fusogenic peptide.

In certain embodiments, the present invention provides a micelle having a polynucleotide encapsulated therein, comprising a triblock copolymer of formula II-b:

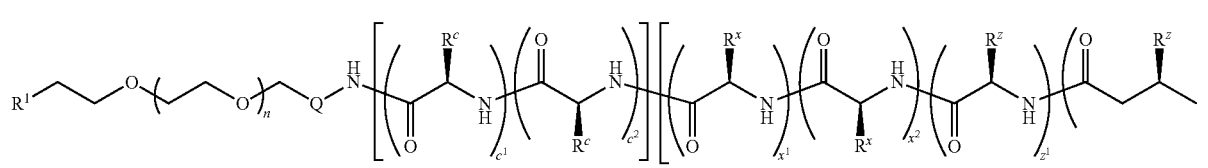

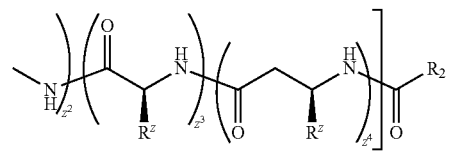

as described above, wherein the polynucleotide is combined with a suitable metal ion. In some embodiments, the polynucleotide combined with a suitable metal ion is DNA. In some embodiments, the polynucleotide combined with a suitable metal ion is pDNA.

In certain embodiments, the present invention provides a micelle having a polynucleotide encapsulated therein, comprising a triblock copolymer of formula II-c:

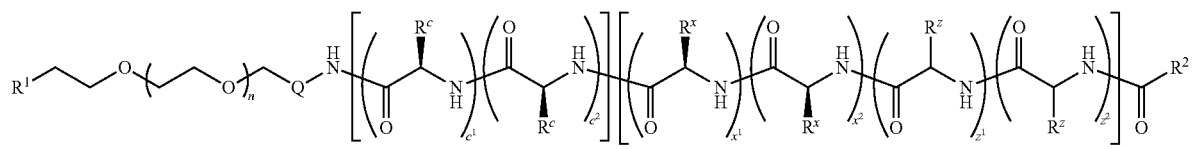

II-c wherein:
n is 50-2500;
$c^1$ is 0 to 100;
$c^2$ is 0 to 100, provided that $c^1$ and $c^2$ are not simultaneously zero;
$x^1$ is 0 to 250;
$x^2$ is 0 to 250;
$z^1$ is 0 to 250, provided that $x^1$ and $z^1$ are not simultaneously zero;
$z^2$ is 0 to 250, provided that $z^1$ and $z^2$ are not simultaneously zero;
$R^c$ is a natural or unnatural amino acid side-chain group that is capable of crosslinking;
$R^x$ is a natural or unnatural amino acid side-chain group that is hydrophobic;
$R^z$ is -L-$R^4$ wherein:
  L is a bivalent, straight or branched, $C_{4-20}$ alkylene chain wherein at least one methylene unit of -L- is replaced by —C(O)NR— and 1-10 additional methylene units are independently replaced by —N(R)— or -Het-;
  Het is a bivalent 5-6 membered saturated, partially unsaturated, or aromatic ring having at least one nitrogen and 0-3 additional heteroatoms independently selected from nitrogen, oxygen, or sulfur;
  $R^4$ is R or N(R)$_2$;
  each R is hydrogen or $C_{1-6}$ aliphatic, or two R on the same nitrogen are taken together with the nitrogen to form a 5-6 membered heterocyclic ring having 1-3 heteroatoms independently selected from nitrogen, oxygen, or sulfur;

$R^1$ is —Z(CH$_2$CH$_2$Y)$_p$(CH$_2$)$_t$R$^3$, wherein:
  Z is a valence bond, a bivalent triazolyl moiety, —O—, —S—, —C≡C—, or —CH$_2$—;
  each Y is independently —O— or —S—;
  p is 0-10;
  t is 0-10; and
  $R^3$ is —N$_3$, —CN, a mono-protected amine, a di-protected amine, a protected aldehyde, a protected hydroxyl, a protected carboxylic acid, a protected thiol, a 9-30 membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety or a targeting group;

Q is a valence bond or a bivalent, saturated or unsaturated, straight or branched $C_{1-12}$ alkylene chain, wherein 0-6 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:

-Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;

$R^2$ is selected from an optionally substituted aliphatic group or a fusogenic peptide.

In certain embodiments, the present invention provides a micelle having a polynucleotide encapsulated therein, comprising a triblock copolymer of formula II-c:

II-c

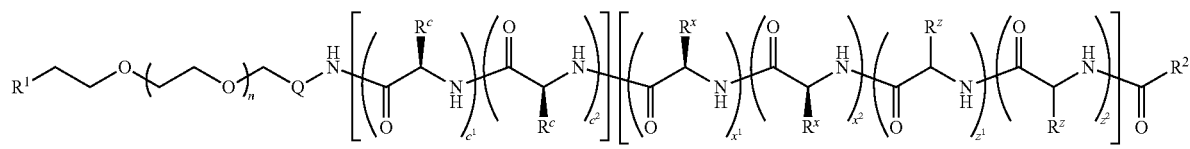

as described above, wherein the polynucleotide is combined with a suitable metal ion. In some embodiments, the polynucleotide combined with a suitable metal ion is DNA. In some embodiments, the polynucleotide combined with a suitable metal ion is pDNA.

In certain embodiments, the present invention provides a micelle having a polynucleotide encapsulated therein, comprising a triblock copolymer of formula II-d:

II-d

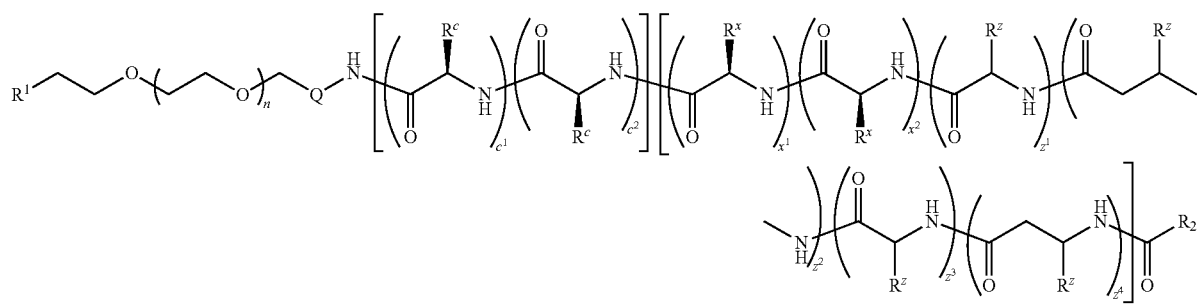

wherein:
n is 50-2500;
$c^1$ is 0 to 100;
$c^2$ is 0 to 100, provided that $c^1$ and $c^2$ are not simultaneously zero;
$x^1$ is 0 to 250;
$x^2$ is 0 to 250;
$z^1$ is 0 to 250;
$z^2$ is 0 to 250;
$z^3$ is 0 to 250, provided that $z^1$ and $z^3$ are not simultaneously zero;
$z^4$ is 0 to 250;
$R^c$ is a natural or unnatural amino acid side-chain group that is capable of crosslinking;
$R^x$ is a natural or unnatural amino acid side-chain group that is hydrophobic;
each $R^z$ is independently -L-$R^4$ wherein:
  L is a bivalent, straight or branched, $C_{4-20}$ alkylene chain wherein at least one methylene unit of -L- is replaced by —C(O)NR— and 1-10 additional methylene units are independently replaced by —N(R)— or -Het-;
  Het is a bivalent 5-6 membered saturated, partially unsaturated, or aromatic ring having at least one nitrogen and 0-3 additional heteroatoms independently selected from nitrogen, oxygen, or sulfur;
  $R^4$ is R or N(R)$_2$;
  each R is hydrogen or $C_{1-6}$ aliphatic, or two R on the same nitrogen are taken together with the nitrogen to form a 5-6 membered heterocyclic ring having 1-3 heteroatoms independently selected from nitrogen, oxygen, or sulfur;

$R^1$ is —Z(CH$_2$CH$_2$Y)$_p$(CH$_2$)$_t$R$^3$, wherein:
  Z is a valence bond, a bivalent triazolyl moiety, —O—, —S—, —C≡C—, or —CH$_2$—;
  each Y is independently —O— or —S—;
  p is 0-10;
  t is 0-10; and
$R^3$ is —N$_3$, —CN, a mono-protected amine, a di-protected amine, a protected aldehyde, a protected hydroxyl, a protected carboxylic acid, a protected thiol, a 9-30 membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety or a targeting group;

Q is a valence bond or a bivalent, saturated or unsaturated, straight or branched $C_{1-12}$ alkylene chain, wherein 0-6 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:
  -Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;

$R^2$ is selected from an optionally substituted aliphatic group or a fusogenic peptide.

In certain embodiments, the present invention provides a micelle having a polynucleotide encapsulated therein, comprising a triblock copolymer of formula II-d:

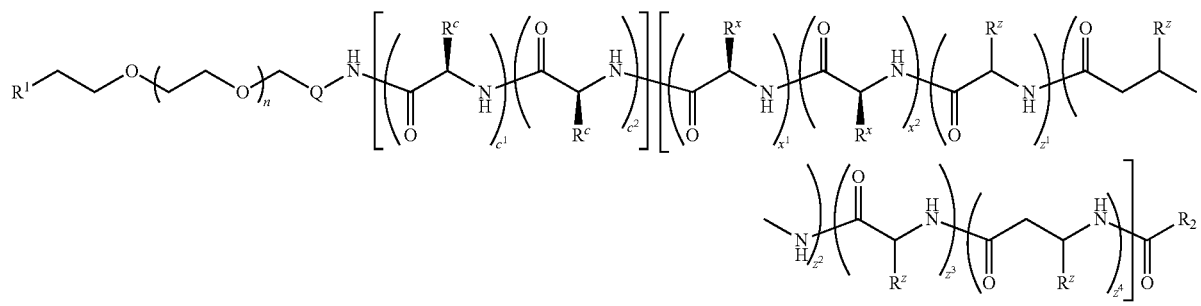

II-d as described above, wherein the polynucleotide is combined with a suitable metal ion. In some embodiments, the polynucleotide combined with a suitable metal ion is DNA. In some embodiments, the polynucleotide combined with a suitable metal ion is pDNA.

chain. In other embodiments, $R^c$ is an aspartic acid side chain. In still other embodiments, $R^c$ is a histidine side-chain. In yet other embodiments, $R^c$ is a benzamidazole derivative.

In certain embodiments, the present invention provides a micelle having a polynucleotide encapsulated therein, comprising a multiblock copolymer of formula III:

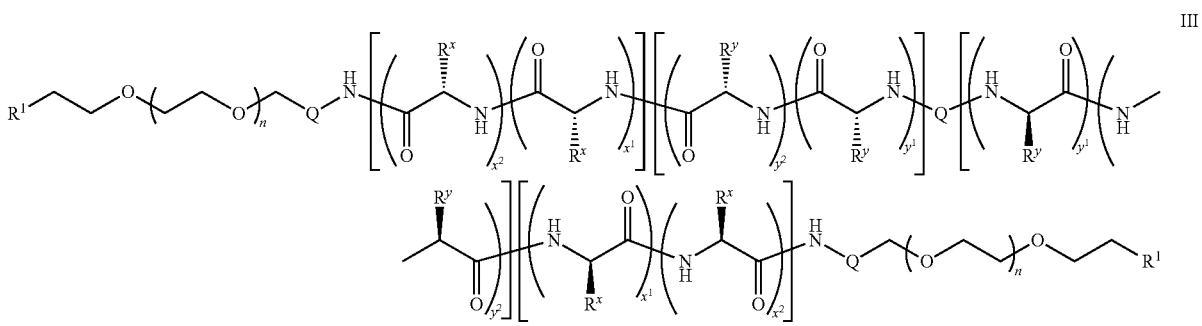

III

In some embodiments, each of the $R^1$, $R^2$, Q, $R^x$, $R^y$, $R^z$, n, $x^1$, $x^2$, $y^1$, $y^2$, $z^1$, $z^2$, $z^3$ and $z^4$ groups of formulae II, II-a, II-b, II-c, or II-d are independently as described with respect to formula I, above.

In certain embodiments, the $R^c$ group of formula II is a crosslinkable amino acid side-chain group. In certain embodiments, such crosslinkable amino acid side-chain groups correspond to that of tyrosine, serine, cysteine, threonine, aspartic acid (also known as aspartate, when charged), glutamic acid (also known as glutamate, when charged), asparagine, histidine, lysine, arginine, glutamine, or a benzimidazole-functionalized amino acid. In some embodiments, $R^c$ is a benzamidazole derivative or an amino acid side-chain group corresponding to that of glutamic acid, aspartic acid, or histidine.

As defined above, the $R^c$ group of formula II is a natural or unnatural amino acid side-chain group capable of forming cross-links. It will be appreciated that a variety of amino acid side-chain functional groups are capable of such cross-linking, including, but not limited to, carboxylate, thiol, amine, and imidazole groups. Examples of $R^c$ moieties having functional groups capable of forming cross-links include a glutamic acid side-chain, —$CH_2C(O)OH$, an aspartic acid side-chain, —$CH_2CH_2C(O)OH$, a cysteine side-chain, a lysine, an ornithine, or a histidine side-chain, —$CH_2$-imidazol-4-yl. In some embodiments, $R^c$ is a glutamic acid side wherein:
n is 50-2500;
$x^1$ is 0 to 250;
$x^2$ is 0 to 250;
$y^1$ is 0 to 250, provided that $x^1$ and $y^1$ are not simultaneously zero;
$y^2$ is 0 to 250, provided that $y^1$ and $y^2$ are not simultaneously zero;
$R^x$ is a natural or unnatural amino acid side-chain group that is hydrophobic;
$R^y$ is a natural or unnatural amino acid side-chain group that contains an ester;
$R^1$ is —$Z(CH_2CH_2Y)_p(CH_2)_tR^3$, wherein:
Z is a valence bond, a bivalent triazolyl moiety, —O—, —S—, —C≡C—, or —$CH_2$—;
each Y is independently —O— or —S—;
p is 0-10;
t is 0-10; and
$R^3$ is —$N_3$, —CN, a mono-protected amine, a di-protected amine, a protected aldehyde, a protected hydroxyl, a protected carboxylic acid, a protected thiol, a 9-30 membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety or a targeting group; and each Q is independently a valence bond or a bivalent, saturated or unsaturated, straight or branched $C_{1-12}$ alkylene chain, wherein 0-6 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:

-Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur.

In certain embodiments, the present invention provides a micelle having a polynucleotide encapsulated therein, comprising a triblock copolymer of formula III-a:

form a 5-6 membered heterocyclic ring having 1-3 heteroatoms independently selected from nitrogen, oxygen, or sulfur;

$R^1$ is —Z(CH$_2$CH$_2$Y)$_p$(CH$_2$)$_t$R$^3$, wherein:
  Z is a valence bond, a bivalent triazolyl moiety, —O—, —S—, —C≡C—, or —CH$_2$—;
  each Y is independently —O— or —S—;
  p is 0-10;
  t is 0-10; and $R^3$ is —N$_3$, —CN, a mono-protected amine, a di-protected amine, a protected aldehyde, a protected hydroxyl, a protected carboxylic acid, a protected thiol, a 9-30 membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety or a targeting group; and each Q is independently a valence bond or a bivalent, saturated or unsaturated, straight or branched $C_{1-12}$ alky-

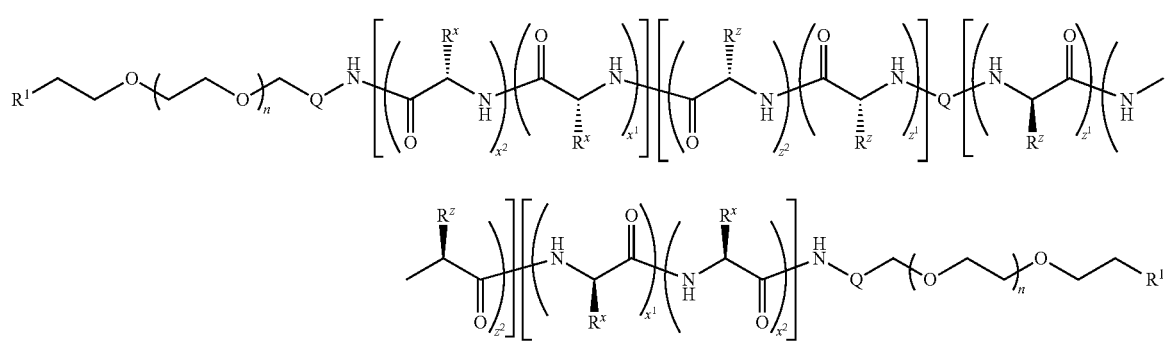

III-a wherein:
n is 50-2500;
$x^1$ is 0 to 250;
$x^2$ is 0 to 250;
$z^1$ is 0 to 250, provided that $x^1$ and $z^1$ are not simultaneously zero;
$z^2$ is 0 to 250, provided that $z^1$ and $z^2$ are not simultaneously zero;
$R^x$ is a natural or unnatural amino acid side-chain group that is hydrophobic;
$R^z$ is -L-R$^4$ wherein:
  L is a bivalent, straight or branched, $C_{4-20}$ alkylene chain wherein at least one methylene unit of -L- is replaced by —C(O)NR— and 1-10 additional methylene units are independently replaced by —N(R)— or -Het-;
  Het is a bivalent 5-6 membered saturated, partially unsaturated, or aromatic ring having at least one nitrogen and 0-3 additional heteroatoms independently selected from nitrogen, oxygen, or sulfur;
  $R^4$ is R or N(R)$_2$;
  each R is hydrogen or $C_{1-6}$ aliphatic, or two R on the same nitrogen are taken together with the nitrogen to lene chain, wherein 0-6 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:

-Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur.

In some embodiments, each Q is independently a $C_{1-12}$ alkylene chain, wherein 0-2 methylene units of Q are independently replaced by -Cy-, —O—, —C(O)—, or —NH—. In certain embodiments, -Cy- is an optionally substituted triazolyl.

In certain embodiments, the present invention provides a micelle having a polynucleotide encapsulated therein, comprising a triblock copolymer of formula III-a:

III-a

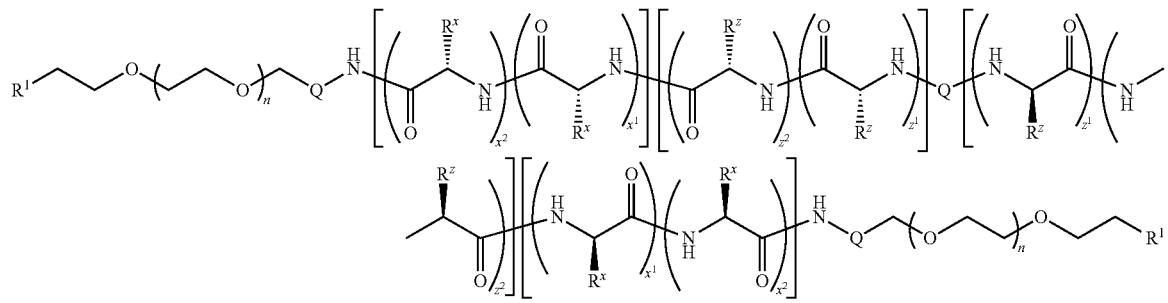

as described above, wherein the polynucleotide is combined with a suitable metal ion. In some embodiments, the polynucleotide combined with a suitable metal ion is DNA. In some embodiments, the polynucleotide combined with a suitable metal ion is pDNA.

Another aspect of the present invention provides a method for preparing a multi-block copolymer of formula III-a:

wherein each of $R^1$, $R^c$, $R^x$, $R^y$, $R^2$, Q, n, $c^1$, $c^2$, $x^1$, $x^2$, $y^1$, and $y^2$ is as defined above and described herein, and b) reacting the compound of formula III with a suitable amine to form the compound of formula III-a.

In certain embodiments, the present invention provides a micelle having a polynucleotide encapsulated therein, comprising a triblock copolymer of formula III-b:

III-a

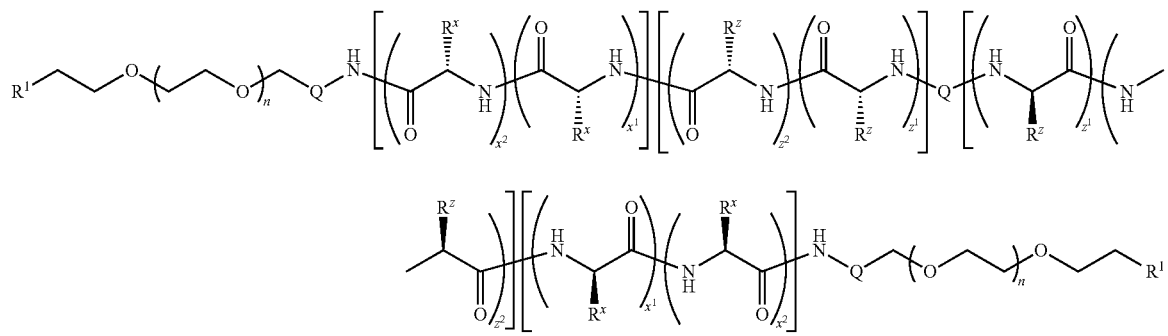

wherein each of $R^1$, $R^x$, $R^z$, $R^2$, Q, n, $x^1$, $x^2$, $z^1$, and $z^2$ is as defined above and described herein, said method comprising the steps of:

a) providing a compound of formula III:

III

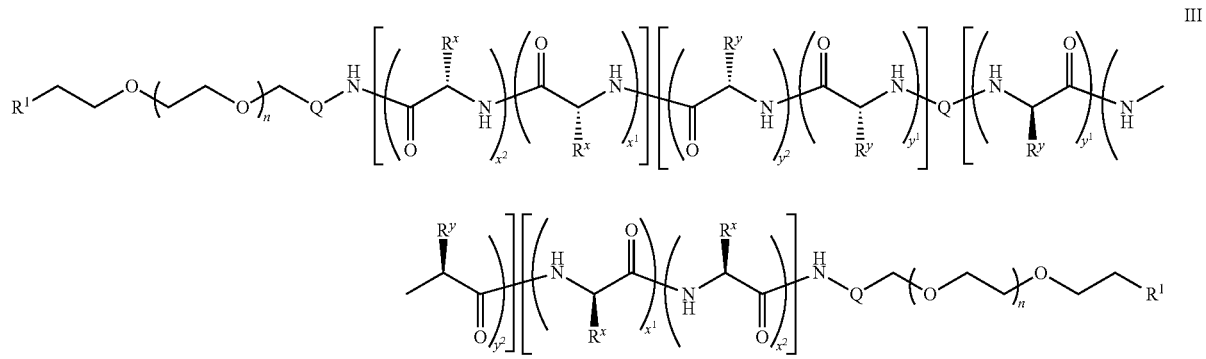

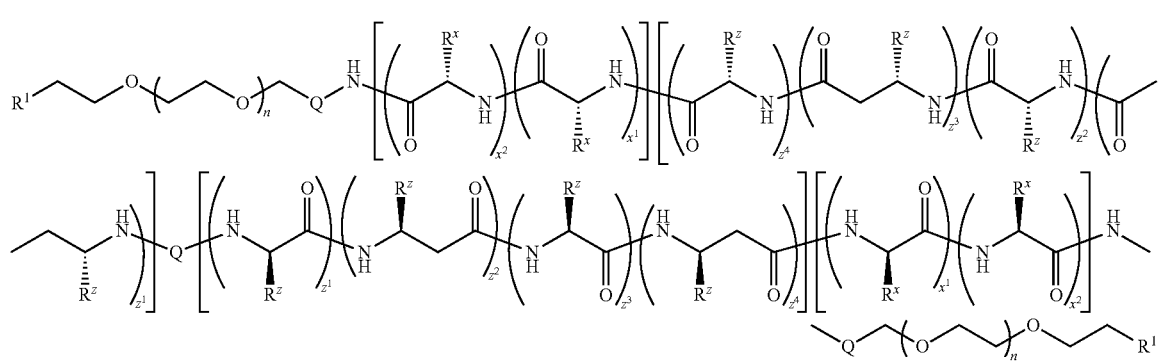

III-b wherein:
n is 50-2500;
$x^1$ is 0 to 250;
$x^2$ is 0 to 250;
$z^1$ is 0 to 250;
$z^2$ is 0 to 250;
$z^3$ is 0 to 250, provided that $z^1$ and $z^3$ are not simultaneously zero;
$z^4$ is 0 to 250;
$R^x$ is a natural or unnatural amino acid side-chain group that is hydrophobic;
each $R^z$ is independently -L-$R^4$ wherein:
  L is a bivalent, straight or branched, $C_{4-20}$ alkylene chain wherein at least one methylene unit of -L- is replaced by —C(O)NR— and 1-10 additional methylene units are independently replaced by —N(R)— or -Het-;
  Het is a bivalent 5-6 membered saturated, partially unsaturated, or aromatic ring having at least one nitrogen and 0-3 additional heteroatoms independently selected from nitrogen, oxygen, or sulfur;
  $R^4$ is R or $N(R)_2$;
  each R is hydrogen or $C_{1-6}$ aliphatic, or two R on the same nitrogen are taken together with the nitrogen to form a 5-6 membered heterocyclic ring having 1-3 heteroatoms independently selected from nitrogen, oxygen, or sulfur;
$R^1$ is —Z(CH$_2$CH$_2$Y)$_p$(CH$_2$)$_t$R$^3$, wherein:
  Z is a valence bond, a bivalent triazolyl moiety, —O—, —S—, —C≡C—, or —CH$_2$—;
  each Y is independently —O— or —S—;
  p is 0-10;
  t is 0-10; and
$R^3$ is —N$_3$, —CN, a mono-protected amine, a di-protected amine, a protected aldehyde, a protected hydroxyl, a protected carboxylic acid, a protected thiol, a 9-30 membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety or a targeting group; and
each Q is independently a valence bond or a bivalent, saturated or unsaturated, straight or branched $C_{1-12}$ alkylene chain, wherein 0-6 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:
  -Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur.

In certain embodiments, the present invention provides a micelle having a polynucleotide encapsulated therein, comprising a triblock copolymer of formula III-b:

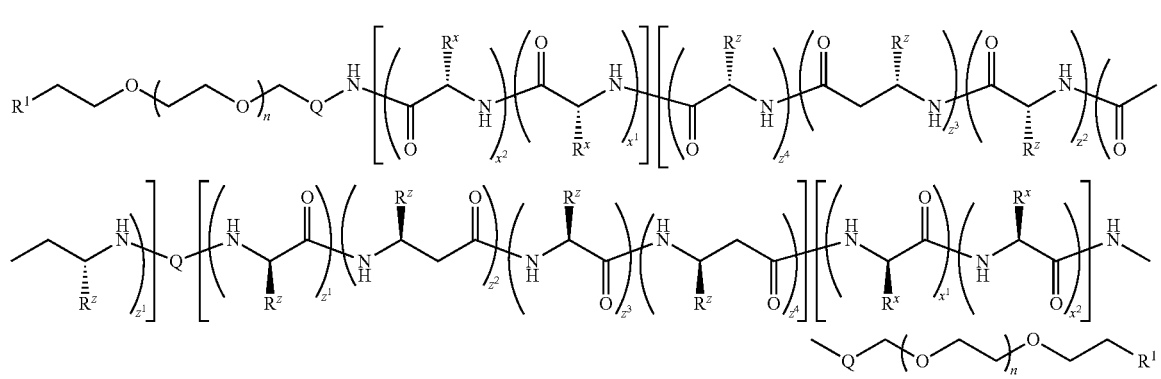

III-b as described above, wherein the polynucleotide is combined with a suitable metal ion. In some embodiments, the polynucleotide combined with a suitable metal ion is DNA. In some embodiments, the polynucleotide combined with a suitable metal ion is pDNA.

In certain embodiments, the present invention provides a micelle having a polynucleotide encapsulated therein, comprising a triblock copolymer of formula III-c:

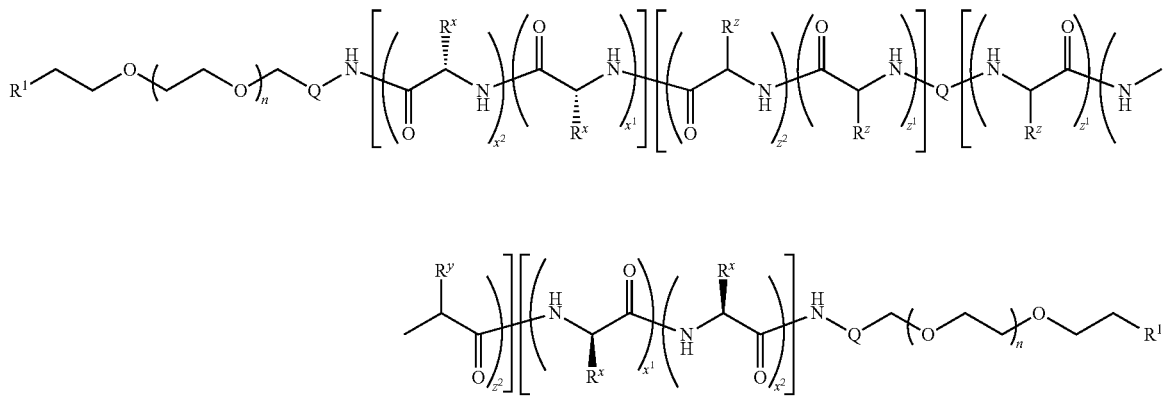

III-c wherein:

n is 50-2500;

$x^1$ is 0 to 250;

$x^2$ is 0 to 250;

$z^1$ is 0 to 250, provided that $x^1$ and $z^1$ are not simultaneously zero;

$z^2$ is 0 to 250, provided that $z^1$ and $z^2$ are not simultaneously zero;

$R^x$ is a natural or unnatural amino acid side-chain group that is hydrophobic;

$R^z$ is -L-$R^4$ wherein:

L is a bivalent, straight or branched, $C_{4\text{-}20}$ alkylene chain wherein at least one methylene unit of -L- is replaced by —C(O)NR— and 1-10 additional methylene units are independently replaced by —N(R)— or -Het-;

Het is a bivalent 5-6 membered saturated, partially unsaturated, or aromatic ring having at least one nitrogen and 0-3 additional heteroatoms independently selected from nitrogen, oxygen, or sulfur;

$R^4$ is R or $N(R)_2$;

each R is hydrogen or $C_{1\text{-}6}$ aliphatic, or two R on the same nitrogen are taken together with the nitrogen to form a 5-6 membered heterocyclic ring having 1-3 heteroatoms independently selected from nitrogen, oxygen, or sulfur;

$R^1$ is —Z(CH$_2$CH$_2$Y)$_p$(CH$_2$)$_t$R$^3$, wherein:

Z is a valence bond, a bivalent triazolyl moiety, —O—, —S—, —C≡C—, or —CH$_2$—;

each Y is independently —O— or —S—;

p is 0-10;

t is 0-10; and $R^3$ is —N$_3$, —CN, a mono-protected amine, a di-protected amine, a protected aldehyde, a protected hydroxyl, a protected carboxylic acid, a protected thiol, a 9-30 membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety or a targeting group; and each Q is independently a valence bond or a bivalent, saturated or unsaturated, straight or branched $C_{1\text{-}12}$ alkylene chain, wherein 0-6 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:

-Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur.

In certain embodiments, the present invention provides a micelle having a polynucleotide encapsulated therein, comprising a triblock copolymer of formula III-c:

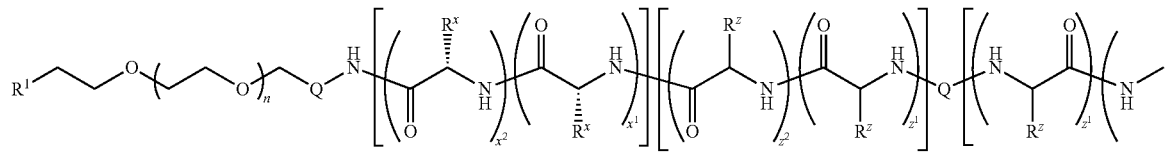
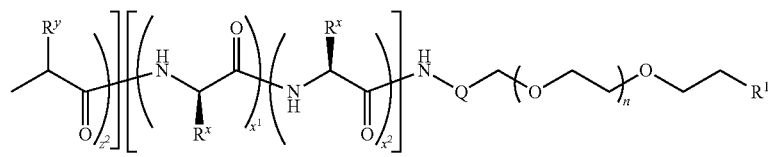

III-c as described above, wherein the polynucleotide is combined with a suitable metal ion. In some embodiments, the polynucleotide combined with a suitable metal ion is DNA. In some embodiments, the polynucleotide combined with a suitable metal ion is pDNA.

In certain embodiments, the present invention provides a micelle having a polynucleotide encapsulated therein, comprising a triblock copolymer of formula III-d:

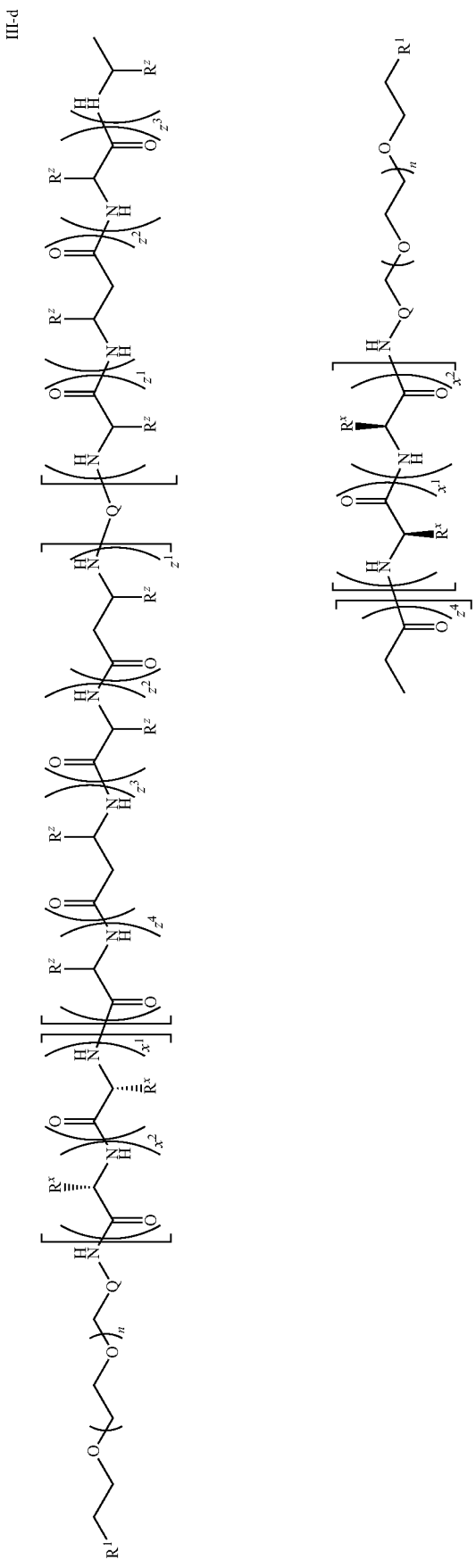

wherein:

n is 50-2500;

$x^1$ is 0 to 250;

$x^2$ is 0 to 250;

$z^1$ is 0 to 250;

$z^2$ is 0 to 250;

$z^3$ is 0 to 250, provided that $z^1$ and $z^3$ are not simultaneously zero;

$z^4$ is 0 to 250;

$R^x$ is a natural or unnatural amino acid side-chain group that is hydrophobic;

each $R^z$ is independently -L-$R^4$ wherein:

L is a bivalent, straight or branched, $C_{4-20}$ alkylene chain wherein at least one methylene unit of -L- is replaced by —C(O)NR— and 1-10 additional methylene units are independently replaced by —N(R)— or -Het-;

Het is a bivalent 5-6 membered saturated, partially unsaturated, or aromatic ring having at least one nitrogen and 0-3 additional heteroatoms independently selected from nitrogen, oxygen, or sulfur;

$R^4$ is R or $N(R)_2$;

each R is hydrogen or $C_{1-6}$ aliphatic, or two R on the same nitrogen are taken together with the nitrogen to form a 5-6 membered heterocyclic ring having 1-3 heteroatoms independently selected from nitrogen, oxygen, or sulfur;

$R^1$ is —Z(CH$_2$CH$_2$Y)$_p$(CH$_2$)$_t$R$^3$, wherein:

Z is a valence bond, a bivalent triazolyl moiety, —O—, —S—, —C≡C—, or —CH$_2$—;

each Y is independently —O— or —S—;

p is 0-10;

t is 0-10; and $R^3$ is —N$_3$, —CN, a mono-protected amine, a di-protected amine, a protected aldehyde, a protected hydroxyl, a protected carboxylic acid, a protected thiol, a 9-30 membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety or a targeting group; and each Q is independently a valence bond or a bivalent, saturated or unsaturated, straight or branched $C_{1-12}$ alkylene chain, wherein 0-6 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:

-Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur.

In certain embodiments, the present invention provides a micelle having a polynucleotide encapsulated therein, comprising a triblock copolymer of formula III-d:

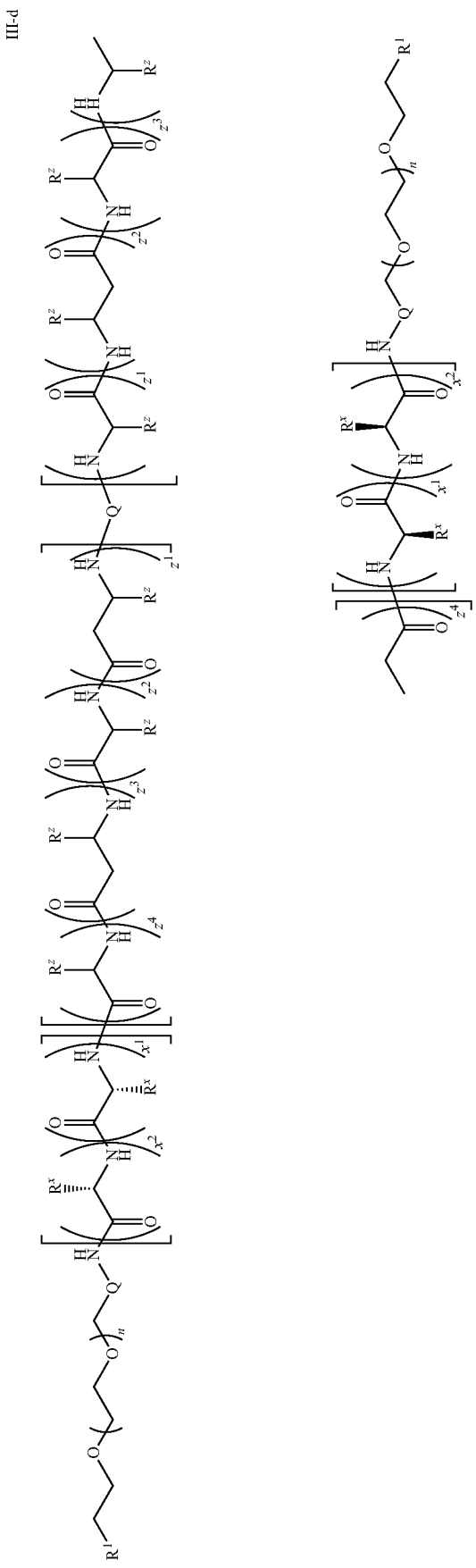

as described above, wherein the polynucleotide is combined with a suitable metal ion. In some embodiments, the polynucleotide combined with a suitable metal ion is DNA. In some embodiments, the polynucleotide combined with a suitable metal ion is pDNA.

In some embodiments, each of the $R^1$, $R^2$, Q, $R^x$, $R^y$, $R^z$, n, $x^1$, $x^2$, $y^1$, $y^2$, $z^1$, $z^2$, $z^3$ and $z^4$ groups of formulae III, III-a, III-b, III-c, or III-d are independently as described with respect to formula I, above.

In certain embodiments, the present invention provides a micelle having a polynucleotide encapsulated therein, comprising a multiblock copolymer of formula IV:

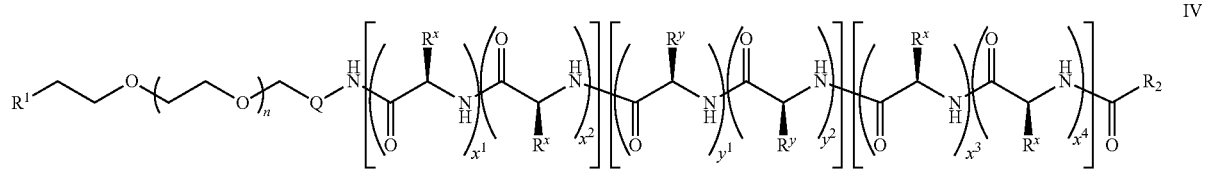

wherein:

n is 50-2500;

$x^1$ is 0 to 250;

$x^2$ is 0 to 250;

$y^1$ is 0 to 250, provided that $x^1$ and $y^1$ are not simultaneously zero;

$y^2$ is 0 to 250, provided that $y^1$ and $y^2$ are not simultaneously zero;

$x^3$ is 0 to 250;

$x^4$ is 0 to 250, provided that $x^3$ and $x^4$ are not simultaneously zero;

$R^x$ is a natural or unnatural amino acid side-chain group that is hydrophobic;

$R^y$ is a natural or unnatural amino acid side-chain group that contains an ester;

$R^1$ is —Z(CH$_2$CH$_2$Y)$_p$(CH$_2$)$_t$R$^3$, wherein:

Z is a valence bond, a bivalent triazolyl moiety, —O—, —S—, —C≡C—, or —CH$_2$—;

each Y is independently —O— or —S—;

p is 0-10;

t is 0-10; and

R$^3$ is —N$_3$, —CN, a mono-protected amine, a di-protected amine, a protected aldehyde, a protected hydroxyl, a protected carboxylic acid, a protected thiol, a 9-30 membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety or a targeting group;

Q is a valence bond or a bivalent, saturated or unsaturated, straight or branched C$_{1-12}$ alkylene chain, wherein 0-6 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:

-Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;

R$^2$ is selected from an optionally substituted aliphatic group or a fusogenic peptide.

In certain embodiments, the present invention provides a micelle having a polynucleotide encapsulated therein, comprising a multiblock copolymer of formula IV:

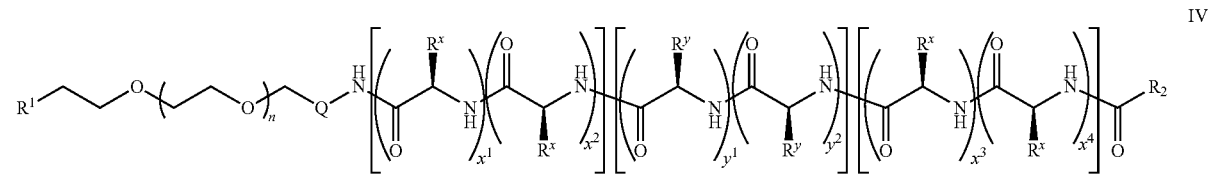

as described above, wherein the polynucleotide is combined with a suitable metal ion. In some embodiments, the polynucleotide combined with a suitable metal ion is DNA. In some embodiments, the polynucleotide combined with a suitable metal ion is pDNA.

In certain embodiments, the present invention provides a micelle having a polynucleotide encapsulated therein, comprising a triblock copolymer of formula IV-a:

IV-a

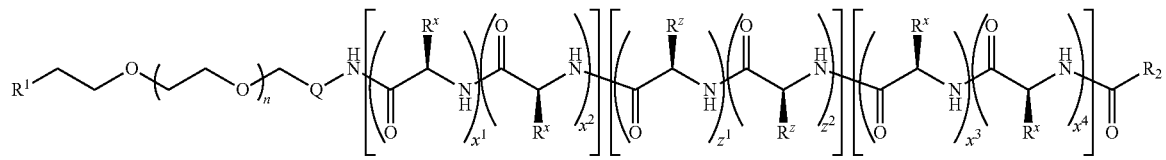

wherein:
n is 50-2500;
$x^1$ is 0 to 250;
$x^2$ is 0 to 250;
$z^1$ is 0 to 250, provided that $x^1$ and $y^1$ are not simultaneously zero;
$z^2$ is 0 to 250, provided that $y^1$ and $y^2$ are not simultaneously zero;
$x^3$ is 0 to 250;
$x^4$ is 0 to 250, provided that $x^3$ and $x^4$ are not simultaneously zero;
$R^x$ is a natural or unnatural amino acid side-chain group that is hydrophobic;
$R^z$ is -L-$R^4$ wherein:
  L is a bivalent, straight or branched, $C_{4-20}$ alkylene chain wherein at least one methylene unit of -L- is replaced by —C(O)NR— and 1-10 additional methylene units are independently replaced by —N(R)— or -Het-;
  Het is a bivalent 5-6 membered saturated, partially unsaturated, or aromatic ring having at least one nitrogen and 0-3 additional heteroatoms independently selected from nitrogen, oxygen, or sulfur;
  $R^4$ is R or N(R)$_2$;
  each R is hydrogen or $C_{1-6}$ aliphatic, or two R on the same nitrogen are taken together with the nitrogen to form a 5-6 membered heterocyclic ring having 1-3 heteroatoms independently selected from nitrogen, oxygen, or sulfur;
$R^1$ is —Z(CH$_2$CH$_2$Y)$_p$(CH$_2$)$_t$R$^3$, wherein:
  Z is a valence bond, a bivalent triazolyl moiety, —O—, —S—, or —CH$_2$—;
  each Y is independently —O— or —S—;
  p is 0-10;
  t is 0-10; and
  $R^3$ is —N$_3$, —CN, a mono-protected amine, a di-protected amine, a protected aldehyde, a protected hydroxyl, a protected carboxylic acid, a protected thiol, a 9-30 membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety or a targeting group;
Q is a valence bond or a bivalent, saturated or unsaturated, straight or branched $C_{1-12}$ alkylene chain, wherein 0-6 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:
  -Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;
$R^2$ is selected from an optionally substituted aliphatic group or a fusogenic peptide.

In certain embodiments, the present invention provides a micelle having a polynucleotide encapsulated therein, comprising a triblock copolymer of formula IV-a:

IV-a

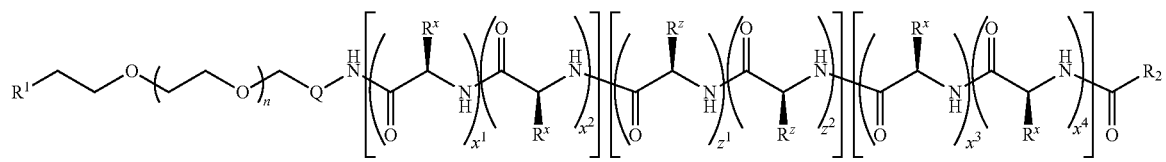

as described above, wherein the polynucleotide is combined with a suitable metal ion. In some embodiments, the polynucleotide combined with a suitable metal ion is DNA. In some embodiments, the polynucleotide combined with a suitable metal ion is pDNA.

In some embodiments for compounds of formulae IV and IV-a, the sum of $x^1$ and $x^2$ is about 25, the sum of $z^1$ and $z^2$ is about 25, and the sum of $x^3$ and $x^4$ is about 25. In some embodiments, the sum of $x^1$ and $x^2$ is about 50, the sum of $z^1$ and $z^2$ is about 50, and the sum of $x^3$ and $x^4$ is about 50. In some embodiments, the sum of $x^1$ and $x^2$ is about 100, the sum of $z^1$ and $z^2$ is about 100, and the sum of $x^3$ and $x^4$ is about 100.

Another aspect of the present invention provides a method for preparing a multi-block copolymer of formula IV-a:

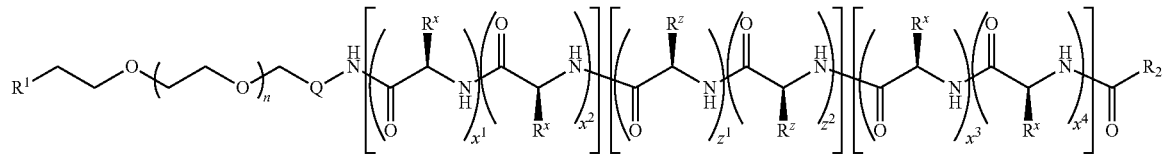

wherein each of $R^1$, $R^x$, $R^z$, $R^2$, Q, n, $x^1$, $x^2$, $x^3$, $x^4$, $z^1$, and $z^2$ is as defined above and described herein, said method comprising the steps of:
a) providing a compound of formula IV:

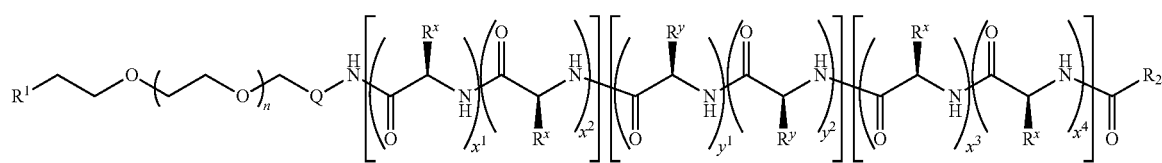

wherein each of $R^1$, $R^x$, $R^z$, $R^2$, Q, n, $x^1$, $x^2$, $x^3$, $x^4$, $z^1$, and $z^2$ is as defined above and described herein, and
b) reacting the compound of formula IV with a suitable amine found to form the compound of formula IV-a.

In certain embodiments, the present invention provides a micelle having a polynucleotide encapsulated therein, comprising a triblock copolymer of formula IV-b:

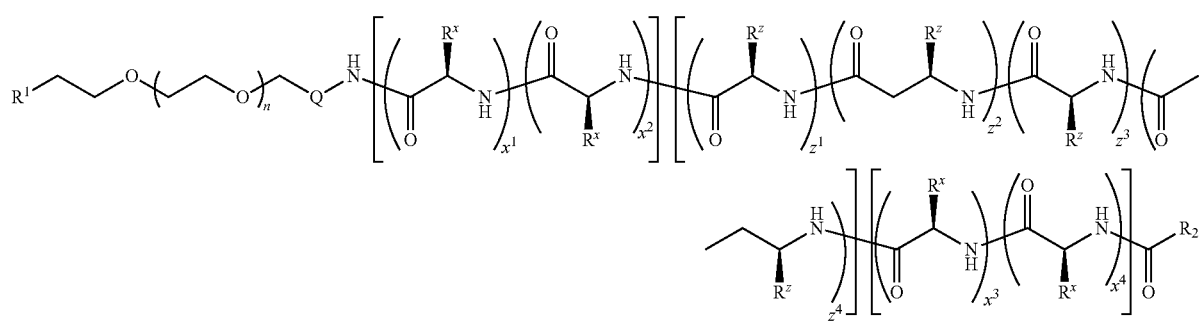

wherein:
n is 50-2500;
$x^1$ is 0 to 250;
$x^2$ is 0 to 250;
$z^1$ is 0 to 250;
$z^2$ is 0 to 250;
$z^3$ is 0 to 250, provided that $z^1$ and $z^3$ are not simultaneously zero;
$z^4$ is 0 to 250;
$x^3$ is 0 to 250;
$x^4$ is 0 to 250, provided that $x^3$ and $x^4$ are not simultaneously zero;
$R^x$ is a natural or unnatural amino acid side-chain group that is hydrophobic;
each $R^z$ is independently -L-$R^4$ wherein:
L is a bivalent, straight or branched, $C_{4-20}$ alkylene chain wherein at least one methylene unit of -L- is replaced by —C(O)NR— and 1-10 additional methylene units are independently replaced by —N(R)— or -Het-;
Het is a bivalent 5-6 membered saturated, partially unsaturated, or aromatic ring having at least one nitrogen and 0-3 additional heteroatoms independently selected from nitrogen, oxygen, or sulfur;

$R^4$ is R or $N(R)_2$;

each R is hydrogen or $C_{1-6}$ aliphatic, or two R on the same nitrogen are taken together with the nitrogen to form a 5-6 membered heterocyclic ring having 1-3 heteroatoms independently selected from nitrogen, oxygen, or sulfur;
$R^1$ is —$Z(CH_2CH_2Y)_p(CH_2)_tR^3$, wherein:
Z is a valence bond, a bivalent triazolyl moiety, —O—, —S—, —C≡C—, or —$CH_2$—;
each Y is independently —O— or —S—;
p is 0-10;
t is 0-10; and
$R^3$ is —$N_3$, —CN, a mono-protected amine, a di-protected amine, a protected aldehyde, a protected hydroxyl, a protected carboxylic acid, a protected thiol, a 9-30 membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety or a targeting group;

Q is a valence bond or a bivalent, saturated or unsaturated, straight or branched $C_{1-12}$ alkylene chain, wherein 0-6 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:

-Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;

$R^2$ is selected from an optionally substituted aliphatic group or a fusogenic peptide.

In certain embodiments, the present invention provides a micelle having a polynucleotide encapsulated therein, comprising a triblock copolymer of formula IV-b:

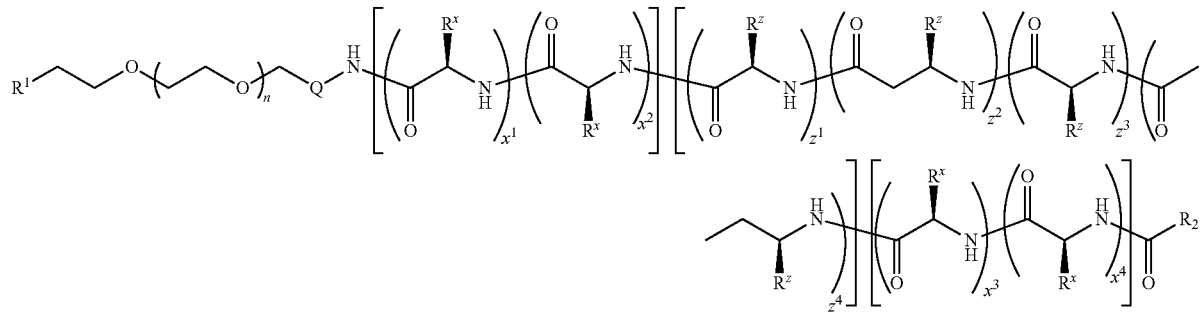

IV-b as described above, wherein the polynucleotide is combined with a suitable metal ion. In some embodiments, the polynucleotide combined with a suitable metal ion is DNA. In some embodiments, the polynucleotide combined with a suitable metal ion is pDNA.

In certain embodiments, the present invention provides a micelle having a polynucleotide encapsulated therein, comprising a triblock copolymer of formula IV-c:

$z^2$ is 0 to 250, provided that $z^1$ and $z^2$ are not simultaneously zero;

$x^3$ is 0 to 250;

$x^4$ is 0 to 250, provided that $x^3$ and $x^4$ are not simultaneously zero;

$R^x$ is a natural or unnatural amino acid side-chain group that is hydrophobic;

$R^z$ is -L-$R^4$ wherein:

L is a bivalent, straight or branched, $C_{4-20}$ alkylene chain wherein at least one methylene unit of -L- is replaced by —C(O)NR— and 1-10 additional methylene units are independently replaced by —N(R)— or -Het-;

Het is a bivalent 5-6 membered saturated, partially unsaturated, or aromatic ring having at least one nitrogen and 0-3 additional heteroatoms independently selected from nitrogen, oxygen, or sulfur;

$R^4$ is R or N(R)$_2$;

each R is hydrogen or $C_{1-6}$ aliphatic, or two R on the same nitrogen are taken together with the nitrogen to form a 5-6 membered heterocyclic ring having 1-3 heteroatoms independently selected from nitrogen, oxygen, or sulfur;

$R^1$ is —Z(CH$_2$CH$_2$Y)$_p$(CH$_2$)$_t$R$^3$, wherein:

Z is a valence bond, a bivalent triazolyl moiety, —O—, —S—, —C≡C—, or —CH$_2$—;

each Y is independently —O— or —S—;

p is 0-10;

t is 0-10; and $R^3$ is —N$_3$, —CN, a mono-protected amine, a di-protected amine, a protected aldehyde, a protected hydroxyl, a protected carboxylic acid, a protected thiol, a 9-30 mem-

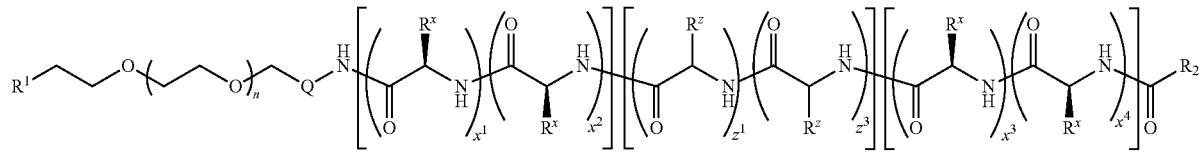

IV-c wherein:

n is 50-2500;

$x^1$ is 0 to 250;

$x^2$ is 0 to 250;

$z^1$ is 0 to 250, provided that $x^1$ and $z^1$ are not simultaneously zero;

bered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety or a targeting group;

Q is a valence bond or a bivalent, saturated or unsaturated, straight or branched $C_{1-12}$ alkylene chain, wherein 0-6 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:

-Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;

$R^2$ is selected from an optionally substituted aliphatic group or a fusogenic peptide.

In certain embodiments, the present invention provides a micelle having a polynucleotide encapsulated therein, comprising a triblock copolymer of formula IV-c:

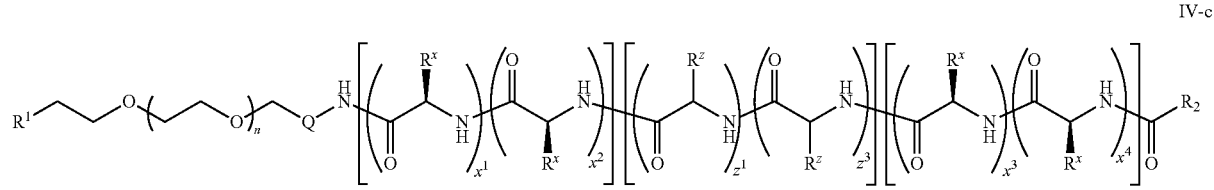

IV-c as described above, wherein the polynucleotide is combined with a suitable metal ion. In some embodiments, the polynucleotide combined with a suitable metal ion is DNA. In some embodiments, the polynucleotide combined with a suitable metal ion is pDNA.

In certain embodiments, the present invention provides a micelle having a polynucleotide encapsulated therein, comprising a triblock copolymer of formula IV-d:

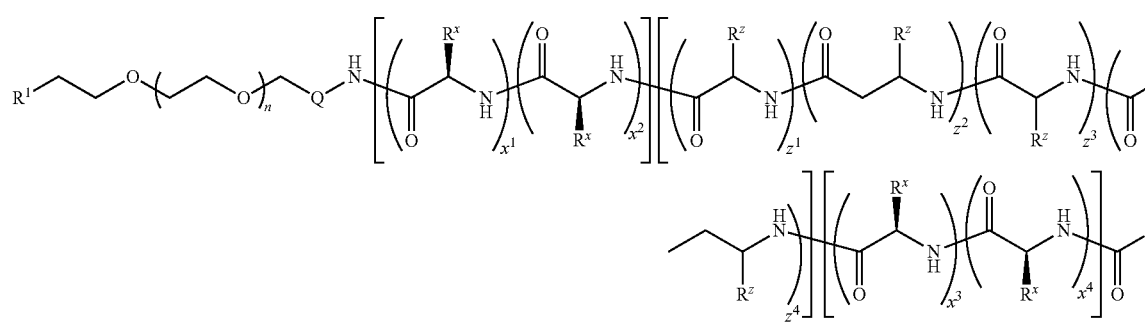

IV-d wherein:
n is 50-2500;
$x^1$ is 0 to 250;
$x^2$ is 0 to 250;
$z^1$ is 0 to 250;
$z^2$ is 0 to 250;
$z^3$ is 0 to 250, provided that $z^1$ and $z^3$ are not simultaneously zero;
$z^4$ is 0 to 250;
$x^3$ is 0 to 250;
$x^4$ is 0 to 250, provided that $x^3$ and $x^4$ are not simultaneously zero;

$R^x$ is a natural or unnatural amino acid side-chain group that is hydrophobic;

each $R^z$ is independently -L-$R^4$ wherein:
L is a bivalent, straight or branched, $C_{4-20}$ alkylene chain wherein at least one methylene unit of -L- is replaced by —C(O)NR— and 1-10 additional methylene units are independently replaced by —N(R)— or -Het-;
Het is a bivalent 5-6 membered saturated, partially unsaturated, or aromatic ring having at least one nitrogen and 0-3 additional heteroatoms independently selected from nitrogen, oxygen, or sulfur;
$R^4$ is R or N(R)$_2$;
each R is hydrogen or $C_{1-6}$ aliphatic, or two R on the same nitrogen are taken together with the nitrogen to form a 5-6 membered heterocyclic ring having 1-3 heteroatoms independently selected from nitrogen, oxygen, or sulfur;

$R^1$ is —Z(CH$_2$CH$_2$Y)$_p$(CH$_2$)$_t$R$^3$, wherein:

Z is a valence bond, a bivalent triazolyl moiety, —O—, —S—, —C≡C—, or —CH$_2$—;
each Y is independently —O— or —S—;
p is 0-10;
t is 0-10; and
$R^3$ is —N$_3$, —CN, a mono-protected amine, a di-protected amine, a protected aldehyde, a protected hydroxyl, a protected carboxylic acid, a protected thiol, a 9-30 membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety or a targeting group;

Q is a valence bond or a bivalent, saturated or unsaturated, straight or branched $C_{1-12}$ alkylene chain, wherein 0-6 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:

-Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;

$R^2$ is selected from an optionally substituted aliphatic group or a fusogenic peptide.

In certain embodiments, the present invention provides a micelle having a polynucleotide encapsulated therein, comprising a triblock copolymer of formula IV-d:

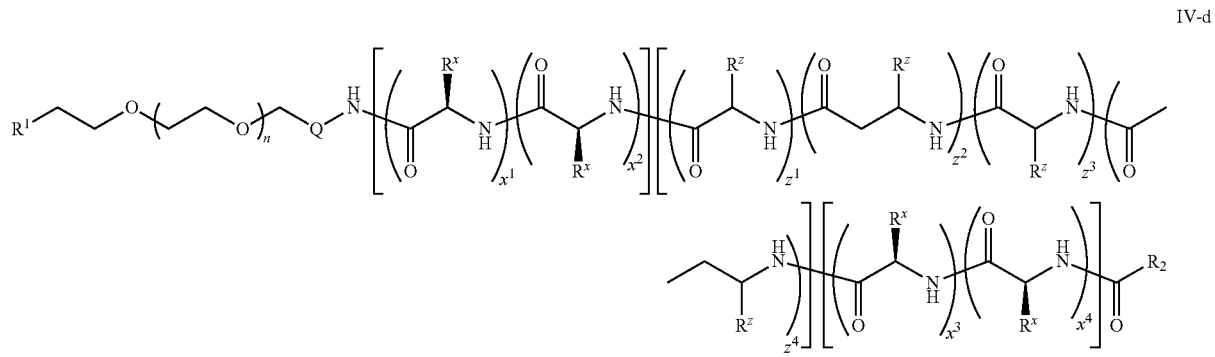

IV-d wherein:
n is 50-2500;
y is 5 to 250; and
z is 5 to 250.

As defined generally above, the n group of compound a is 50-2500. In some embodiments, n is about 110 to about 460. In certain embodiments, the present invention provides compounds of compound a as described above, wherein n is about 270. In some embodiments, n is about 225. In other embodiments, n is about 350. In some embodiments, n is about 110. In some embodiments, n is about 454. In some embodiments, n is selected from 110±10, 180±10, 225±10, 275±10, 315±10, or 450±10.

In certain embodiments, the y group of compound a is about 5 to about 250. In certain embodiments, the y group of compound a is about 10. In some embodiments, y is about 5-50. In some embodiments, y is about 0-50. In some embodiments, y is about 20. In some embodiments, y is about 30. In other embodiments, y is about 40. In some embodiments, y is selected from 10±5, 20±5, 30±5, 40±5, or 50±5.

In certain embodiments, the z group of compound a is about 5 to about 250. In other embodiments, z is about 100-200. In certain embodiments, z is about 140. In some embodiments, z is about 160. In some embodiments, z is about 180. In some embodiments, z is selected from 150±10, 160±10, 170±10, 180±10, or 190±10.

In some embodiments, y is about 25 and z is about 25. In some embodiments, y is about 50 and z is about 50. In some embodiments, y is about 100 and z is about 100.

In certain embodiments, the present invention provides a micelle having a polynucleotide encapsulated therein, comprising a diblock copolymer of compound a:

as described above, wherein the polynucleotide is combined with a suitable metal ion. In some embodiments, the polynucleotide combined with a suitable metal ion is DNA. In some embodiments, the polynucleotide combined with a suitable metal ion is pDNA.

In some embodiments, each of the $R^1$, $R^2$, Q, $R^x$, $R^y$, $R^z$, n, $x^1$, $x^2$, $y^1$, $y^2$, $z^1$, $z^2$, $z^3$ and $z^4$ groups of formulae IV, IV-a, IV-b, IV-c, or IV-d are independently as described with respect to formula I, above.

In certain embodiments, the $x^3$ group of formulae IV, IV-a, IV-b, IV-c, or IV-d is about 0 to about 250. In certain embodiments, the $x^3$ group of formulae IV, IV-a, IV-b, IV-c, or IV-d is about 10. In some embodiments $x^3$ is about 0 to about 50. In some embodiments, $x^3$ is about 20. In some embodiments, $x^3$ is about 30. In some embodiments, $x^3$ is about 40. In some embodiments, $x^3$ is selected from 10±5, 20±5, 30±5, 40±5, or 50±5.

In certain embodiments, the $x^4$ group of formulae IV, IV-a, IV-b, IV-c, or IV-d is about 0 to about 250. In certain embodiments, the $x^4$ group of formulae IV, IV-a, IV-b, IV-c, or IV-d is about 10. In some embodiments $x^4$ is about 0 to about 50. In some embodiments, $x^4$ is about 20. In some embodiments, $x^4$ is about 30. In some embodiments, $x^4$ is about 40. In some embodiments, $x^4$ is selected from 10±5, 20±5, 30±5, 40±5, or 50±5.

In certain embodiments, the present invention provides a micelle having a polynucleotide encapsulated therein, comprising a diblock copolymer of compound a:

a

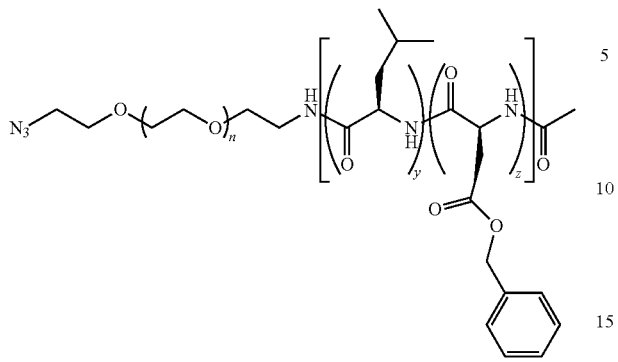

as described above, wherein the polynucleotide is combined with a suitable metal ion. In some embodiments, the polynucleotide combined with a suitable metal ion is DNA. In some embodiments, the polynucleotide combined with a suitable metal ion is pDNA.

In certain embodiments, the present invention provides a micelle having a polynucleotide encapsulated therein, comprising a diblock copolymer of compound b:

b

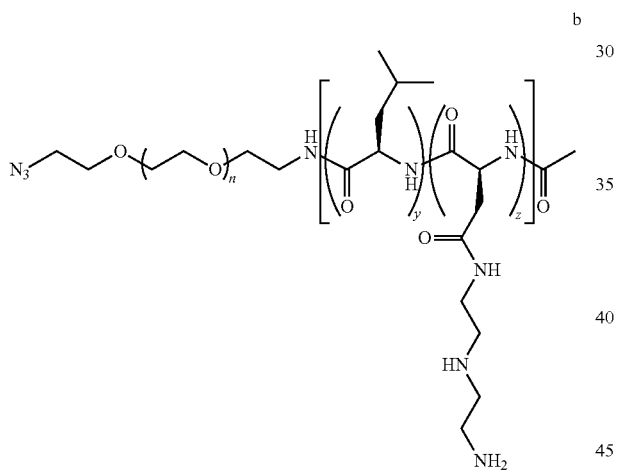

wherein:
n is 50-2500;
y is 5 to 250; and
z is 5 to 250.

As defined generally above, the n group of compound b is 50-2500. In some embodiments, n is about 110 to about 460. In certain embodiments, the present invention provides compounds of compound b as described above, wherein n is about 270. In some embodiments, n is about 225. In some embodiments, n is about 350. In some embodiments, n is about 110. In some embodiments, n is about 454. In some embodiments, n is selected from 110±10, 180±10, 225±10, 275±10, 315±10, or 450±10.

In certain embodiments, the y group of compound b is about 5 to about 250. In certain embodiments, the y group of compound b is about 10. In some embodiments y is about 5-50. In some embodiments y is about 0-50. In some embodiments, y is about 20. In some embodiments, y is about 30. In some embodiments, y is about 40. In other embodiments, y is selected from 10±5, 20±5, 30±5, 40±5, or 50±5.

In certain embodiments, the z group of compound b is about 5 to about 250. In some embodiments, z is about 100-200. In some embodiments, z is about 140. In some embodiments, z is about 160. In some embodiments, z is about 180. In some embodiments, z is selected from 150±10, 160±10, 170±10, 180±10, or 190±10.

In some embodiments, y is about 25 and z is about 25. In some embodiments, y is about 50 and z is about 50. In some embodiments, y is about 100 and z is about 100.

In certain embodiments, the present invention provides a micelle having a polynucleotide encapsulated therein, comprising a diblock copolymer of compound b:

b

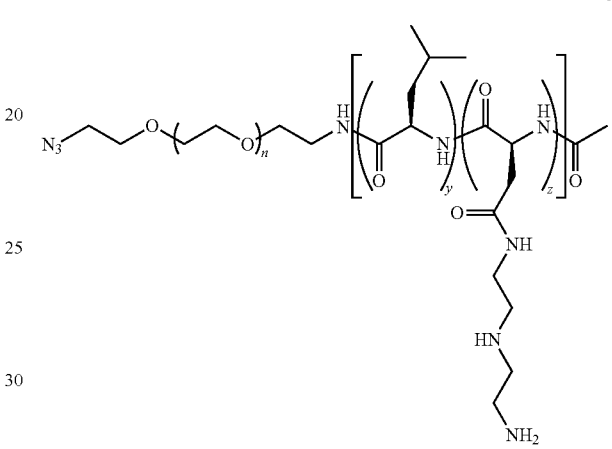

as described above, wherein the polynucleotide is combined with a suitable metal ion. In some embodiments, the polynucleotide combined with a suitable metal ion is DNA. In some embodiments, the polynucleotide combined with a suitable metal ion is pDNA.

In certain embodiments, the present invention provides a micelle having a polynucleotide encapsulated therein, comprising a diblock copolymer of compound c:

c

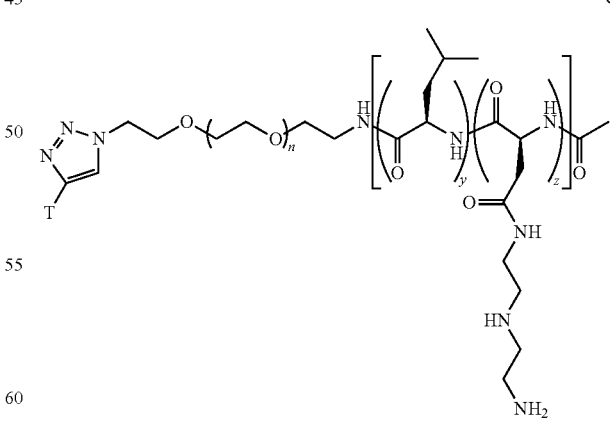

wherein:
n is 50-2500;
y is 5 to 250;
z is 5 to 250; and
T is a targeting group moiety.

As defined generally above, the n group of compound c is 50-2500. In some embodiments, n is about 110 to about 460. In certain embodiments, the present invention provides compounds of compound c as described above, wherein n is about 270. In some embodiments, n is about 225. In some embodiments, n is about 350. In some embodiments, n is about 110. In some embodiments, n is about 454. In some embodiments, n is selected from 110±10, 180±10, 225±10, 275±10, 315±10, or 450±10.

In certain embodiments, the y group of compound c is about 5 to about 250. In certain embodiments, the y group of compound c is about 10. In some embodiments y is about 5-50. In some embodiments y is about 0-50. In some embodiments, y is about 20. In some embodiments, y is about 30. In some embodiments, y is about 40. In some embodiments, y is selected from 10±5, 20±5, 30±5, 40±5, or 50±5.

In certain embodiments, the z group of compound c is about 5 to about 250. In some embodiments, z is about 100-200. In some embodiments, z is about 140. In some embodiments, z is about 160. In some embodiments, z is about 180. In some embodiments, z is selected from 150±10, 160±10, 170±10, 180±10, or 190±10.

In some embodiments, y is about 25 and z is about 25. In some embodiments, y is about 50 and z is about 50. In some embodiments, y is about 100 and z is about 100.

As defined generally above, the T group of compound c is a targeting group moiety. Targeting groups are well known in the art and include those described in International application publication number WO 2008/134731, published Nov. 6, 2008, the entirety of which is hereby incorporated by reference. In some embodiments, the T targeting group is a moiety selected from folate, a Her-2 binding peptide, a urokinase-type plasminogen activator receptor (uPAR) antagonist, a CXCR4 chemokine receptor antagonist, a GRP78 peptide antagonist, an RGD peptide, an RGD cyclic peptide, a luteinizing hormone-releasing hormone (LHRH) antagonist peptide, an aminopeptidase targeting peptide, a brain homing peptide, a kidney homing peptide, a heart homing peptide, a gut homing peptide, an integrin homing peptide, an angiogencid tumor endothelium homing peptide, an ovary homing peptide, a uterus homing peptide, a sperm homing peptide, a microglia homing peptide, a synovium homing peptide, a urothelium homing peptide, a prostate homing peptide, a lung homing peptide, a skin homing peptide, a retina homing peptide, a pancreas homing peptide, a liver homing peptide, a lymph node homing peptide, an adrenal gland homing peptide, a thyroid homing peptide, a bladder homing peptide, a breast homing peptide, a neuroblastoma homing peptide, a lymphona homing peptide, a muscle homing peptide, a wound vasculature homing peptide, an adipose tissue homing peptide, a virus binding peptide, or a fusogenic peptide. Such targeting groups are well known in the art and are described in detail in WO 2008/134731.

In certain embodiments, a T targeting group is a peptide moiety. In some embodiments, a T targeting group is a moiety selected from a tumor homing group, a prostate specific membrane antigen homing peptide, an aminopeptidate N homing peptide, a Her-2 homing peptide, a colong cancer homing peptide, a VEGFR1 homing peptide, or a CXCR4 homing peptide.

In certain embodiments, the present invention provides a micelle having a polynucleotide encapsulated therein, comprising a diblock copolymer of compound c:

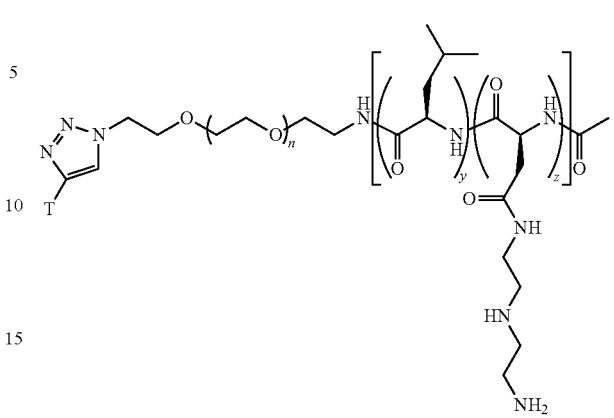

as described above, wherein the polynucleotide is combined with a suitable metal ion. In some embodiments, the polynucleotide combined with a suitable metal ion is DNA. In some embodiments, the polynucleotide combined with a suitable metal ion is pDNA.

In certain embodiments, the present invention provides a micelle having a polynucleotide encapsulated therein, comprising a diblock copolymer of compound d:

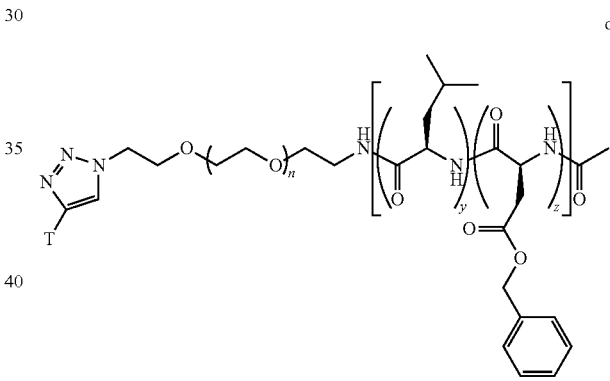

wherein:
n is 50-2500;
y is 5 to 250;
z is 5 to 250; and
T is a targeting group moiety.

As defined generally above, the n group of compound d is 50-2500. In some embodiments, n is about 110 to about 460. In certain embodiments, the present invention provides a micelle having a polynucleotide encapsulated therein, comprising compounds of compound d as described above, wherein n is about 270. In some embodiments, n is about 225. In some embodiments, n is about 350. In some embodiments, n is about 110. In some embodiments, n is about 454. In some embodiments, n is selected from 110±10, 180±10, 225±10, 275±10, 315±10, or 450±10.

In certain embodiments, the y group of compound d is about 5 to about 250. In certain embodiments, the y group of compound d is about 10. In some embodiments, y is about 5-50. In some embodiments, y is about 0-50. In some embodiments, y is about 20. In some embodiments, y is about 30. In some embodiments, y is about 40. In some embodiments, y is selected from 10±5, 20±5, 30±5, 40±5, or 50±5.

In certain embodiments, the z group of compound d is about 5 to about 250. In some embodiments, z is about 100-200. In some embodiments, z is about 140. In some embodiments, z is about 160. In some embodiments, z is about 180. In some embodiments, z is selected from 150±10, 160±10, 170±10, 180±10, or 190±10.

In some embodiments, y is about 25 and z is about 25. In some embodiments, y is about 50 and z is about 50. In some embodiments, y is about 100 and z is about 100.

As defined generally above, the T group of compound d is a targeting group moiety. Targeting groups are well known in the art and include those described in International application publication number WO 2008/134731, published Nov. 6, 2008, the entirety of which is hereby incorporated by reference. In some embodiments, the T targeting group is a moiety selected from folate, a Her-2 binding peptide, a urokinase-type plasminogen activator receptor (uPAR) antagonist, a CXCR4 chemokine receptor antagonist, a GRP78 peptide antagonist, an RGD peptide, an RGD cyclic peptide, a luteinizing hormone-releasing hormone (LHRH) antagonist peptide, an aminopeptidase targeting peptide, a brain homing peptide, a kidney homing peptide, a heart homing peptide, a gut homing peptide, an integrin homing peptide, an angiogencid tumor endothelium homing peptide, an ovary homing peptide, a uterus homing peptide, a sperm homing peptide, a microglia homing peptide, a synovium homing peptide, a urothelium homing peptide, a prostate homing peptide, a lung homing peptide, a skin homing peptide, a retina homing peptide, a pancreas homing peptide, a liver homing peptide, a lymph node homing peptide, an adrenal gland homing peptide, a thyroid homing peptide, a bladder homing peptide, a breast homing peptide, a neuroblastoma homing peptide, a lymphona homing peptide, a muscle homing peptide, a wound vasculature homing peptide, an adipose tissue homing peptide, a virus binding peptide, or a fusogenic peptide. Such targeting groups are well known in the art and are described in detail in WO 2008/134731.

In some embodiments, the T targeting group is a moiety selected from a tumor homing group, a prostate specific membrane antigen homing peptide, an aminopeptidate N homing peptide, a Her-2 homing peptide, a colong cancer homing peptide, a VEGFR1 homing peptide, or a CXCR4 homing peptide.

In certain embodiments, the present invention provides a micelle having a polynucleotide encapsulated therein, comprising a diblock copolymer of compound d:

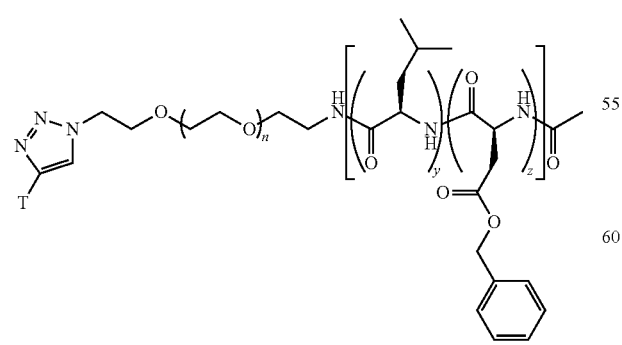

as described above, wherein the polynucleotide is combined with a suitable metal ion. In some embodiments, the polynucleotide combined with a suitable metal ion is DNA. In some embodiments, the polynucleotide combined with a suitable metal ion is pDNA.

Another embodiment of the present invention provides a method for preparing compound c:

wherein:
n is 50-2500;
y is 5 to 250;
z is 5 to 250; and
T is a targeting group moiety,
wherein said method comprises the steps of:
a) providing compound a:

wherein:
n is 50-2500;
y is 5 to 250; and
z is 5 to 250, wherein said method comprises the steps of:
a) providing compound a:

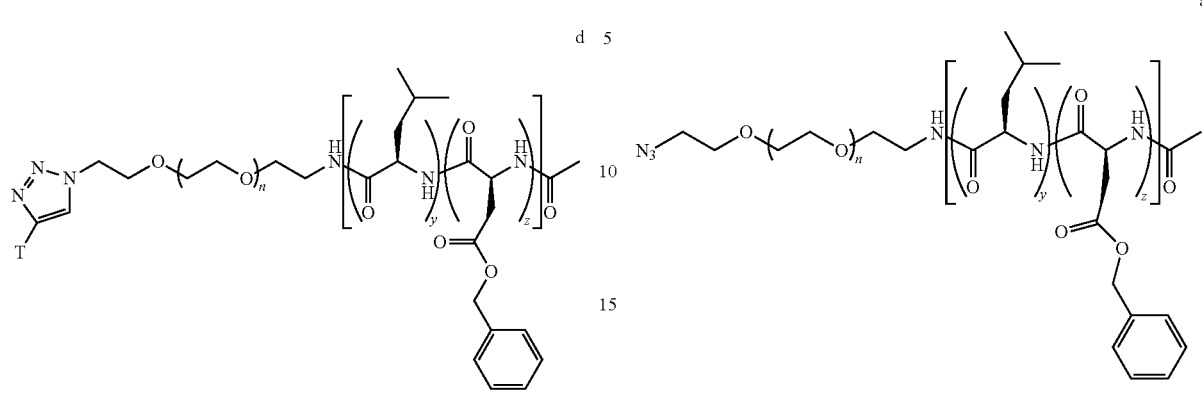

wherein:
n is 50-2500;
y is 5 to 250; and
z is 5 to 250,
b) performing an aminolysis reaction with diethylene triamine and compound a to give compound b

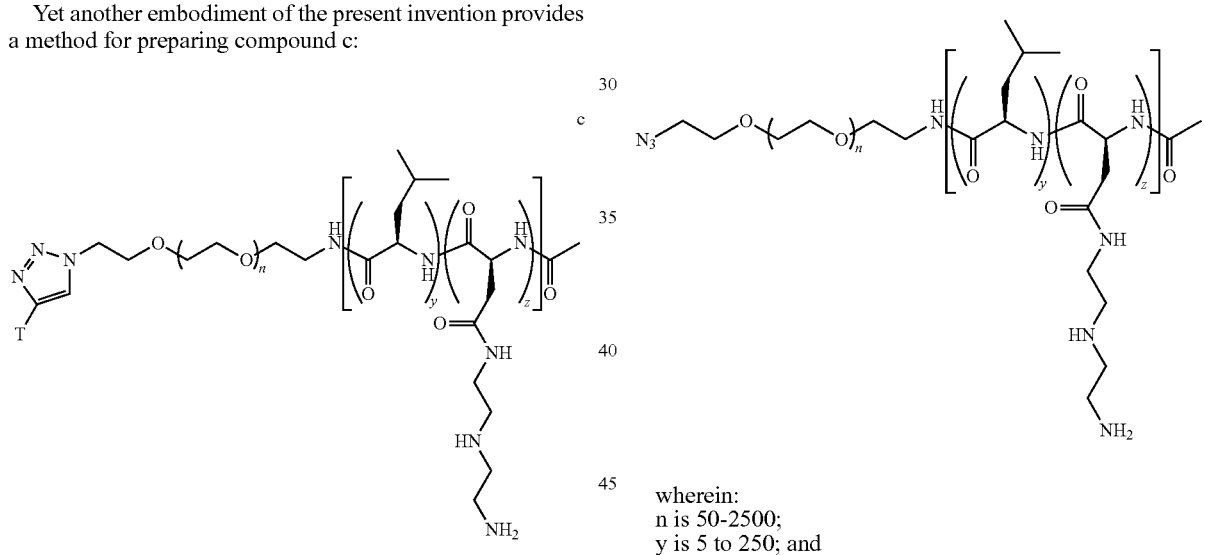

wherein:
n is 50-2500;
y is 5 to 250; and
z is 5 to 250
and c) performing a "click" reaction on compound b.

In certain embodiments, the present invention provides a method of polynucleotide encapsulation, the method comprising the steps of:
a) optionally combining a nucleotide with a suitable metal ion; and
b) combining the nucleotide with a compound of formula I-b:

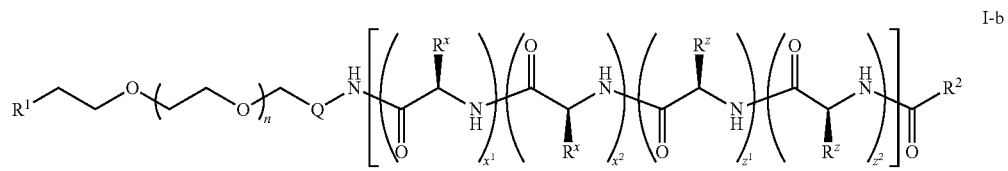

b) performing a "click" reaction on compound a to provide compound d:

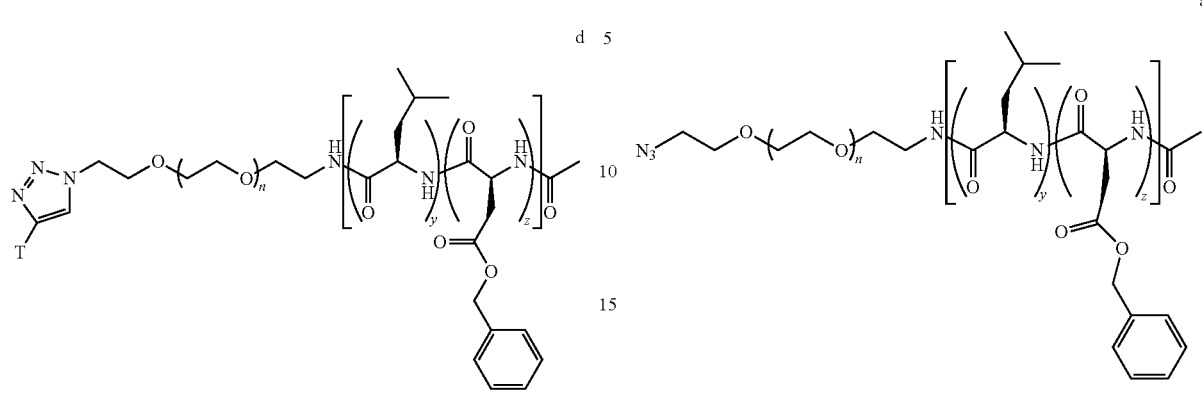

wherein:
n is 50-2500;
y is 5 to 250;
z is 5 to 250; and
T is a targeting group moiety, and
c) performing an aminolysis reaction with diethylene triamine and compound d.

Yet another embodiment of the present invention provides a method for preparing compound c:

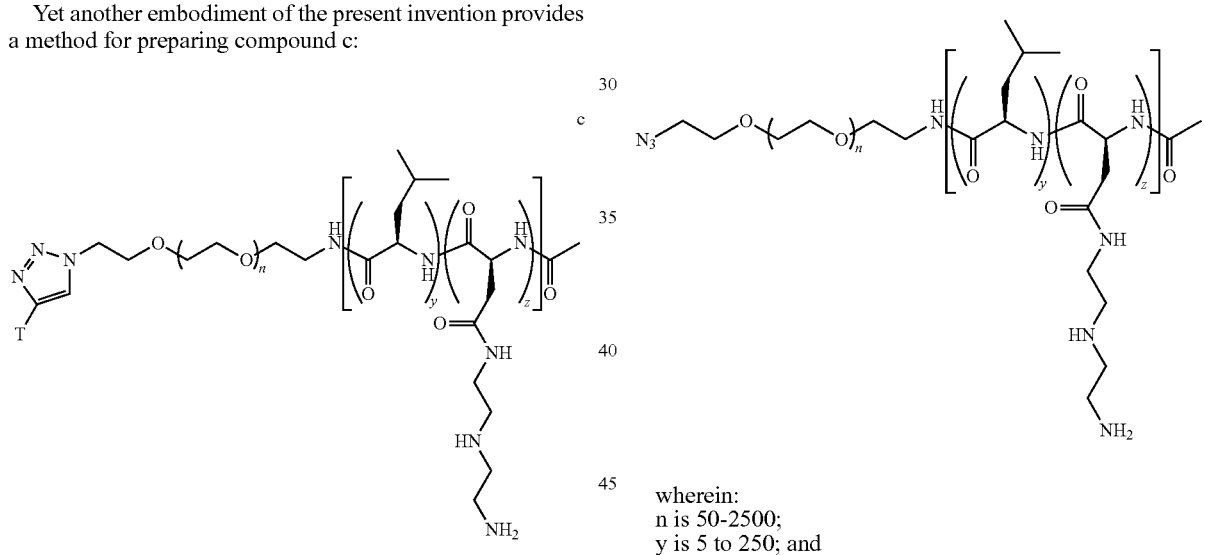

wherein:
n is 50-2500;
y is 5 to 250;
z is 5 to 250; and
T is a targeting group moiety wherein:

n is 50-2500;

$x^1$ is 0 to 250;

$x^2$ is 0 to 250;

$z^1$ is 0 to 250, provided that $x^1$ and $z^1$ are not simultaneously zero;

$z^2$ is 0 to 250, provided that $z^1$ and $z^2$ are not simultaneously zero;

$R^x$ is a natural or unnatural amino acid side-chain group that is hydrophobic;

$R^z$ is -L-$R^4$ wherein:

L is a bivalent, straight or branched, $C_{4-20}$ alkylene chain wherein at least one methylene unit of -L- is replaced by —C(O)NR— and 1-10 additional methylene units are independently replaced by —N(R)— or -Het-;

Het is a bivalent 5-6 membered saturated, partially unsaturated, or aromatic ring having at least one nitrogen and 0-3 additional heteroatoms independently selected from nitrogen, oxygen, or sulfur;

$R^4$ is R or $N(R)_2$;

each R is hydrogen or $C_{1-6}$ aliphatic, or two R on the same nitrogen are taken together with the nitrogen to form a 5-6 membered heterocyclic ring having 1-3 heteroatoms independently selected from nitrogen, oxygen, or sulfur;

$R^1$ is —Z(CH$_2$CH$_2$Y)$_p$(CH$_2$)$_t$R$^3$, wherein:

Z is a valence bond, a bivalent triazolyl moiety, —O—, —S—, —C≡C—, or —CH$_2$—;

each Y is independently —O— or —S—;

p is 0-10;

t is 0-10; and $R^3$ is hydrogen, —$N_3$, —CN, a mono-protected amine, a di-protected amine, a protected aldehyde, a protected hydroxyl, a protected carboxylic acid, a protected thiol, a 9-30 membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety or a targeting group;

Q is a valence bond or a bivalent, saturated or unsaturated, straight or branched $C_{1-12}$ alkylene chain, wherein 0-6 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:

-Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;

$R^2$ is selected from an optionally substituted aliphatic group or a fusogenic peptide; to form a micelle having the polynucleotide encapsulated therein.

In certain embodiments, step (a) comprises combining DNA with a suitable metal ion. In certain embodiments, step (a) comprises combining pDNA with a suitable metal ion. In certain embodiments, the combination of a suitable metal ion with a polynucleotide results in pre-compaction of the polynucleotide. In some embodiments, the step of combining a nucleotide with a suitable metal ion comprises incubating the nucleotide in the presence of the metal ion such that the nucleotide is pre-compacted prior to encapsulation. In certain embodiments, a nucleotide combined with a suitable metal ion is characterized in that the nucleotide is pre-compacted. In some embodiments, a suitable metal ion is selected from Mg, Ca, Cu, Mn, Zn, Ni, Fe, or combinations thereof. In some embodiments, a suitable metal ion is copper. In some embodiments, a suitable metal ion is calcium.

It will be appreciated that, in accordance with the present invention, any of formulae I-b, I-c, I-d, I-e, II-a, II-b, II-c, II-d, III-a, III-b, III-c, III-d, IV-a, IV-b, IV-c, IV-d, b, c, or combinations thereof, may be combined with a nucleotide in step (b) to form a micelle having the polynucleotide encapsulated therein.

C. Crosslinking Chemistries

In addition to advances in polymer micelle technology, significant efforts have been made in the development of stimuli-responsive polymeric materials that can respond to environmental pH changes. See Chatterjee, J.; Haik, Y.; Chen, C. J. *J. App. Polym. Sci.* 2004, 91, 3337-3341; Du, J. Z.; Armes, S. P. *J. Am. Chem. Soc.* 2005, 127, 12800-12801; and Twaites, B. R.; de las Heras Alarcon, C.; Cunliffe, D.; Lavigne, M.; Pennadam, S.; Smith, J. R.; Gorecki, D. C.; Alexander, C. *J. Control. Release* 2004, 97, 551-566. This is of importance for sensitive protein and nucleic acid-based drugs where escape from acidic intracellular compartments (i.e. endosome and lysosome) and cytoplasmic release are required to achieve therapeutic value. See Murthy, N.; Campbell, J.; Fausto, N.; Hoffman, A. S.; Stayton, P. S. *J. Control. Release* 2003, 89, 365-374; El-Sayed, M. E. H.; Hoffman, A. S.; Stayton, P. S. *J. Control. Release* 2005, 104, 417-427; and Liu, Y.; Wenning, L.; Lynch, M.; Reineke, T. *J. Am. Chem. Soc.* 2004, 126, 7422-7423. Acid-sensitive delivery systems that can successfully escape the endosome and transport small-molecule chemotherapeutic drugs into the cytoplasm are also of interest since these carriers can bypass many of the cellular mechanisms responsible for multi-drug resistance. In some of these cases, the polymers are designed to respond to the significant pH gradient between the blood (pH 7.4) and the late-early endosome (pH ~5.0-6.0).

In contrast to shell-crosslinked micelles, the crosslinking of multiblock copolymer micelles in accordance with the present invention is accomplished without large dilution volumes because micelle-micelle coupling does not occur. Such crosslinking will enhance post-administration circulation time leading to more efficient passive drug targeting by the EPR effect and improved active targeting using cancer-specific targeting groups. In addition, stimuli-responsive crosslinking may offer another targeting mechanism to isolate the release of the chemotherapy drug exclusively within the tumor tissue and cancer cell cytoplasm.

Crosslinking reactions designed for drug delivery preferably meet a certain set of requirements to be deemed safe and useful for in vivo applications. For example, in some embodiments, the crosslinking reaction would utilize non-cytotoxic reagents, would be insensitive to water, would not alter the drug to be delivered, and in the case of cancer therapy, would be reversible at pH levels commonly encountered in tumor tissue (pH ~6.8) or acidic organelles in cancer cells (pH ~5.0-6.0).

Scheme 2

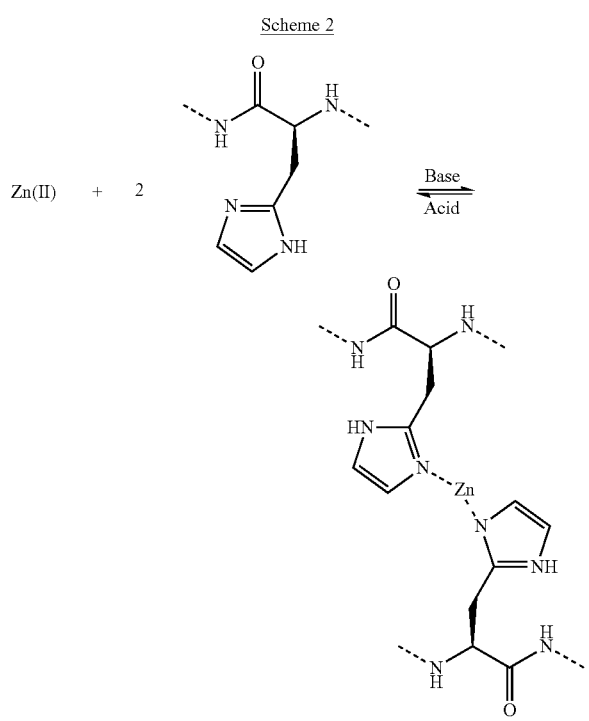

Scheme 2 above illustrates the reaction of an aqueous zinc (II) ion (e.g. from zinc chloride or zinc acetate) with two equivalents of an appropriate imidazole (e.g. histidine) to form a zinc-histidine complex. This reaction occurs rapidly in a slightly basic pH environment and is reversible upon acidification to pH less than 6. (Tezcan, et. al. *J. Am. Chem. Soc.* 2007, 129, 13347-13375.)

In certain embodiments, $R^c$ is a histidine side-chain crosslinked with zinc. Without wishing to be bound by any particular theory, it is believed that zinc-histidine crosslinks are stable in the blood compartment (pH 7.4), allowing for effective accumulation of therapeutic loaded micelles in solid tumors by passive and/or active targeting mechanisms. In the presence of lactic acid concentrations commonly encountered in solid tumors or hydrochloric acid in acidic organelles of cancer cells, rapid degradation of the metal crosslinks occurs which leads to micelle dissociation and release of the polynucleotide at the tumor site.

The choice of zinc as a crosslinking metal is advantageous for effective micelle crosslinking. Zinc chloride and the zinc lactate by-product are generally recognized as non-toxic, and other safety concerns are not anticipated. Pharmaceutical grade zinc chloride is commonly used in mouthwash and as a chlorophyll stabilizer in vegetables while zinc lactate is used as an additive in toothpaste and drug preparation. While zinc has been chosen as an exemplary metal for micelle crosslinking, it should be noted that many other metals undergo acid sensitive coupling with imidazole derivatives. These metals include calcium, iron, copper, nickel and other transition metals. One or more of these metals can be substituted for zinc.

The ultimate goal of metal-mediated crosslinking is to ensure micelle stability when diluted in the blood (pH 7.4) followed by rapid dissolution and polynucleotide release in response to a finite pH change such as those found in tumor environments or in intracellular compartments. Previous reports suggest that the zinc-histidine bonds are stable above a threshold pH, below which dissociation to zinc ions and histidine occurs. (Tezcan, et. al. *J. Am. Chem. Soc.* 2007, 129, 13347-13375.)

D. Polymer Conjugation

In addition to their core-shell morphology, polymer micelles can be modified to enable passive and active cell-targeting to maximize the benefits of current and future therapeutic agents. Because drug-loaded micelles typically possess diameters greater than 20 nm, they exhibit dramatically increased circulation time when compared to stand-alone drugs due to minimized renal clearance. This unique feature of nanovectors and polymeric drugs leads to selective accumulation in diseased tissue, especially cancerous tissue due to the enhanced permeation and retention effect ("EPR"). The EPR effect is a consequence of the disorganized nature of the tumor vasculature, which results in increased permeability of polymer therapeutics and drug retention at the tumor site. In addition to passive cell targeting by the EPR effect, micelles are designed to actively target tumor cells through the chemical attachment of targeting groups to the micelle periphery. The incorporation of such groups is most often accomplished through end-group functionalization of the hydrophilic block using chemical conjugation techniques. Like viral particles, micelles functionalized with targeting groups utilize receptor-ligand interactions to control the spatial distribution of the micelles after administration, further enhancing cell-specific delivery of therapeutics. In cancer therapy, targeting groups are designed to interact with receptors that are over-expressed in cancerous tissue relative to normal tissue such as folic acid, oligopeptides, sugars, and monoclonal antibodies. See Pan, D.; Turner, J. L.; Wooley, K. L. *Chem. Commun.* 2003, 2400-2401; Gabizon, A.; Shmeeda, H.; Horowitz, A. T.; Zalipsky, S. *Adv. Drug Deliv. Rev.* 2004, 56, 1177-1202; Reynolds, P. N.; Dmitriev, I.; Curiel, D. T. Vector. *Gene Ther.* 1999, 6, 1336-1339; Derycke, A. S. L.; Kamuhabwa, A.; Gijsens, A.; Roskams, T.; De Vos, D.; Kasran, A.; Huwyler, J.; Missiaen, L.; de Witte, P. A. M. T *J. Nat. Cancer Inst.* 2004, 96, 1620-30; Nasongkla, N., Shuai, X., Ai, H.; Weinberg, B. D. P., J.; Boothman, D. A.; Gao, *J. Angew. Chem. Int. Ed.* 2004, 43, 6323-6327; Jule, E.; Nagasaki, Y.; Kataoka, K. *Bioconj. Chem.* 2003, 14, 177-186; Stubenrauch, K.; Gleiter, S.; Brinkmann, U.; Rudolph, R.; Lilie, H. *Biochem. J.* 2001, 356, 867-873; Kurschus, F. C.; Kleinschmidt, M.; Fellows, E.; Dornmair, K.; Rudolph, R.; Lilie, H.; Jenne, D. E. *FEBS Lett.* 2004, 562, 87-92; and Jones, S. D.; Marasco, W. A. *Adv. Drug Del. Rev.* 1998, 31, 153-170.

After incorporating the poly (amino acid) block portions into the multi-block copolymer of the present invention resulting in a multi-block copolymer of the form W—X—X', the other end-group functionality, corresponding to the $R^1$ or $R^{1a}$ moiety of any of formulae I to IV-d can be used to attach targeting groups for cell specific delivery including, but not limited to, attach targeting groups for cell specific delivery including, but not limited to, proteins, oligopeptides, antibodies, monosaccharides, oligosaccharides, vitamins, or other small biomolecules. Such targeting groups include, but or not limited to monoclonal and polyclonal antibodies (e.g. IgG, IgA, IgM, IgD, IgE antibodies), sugars (e.g. mannose, mannose-6-phosphate, galactose), proteins (e.g. Transferrin), oligopeptides (e.g. cyclic and acyclic RGD-containing oligopeptides), and vitamins (e.g. folate). Alternatively and/or additionally, the $R^1$ or $R^{1a}$ moiety of any of formulae I to IV-d is bonded to a biomolecule, drug, cell, or other suitable substrate.

In some embodiments, the $R^1$ or $R^{1a}$ moiety of any of formulae I to IV-d is bonded to biomolecules which promote cell entry and/or endosomal escape. Such biomolecules include, but are not limited to, oligopeptides containing protein transduction domains such as the HIV Tat peptide sequence (GRKKRRQRRR) or oligoarginine (RRRRRRRR). Oligopeptides which undergo conformational changes in varying pH environments such oligohistidine (HHHHH) also promote cell entry and endosomal escape.

In certain embodiments, micelles of the present invention are mixed micelles comprising one or more compounds of formula I to IV-d. It will be appreciated that mixed micelles having different $R^1$ or $R^{1a}$ groups, as described herein, can be conjugated to multiple other compounds and/or macromolecules. For example, a mixed micelle of the present invention can have one $R^1$ or $R^{1a}$ group suitable for click chemistry and another $R^1$ or $R^{1a}$ group suitable for covalent attachment via a variety of coupling reactions. Such a mixed micelle can be conjugated to different compounds and/or macromolecules via these different $R^1$ or $R^{1a}$ groups. Such conjugation reactions are well known to one of ordinary skill in the art and include those described herein.

4. Uses, Methods, and Compositions

As described herein, micelles of the present invention can encapsulate a wide variety of therapeutic agents useful for treating a wide variety of diseases. In certain embodiments, the present invention provides a nucleotide-loaded micelle, as described herein, wherein said micelle is useful for treating the disorder for which the nucleotide is known to treat. In some embodiments, the present invention provides methods for treating one or more disorders selected from pain, inflammation, arrhythmia, arthritis (rheumatoid or osteoarthritis), atherosclerosis, restenosis, bacterial infection, viral infection, depression, diabetes, epilepsy, fungal infection, gout, hypertension, malaria, migraine, cancer or other proliferative disorder, erectile dysfunction, a thyroid disorder, neurological disorders and hormone-related diseases, Parkinson's disease, Huntington's disease, Alzheimer's disease, a gastrointestinal disorder, allergy, an autoimmune disorder, such as asthma or psoriasis, osteoporosis, obesity and comorbidities, a cognitive disorder, stroke, AIDS-associated dementia, amyotrophic lateral sclerosis (ALS, Lou Gehrig's disease), multiple sclerosis (MS), schizophrenia, anxiety, bipolar disorder, tauopothy, a spinal cord or peripheral nerve injury, myocardial infarction, cardiomyocyte hypertrophy, glaucoma, an attention deficit disorder (ADD or ADHD), a sleep disorder, reperfusion/ischemia, an angiogenic disorder, or urinary incontinence, comprising administering to a patient in need thereof a micelle comprising a multiblock copolymer which comprises a polymeric hydrophilic block, a crosslinked poly(amino acid block), and a poly(amino acid block), characterized in that said micelle has a drug-loaded inner core, a crosslinked outer core, and a hydrophilic shell, wherein said micelle encapsulates a therapeutic agent suitable for treating said disorder.

In certain embodiments, the present invention provides methods for treating one or more disorders selected from autoimmune disease, an inflammatory disease, a metabolic disorder, a psychiatric disorder, diabetes, an angiogenic disorder, tauopothy, a neurological or neurodegenerative disorder, a spinal cord injury, glaucoma, baldness, or a cardiovascular disease, comprising administering to a patient in need thereof a micelle comprising multiblock copolymers which comprise a polymeric hydrophilic block and a mixed random copolymer block consisting of hydrophobic and amine-containing amino acid residues; characterized in that said micelle has an inner core suitable for polynucleotide encapsulation and a hydrophilic shell, wherein said micelle encapsulates a therapeutic polynucleotide suitable for treating said disorder.

In some embodiments, micelles of the present invention are for use in medicine. In certain embodiments, nucleotide-loaded micelles of the present invention are useful for treating cancer. Accordingly, in some embodiments the present invention provides methods for treating cancer in a patient comprising administering to a patient in need thereof a micelle comprising multiblock copolymers which comprise a polymeric hydrophilic block and a mixed random copolymer block consisting of hydrophobic and amine-containing amino acid derivatives; characterized in that said micelle has an inner core suitable for polynucleotide encapsulation and a hydrophilic shell, wherein said micelle encapsulates a therapeutic polynucleotide suitable for treating said cancer. In certain embodiments, the present invention relates to methods of treating a cancer selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon-rectum, large intestine, rectum, brain and central nervous system, and leukemia, comprising administering a micelle in accordance with the present invention wherein said micelle encapsulates a therapeutic polynucleotide suitable for treating said cancer.

Compositions

In certain embodiments, the invention provides a composition comprising a micelle of this invention or a pharmaceutically acceptable derivative thereof and a pharmaceutically acceptable carrier, adjuvant, or vehicle. In certain embodiments, a composition of this invention is formulated for administration to a patient in need of such composition. In certain embodiments, a composition of this invention is formulated for oral administration to a patient.

The term "patient", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N+(C_{1-4}alkyl)_4$ salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added. In certain embodiments, pharmaceutically acceptable compositions of the present invention are enterically coated.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In certain embodiments, the pharmaceutically acceptable compositions of this invention are formulated for oral administration.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the drug can be administered to a patient receiving these compositions.

It will be appreciated that dosages typically employed for the encapsulated drug are contemplated by the present invention. In certain embodiments, a patient is administered a drug-loaded micelle of the present invention wherein the dosage of the drug is equivalent to what is typically administered for that drug. In some embodiments, a patient is administered a drug-loaded micelle of the present invention wherein the dosage of the drug is lower than is typically administered for that drug.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

In order that the invention described herein may be more fully understood, the following examples are set forth. It will be understood that these examples are for illustrative purposes only and are not to be construed as limiting this invention in any manner.

EXAMPLES

Preparation of Bifunctional PEGs and Multiblock Copolymers of the Present Invention As described generally above, multiblock copolymers of the present invention are prepared using the heterobifunctional PEGs described herein and in U.S. patent application Ser. No. 11/256,735, filed Oct. 24, 2005, published as WO2006/047419 on May 4, 2006 and published as US 20060142506 on Jun. 29, 2006, the entirety of which is hereby incorporated herein by reference. The preparation of multiblock polymers in accordance with the present invention is accomplished by methods known in the art, including those described in detail in U.S. patent application Ser. No. 11/325,020, filed Jan. 4, 2006, published as WO2006/74202 on Jul. 13, 2006 and published as US 20060172914 on Aug. 3, 2006, the entirety of which is hereby incorporated herein by reference.

In each of the Examples below, where an amino acid, or corresponding NCA, is designated "D", then that amino acid, or corresponding NCA, is of the D-configuration. Where no such designation is recited, then that amino acid, or corresponding NCA, is of the L-configuration.

Example 1

Synthesis of dibenzyl amino ethanol

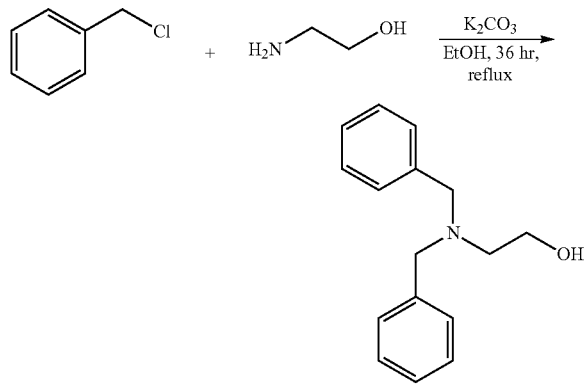

Benzyl chloride (278.5 g, 2.2 mol), ethanol amine (60 mL, 1 mol), potassium carbonate (283.1 g, 2.05 mol) and ethanol (2 L) were mixed together in a 3 L 3-neck flask, fitted with an overhead stirrer, a condenser and a glass plug. The whole setup was heated up to reflux for 36 hr, after which the insoluble solid was filtered through a medium frit. The filtrate was recovered and ethanol was removed by rotovapor. The viscous liquid was redissolved in ether, the solid suspension removed by filtration and extracted twice against water. The ether solution was kept and the aqueous layer was extracted twice with dichloromethane (2×400 mL). The fraction were recombined, dried over MgSO$_4$, stirred over carbon black for 15 min and filtered through a celite pad. Dichloromethane was removed and the solid was redissolved into a minimal amount of ether (combined volume of 300 mL with the first ether fraction, 300 mL). Hexanes (1700 mL) was added and the solution was heated up gently till complete dissolution of the product. The solution was then cooled down gently, placed in the fridge (+4° C.) overnight and white crystals were obtained. The recrystallization was done a second time. 166.63 g, 69% yield. $^1$H NMR (d$_6$-DMSO) δ 7.39-7.24 (10H), 4.42 (1H), 3.60 (4H), 3.52 (2H), 2.52 (2H).

Example 2

Synthesis of (Dibenzyl)-N-EO270-OH

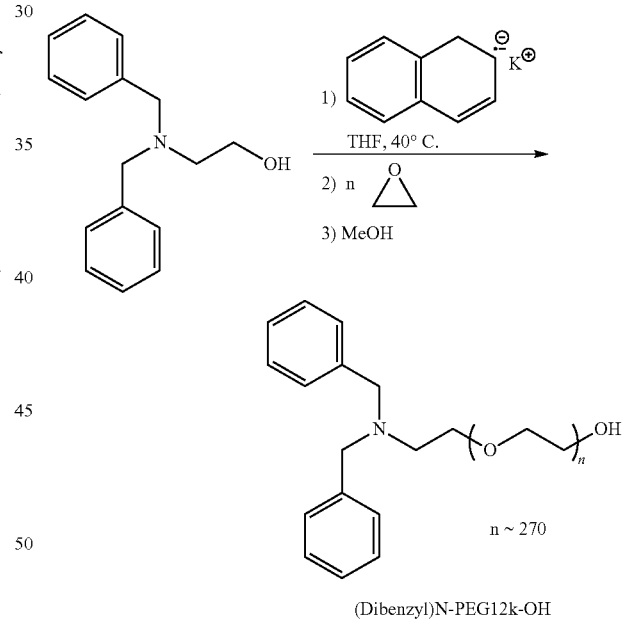

The glassware was assembled while still warm. Vacuum was then applied to the assembly and the ethylene oxide line to about 10 mTorr. The setup was backfilled with argon. 2-Dibenzylamino ethanol (3.741 g, 40.4 mmol) was introduced via the sidearm of the jacketed flask under argon overpressure. Two vacuum/argon backfill cycles were applied to the whole setup. THF line was connected to the 14/20 sidearm and vacuum was applied to the whole setup. At this stage, the addition funnel was closed and left under vacuum. THF (4 L) was introduced via the side-arm in the round bottom flask under an argon overpressure. An aliquot of the THF added to the reaction vessel was collected and analyzed by Karl-Fisher colorometric titration to ensure water content of the THF is less than 6 ppm. Next, 2-dibenzylamino ethanol was converted to potassium 2-dibenzylamino ethoxide via addition of potassium naphthalenide (200 mL). Ethylene oxide (500 ml, 10.44 mol) was condensed under vacuum at −30° C. into the jacketed addition funnel, while the alkoxide solution was cooled to 10° C. Once the appropriate amount of ethylene oxide was condensed, the flow of ethylene oxide was stopped, and the liquid ethylene oxide added directly to the cooled alkoxide solution. After complete ethylene oxide addition, the addition funnel was closed and the reaction flask back-filled with argon. While stirring, the following temperature ramp was applied to the reaction: 12 hrs at 20° C., 1 hr from 20° C. to 40° C. and 3 days at 40° C. The reaction went from a light green tint to a golden yellow color. Upon termination with an excess methanol, the solution color changed to light green. The solution was precipitated into ether and isolated by filtration. 459 g, 99% yield was recovered after drying in a vacuum oven overnight. $^1$H NMR (d6-DMSO) δ, 7.4-7.2 (10H), 4.55 (1H), 3.83-3.21 (910H) ppm.

Example 3

Synthesis of H$_2$N-EO270-OH

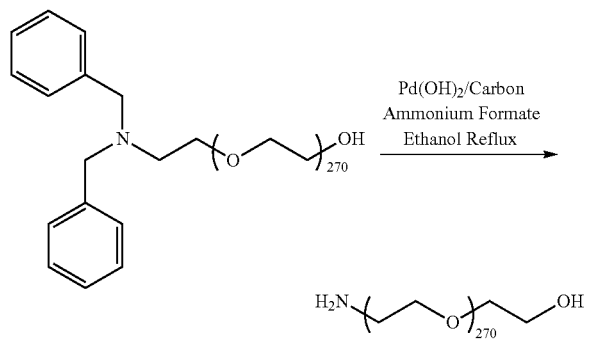

Batch Bz-EO270-OH-A (455 g, 39.56 mmol) was split into two equal amounts and was introduced into two 2 L flasks. Batch Bz-EO270-OH—B (273 g, 23.74 mmol) was put into a 2 L flask as well. The following steps were repeated for each flask. H$_2$N-EO270-OH (~0.225 g), Pd(OH)$_2$/C (32 g, 45.6 mmol), ammonium formate (80 g, 1.27 mol) and ethanol (1.2 L) were mixed together in a 2 L flask. The reaction was heated to 80° C. while stirring for 24 hrs. The reaction was cooled to room temperature and filtered through a triple layer Celite/MgSO$_4$/Celite pad. The MgSO$_4$ powder is fine enough that very little Pd(OH)$_2$/C permeates through the pad. Celite helps prevent the MgSO$_4$ layer from cracking. At this stage, the three filtrates were combined, precipitated into ~30 L of ether and filtered through a medium glass frit. The wet polymer was then dissolved into 4 L of water, 1 L of brine and 400 mL of saturated K$_2$CO$_3$ solution. The pH was checked to be ~11 by pH paper. The aqueous solution was introduced into a 12 L extraction funnel, rinsed once with 4 L of ether and extracted 4 times with dichloromethane (6 L, 6 L, 6 L, 2 L). Dichloromethane fractions were recombined, dried over MgSO$_4$ (3 kg), filtered, concentrated to ~3 L by rotary evaporation and precipitated into diethyl ether (30 L). 555 g, 75% yield was recovered after filtration and evaporation to dryness in a vacuum oven. $^1$H NMR (d6-DMSO) 4.55 (1H), 3.83-3.21 (910H), 2.96 (2H) ppm.

Example 4

Synthesis of H$_2$N-EO270-OH

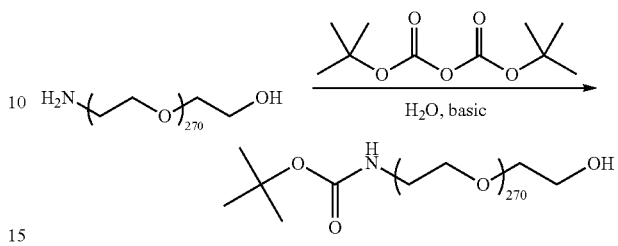

H$_2$N-EO270-OH (555 g, 48.26 mmol) was dissolved into 4 L of DI water. A saturated solution of K$_2$CO$_3$ (120 mL) was added, to keep the pH basic (pH ~11 with pH paper). Di-tert-butyl dicarbonate (105 g, 0.48 mol) was added to the aqueous solution of H$_2$N-EO270-OH and allowed to stir at room temperature overnight. At this stage, a 5 mL aliquot of the reaction was extracted with 10 mL of dichloromethane and the dichloromethane extract precipitated into ether. A $^1$H NMR was run to ensure completion of the reaction. Thereafter, the aqueous solution was placed into a 12 L extraction funnel, was rinsed once with ether (4 L) and extracted three times with dichloromethane (6 L, 6 L and 6 L). The organic fractions were recombined, dried over MgSO$_4$ (3 kg), filtered, concentrated to ~4 L and precipitated into 30 L of ether. The white powder was filtered and dried overnight in a vacuum oven, giving 539 g, 97% yield. $^1$H NMR (d$_6$-DMSO) δ 6.75 (1H), 4.55 (1H), 3.83-3.21 (910H), 3.06 (2H), 1.37 (9H) ppm Example 5

Reaction of Boc-HN-EO270-OH with methanesulfonyl chloride and sodium azide to obtain Boc-HN-EO270-N3

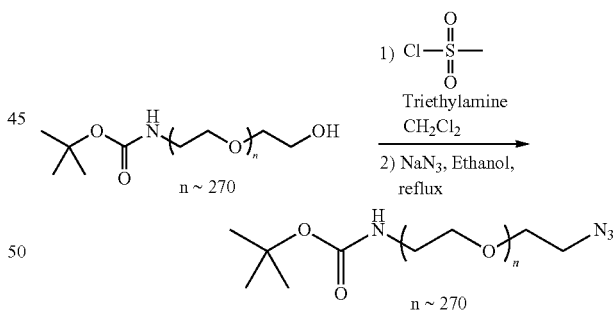

Boc-EO270-OH (539 g, 49.9 mmol) were placed into a 6 L jacketed flask and dried by azeotropic distillation from toluene (3 L). It was then dissolved into 3 L of dry dichloromethane under inert atmosphere. The solution was cooled to 0° C., methanesulfonyl chloride (10.9 mL, 140.8 mmol) was added followed by triethylamine (13.1 mL, 94 mmol). The reaction was allowed to warm to room temperature and proceeded overnight under inert atmosphere. The solution was evaporated to dryness by rotary evaporation and used as-is for the next step.

NaN$_3$ (30.5 g, 470 mmol) and 3 L of ethanol were added to the flask containing the polymer. The solution was heated to 80° C. and allowed to react overnight. It was then evaporated to dryness by rotary evaporation (bath temperature of 55° C.) and dissolved in 2 L of dichloromethane. The latter solution was the filtered through a Büchner funnel fitted with a Whatman paper #1 to remove most of the salts. The solution was concentrated down to ~1 L by rotary evaporation. The product was purified by silica gel flash column chromatography using a 8 in. diameter column with a coarse frit. About 7 L of dry silica gel were used. The column was packed with 1:99 MeOH/CH$_2$Cl$_2$ and the product was loaded and eluted onto the column by pulling vacuum from the bottom of the column. The elution profile was the following: 1:99 MeOH/CH$_2$Cl$_2$ for 1 column volume (CV), 3:97 MeOH/CH$_2$Cl$_2$ for 2 CV and 10:90 MeOH/CH$_2$Cl$_2$ for 6 CV. The different polymer-containing fractions were recombined (~40 L of dichloromethane), concentrated by rotary evaporation and precipitated into a 10-fold excess of diethyl ether. The polymer was recovered by filtration as a white powder and dried overnight in vacuo, giving 446.4 g, 82% yield. $^1$H NMR (d$_6$-DMSO) δ 6.75 (1H), 3.83-3.21 (910H), 3.06 (2H), 1.37 (9H) ppm. M. (MALDI-TOF)=11,554 g/mol. PDI (DMF GPC)=1.04

Example 6

Synthesis of N$_3$-EO270-NH$_3$/DFA Salt from N$_3$-EO270-NH-Boc

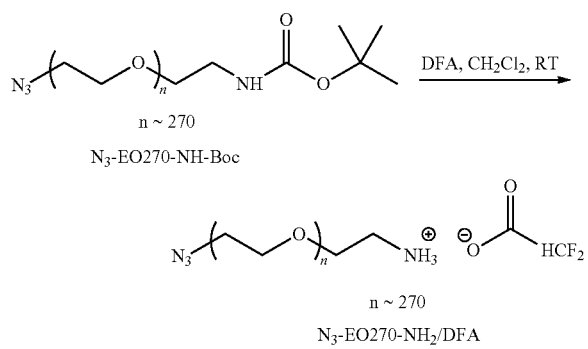

N$_3$-EO270-NH-Boc (313 g, 27.2 mmol) was weighed into a 2 L beaker, 600 mL of DFA, 600 mL of dichloromethane were added. The solution was stirred at room temperature for 32 hr and the polymer was recovered by two consecutive precipitation in ether (2×30 L). The white powder was dried overnight in a vacuum oven. (306 g, 98% yield). $^1$H NMR (d$_6$-DMSO) δ 7.67 (3H), 6.13 (1H), 3.82-3.00 (1060H), 2.99 (2H).

Example 7

Synthesis of D-Leucine NCA

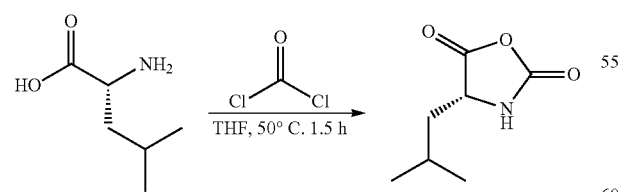

H-DLeu-OH (20.0 g, 152.5 mmol) was suspended in 300 mL of anhydrous THF and heated to 50° C. Phosgene (20% in toluene) (99.3 mL, 198.3 mmol) was added to the amino acid suspension. The amino acid dissolved over the course of approx. 1 hr, forming a clear solution. The solution was concentrated on the rotovap, transferred to a beaker, and hexane was added to precipitate the product. The white solid was isolated by filtration and dissolved in a toluene/THF mixture. The solution was filtered over a bed of Celite to remove any insoluble material. An excess of hexane was added to the filtrate to precipitate the product. The NCA was isolated by filtration and dried in vacuo. 13.8 g (58% yield) of DLeu NCA was isolated as a white, crystalline solid. $^1$H NMR (d$_6$-DMSO) δ 9.13 (1H), 4.44 (1H), 1.74 (1H), 1.55 (2H), 0.90 (6H) ppm.

Example 8

Synthesis of Asp(O$^t$Bu)NCA

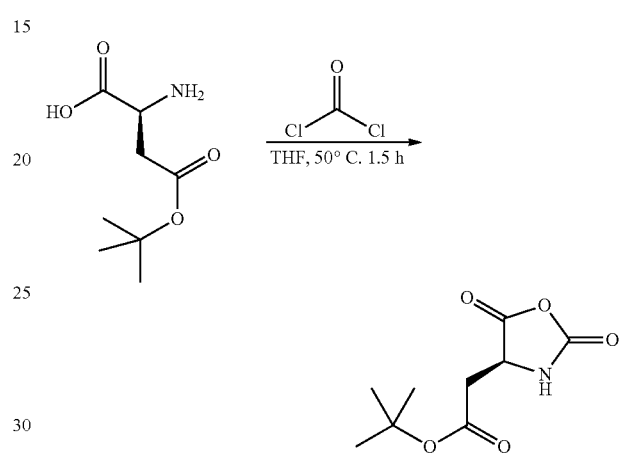

H-Asp(O$^t$Bu)-OH (25.0 g, 132 mmol) was suspended in 500 mL of anhydrous THF and heated to 50° C. Phosgene (20% in toluene) (100 mL, 200 mmol) was added to the amino acid suspension, and the amino acid dissolved over the course of approx. 1 hr, forming a clear solution. The solution was concentrated on by rotary evaporation, transferred to a beaker, and hexane was added to precipitate the product. The white solid was isolated by filtration and dissolved in anhydrous THF. The solution was filtered over a bed of Celite to remove any insoluble material. An excess of hexane was added on the top of the filtrate and the bilayer solution was left in the freezer overnight. The NCA was isolated by filtration and dried in vacuo. 13.1 g (46% yield) of Asp(O$^t$Bu)NCA was isolated as a white, crystalline solid. $^1$H NMR (d$_6$-DMSO) δ 8.99 (1H), 4.61 (1H), 2.93 (1H), 2.69 (1H), 1.38 (9H) ppm.

Example 9

Synthesis of Asp(OBzl)NCA

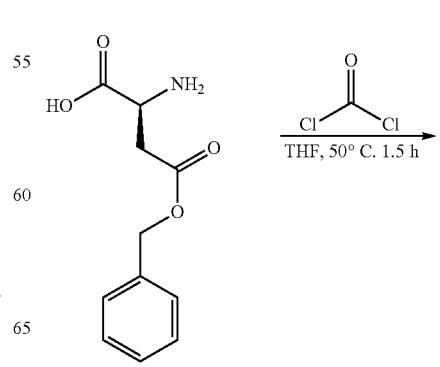

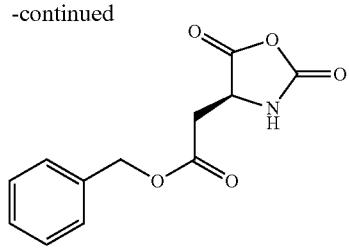

H-Asp(OBzl)-OH (14.0 g, 62.7 mmol) was suspended in 225 mL of anhydrous THF and heated to 50° C. Phosgene (20% in toluene) (40 mL, 80 mmol) was added the amino acid suspension. The amino acid dissolved to give a clear solution over the course of approx. 15 min and was left reacting for another 25 min. The solution was concentrated on the rotovap, the white solid redissolved in a toluene/THF mixture (100 mL/50 mL) and the clear solution rotovaped to dryness. The white solid obtained was redissolved into 100 mL of THF, transferred to a beaker, and dry hexanes were added to precipitate the product. The white solid was isolated by filtration and rinsed twice with dry hexanes (2×200 mL) The NCA was isolated by filtration and dried in vacuo. 14.3 g (65% yield) of Asp(OBzl)NCA was isolated as a white solid. $^1$H NMR (d$_6$-DMSO) δ 9.00 (1H), 7.48-7.25 (5H), 5.13 (2H), 4.69 (1H), 3.09 (1H), 2.92 (1H) ppm Example 10

Synthesis of D-Asp(OBzl)NCA

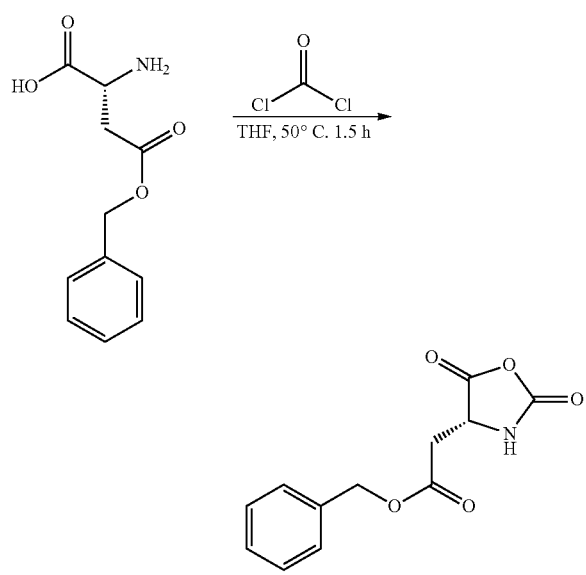

H-D-Asp(OBzl)-OH (30.0 g, 134 mmol) was suspended in 450 mL of anhydrous THF and heated to 50° C. Phosgene (20% in toluene) (100 mL, 100 mmol) was added the amino acid suspension. The amino acid dissolved over the course of approx. 50 min and was left reacting for another 30 min. The solution was concentrated on the rotovap, the white solid redissolved in a toluene/THF mixture (250 mL/50 mL) and the clear solution rotovaped to dryness. The white solid obtained was redissolved into 250 mL of THF, transferred to a beaker, and dry hexanes were added to precipitate the product. The white solid was isolated by filtration and rinsed twice with dry hexanes (2×400 mL) The NCA was isolated by filtration and dried in vacuo. 26.85 g (83.2% yield) of D-Asp (OBzl)NCA was isolated as a white solid. $^1$H NMR (d$_6$-DMSO) δ 9.00 (1H), 7.48-7.25 (5H), 5.13 (2H), 4.69 (1H), 3.09 (1H), 2.92 (1H) ppm Example 11

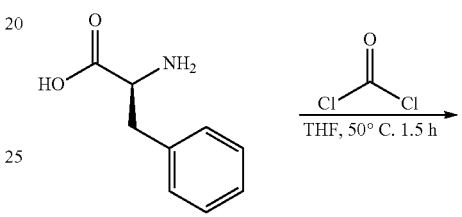

H-L-Phe-OH (20.0 g, 132 mmol) was suspended in 300 mL of anhydrous THF and heated to 50° C. Phosgene (20% in toluene) (90 mL, 182 mmol) was added to the amino acid suspension, and the amino acid dissolved over the course of approx. 1 hr, forming a cloudy solution. The solution was filtered through a paper filter (Whatman #1), concentrated on by rotary evaporation, transferred to a beaker, and hexane was added to precipitate the product. The white solid was isolated by filtration and dissolved in anhydrous THF. The solution was filtered over a bed of Celite to remove any insoluble material. An excess of hexanes were added on the filtrate while stirring with a spatula. The NCA was isolated by filtration and dried in vacuo. 20.0 g (86% yield) of D-PheNCA was isolated as a white, crystalline solid. $^1$H NMR (d$_6$-DMSO) δ 9.09 (1H), 7.40-7.08 (5H), 4.788 (1H), 3.036 (2H) ppm.

Example 12

Synthesis of N$_3$-PEG12K-b-P(Asp(O$^t$Bu)$_{25}$-co-D-Leu$_{50}$-co-Orn(Z)$_{25}$)—Ac

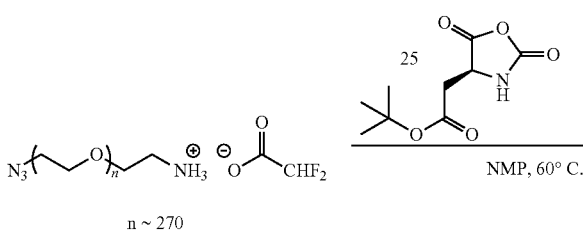

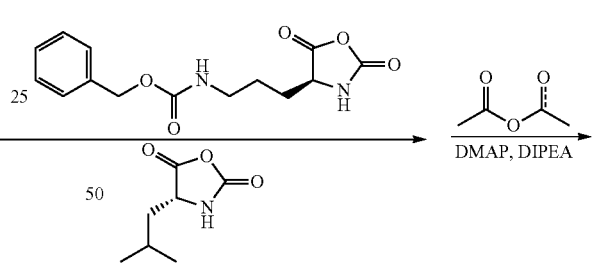

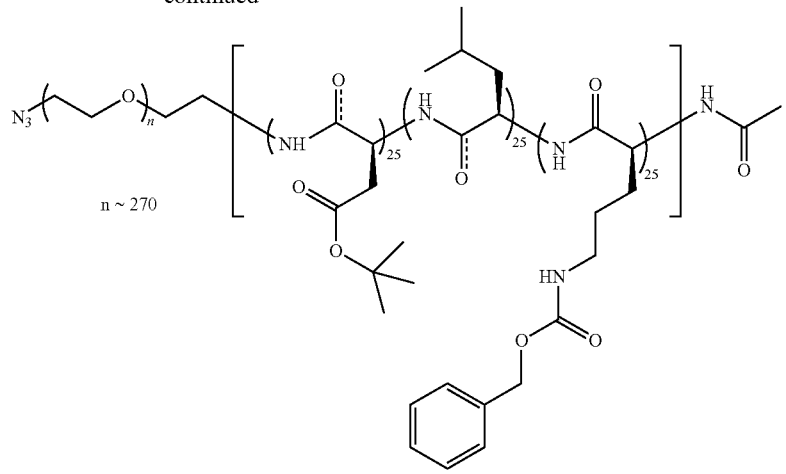

N₃-PEG12k-NH₂/DFA salt, (10.0 g, 0.83 mmol) was weighed into an oven-dried, round-bottom flask, dissolved in toluene, and dried by azeotropic distillation. Excess toluene was removed under vacuum. Asp(O'Bu)NCA (2.15 g, 10 mmol), D-Leu NCA (6.55 g, 41.7 mmol) and Orn(Z)NCA (5.02 g, 17.2 mmol) was added to the flask, the flask was evacuated under reduced pressure, and subsequently backfilled with nitrogen gas. Dry N-methylpyrrolidone (NMP) (130 mL) was introduced by syringe and the solution was heated to 60° C. The reaction mixture was allowed to stir for 5 days at 60° C. under nitrogen gas. The solution was cooled to room temperature and DIPEA (2.0 mL), DMAP (100 mg), and acetic anhydride (2.0 mL) were added. Stirring was continued for 1 hour at room temperature. The polymer was precipitated into diethyl ether (cooled down to −20° C.) and isolated by filtration. The solid was redissolved in dichloromethane and precipitated into diethyl ether (cooled down to −20° C.). The product was isolated by filtration and dried in vacuo to give the block copolymer as an off-white powder. ¹H NMR (d₆-DMSO) δ 8.44-7.58, 7.38-7.08, 5.04-4.89, 4.63-4.38, 4.35-4.14, 3.50, 3.05-2.88, 2.75-2.61, 2.48, 1.75-1.15, 0.95-0.71 ppm Example 13

Synthesis of N₃-PEG5K-b-P(Asp(O'Bu)₅₀-co-D-Leu₂₅-co-Orn(Z)₅₀)—Ac

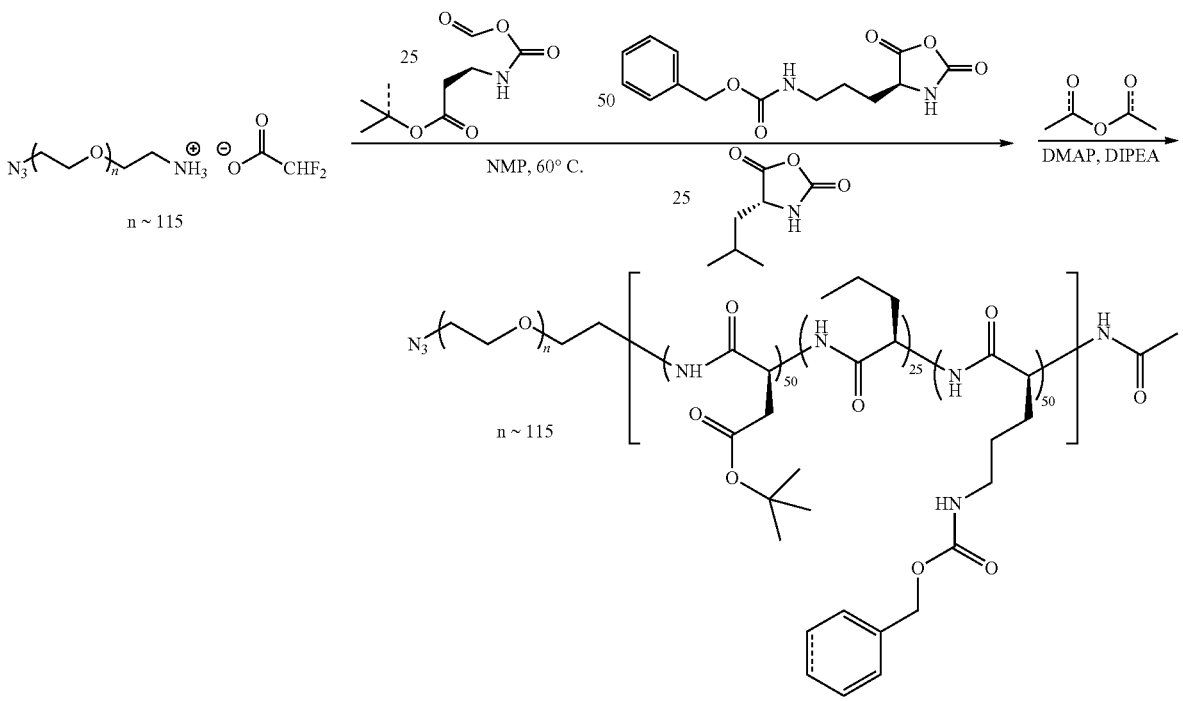

N₃-PEG5K-b-P(Asp(O'Bu)₅₀-co-D-Leu₂₅-co-Orn(Z)₅₀)—Ac was synthesized as described in Example 12 from N₃-PEG-NH₂/DFA salt, 5 kDa (0.5 g, 0.1 mmol), Asp(O'Bu) NCA (1.08 g, 5 mmol), D-Leu NCA (0.39 g, 2.5 mmol), Orn(Z)NCA (1.46 g, 5 mmol) and 23 mL of NMP. The block copolymer was isolated as an off-white powder (1.6 g, 56% yield). ¹H NMR (d₆-DMSO) δ 8.44-7.58, 7.38-7.08, 5.04-4.89, 4.63-4.38, 4.35-4.14, 3.50, 3.05-2.88, 2.75-2.61, 2.48, 1.75-1.15, 0.95-0.71 ppm

Example 14

Synthesis of $N_3$-PEG5K-b-P(Asp(O$^t$Bu)$_{75}$-co-D-Leu$_{25}$-co-Orn(Z)$_{50}$)—Ac

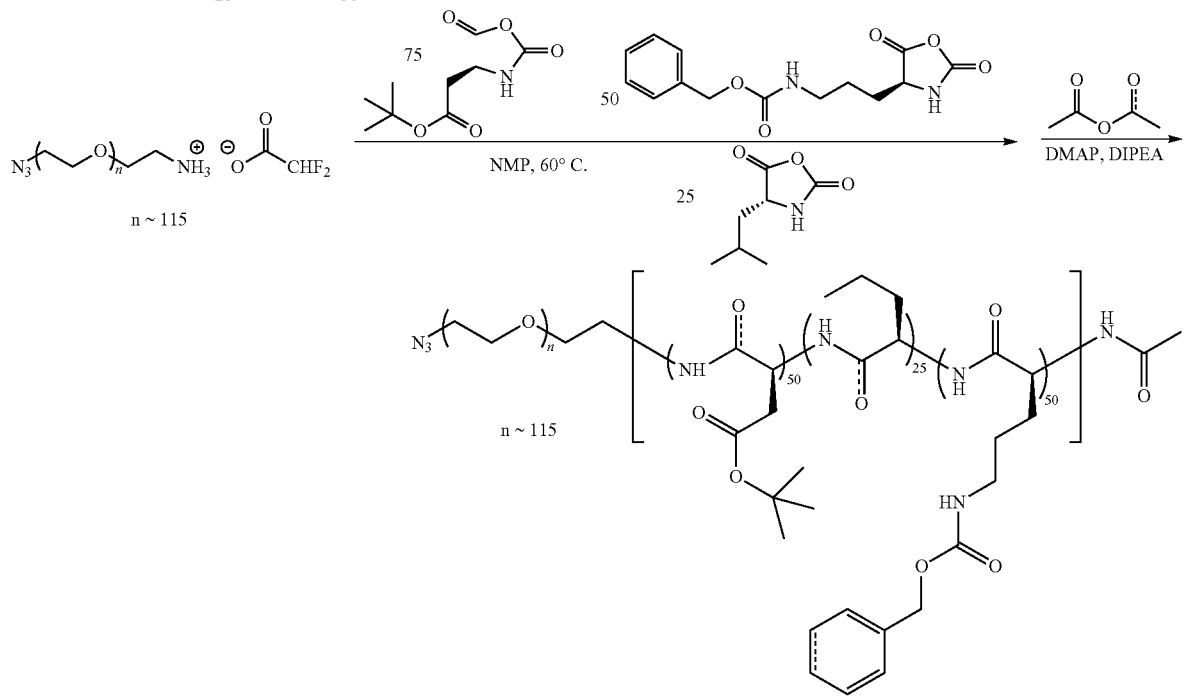

$N_3$-PEG5K-b-P(Asp(O$^t$Bu)$_{75}$-co-D-Leu$_{25}$-co-Orn(Z)$_{50}$)—Ac was synthesized as described in Example 12 from $N_3$-PEG-NH$_2$/DFA salt, 5 kDa (0.5 g, 0.1 mmol), Asp(O$^t$Bu) NCA (1.61 g, 7.5 mmol), D-Leu NCA (0.39 g, 2.5 mmol), Orn(Z)NCA (1.46 g, 5 mmol) and 26 mL of NMP. The block copolymer was isolated as an off-white powder (1.3 g, 39% yield). $^1$H NMR (d$_6$-DMSO) δ 8.44-7.58, 7.38-7.08, 5.04-4.89, 4.63-4.38, 4.35-4.14, 3.50, 3.05-2.88, 2.75-2.61, 2.48, 1.75-1.15, 0.95-0.71 ppm

Example 15

Synthesis of $N_3$-PEG5K-b-P(Asp(O$^t$Bu)$_{100}$-co-D-Leu$_{25}$-co-Orn(Z)$_{50}$)—Ac

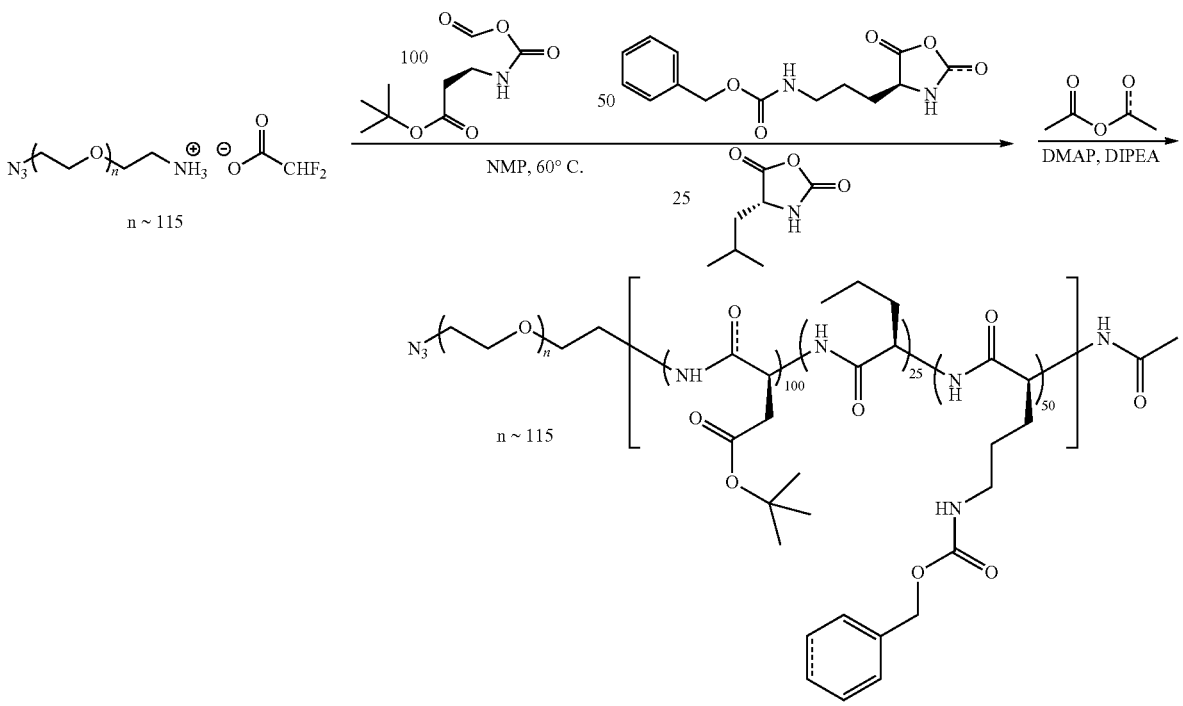

$N_3$-PEG5K-b-P(Asp(O$^t$Bu)100-co-D-Leu$_{25}$-co-Orn(Z)$_{50}$)—Ac was synthesized as described in Example 12 from $N_3$-PEG-NH$_2$/DFA salt, 5 kDa (0.5 g, 0.1 mmol), Asp(O$^t$Bu)NCA (2.15 g, 10 mmol), D-Leu NCA (0.39 g, 2.5 mmol), Orn(Z)NCA (1.46 g, 5 mmol) and 30 mL of NMP. The block copolymer was isolated as an off-white powder (1.9 g, 51% yield). $^1$H NMR (d$_6$-DMSO) δ 8.44-7.58, 7.38-7.08, 5.04-4.89, 4.63-4.38, 4.35-4.14, 3.50, 3.05-2.88, 2.75-2.61, 2.48, 1.75-1.15, 0.95-0.71 ppm

Example 16

Synthesis of $N_3$-PEG5K-b-P(Asp(O$^t$Bu)$_{100}$-co-D-Leu$_{25}$-co-Orn(Z)$_{100}$)—Ac

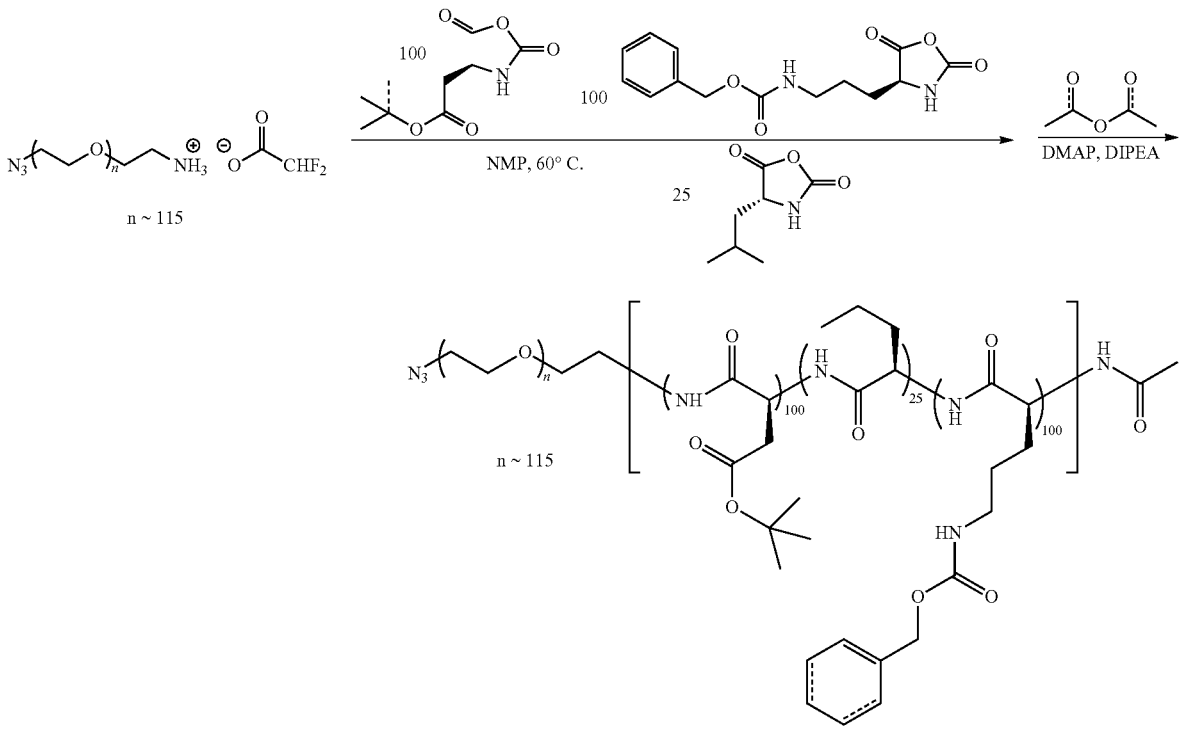

$N_3$-PEG5K-b-P(Asp(O$^t$Bu)100-co-D-Leu$_{25}$-co-Orn(Z)$_{100}$)—Ac was synthesized as described in Example 12 from $N_3$-PEG-NH$_2$/DFA salt, 5 kDa (0.5 g, 0.1 mmol), Asp(O$^t$Bu)NCA (2.15 g, 10 mmol), D-Leu NCA (0.39 g, 2.5 mmol), Orn(Z)NCA (2.92 g, 10 mmol) and 40 mL of NMP. The block copolymer was isolated as an off-white powder. $^1$H NMR (d$_6$-DMSO) δ 8.44-7.58, 7.38-7.08, 5.04-4.89, 4.63-4.38, 4.35-4.14, 3.50, 3.05-2.88, 2.75-2.61, 2.48, 1.75-1.15, 0.95-0.71 ppm

Example 17

Synthesis of $N_3$-PEG5K-b-P(Asp(O$^t$Bu)$_{75}$-co-D-Leu$_{25}$-co-Orn(Z)$_{100}$)—Ac

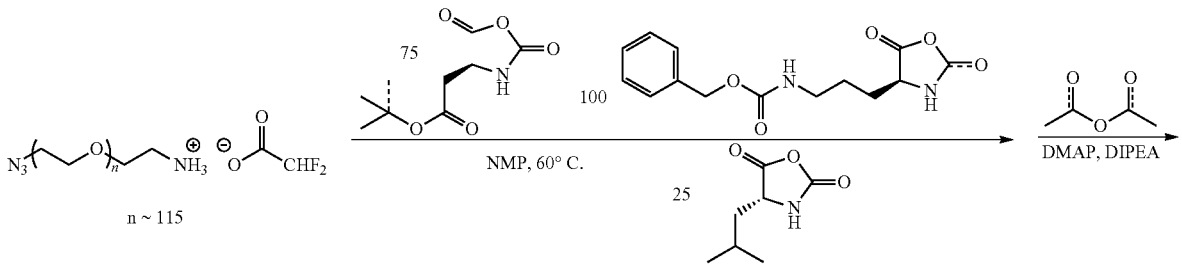

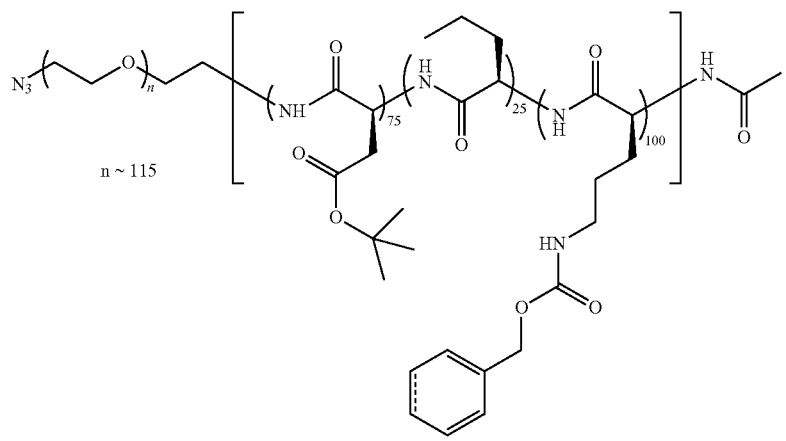

$N_3$-PEG5K-b-P(Asp(O$^t$Bu)$_{75}$-co-D-Leu$_{25}$-co-Orn(Z)$_{100}$)—Ac was synthesized as described in Example 12 from $N_3$-PEG-NH$_2$/DFA salt, 5 kDa (0.5 g, 0.1 mmol), Asp(O$^t$Bu) NCA (1.61 g, 7.5 mmol), D-Leu NCA (0.39 g, 2.5 mmol), Orn(Z)NCA (2.92 g, 10 mmol) and 36 mL of NMP. The block copolymer was isolated as an off-white powder. $^1$H NMR (d$_6$-DMSO) δ 8.44-7.58, 7.38-7.08, 5.04-4.89, 4.63-4.38, 4.35-4.14, 3.50, 3.05-2.88, 2.75-2.61, 2.48, 1.75-1.15, 0.95-0.71 ppm $N_3$-PEG5K-b-P(Asp(O$^t$Bu)$_{100}$-co-D-Leu$_{50}$-co-Orn(Z)$_{50}$)—Ac was synthesized as described in Example 12 from $N_3$-PEG-NH$_2$/DFA salt, 5 kDa (0.5 g, 0.1 mmol), Asp(O$^t$Bu) NCA (2.15 g, 10 mmol), D-Leu NCA (0.79 g, 5 mmol), Orn(Z)NCA (1.46 g, 5 mmol) and 33 mL of NMP. The block copolymer was isolated as an off-white powder (2.52 g, 63% yield). $^1$H NMR (d$_6$-DMSO) δ 8.44-7.58, 7.38-7.08, 5.04-4.89, 4.63-4.38, 4.35-4.14, 3.50, 3.05-2.88, 2.75-2.61, 2.48, 1.75-1.15, 0.95-0.71 ppm Example 18

Synthesis of $N_3$-PEG5K-b-P(Asp(O$^t$Bu)$_{100}$-co-D-Leu$_{50}$-co-Orn(Z)$_{50}$)—Ac

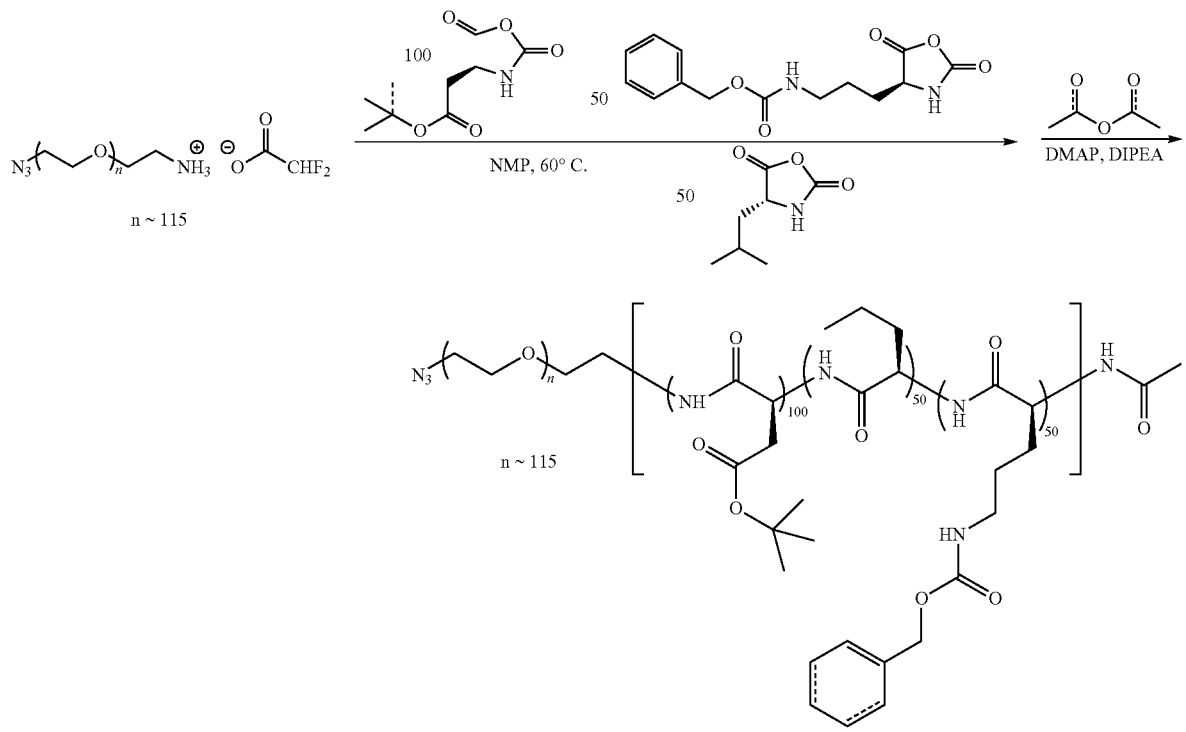

Example 19

Synthesis of N₃-PEG5K-b-P(Asp(O$^t$Bu)₅₀-b-P(D-Leu₅₀-co-Orn(Z)₅₀)—Ac

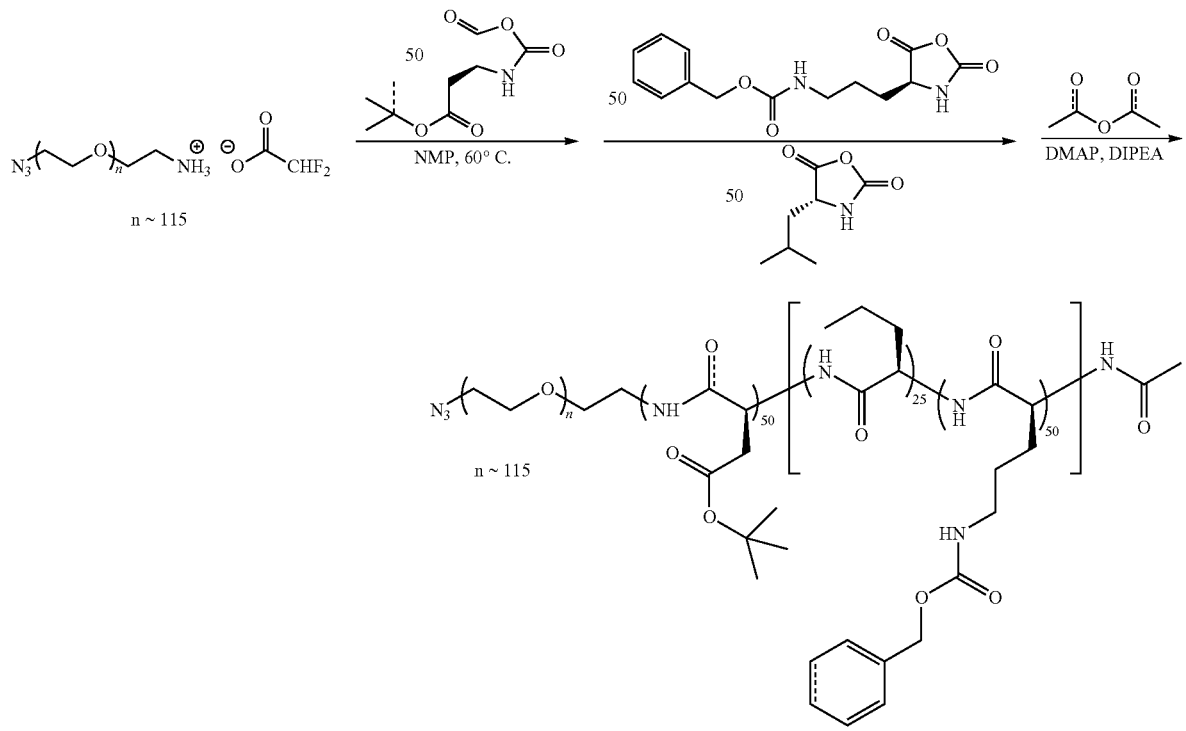

N₃-PEG5 k-NH₂/DFA salt, (0.5 g, 0.1 mmol) was weighed into an oven-dried, round-bottom flask, dissolved in toluene, and dried by azeotropic distillation. Excess toluene was removed under vacuum. Asp(O$^t$Bu)NCA (1.08 g, 5 mmol) was added to the flask, the flask was evacuated under reduced pressure, and subsequently backfilled with nitrogen gas (repeated twice). Dry N-methylpyrrolidone (NMP) (10.5 mL) was introduced by syringe and the solution was heated to 60° C. The reaction mixture was allowed to stir for 2 days at 60° C. under nitrogen gas. In an oven-dried 2-neck round-bottom flask, D-Leu NCA (0.79 g, 5 mmol) and Orn(Z)NCA (1.46 g, 5 mmol) were combined, 3 vacuum/N2 cycles were applied and the white powder was dissolved in 15 ml of dry NMP under nitrogen gas. This solution was then transferred to the polymerization by syringe and allowed to stir for an additional 4 days 15 h at 60° C. The solution was cooled to room temperature and DIPEA (1.0 mL), DMAP (100 mg), and acetic anhydride (1.0 mL) were added. Stirring was continued for 1 hour at room temperature. The polymer was precipitated into diethyl ether and isolated by filtration. The solid was redissolved in dichloromethane and precipitated into diethyl ether. The product was isolated by filtration and dried in vacuo to give 2.39 g (75% yield) of the block copolymer as an off-white powder. ¹H NMR (d₆-DMSO) δ 8.44-7.58, 7.38-7.08, 5.04-4.89, 4.63-4.38, 4.35-4.14, 3.50, 3.05-2.88, 2.75-2.61, 2.48, 1.75-1.15, 0.95-0.71 ppm

Example 20

Synthesis of N₃-PEG5K-b-P(Asp(O$^t$Bu)₇₅-b-P(D-Leu₅₀-co-Orn(Z)₅₀)—Ac

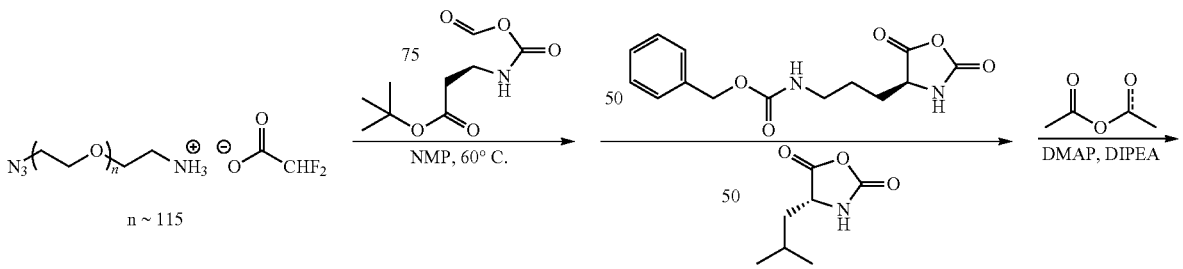

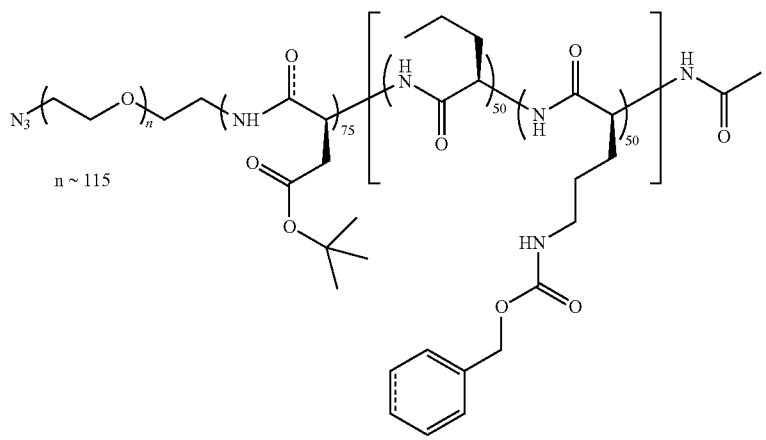

N$_3$-PEG5K-b-P(Asp(O$^t$Bu))$_{75}$-b-P(D-Leu$_{50}$-co-Orn(Z)$_{50}$)—Ac was synthesized as described in Example 19 from N$_3$-PEG-NH$_2$/DFA salt, 5 kDa (0.5 g, 0.1 mmol), Asp(O$^t$Bu) NCA (1.61 g, 7.5 mmol), D-Leu NCA (0.79 g, 5 mmol), Orn(Z)NCA (1.46 g, 5 mmol) and 36 mL of NMP (21 mL of NMP for the second block and 15 mL for the third block). The block copolymer was isolated as an off-white powder (2.7 g, 75% yield). $^1$H NMR (d$_6$-DMSO) δ 8.44-7.58, 7.38-7.08, 5.04-4.89, 4.63-4.38, 4.35-4.14, 3.50, 3.05-2.88, 2.75-2.61, 2.48, 1.75-1.15, 0.95-0.71 ppm Example 21

Synthesis of N$_3$-PEG5K-b-P(Asp(O$^t$Bu))$_{100}$-b-P(D-Leu$_{50}$-co-Orn(Z)$_{50}$)—Ac N$_3$-PEG5K-b-P(Asp(O$^t$Bu))$_{100}$-b-P(D-Leu$_{50}$-co-Orn(Z)$_{50}$)—Ac was synthesized as described in Example 19 from N$_3$-PEG-NH$_2$/DFA salt, 5 kDa (0.5 g, 0.1 mmol), Asp(O$^t$Bu) NCA (2.15 g, 10 mmol), D-Leu NCA (0.79 g, 5 mmol), Orn(Z)NCA (1.46 g, 5 mmol) and 41 mL of NMP (26 mL of NMP for the second block and 15 mL for the third block). The block copolymer was isolated as an off-white powder (1.86 g, 46% yield). $^1$H NMR (d$_6$-DMSO) δ 8.44-7.58, 7.38-7.08, 5.04-4.89, 4.63-4.38, 4.35-4.14, 3.50, 3.05-2.88, 2.75-2.61, 2.48, 1.75-1.15, 0.95-0.71 ppm

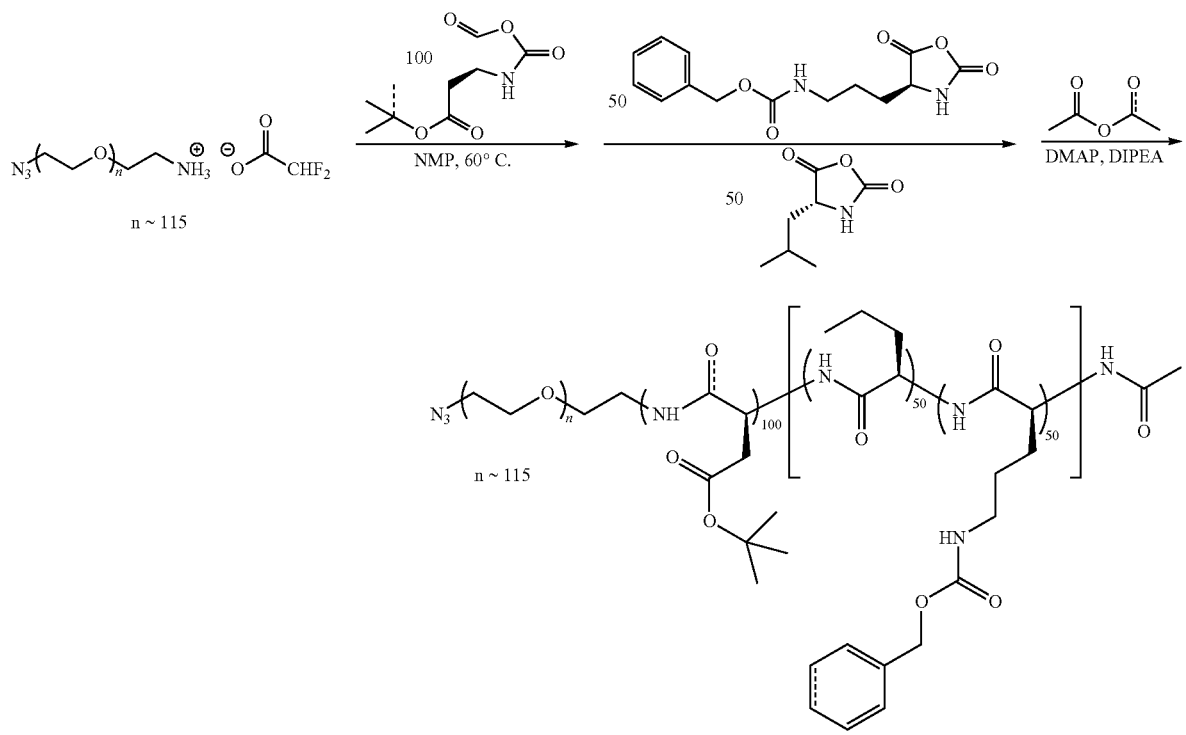

Example 22

Synthesis of N$_3$-PEG5K-b-P(Asp(OBzl)$_{50}$)—Ac

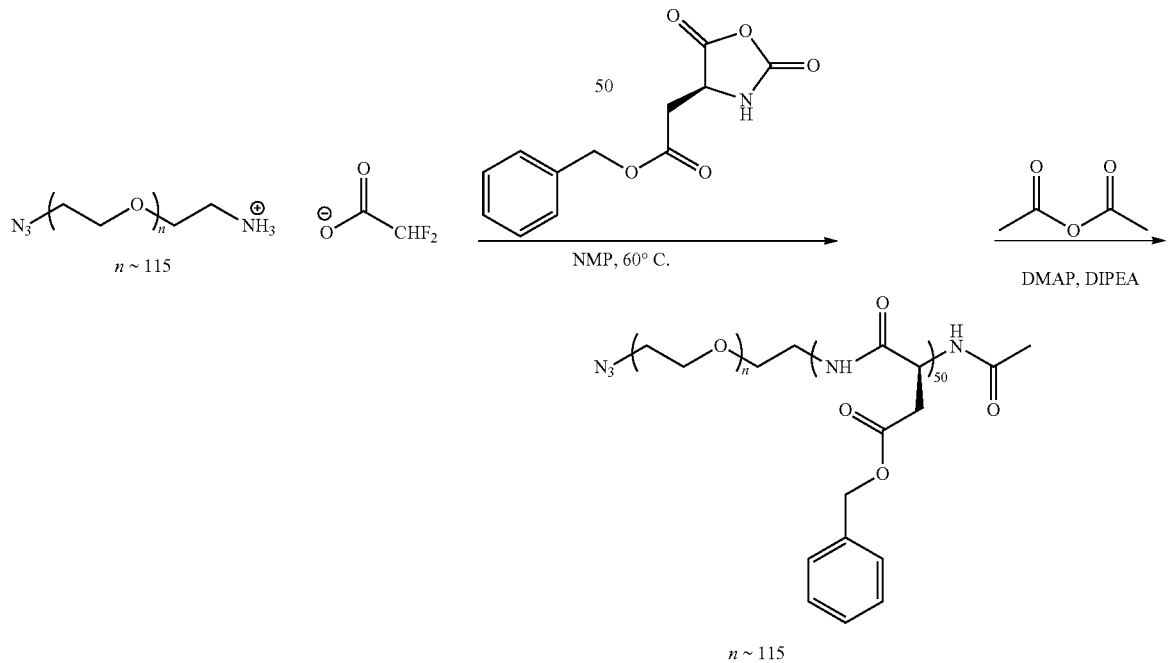

N$_3$-PEG5 k-NH$_2$/DFA salt, (1 g, 0.2 mmol) was weighed into an oven-dried, round-bottom flask, dissolved in toluene, and dried by azeotropic distillation. Excess toluene was removed under vacuum. Asp(O$^t$Bu)NCA (2.49 g, 10 mmol) was added to the flask, the flask was evacuated under reduced pressure, and subsequently backfilled with nitrogen gas (repeated twice). Dry N-methylpyrrolidone (NMP) (17.5 mL) was introduced by syringe and the solution was heated to 60° C. The reaction mixture was allowed to stir for 2 days at 60° C. under nitrogen gas. The solution was cooled to room temperature and DIPEA (1.0 mL), DMAP (100 mg), and acetic anhydride (1.0 mL) were added. Stirring was continued for 1 hour at room temperature. The polymer was then placed in a 3500 g/mol molecular weight cut-off dialysis bag, dialyzed three times against 0.1 N methanol, three times against deionized water and freeze-dried. A white solid was obtained (2.03 g, 66% yield). $^1$H NMR (d$_6$-DMSO) δ 8.54-8.09, 7.44-7.17, 5.23-4.88, 4.63-4.43, 3.63, 3.25, 2.89-2.69, 2.67-2.54 ppm.

Example 23

Synthesis of N$_3$-PEG5K-b-P(Asp(OBzl)$_{75}$)—Ac

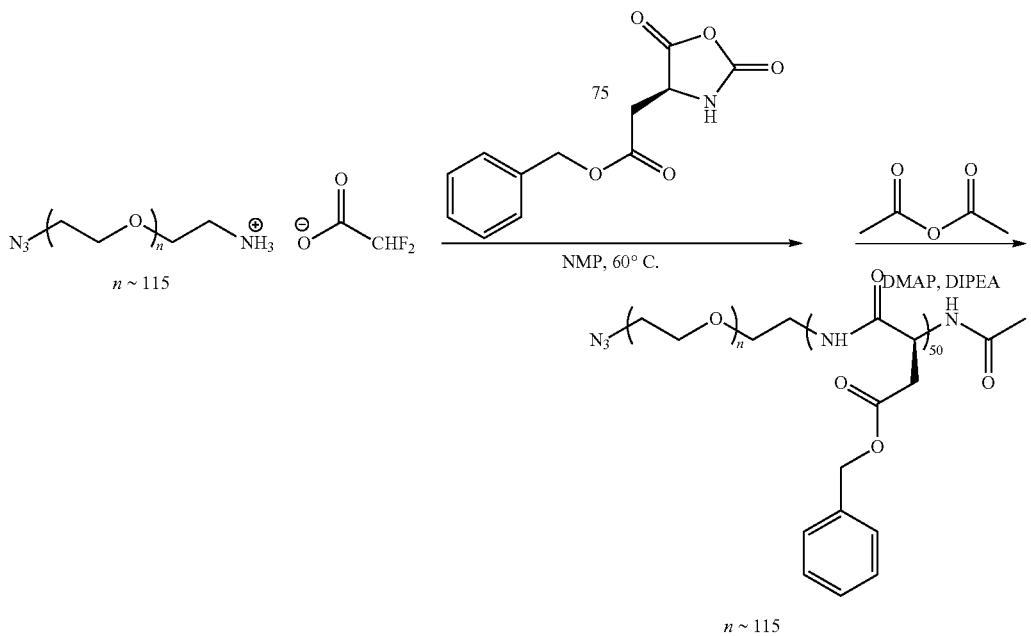

N₃-PEG5K-b-P(Asp(OBzl)₇₅)—Ac was synthesized as described in Example 22 from N₃-PEG-NH₂/DFA salt, 5 kDa (1 g, 0.2 mmol), Asp(OᵗBu)NCA (3.74 g, 15 mmol) and 48 mL of NMP. The block copolymer was isolated as an off-white powder. ¹H NMR (d₆-DMSO) δ 8.54-8.09, 7.44-7.17, 5.23-4.88, 4.63-4.43, 3.63, 3.25, 2.89-2.69, 2.67-2.54 ppm.

Example 24

Synthesis of N₃-PEG5K-b-P(Asp(OBzl)₁₀₀)—Ac

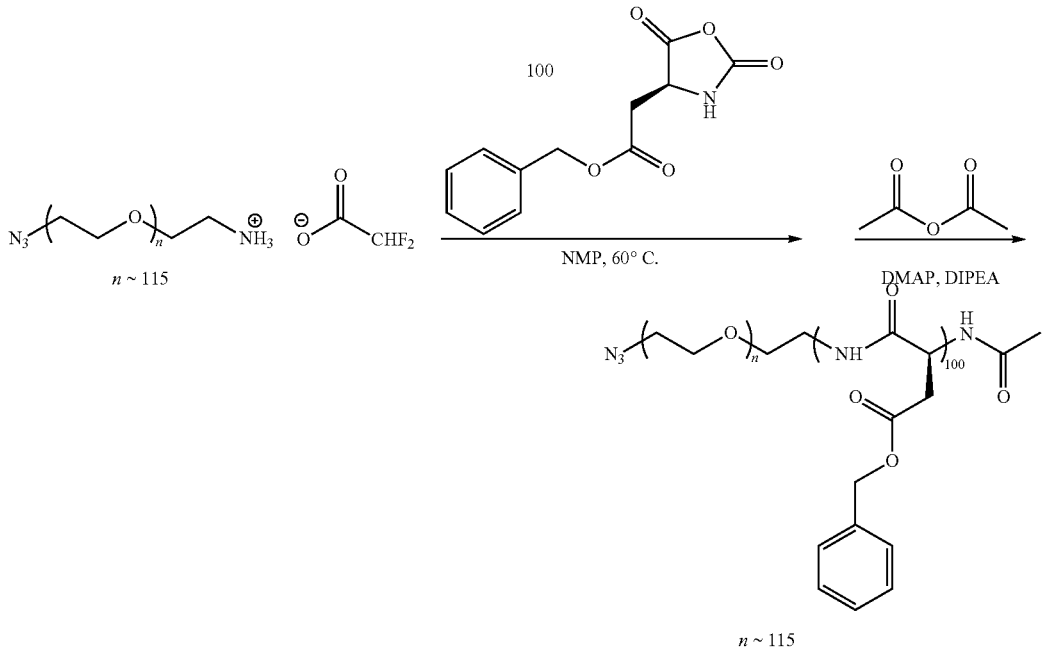

N₃-PEG5K-b-P(Asp(OBzl)₁₀₀)—Ac was synthesized as described in Example 22 from N₃-PEG-NH₂/DFA salt, 5 kDa (1 g, 0.2 mmol), Asp(OᵗBu)NCA (4.98 g, 20 mmol) and 60 mL of NMP. The block copolymer was isolated as an off-white powder. ¹H NMR (d₆-DMSO) δ 8.54-8.09, 7.44-7.17, 5.23-4.88, 4.63-4.43, 3.63, 3.25, 2.89-2.69, 2.67-2.54 ppm.

Example 25

Synthesis of N₃-PEG5K-b-P(Asp(OBzl)₂₅-co-D-Asp(OBzl)₂₅)—Ac

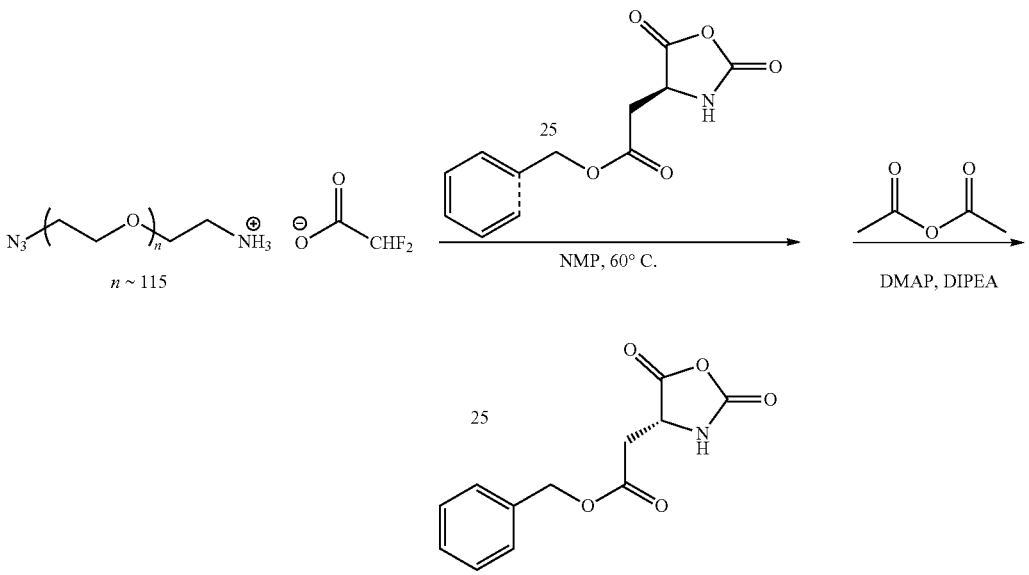

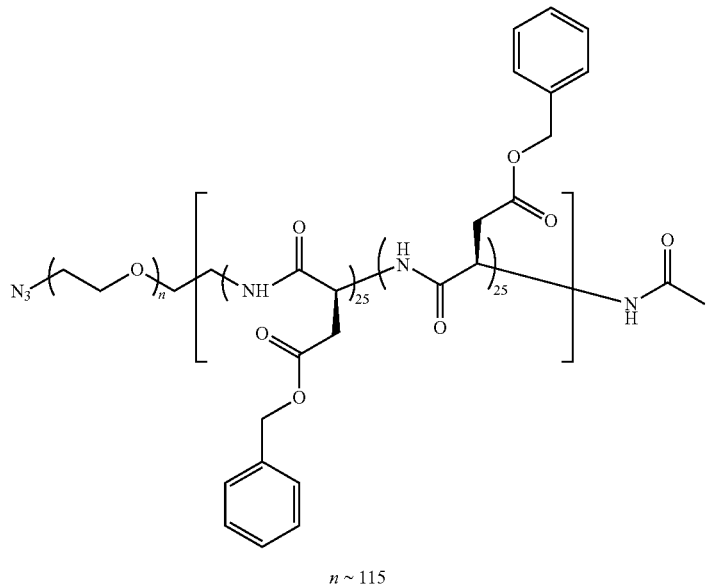
$n \sim 115$
$N_3$-PEG5K-b-P(Asp(OBzl))$_{25}$-co-D-Asp(OBzl)$_{25}$)—Ac was synthesized as described in Example 22 from $N_3$-PEG-NH$_2$/DFA salt, 5 kDa (1 g, 0.2 mmol), Asp(O$^t$Bu)NCA (1.25 g, 5 mmol), D-Asp(O$^t$Bu)NCA (1.25 g, 5 mmol) and 18 mL of NMP. The block copolymer was isolated as an off-white powder. $^1$H NMR (d$_6$-DMSO) δ 8.54-8.09, 7.44-7.17, 5.23-4.88, 4.63-4.43, 3.63, 3.25, 2.89-2.69, 2.67-2.54 ppm.
Example 26
Synthesis of $N_3$-PEG5K-b-P(Asp(OBzl))$_{37}$-co-D-Asp(OBzl)$_{37}$)—Ac
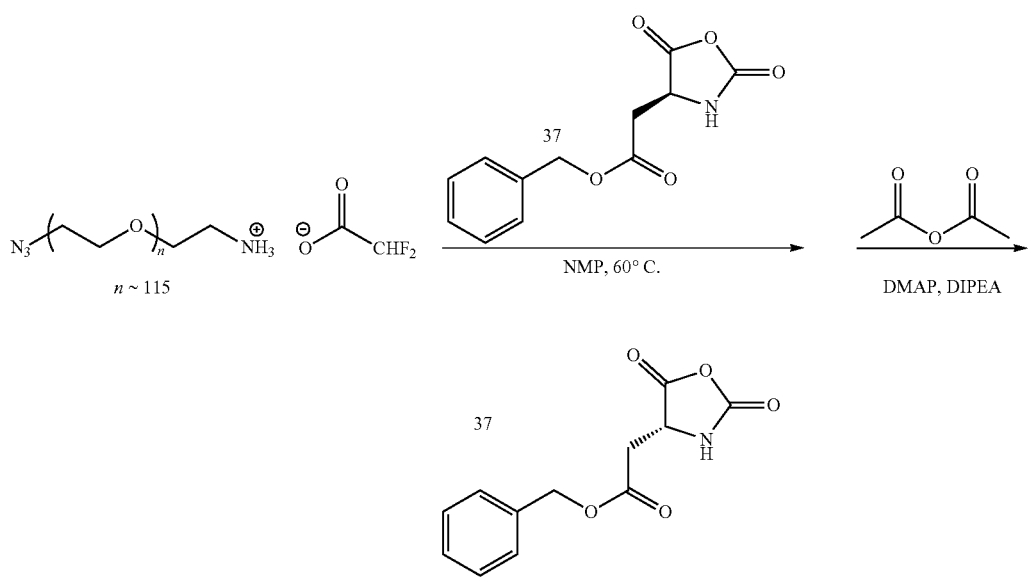

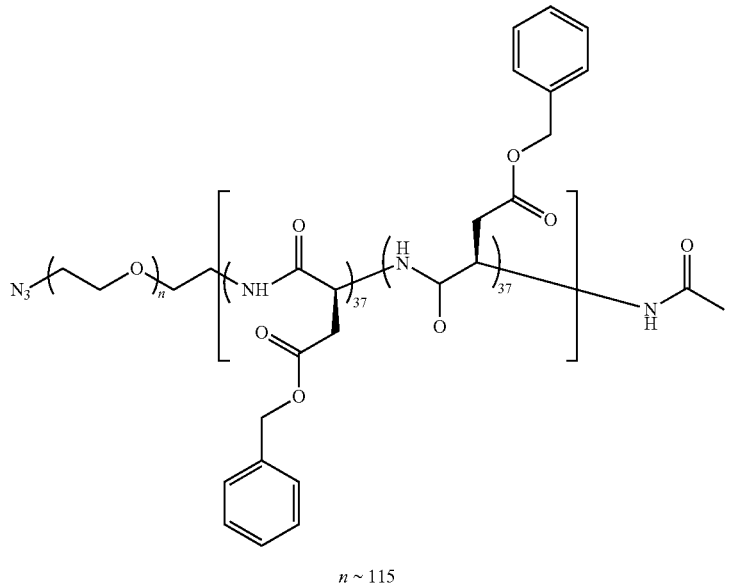
N$_3$-PEG5K-b-P(Asp(OBzl)$_{37}$-co-D-Asp(OBzl)$_{37}$)—Ac was synthesized as described in Example 22 from N$_3$-PEG-NH$_2$/DFA salt, 5 kDa (1 g, 0.2 mmol), Asp(O$^t$Bu)NCA (1.84 g, 7.4 mmol), D-Asp(O$^t$Bu)NCA (1.84 g, 7.4 mmol) and 47 mL of NMP. The block copolymer was isolated as an off-white powder. $^1$H NMR (d$_6$-DMSO) δ 8.54-8.09, 7.44-7.17, 5.23-4.88, 4.63-4.43, 3.63, 3.25, 2.89-2.69, 2.67-2.54 ppm.
Example 27
Synthesis of N$_3$-PEG5K-b-P(Asp(OBzl)$_{50}$-co-D-Asp(OBzl)$_{50}$)—Ac
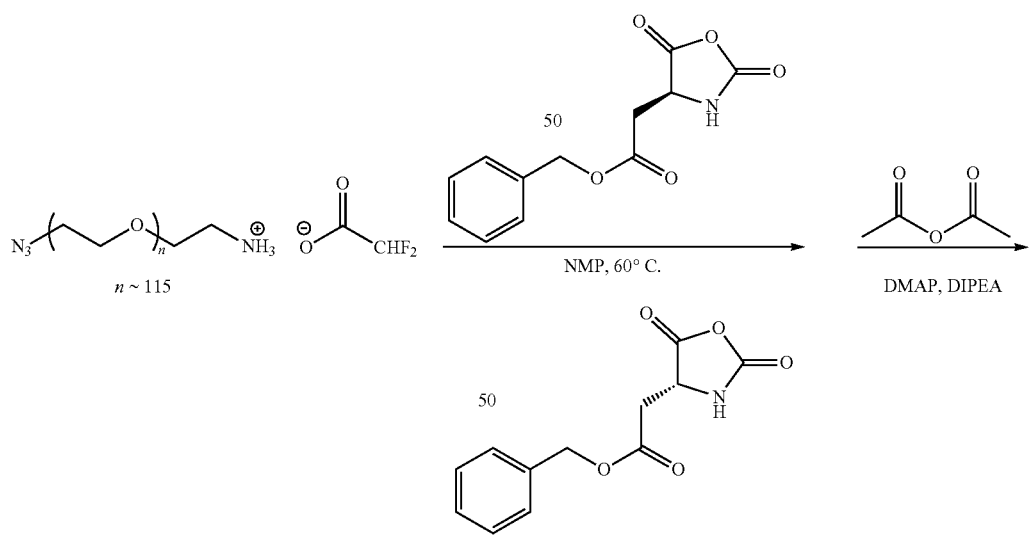

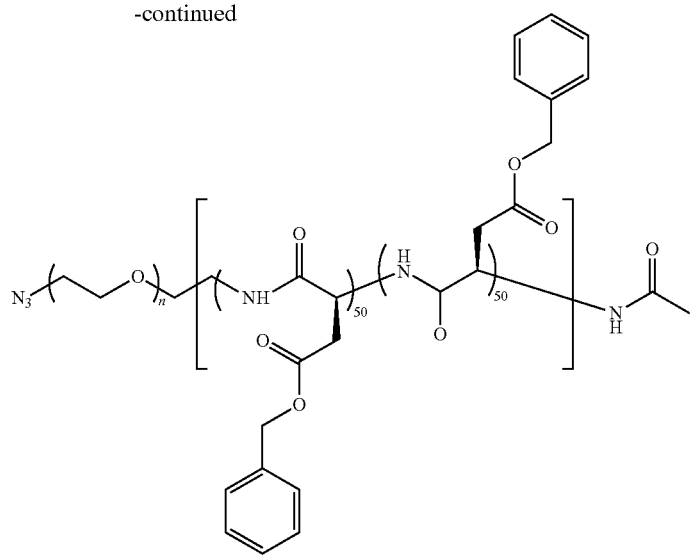
N₃-PEG5K-b-P(Asp(OBzl)₅₀-co-D-Asp(OBzl)₅₀)—Ac was synthesized as described in Example 22 from N₃-PEG-NH₂/DFA salt, 5 kDa (1 g, 0.2 mmol), Asp(O'Bu)NCA (2.49 g, 10 mmol), D-Asp(O'Bu)NCA (2.49 g, 10 mmol) and 60 mL of NMP. The block copolymer was isolated as an off-white powder. ¹H NMR (d₆-DMSO) δ 8.54-8.09, 7.44-7.17, 5.23-4.88, 4.63-4.43, 3.63, 3.25, 2.89-2.69, 2.67-2.54 ppm.
Example 28
Synthesis of N₃-PEG5K-b-P(Orn(Z)₅₀)—Ac
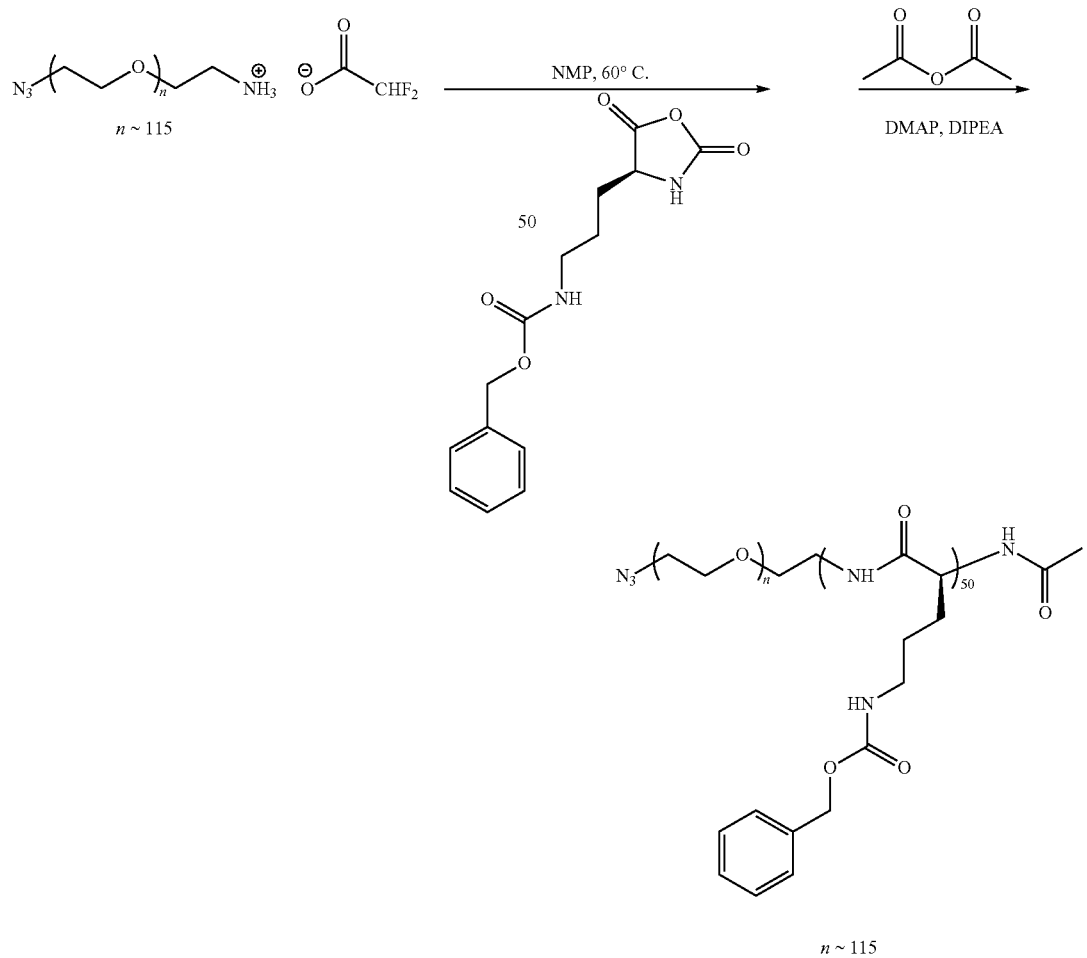

N$_3$-PEG12k-NH$_2$/DFA salt, (1 g, 0.2 mmol) was weighed into an oven-dried, round-bottom flask, dissolved in toluene, and dried by azeotropic distillation. Excess toluene was removed under vacuum. Orn(Z)NCA (2.92 g, 10 mmol) was added to the flask, the flask was evacuated under reduced pressure, and subsequently backfilled with nitrogen gas. Dry N-methylpyrrolidone (NMP) (20 mL) was introduced by syringe and the solution was heated to 60° C. The reaction mixture was allowed to stir for 4 days at 60° C. under nitrogen gas. The solution was cooled to room temperature and DIPEA (2.0 mL), DMAP (100 mg), and acetic anhydride (2.0 mL) were added. Stirring was continued for 1 hour at room temperature. The polymer was precipitated into diethyl ether (cooled down to −20° C.) and isolated by filtration. The product was isolated by filtration and dried in vacuo to give the block copolymer as an off-white powder.

Example 29

Synthesis of N$_3$-PEG5K-b-P(Orn(Z))$_{100}$—Ac

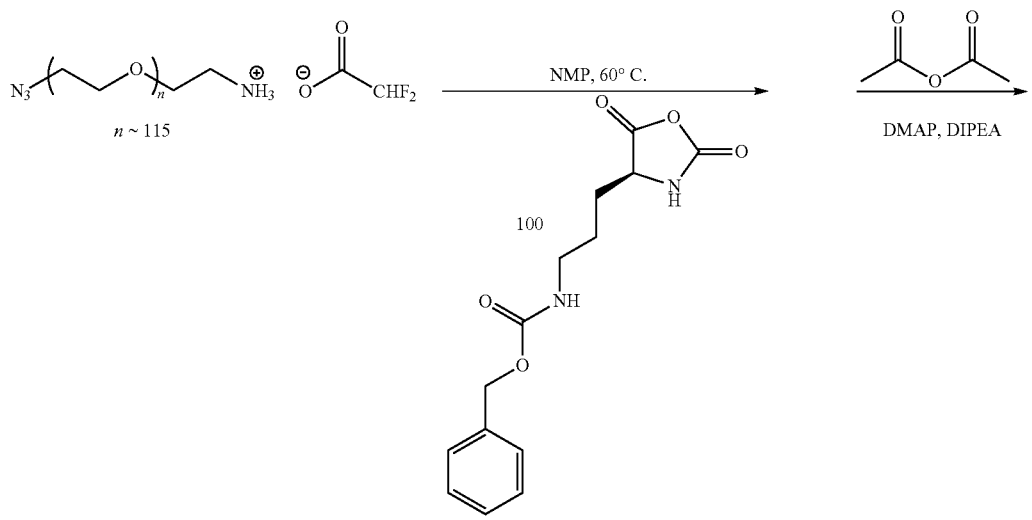

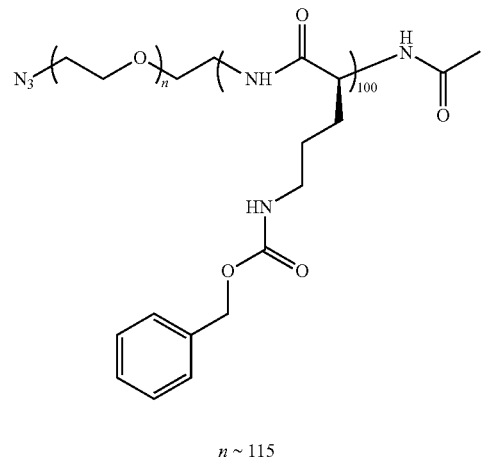

N₃-PEG5K-b-P(Orn(Z)₁₀₀)—Ac was synthesized as described in Example 28 from N₃-PEG-NH₂/DFA salt, 5 kDa (1 g, 0.2 mmol), Orn(Z))NCA (5.85 g, 20 mmol) and 68 mL of NMP. The block copolymer was isolated as an off-white powder.

Example 30

Synthesis of N₃-PEG5K-b-P(Orn₅₀)—Ac

N₃-PEG5K-b-P(Orn(Z)₁₀₀)—Ac (1.5 g, 86 μmol) was dissolved in 37 mL of a 0.5 M solution of pentamethylbenzene (PMB) in trifluoroacetic acid (TFA). The reaction was allowed to stir for 3 hours at room temperature with a white precipitate forming after approximately 1 hour. The solution was placed into a 2000 g/mol molecular weight cut-off dialysis bag and dialyzed twice against 0.1 N MeOH, twice against deionized water and freeze-dried to yield a white powder (0.50 g, 48% yield).

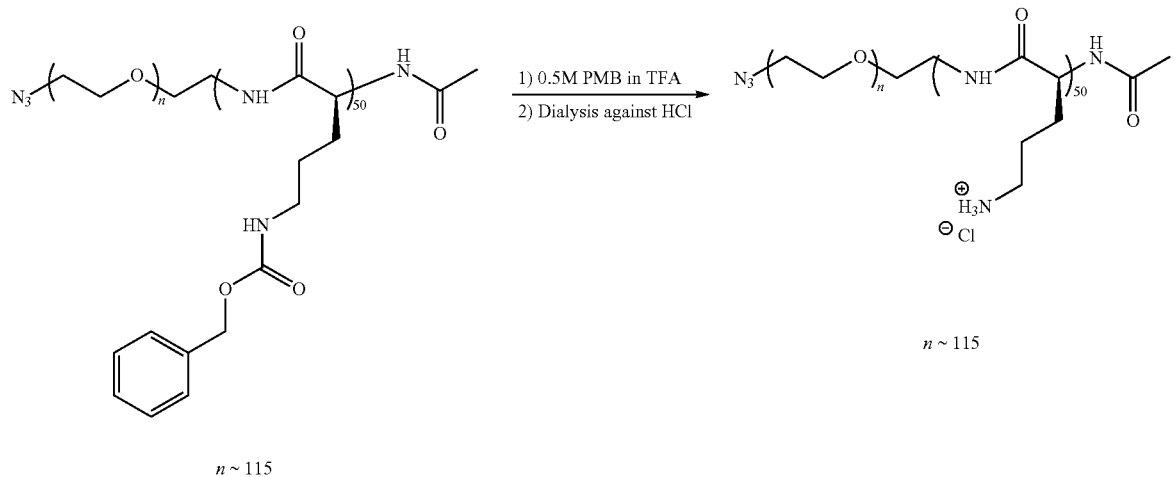

N₃-PEG5K-b-P(Orn(Z)₅₀)—Ac (1.5 g, 86 μmol) was dissolved in 37 mL of a 0.5 M solution of pentamethylbenzene (PMB) in trifluoroacetic acid (TFA). The reaction was allowed to stir for 3 hours at room temperature with a white precipitate forming after approximately 1 hour. The solution was placed into a 2000 g/mol molecular weight cut-off dialysis bag and dialyzed twice against 0.1 N MeOH, twice against deionized water and freeze-dried to yield a white powder (0.49 g, 45% yield).

Example 31

Synthesis of N₃-PEG5K-b-P(Orn₁₀₀)—Ac

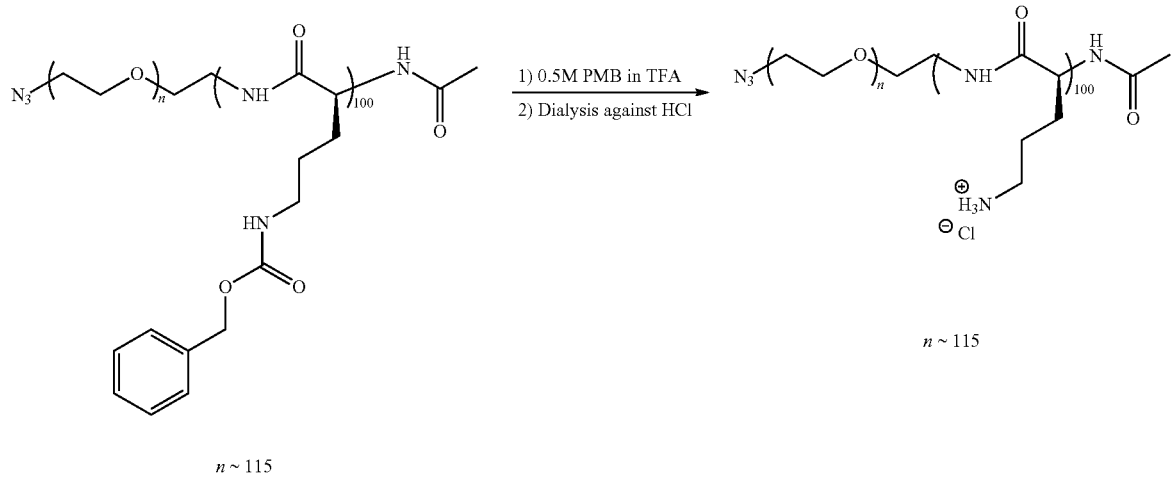

Example 32
Synthesis of N$_3$-PEG5K-b-P(Asp(OBzl))$_{25}$-co-Asp(O$^t$Bu)$_{25}$)—Ac
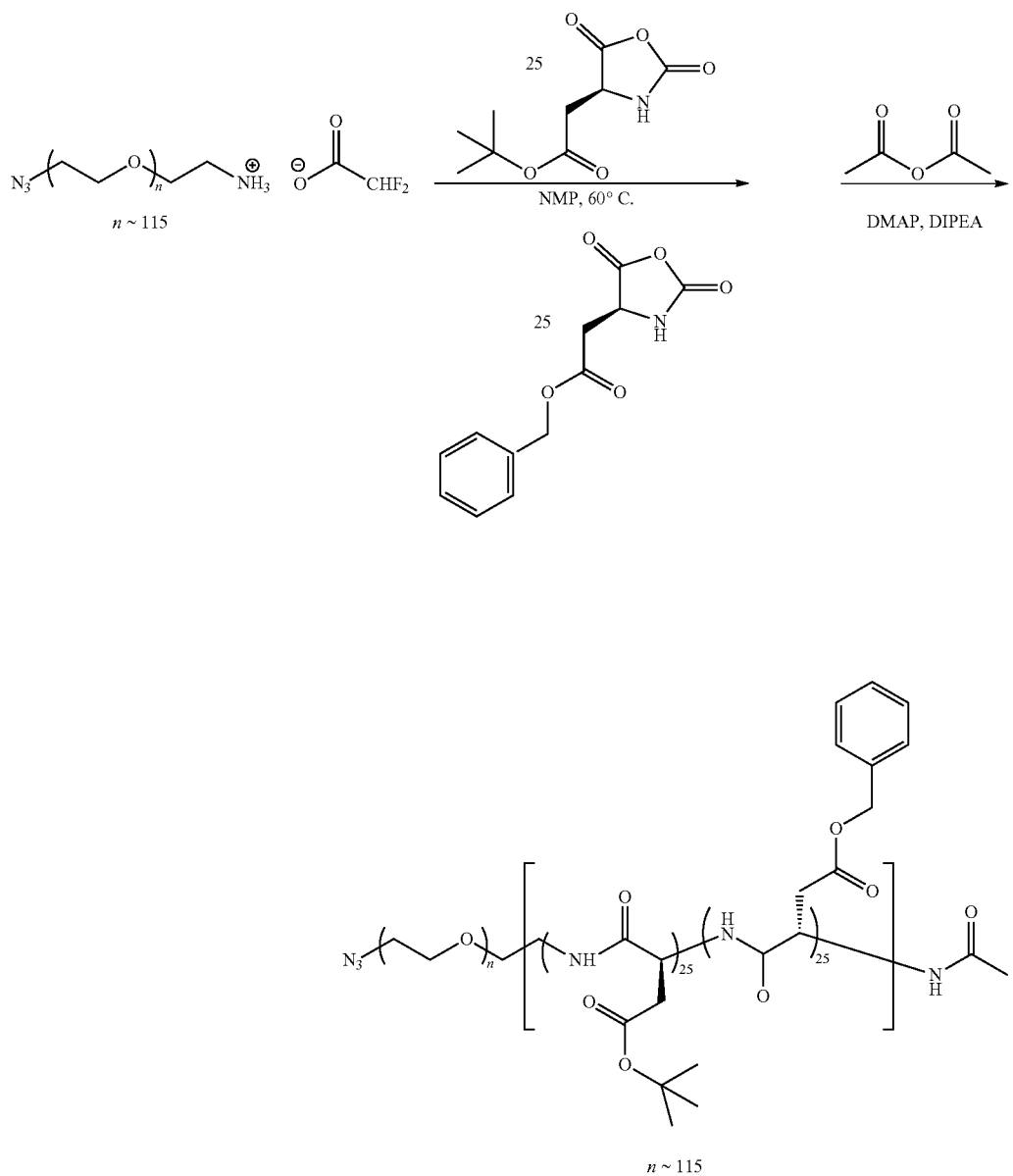
N$_3$-PEG5K-b-P(Asp(OBzl)$_{25}$-co-D-Asp($^t$Bu)$_{25}$)—Ac was synthesized as described in Example 22 from N$_3$-PEG-NH$_2$/DFA salt, 5 kDa (1 g, 0.2 mmol), Asp(O$^t$Bu)NCA (1.25 g, 5 mmol), D-Asp(O$^t$Bu)NCA (1.08 g, 5 mmol) and 17 mL of NMP. The block copolymer was isolated as an off-white powder (1.81 g, 63% yield). $^1$H NMR (d$_6$-DMSO) δ 8.50-7.67, 7.48-7.14, 5.18-4.91, 4.73-4.45, 3.71-3.38, 2.90-2.22, 1.52-1.12 ppm

Example 33
Synthesis of $N_3$-PEG5K-b-P(Asp(OBzl)$_{50}$-co-Asp(O$^t$Bu)$_{50}$)—Ac
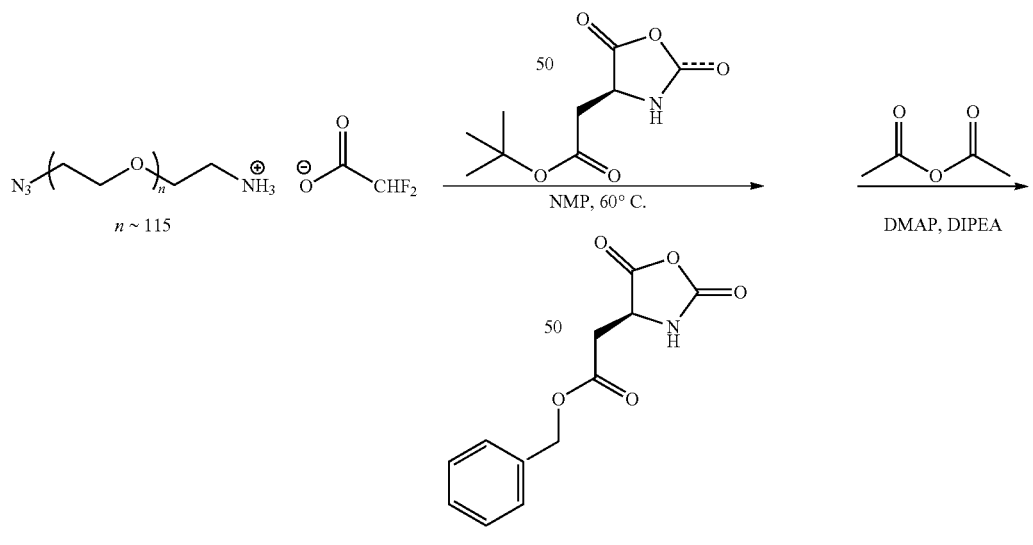
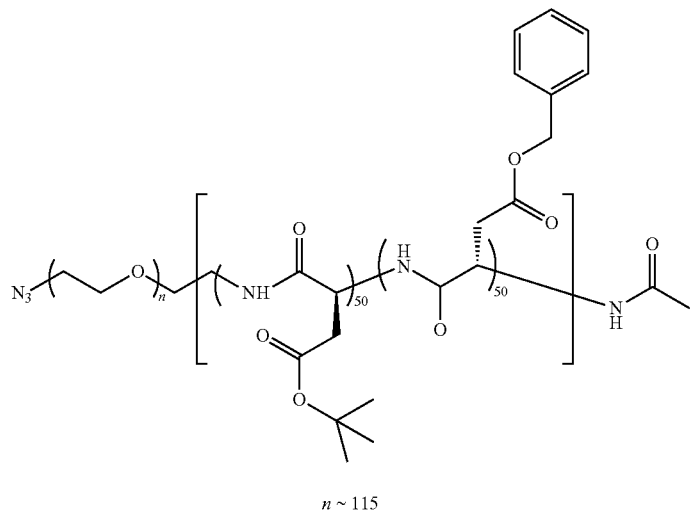
$N_3$-PEG5K-b-P(Asp(OBzl)$_{25}$-co-D-Asp($^t$Bu)$_{25}$)—Ac was synthesized as described in Example 22 from $N_3$-PEG-NH$_2$/DFA salt, 5 kDa (1 g, 0.2 mmol), Asp(O$^t$Bu)NCA (2.49 g, 10 mmol), D-Asp(O$^t$Bu)NCA (2.15 g, 10 mmol) and 60 mL of NMP. The block copolymer was isolated as an off-white powder (2.74 g, 57% yield). $^1$H NMR (d$_6$-DMSO) δ 8.50-7.67, 7.48-7.14, 5.18-4.91, 4.73-4.45, 3.71-3.38, 2.90-2.22, 1.52-1.12 ppm

Example 34

Synthesis of $N_3$-PEG5K-b-P(Asp(OBzl)$_{25}$-co-Asp(Morph)$_{25}$)—Ac

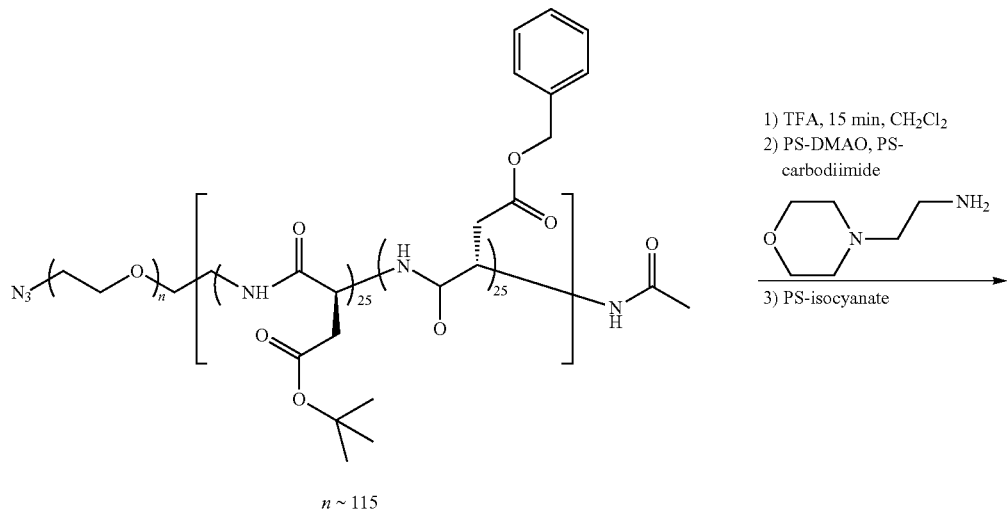

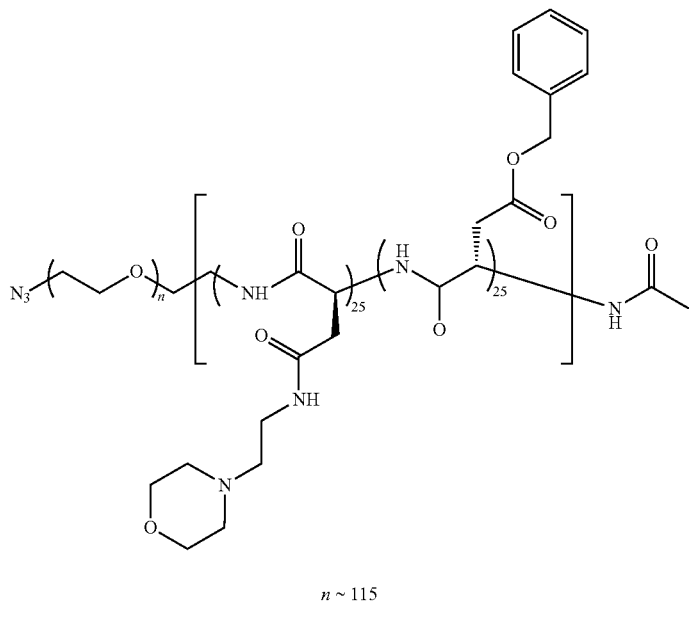

$N_3$-PEG5K-b-P(Asp(OBzl)$_{25}$-co-Asp(O$^t$Bu)$_{25}$)—Ac (1 g, 69.4 μmol) was dissolved in 5 mL of dichloromethane and 5 mL of trifluoroacetic acid (TFA), after which the solution was precipitated into 100 mL of cold ether (−20° C.). The precipitated was redissolved in 10 mL of dichloromethane and reprecipitated into 100 mL of cold ether (−20° C.). After filtration, the product was dried overnight in a vacuum oven. The polymer (250 mg, 0.019 mmol) was weighed into a 50 mL flask, along with PS-DMAP (1.47 mmol/g resin, 0.33 g, 0.48 mmol) and PS carbodiimide (1.33 mmol/g resin, 1.80 g, 2.4 mmol). 4-(2-Aminoethyl)morpholine (0.25 mL, 1.92 mmol) and DMF (dry, 15 mL) were syringed in the flask and the reaction was left at room temperature overnight. The following day, MP-isocyanate resin (1.11 mmol/g, 2.59 g, 2.875 mmol) was introduced in the reaction media and allowed to react to remove the excess 4-(2-aminoethyl)morpholine for 4 hours. The resin was removed from the reaction by filtration through a Whatman paper no. 1 and the solution was used as such for further polymer modification (Example 36).

Example 35
Synthesis of $N_3$-PEG5K-b-P(Asp(OBzl)$_{50}$-co-Asp(Morph)$_{50}$)—Ac
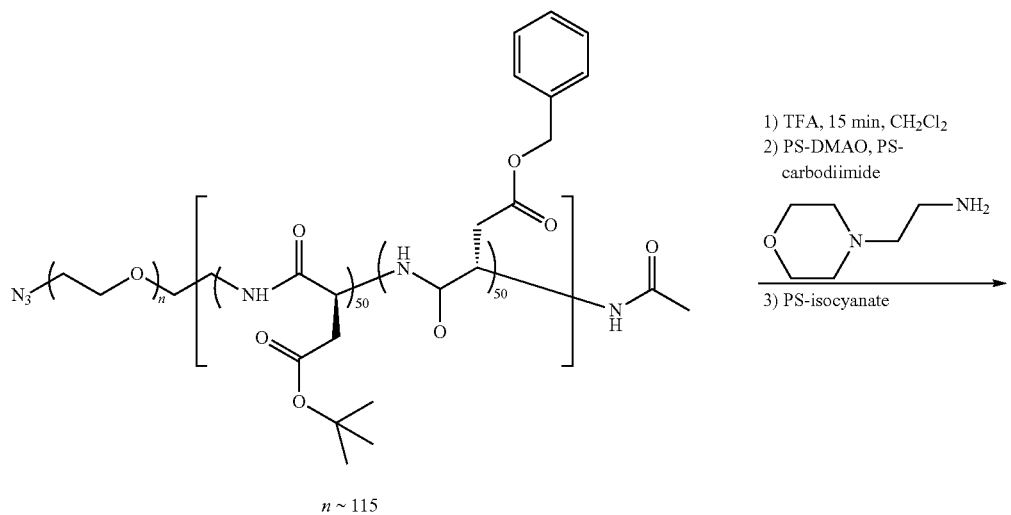
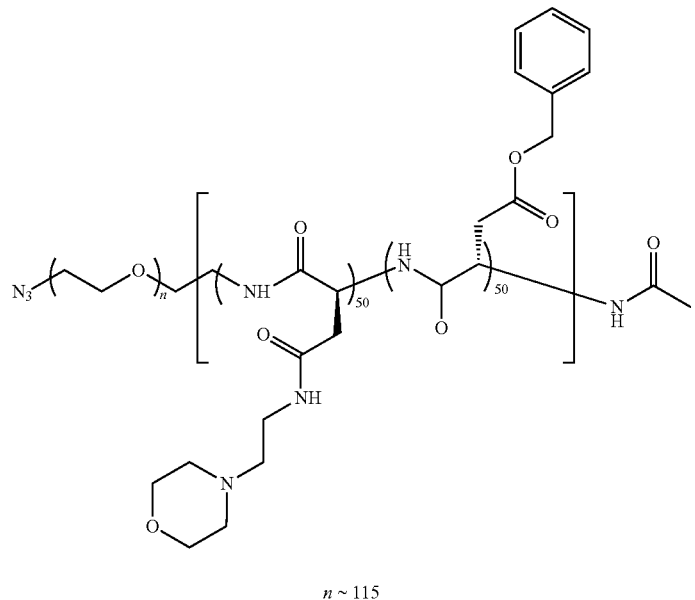
$N_3$-PEG5K-b-P(Asp(OBzl)$_{50}$-co-Asp(Morph)$_{50}$)—Ac was synthesized as in Example 34 from $N_3$-PEG5K-b-P(Asp(OBzl)$_{50}$-co-Asp(O$^t$Bu)$_{50}$)—Ac (0.25 g, 12 μmol), TFA (5 mL), PS-DMAP (0.41 g, 0.595 mmol), PS-carbodiimide (2.24 g, 2.98 mmol), 4-(2-aminoethyl)morpholine (0.31 mL, 2.38 mmol), MP-isocyanate (3.22 g, 3.57 mmol), DMF (15 mL). The final solution was used as such for further modification (Example 37)

Example 36

Synthesis of N$_3$-PEG5K-b-P(Asp(DET)$_{25}$-co-Asp(Morph)$_{25}$)—Ac

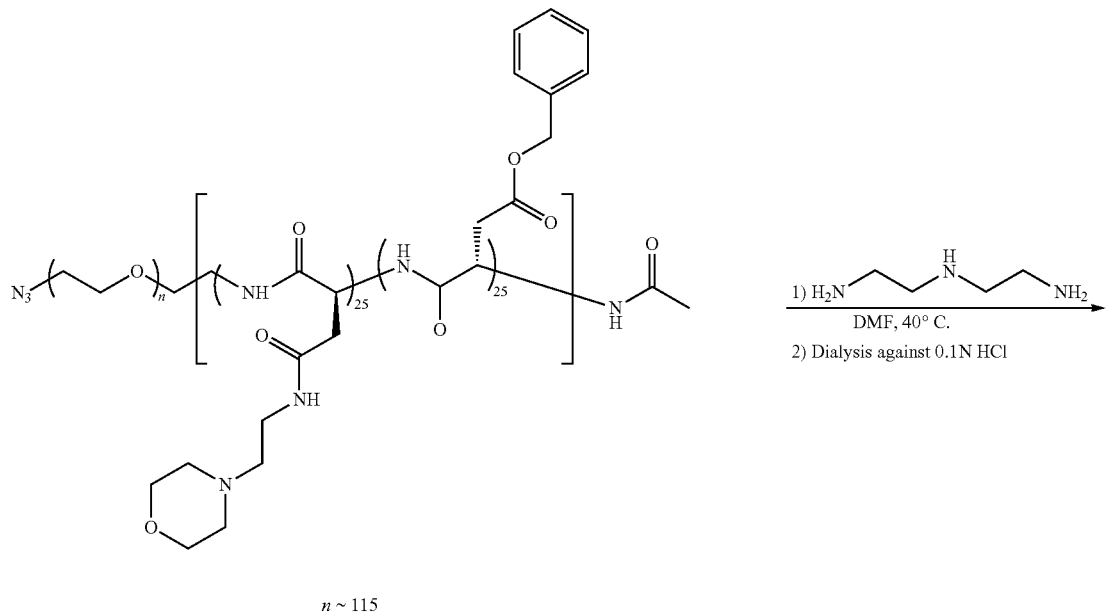

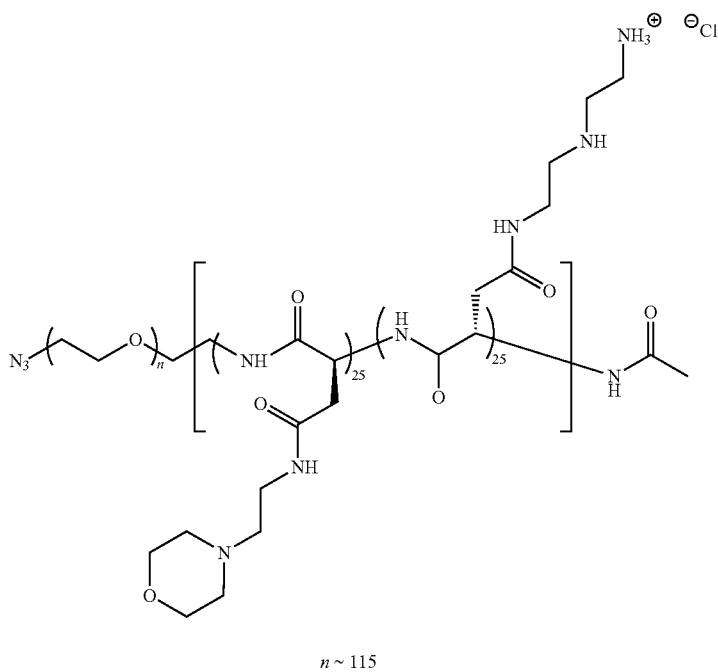

N$_3$-PEG5K-b-P(Asp(OBzl)$_{25}$-co-Asp(Morph)$_{25}$)—Ac (0.25 g, 16.1 μmol) was introduced into an oven-dried two-neck flask and three vacuum/N$_2$ cycles were done. Diethylenetriamine (DET, vacuum distilled from CaH$_2$, 2 mL, 18.6 mmol) and dry DMF (20 mL) were syringed in the reaction flask. The reaction was stirred at 40° C. overnight under inert atmosphere. The reaction solution was then introduced into a 3500 molecular weight cut-off dialysis bag and dialyzed three times against 0.1 M HCl and three times against deionized water. The solution was filtered through a 0.45 μm filter and the solution was freeze-dried. A white fluffy solid was recovered. $^1$H NMR (D$_2$O) δ 4-3.33, 3.33-2.58 ppm

Example 37
Synthesis of N$_3$-PEG5K-b-P(Asp(DET)$_{50}$-co-Asp(Morph)$_{50}$)—Ac
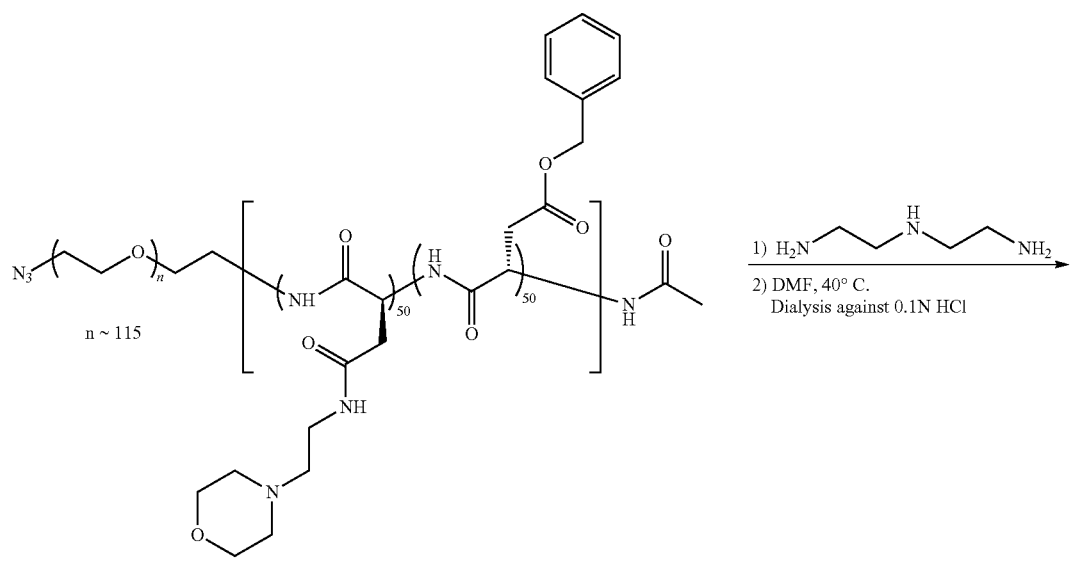
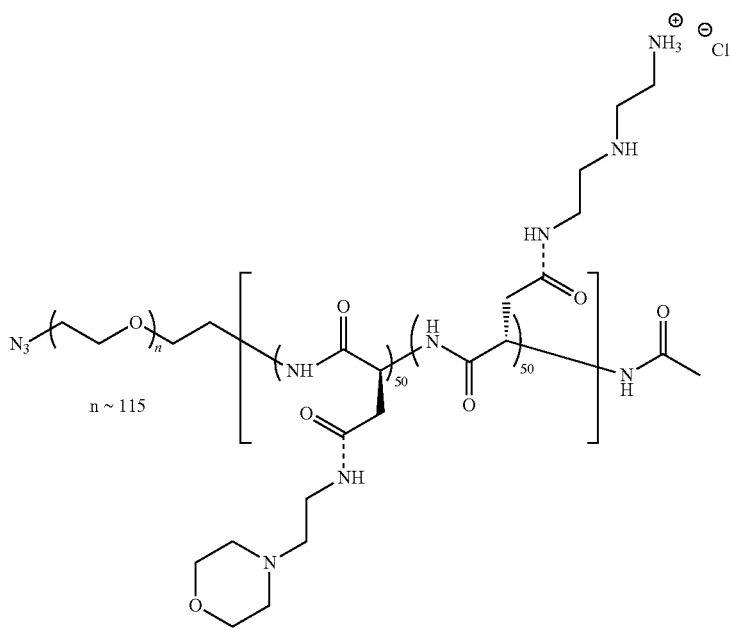
N$_3$-PEG5K-b-P(Asp(DET)$_{50}$-co-Asp(Morph)$_{50}$)—Ac was made as described in Example 36 from N$_3$-PEG5K-b-P(Asp(OBzl)$_{50}$-co-Asp(Morph)$_{50}$)—Ac (0.25 g, 9.6 μmol), diethylenetriamine (2 mL, 18.6 mmol) and DMF (20 mL). A white fluffy solid was recovered. $^1$H NMR (D$_2$O) δ 4-3.33, 3.33-2.58 ppm

Example 38

Synthesis of N3-PEG12K-b-P(Asp(DET)$_{50}$-co-D-Asp(DET)$_{50}$)—Ac

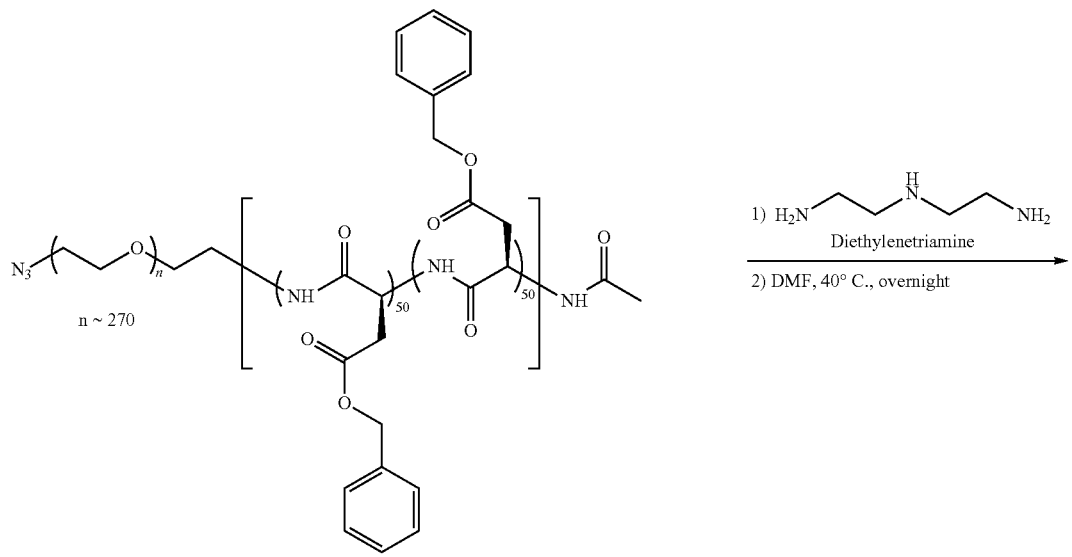

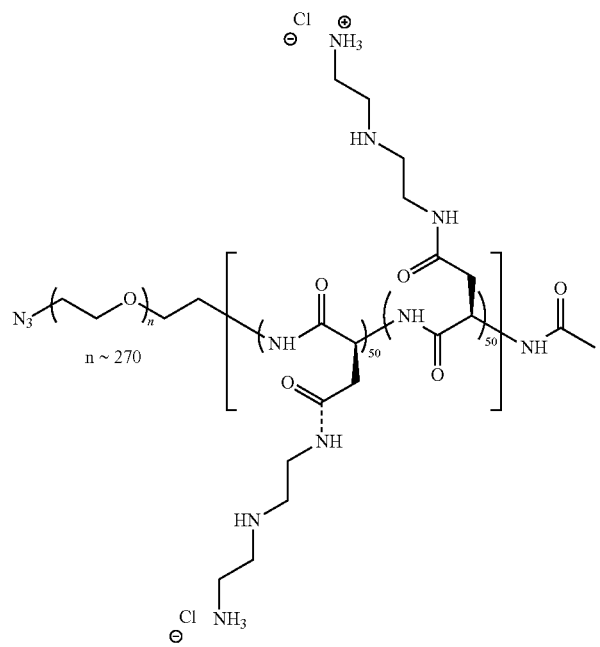

N$_3$-PEG12K-b-P(Asp(OBzl)$_{50}$-co-D-Asp(AspOBzl)$_{50}$)—Ac (0.631 g, 19.7 µmol) was introduced into an oven-dried two-neck flask and three vacuum/N$_2$ cycles were done. Diethylenetriamine (DET, vacuum distilled from CaH$_2$, 4 mL, 37.2 mmol) and dry DMF (0.4 mL) were syringed in the reaction flask. The reaction was stirred at 40° C. overnight under inert atmosphere. The reaction solution was then introduced into a 3500 molecular weight cut-off dialysis bag and dialyzed three times against 0.1 M HCl and three times against deionized water. The solution was filtered through a 0.45 µm filter and the solution was freeze-dried. A white fluffy solid was recovered (0.311 g, 45% yield). $^1$H NMR (D$_2$O) δ 3.90-3.85, 3.83-3.63, 3.61-3.35, 3.35-2.60 ppm

Example 39
Synthesis of N3-PEG12K-b-P(Asp(TET)$_{50}$-co-D-Asp(TET)$_{50}$)—Ac
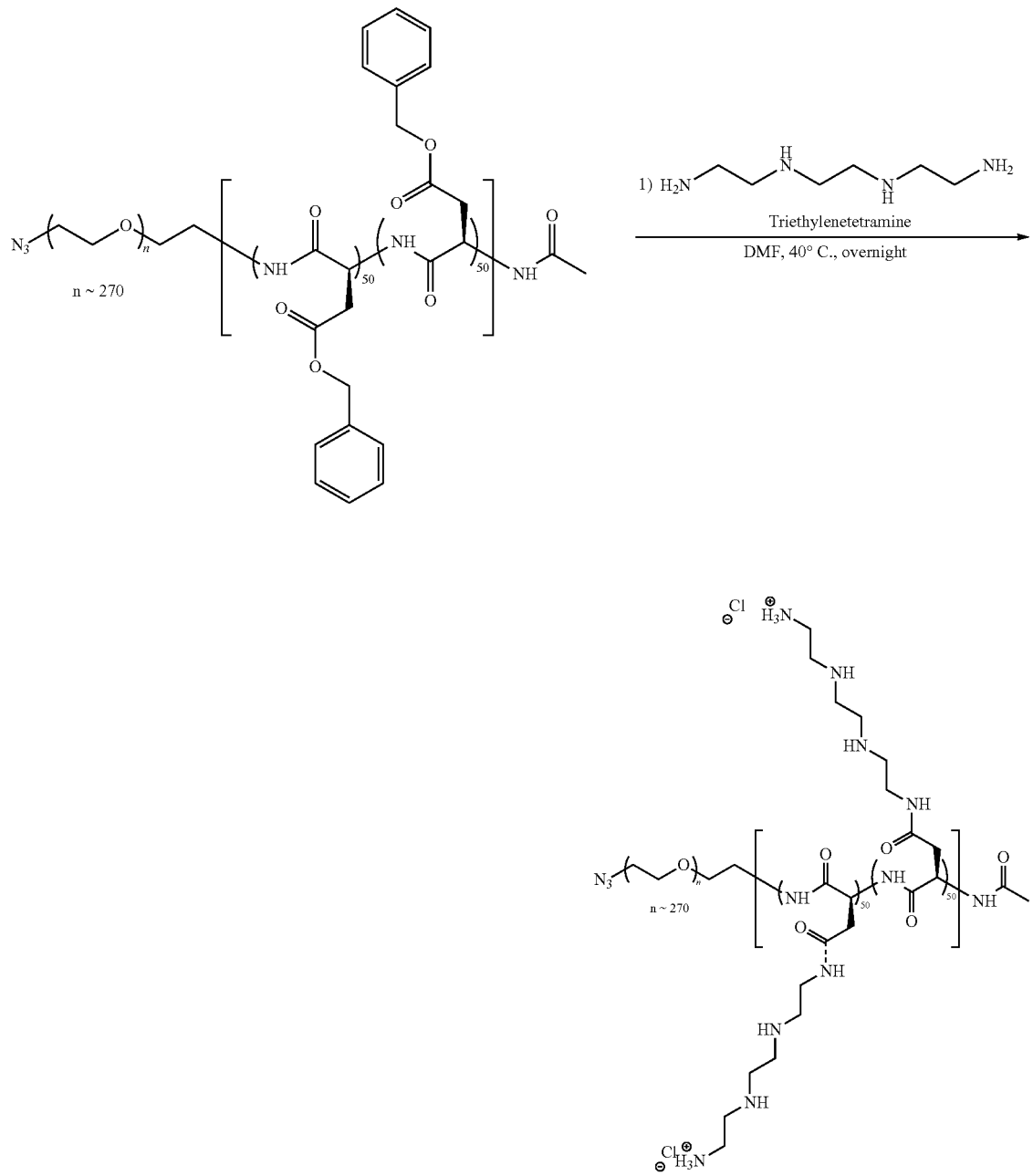
N$_3$-PEG12K-b-P(Asp(TET)$_{50}$-co-D-Asp(TET)$_{50}$)—Ac was synthesized as described in Example 38 from N$_3$-PEG12K-b-P(Asp(OBzl)$_{50}$-co-D-Asp(AspOBzl)$_{50}$)—Ac (0.557 g, 17.4 μmol), triethylenetetramine (TET, 5 mL, 33.3 mmol) and DMF (dry, 10 mL). A white fluffy powder was recovered (0.219 g, 32% yield). $^1$H NMR (D$_2$O) δ 3.90-3.85, 3.83-3.63, 3.61-3.35, 3.35-2.60 ppm

Example 40
Synthesis of N₃-PEG12K-b-P(Asp(TEP)₅₀-co-D-Asp(TEP)₅₀)—Ac
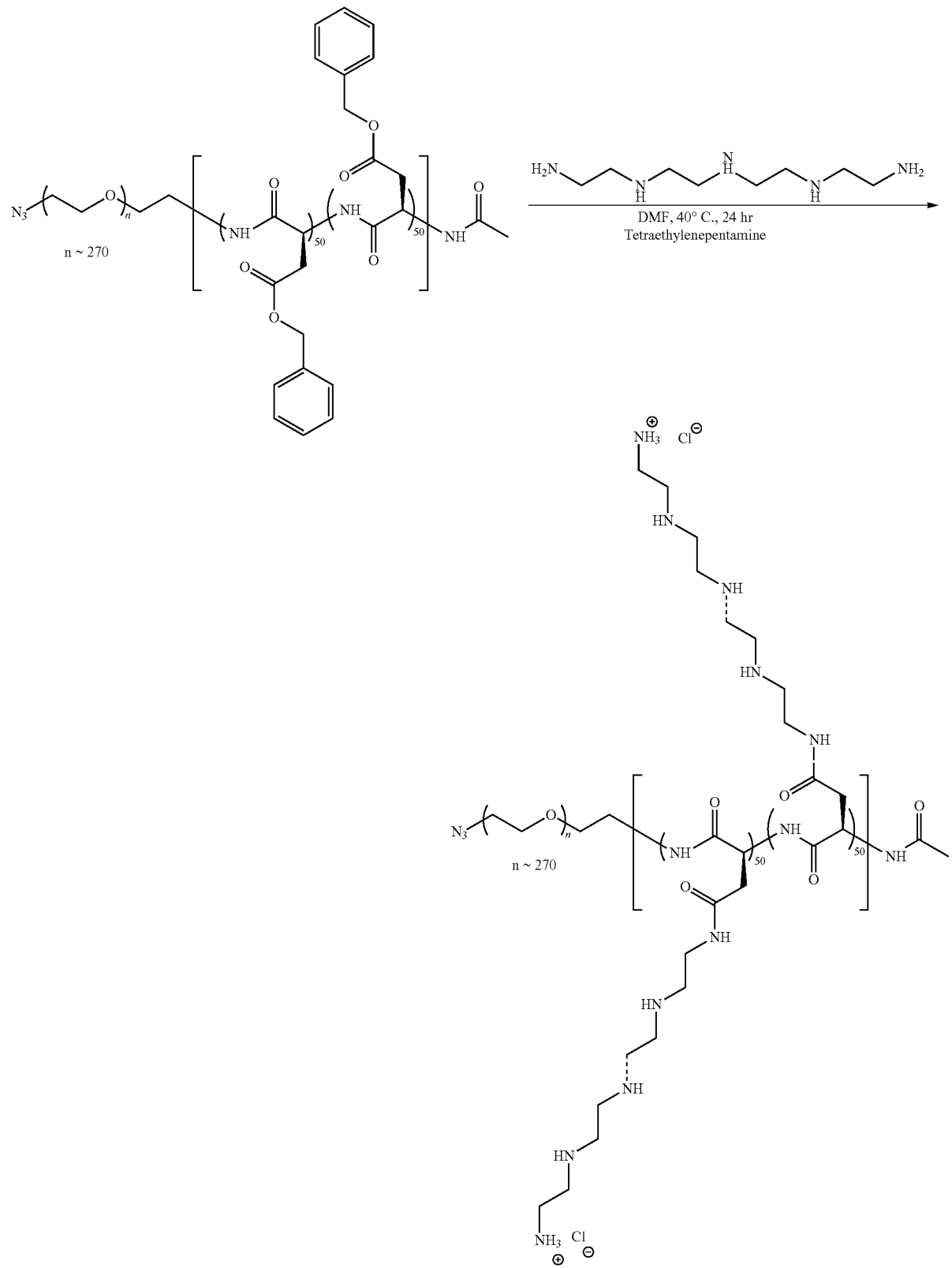

N₃-PEG12K-b-P(Asp(TEP)₅₀-co-D-Asp(TEP)₅₀)—Ac was synthesized as described in Example 38 from N₃-PEG12K-b-P(Asp(OBzl)₅₀-co-D-Asp(AspOBzl)₅₀)—Ac (0.58 g, 18.1 μmol), tetraethylenepentamine (TEP, 7 mL, 36.6 mmol) and DMF (dry, 10 mL). A white fluffy powder was recovered (0.184 g, 23% yield). ¹H NMR (D₂O) δ 3.90-3.85, 3.83-3.43, 3.43-3.02, 3.02-2.58 ppm
Example 41
Synthesis of N₃-PEG12K-b-P(Asp(PEH)₅₀-co-D-Asp(PEH)₅₀)—Ac
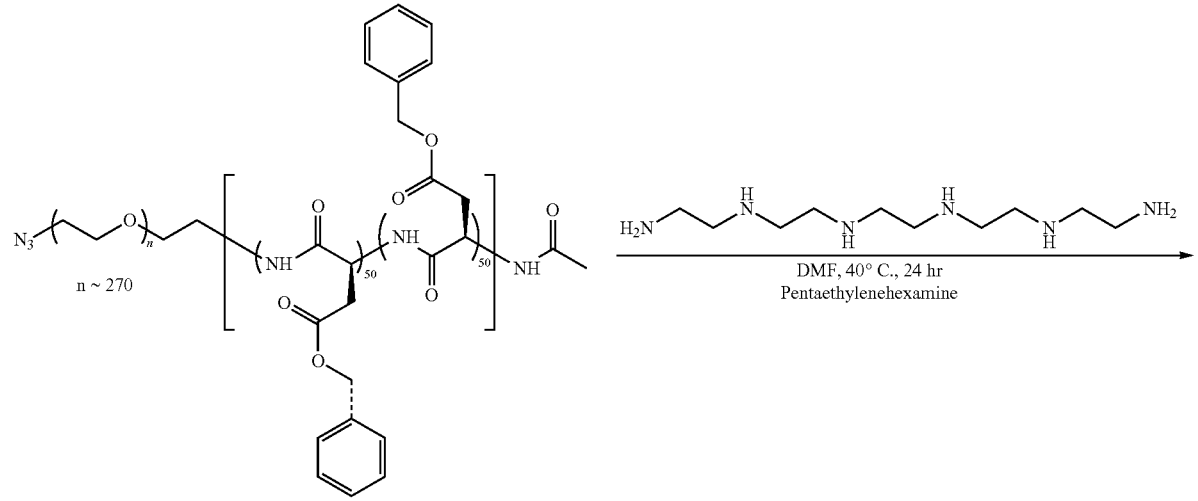
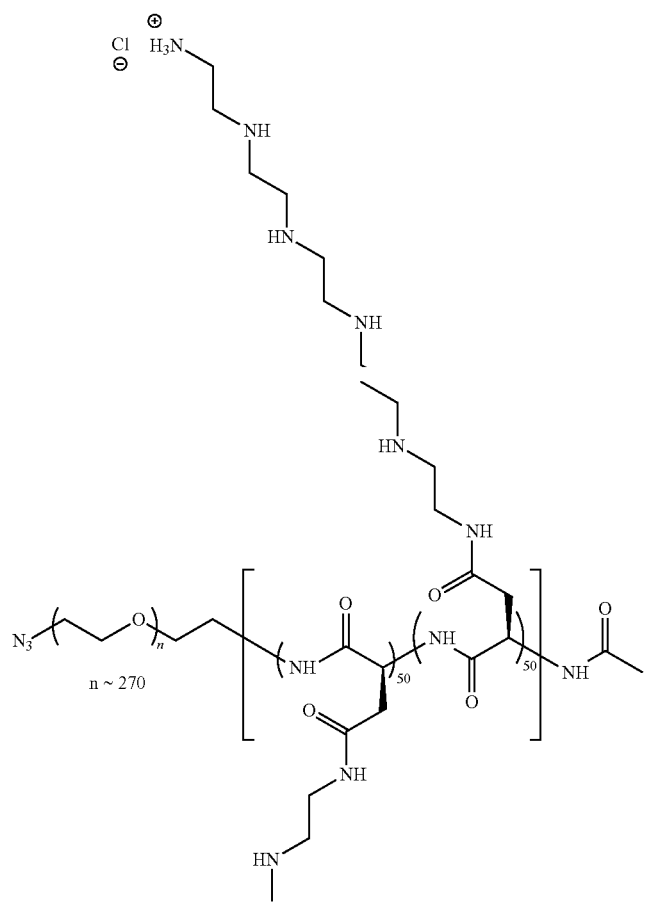

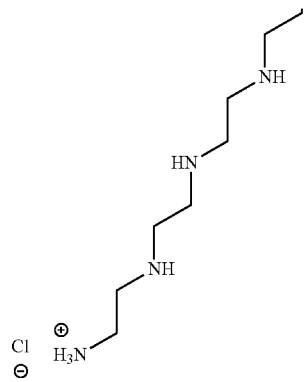
N₃-PEG12K-b-P(Asp(PEH)₅₀-co-D-Asp(PEH)₅₀)—Ac was synthesized as described in Example 38 from N₃-PEG12K-b-P(Asp(OBzl)₅₀-co-D-Asp(AspOBzl)₅₀)—Ac (0.56 g, 17.5 mmol), pentaethylenehexamine (PEH, 8 mL, 34.4 mmol) and DMF (dry, 10 mL). A white fluffy powder was recovered. $^1$H NMR (D₂O) δ 3.90-3.85, 3.83-3.43, 3.43-3.02, 3.02-2.58 ppm
Example 42
Synthesis of N₃-PEG12K-b-P(Asp(Tris)₅₀-co-D-Asp(Tris)₅₀)—Ac
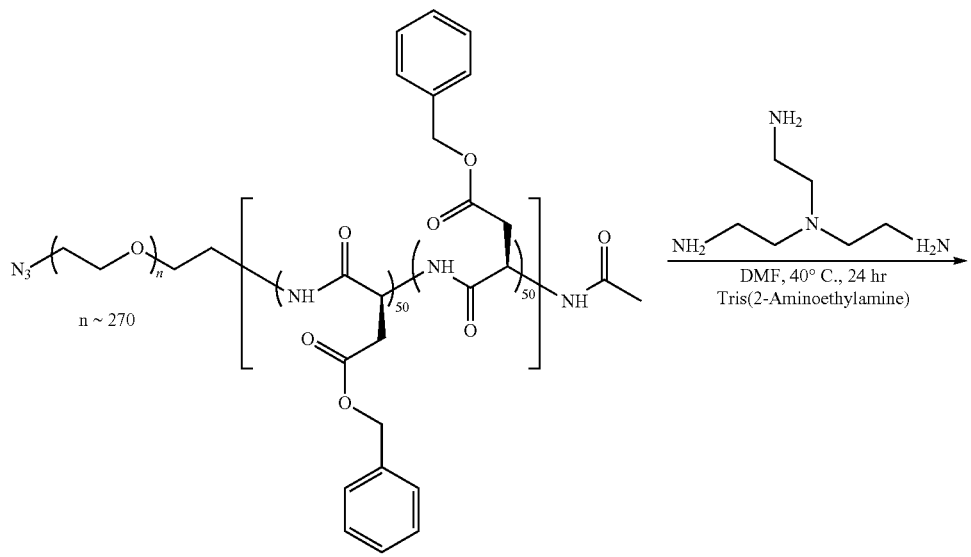

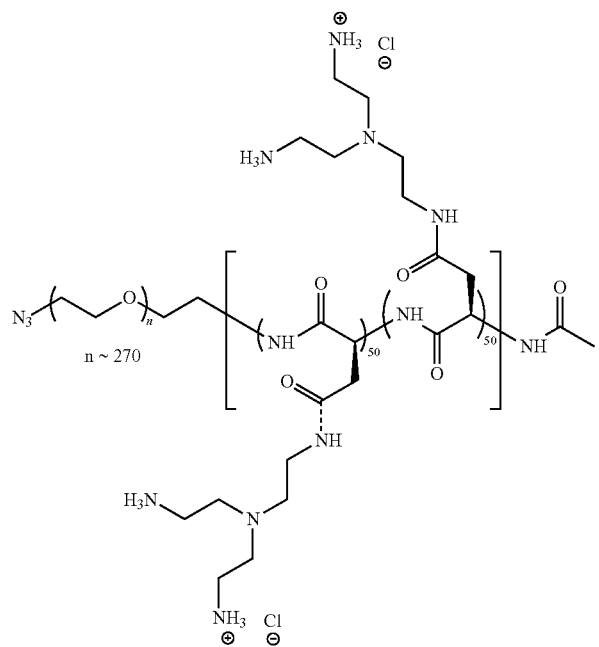
N$_3$-PEG12K-b-P(Asp(Tris)$_{50}$-co-D-Asp(Tris)$_{50}$)—Ac was synthesized as described in Example 38 from N$_3$-PEG12K-b-P(Asp(OBzl)$_{50}$-co-D-Asp(AspOBzl)$_{50}$)—Ac (0.542 g, 16.9 μmol), tris(2-aminoethylamine) (Tris, 8 mL, 34.4 mmol) and DMF (dry, 4 mL). A white fluffy powder was recovered. (0.209 g, 31% yield)
Example 43
Synthesis of N$_3$-PEG12K-b-P(Asp(Pip)$_{50}$-co-D-Asp(Pip)$_{50}$)—Ac
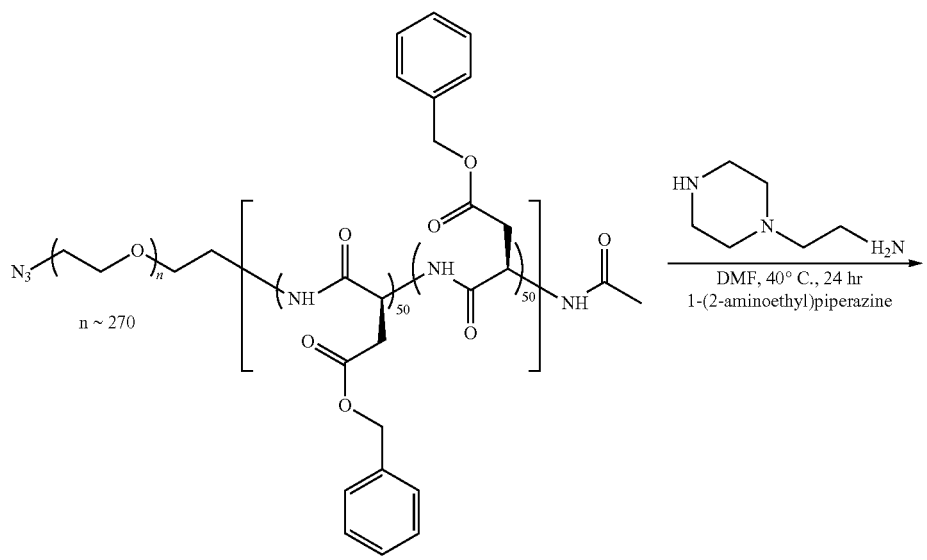

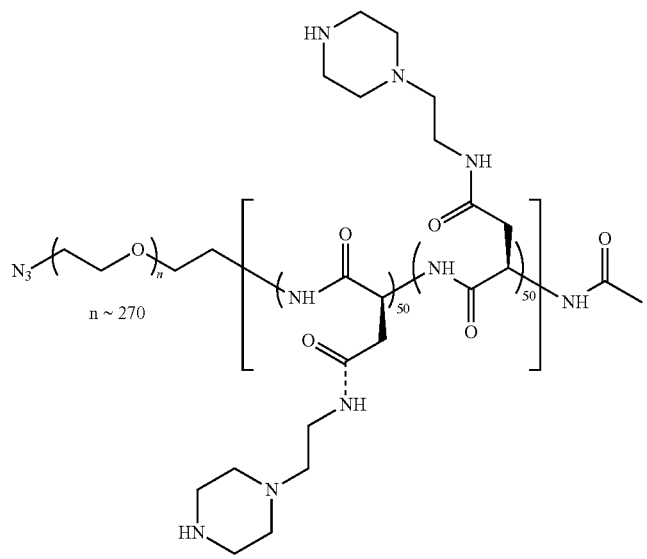
N$_3$-PEG12K-b-P(Asp(Pip)$_{50}$-co-D-Asp(Pip)$_{50}$)—Ac was synthesized as described in Example 38 from N$_3$-PEG12K-b-P(Asp(OBzl)$_{50}$-co-D-Asp(AspOBzl)$_{50}$)—Ac (0.55 g, 16.9 μmol), piperazine (Pip, 8.8 mL, 67.1 mmol) and DMF (dry, 4 mL). A white fluffy powder was recovered. (0.343 g, 58.6% yield) $^1$H NMR (D$_2$O) δ 3.90-3.85, 3.83-3.43, 3.43-3.02, 3.02-2.58 ppm
Example 44
Synthesis of N$_3$-PEG12K-b-P(Asp(DEDET)$_{50}$-co-D-Asp(DEDET)$_{50}$)—Ac
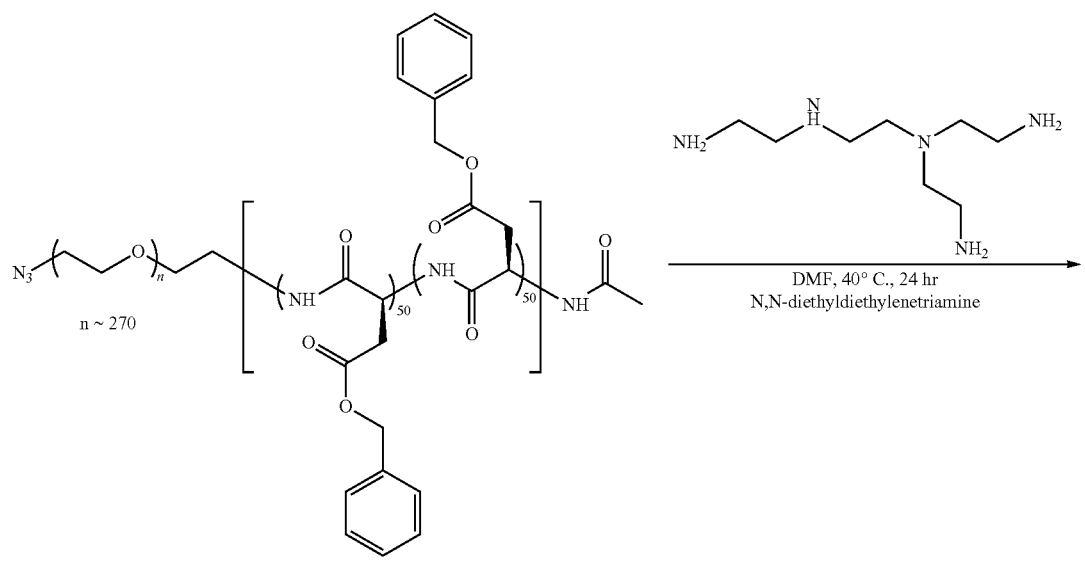

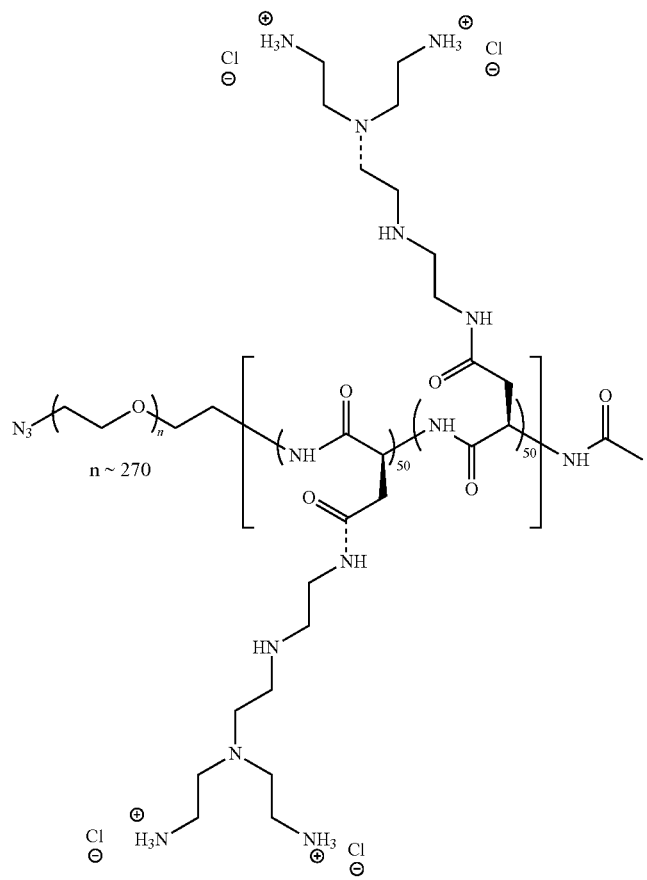
N₃-PEG12K-b-P(Asp(DEDET)₅₀-co-D-Asp(DEDET)₅₀)—Ac was synthesized as described in Example 38 from N₃-PEG12K-b-P(Asp(OBzl)₅₀-co-D-Asp(AspOBzl)₅₀)—Ac (0.55 g, 16.9 mmol), N,N-diethyldiethylenetriamine (DE-DET, 5.3 mL, 28.8 mmol) and DMF (dry, 4 mL). A white fluffy powder was recovered. (0.160 g, 36% yield) ¹H NMR (D₂O)
Example 45
Synthesis of N₃-PEG12K-b-P(Asp(OBzl)₉₀-co-DLeu₁₀)—Ac
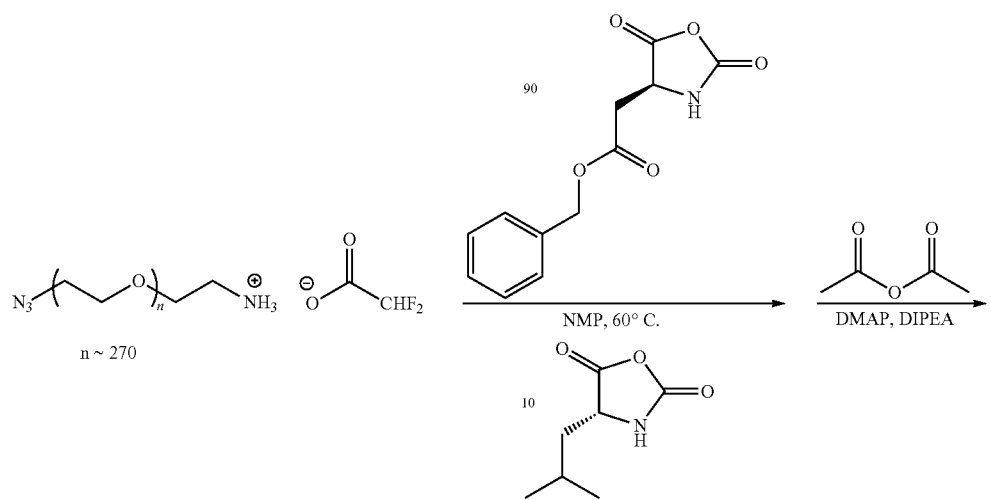

-continued

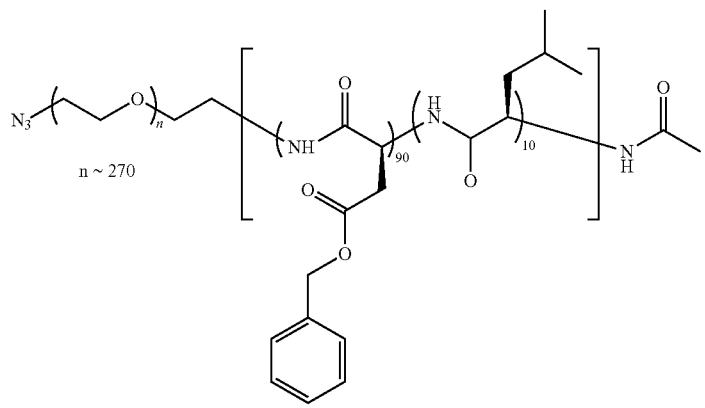

N₃-PEG12k-NH₂/DFA salt, (2 g, 0.17 mmol) was weighed into an oven-dried, round-bottom flask, dissolved in toluene, and dried by azeotropic distillation. Excess toluene was removed under vacuum. Asp(OBzl)NCA (3.90 g, 15.7 mmol) and D-Leu NCA (0.27 g, 1.74 mmol) was added to the flask, the flask was evacuated under reduced pressure, and subsequently backfilled with nitrogen gas (repeated twice). Dry N-methylpyrrolidone (NMP) (40 mL) was introduced by syringe and the solution was heated to 60° C. The reaction mixture was allowed to stir for 3 days at 60° C. under nitrogen gas. The solution was cooled to room temperature and DIPEA (2.0 mL), DMAP (200 mg), and acetic anhydride (2.0 mL) were added. Stirring was continued for 1 hour at room temperature. The polymer was then placed in a 3500 g/mol molecular weight cut-off dialysis bag, dialyzed three times against 0.1 N HCl in methanol, three times against deionized water and freeze-dried. A white solid was obtained (2.441 g, 45% yield). ¹H NMR (d₆-DMSO) δ 8.43-8.07, 7.45-7.16, 5.01, 4.61, 4.3-4.1, 3.68-3.38, 2.94-2.75, 2.75-2.5, 1.57-1.33, 0.84-0.63 ppm Example 46

Synthesis of N₃-PEG12K-b-P(Asp(OBzl)₇₀-co-DLeu₃₀)—Ac

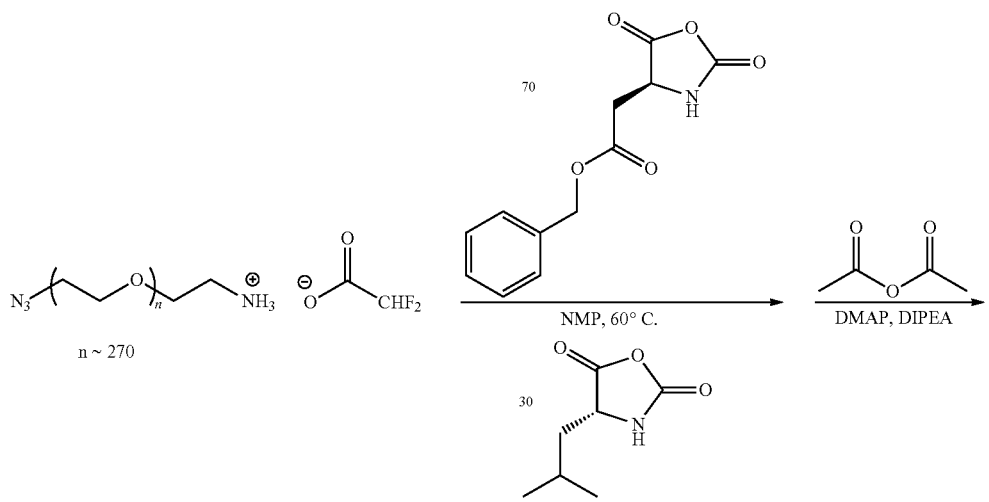

-continued
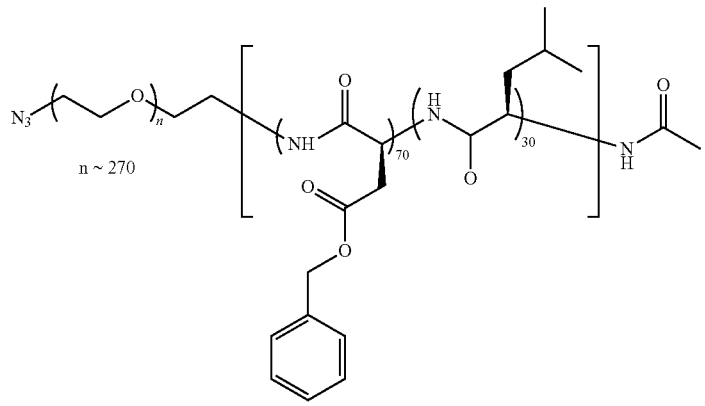
$N_3$-PEG12K-b-P(Asp(OBzl)$_{70}$-co-DLeu$_{30}$)—Ac was synthesized as described in Example 45 from $N_3$-PEG-NH$_2$/DFA salt, 12 kDa (2 g, 0.17 mmol), Asp(OBzl)NCA (3.03 g, 12.2 mmol), D-Leu NCA (0.82 g, 5.2 mmol) and 40 mL of NMP. The block copolymer was isolated as a white powder (3.395 g, 67% yield). $^1$H NMR (d$_6$-DMSO) δ 8.43-8.07, 7.45-7.16, 5.01, 4.61, 4.3-4.1, 3.68-3.38, 2.94-2.75, 2.75-2.5, 1.57-1.33, 0.84-0.63 ppm
Example 47
Synthesis of $N_3$-PEG12K-b-P(Asp(OBzl)$_{50}$-co-DLeu$_{50}$)—Ac
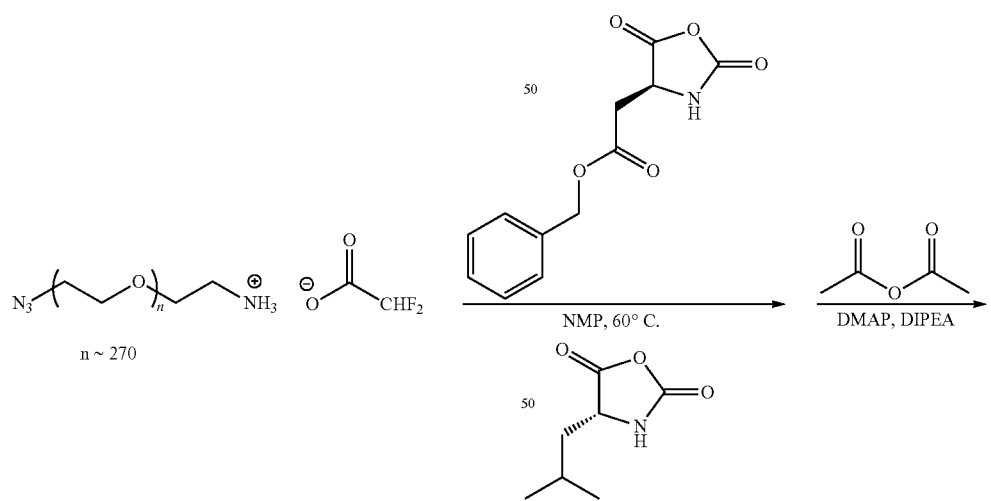

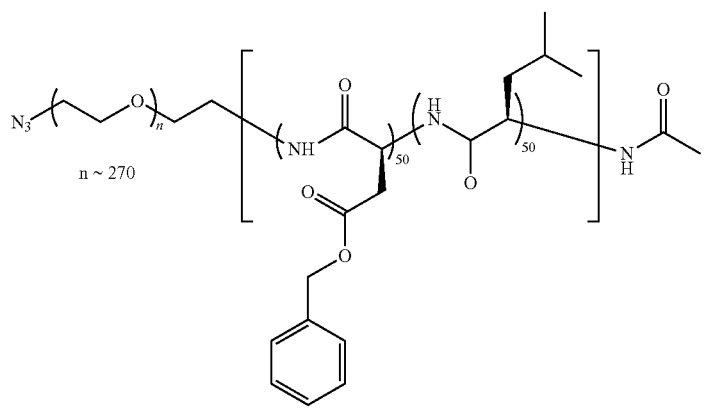
N$_3$-PEG12K-b-P(Asp(OBzl)$_{50}$-co-DLeu$_{50}$)—Ac was synthesized as described in Example 45 from N$_3$-PEG-NH$_2$/DFA salt, 12 kDa (2 g, 0.17 mmol), Asp(OBzl)NCA (2.17 g, 8.7 mmol), D-Leu NCA (1.37 g, 8.7 mmol) and 37 mL of NMP. The block copolymer was isolated as a white powder (2.887 g, 60.5% yield). $^1$H NMR (d$_6$-DMSO) δ 8.43-8.07, 7.45-7.16, 5.01, 4.61, 4.3-4.1, 3.68-3.38, 2.94-2.75, 2.75-2.5, 1.57-1.33, 0.84-0.63 ppm
Example 48
Synthesis of N$_3$-PEG12K-b-P(Asp(OBzl)$_{180}$-co-DLeu$_{20}$)—Ac
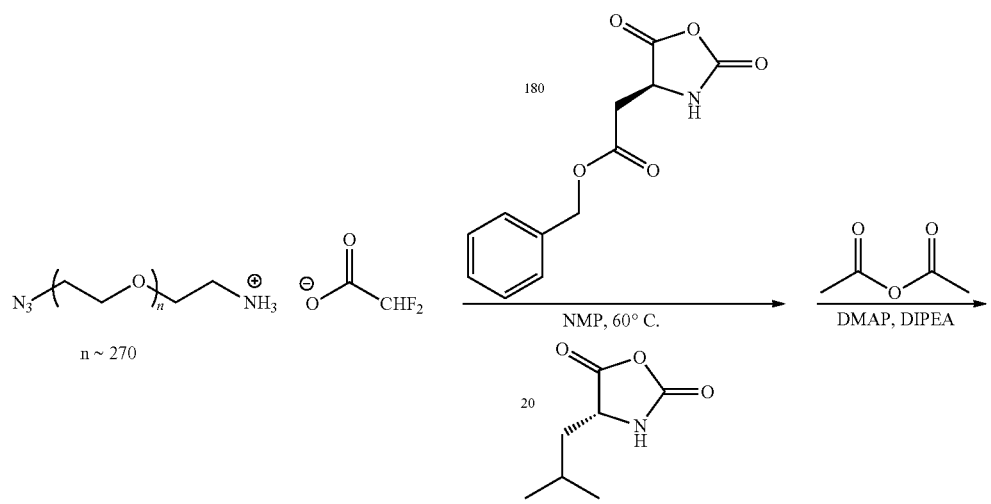

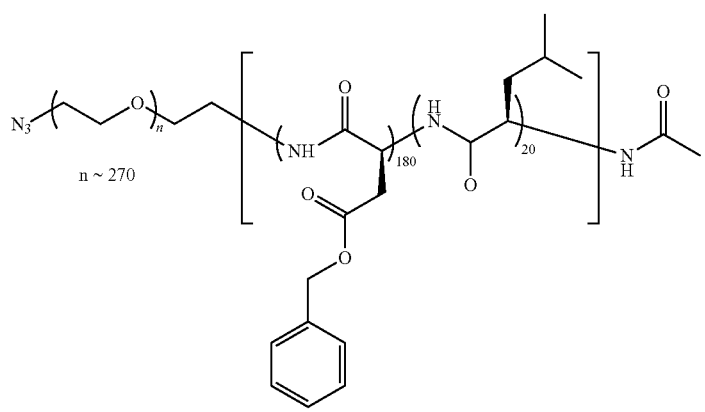
N$_3$-PEG12K-b-P(Asp(OBzl)$_{180}$-co-DLeu$_{20}$)—Ac was synthesized as described in Example 45 from N$_3$-PEG-NH$_2$/DFA salt, 12 kDa (1 g, 0.087 mmol), Asp(OBzl)NCA (3.90 g, 15.6 mmol), D-Leu NCA (0.27 g, 17.4 mmol) and 35 mL of NMP. The block copolymer was isolated as a white powder (1.685 g, 38% yield). $^1$H NMR (d$_6$-DMSO) δ 8.43-8.07, 7.45-7.16, 5.01, 4.61, 4.3-4.1, 3.68-3.38, 2.94-2.75, 2.75-2.5, 1.57-1.33, 0.84-0.63 ppm
Example 49
Synthesis of N$_3$-PEG12K-b-P(Asp(OBzl)$_{140}$-co-DLeu$_{60}$)—Ac
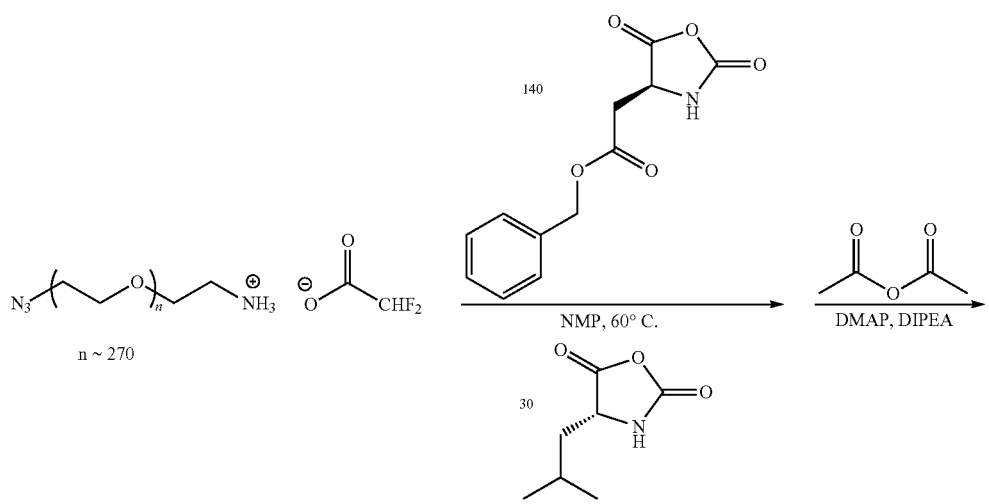

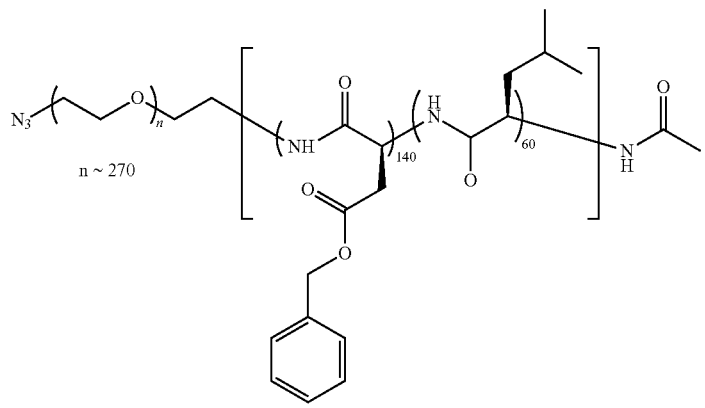
N₃-PEG12K-b-P(Asp(OBzl)₁₄₀-co-DLeu₆₀)—Ac was synthesized as described in Example 45 from N₃-PEG-NH₂/DFA salt, 12 kDa (1 g, 0.087 mmol), Asp(OBzl)NCA (3.03 g, 12.2 mmol), D-Leu NCA (0.82 g, 5.2 mmol) and 40 mL of NMP. The block copolymer was isolated as a white powder (1.784 g, 44% yield). $^1$H NMR (d₆-DMSO) δ 8.43-8.07, 7.45-7.16, 5.01, 4.61, 4.3-4.1, 3.68-3.38, 2.94-2.75, 2.75-2.5, 1.57-1.33, 0.84-0.63 ppm.
Example 50
Synthesis of N₃-PEG12K-b-P(Asp(OBzl)₁₀₀-co-DLeu₁₀₀)—Ac
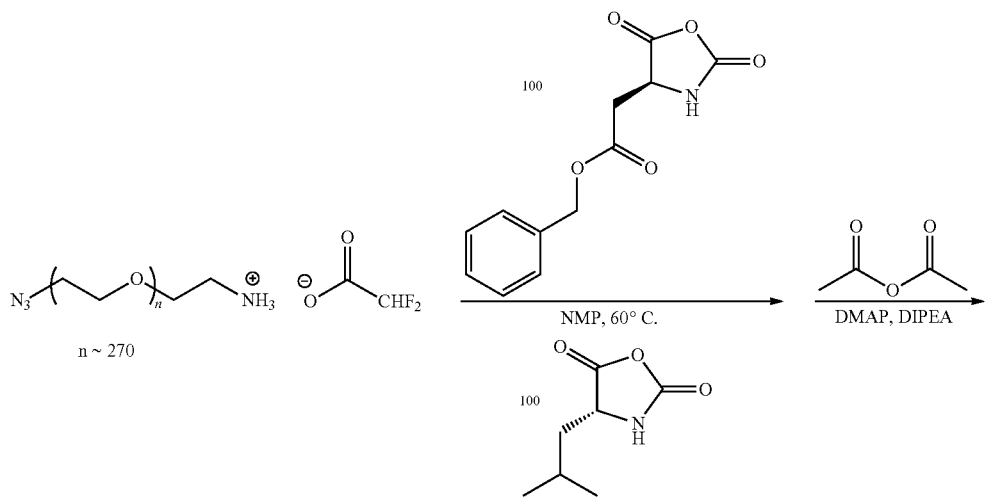

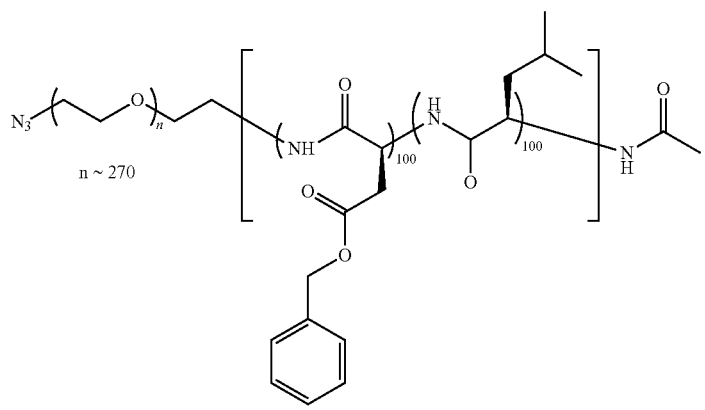
N₃-PEG12K-b-P(Asp(OBzl)₁₀₀-co-DLeu₁₀₀)—Ac was synthesized as described in Example 45 from N₃-PEG-NH₂/DFA salt, 12 kDa (1 g, 0.087 mmol), Asp(OBzl)NCA (2.17 g, 8.7 mmol), D-Leu NCA (1.37 g, 8.7 mmol) and 30 mL of NMP. The block copolymer was isolated as a white powder (2.792 g, 74% yield). ¹H NMR (d₆-DMSO) δ 8.43-8.07, 7.45-7.16, 5.01, 4.61, 4.3-4.1, 3.68-3.38, 2.94-2.75, 2.75-2.5, 1.57-1.33, 0.84-0.63 ppm
Example 51
Synthesis of N₃-PEG12K-b-P(Asp(OBzl)₁₉₀-co-DLeu₁₀)—Ac
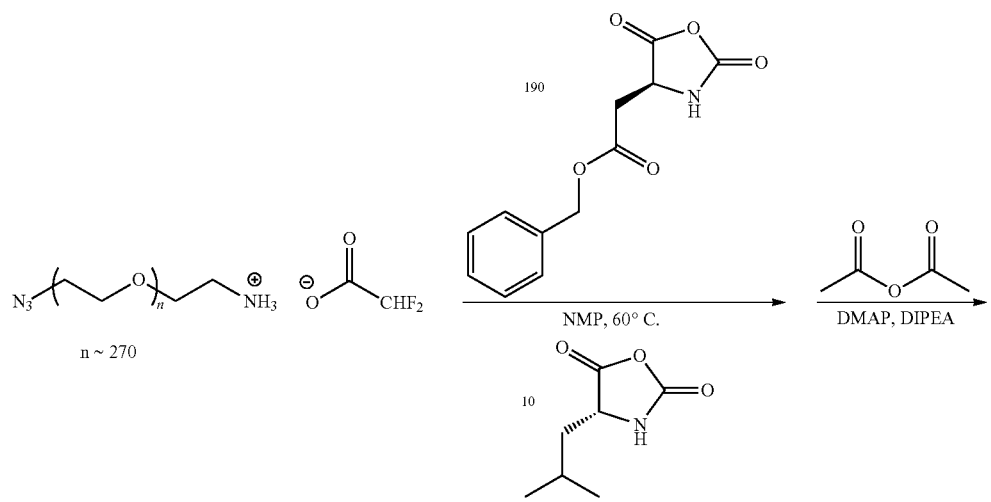

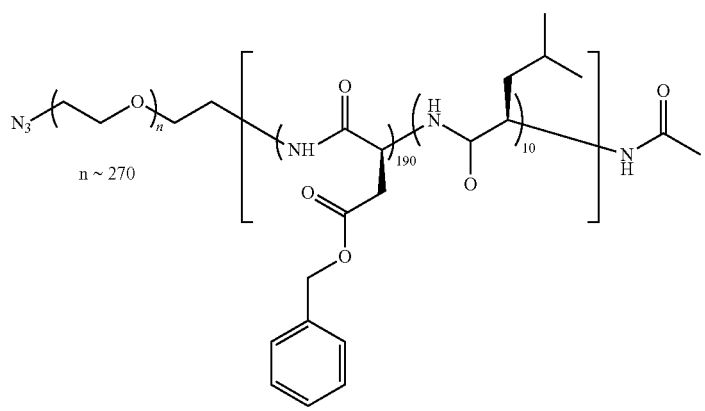
N$_3$-PEG12K-b-P(Asp(OBzl)$_{190}$-co-DLeu$_{10}$)—Ac was synthesized as described in Example 45 from N$_3$-PEG-NH$_2$/DFA salt, 12 kDa (1 g, 0.087 mmol), Asp(OBzl)NCA (4.12 g, 16.5 mmol), D-Leu NCA (0.14 g, 0.87 mmol) and 35 mL of NMP. The block copolymer was isolated as a white powder (1.83 g, 40.7% yield). $^1$H NMR (d$_6$-DMSO) δ 8.43-8.07, 7.45-7.16, 5.01, 4.61, 4.3-4.1, 3.68-3.38, 2.94-2.75, 2.75-2.5, 1.57-1.33, 0.84-0.63 ppm
Example 52
Synthesis of N$_3$-PEG12K-b-P(Asp(OBzl)$_{170}$-co-DLeu$_{30}$)—Ac
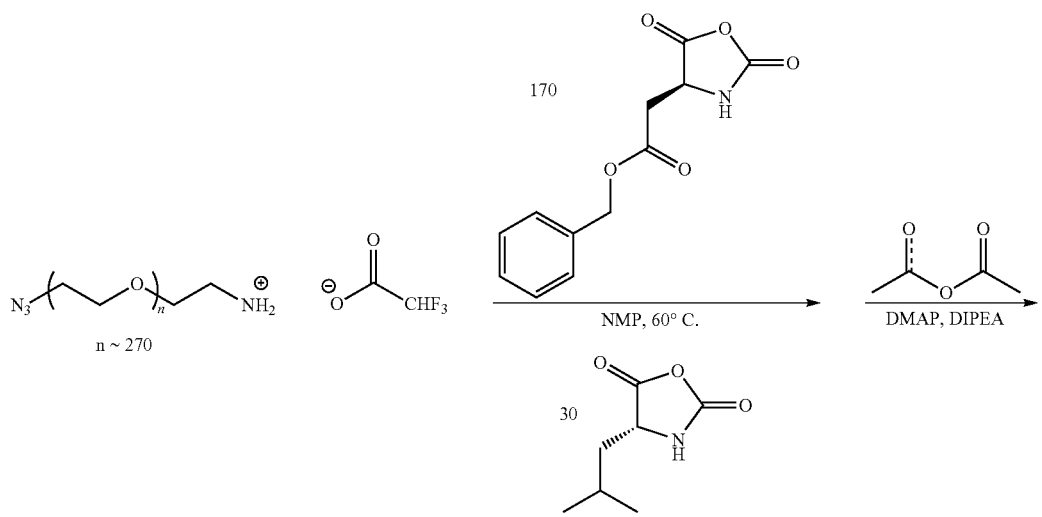

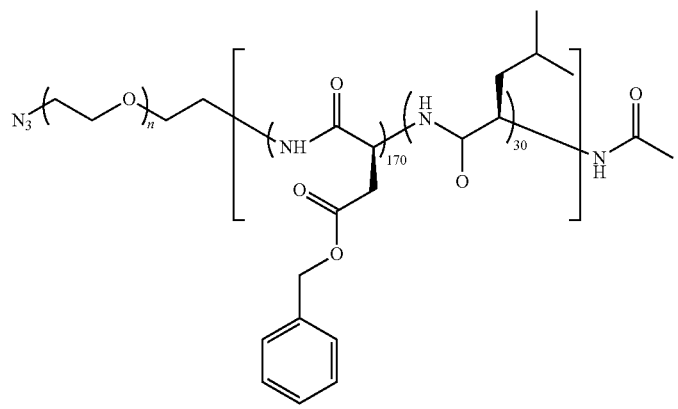
n ~ 270
$N_3$-PEG12K-b-P(Asp(OBzl)$_{170}$-co-DLeu$_{30}$)—Ac was synthesized as described in Example 45 from $N_3$-PEG-NH$_2$/DFA salt, 12 kDa (1 g, 0.087 mmol), Asp(OBzl)NCA (3.68 g, 14.8 mmol), D-Leu NCA (0.41 g, 2.6 mmol) and 35 mL of NMP. The block copolymer was isolated as a white powder (1.38 g, 32% yield). $^1$H NMR (d$_6$-DMSO) δ 8.43-8.07, 7.45-7.16, 5.01, 4.61, 4.3-4.1, 3.68-3.38, 2.94-2.75, 2.75-2.5, 1.57-1.33, 0.84-0.63 ppm
Example 53
Synthesis of $N_3$-PEG12K-b-P(Asp(OBzl)$_{150}$-co-DLeu$_{50}$)—Ac
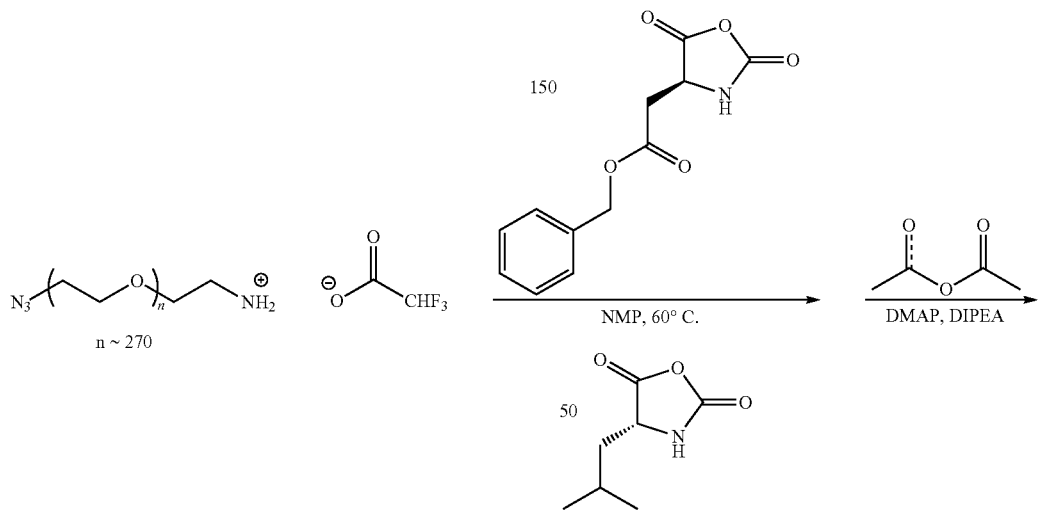

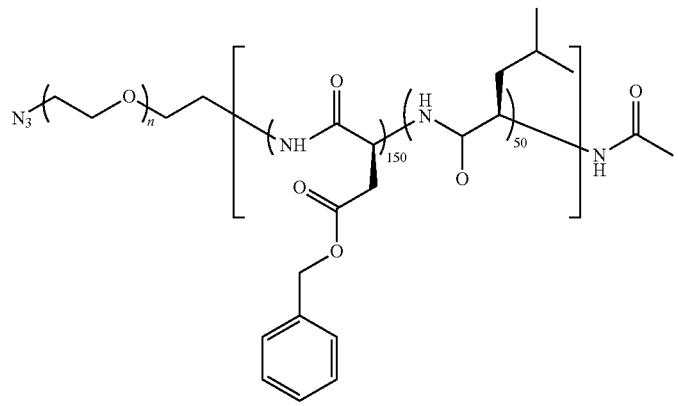
N$_3$-PEG12K-b-P(Asp(OBzl)$_{150}$-co-DLeu$_{50}$)—Ac was synthesized as described in Example 45 from N$_3$-PEG-NH$_2$/DFA salt, 12 kDa (1 g, 0.087 mmol), Asp(OBzl)NCA (3.25 g, 13 mmol), D-Leu NCA (0.68 g, 4.3 mmol) and 35 mL of NMP. The block copolymer was isolated as a white powder (1.82 g, 43.7% yield). $^1$H NMR (d$_6$-DMSO) δ 8.43-8.07, 7.45-7.16, 5.01, 4.61, 4.3-4.1, 3.68-3.38, 2.94-2.75, 2.75-2.5, 1.57-1.33, 0.84-0.63 ppm
Example 54
Synthesis of N$_3$-PEG12K-b-P(Asp(DET)$_{90}$-co-DLeu$_{10}$)—Ac
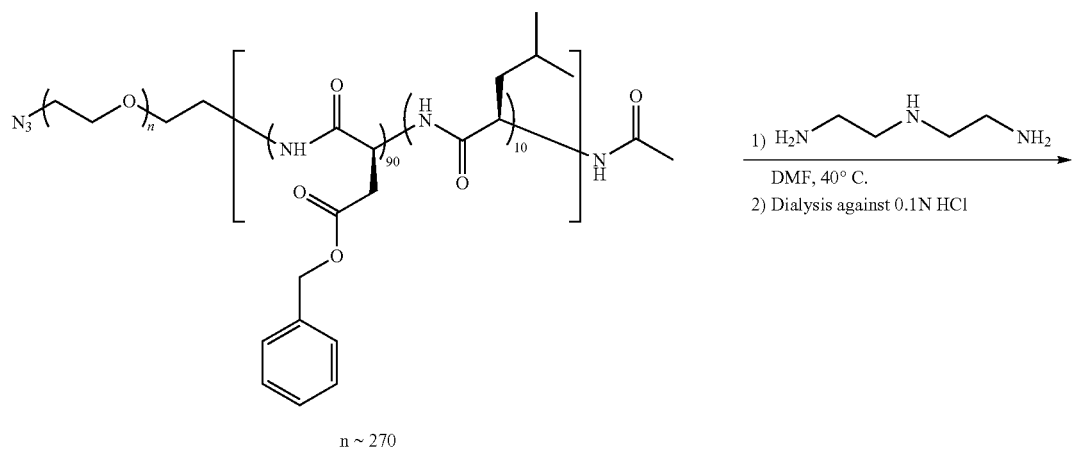

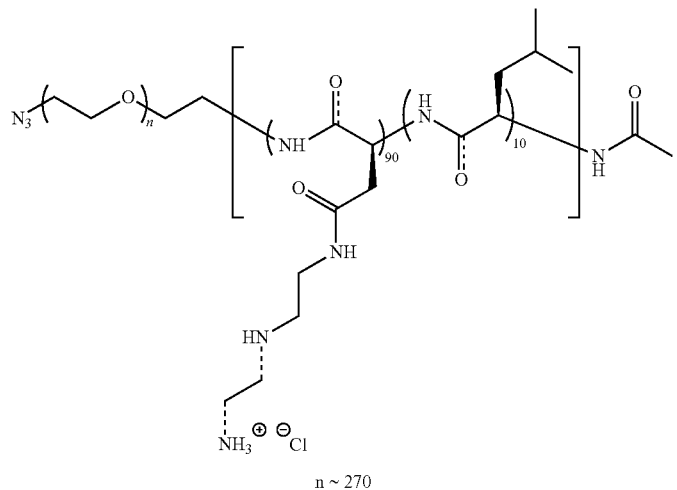
n ~ 270
N₃-PEG12K-b-P(Asp(DET)₉₀-co-DLeu₁₀)—Ac was synthesized as described in Example 38 from N₃-PEG12K-b-P(Asp(OBzl)₉₀-co-DLeu₁₀)—Ac (1 g, 32.1 μmol), diethylenetriamine (DET, vacuum distilled from CaH₂, 5 mL, 46.5 mmol) and DMF (dry, 5 mL). A white fluffy powder was recovered. (0.4505 g, 41.3% yield) $^1$H NMR (D₂O) δ 4.40-4.16, 3.90-3.85, 3.85-3.43, 3.43-3.28, 3.28-3.11, 3.03-2.58, 1.74-1.39, 1.00-0.75 ppm
Example 55
Synthesis of N₃-PEG12K-b-P(Asp(DET)₇₀-co-DLeu₃₀)—Ac
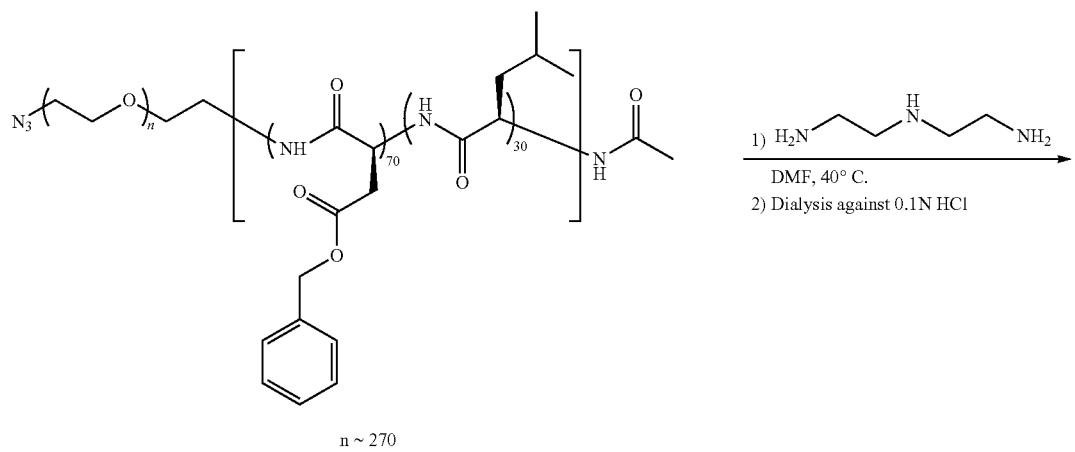
n ~ 270

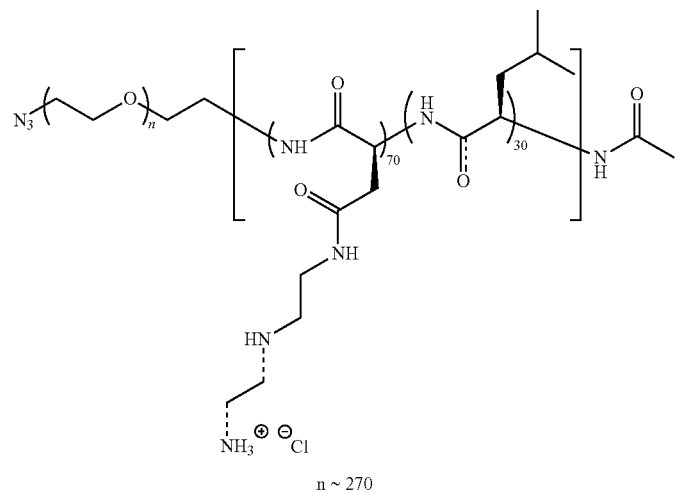
n ~ 270
$N_3$-PEG12K-b-P(Asp(DET)$_{70}$-co-DLeu$_{30}$)—Ac was synthesized as described in Example 38 from $N_3$-PEG12K-b-P(Asp(OBzl)$_{70}$-co-DLeu$_{30}$)—Ac (1 g, 34.1 μmol), diethylenetriamine (DET, vacuum distilled from CaH$_2$, 5 mL, 46.5 mmol) and DMF (dry, 5 mL). A white fluffy powder was recovered. (0.5099 g, 47.4% yield) $^1$H NMR (D$_2$O) δ 4.40-4.16, 3.90-3.85, 3.85-3.43, 3.43-3.28, 3.28-3.11, 3.03-2.58, 1.74-1.39, 1.00-0.75 ppm
Example 56
Synthesis of $N_3$-PEG12K-b-P(Asp(DET)$_{50}$-co-DLeu$_{50}$)—Ac
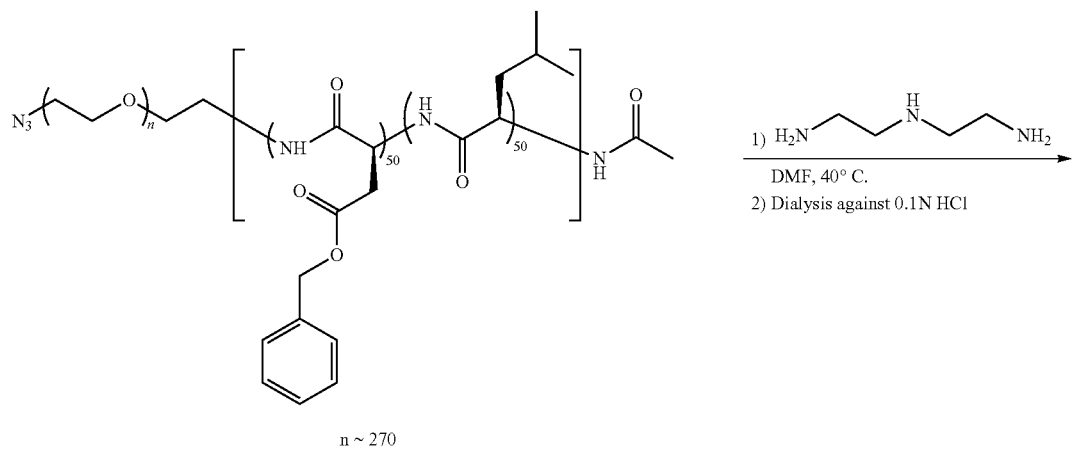
n ~ 270

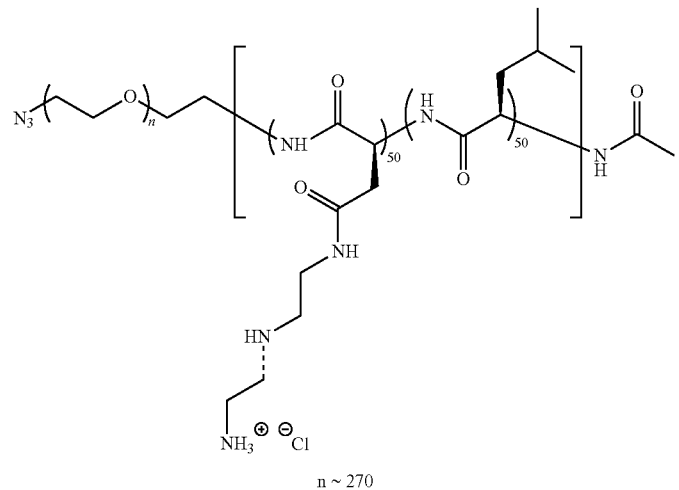
n ~ 270
N₃-PEG12K-b-P(Asp(DET)₅₀-co-DLeu₅₀)—Ac was synthesized as described in Example 38 from N₃-PEG12K-b-P(Asp(OBzl)₅₀-co-DLeu₅₀)—Ac (1 g, 36.5 μmol), diethylenetriamine (DET, vacuum distilled from CaH₂, 5 mL, 46.5 mmol) and DMF (dry, 5 mL). A white fluffy powder was recovered. (0.789 g, 74.5% yield) $^1$H NMR (D₂O) δ 4.40-4.16, 3.90-3.85, 3.85-3.43, 3.43-3.28, 3.28-3.11, 3.03-2.58, 1.74-1.39, 1.00-0.75 ppm
Example 57
Synthesis of N₃-PEG12K-b-P(Asp(DET)₁₈₀-co-DLeu₂₀)—Ac
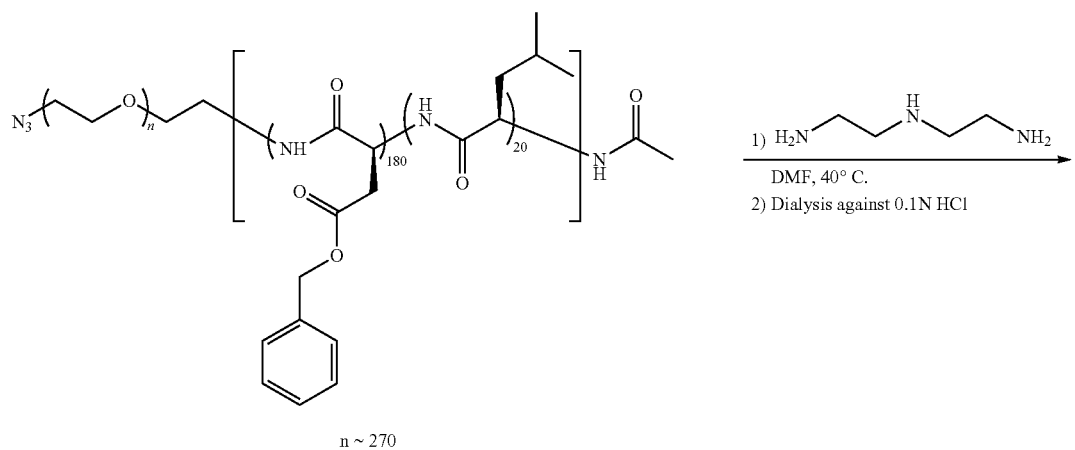
n ~ 270

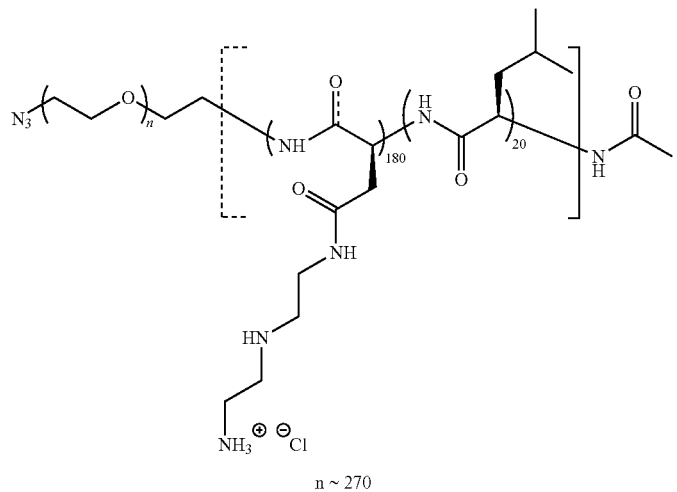
n ~ 270
$N_3$-PEG12K-b-P(Asp(DET)$_{180}$-co-DLeu$_{20}$)—Ac was synthesized as described in Example 38 from $N_3$-PEG12K-b-P(Asp(OBzl)$_{180}$-co-DLeu$_{20}$)—Ac (1 g, 19.7 μmol), diethylenetriamine (DET, vacuum distilled from CaH$_2$, 5 mL, 46.5 mmol) and DMF (dry, 5 mL). A white fluffy powder was recovered. (0.4788 g, 43.0% yield) $^1$H NMR (D$_2$O) δ 4.40-4.16, 3.90-3.85, 3.85-3.43, 3.43-3.28, 3.28-3.11, 3.03-2.58, 1.74-1.39, 1.00-0.75 ppm
Example 58
Synthesis of $N_3$-PEG12K-b-P(Asp(DET)$_{140}$-co-DLeu$_{60}$)—Ac
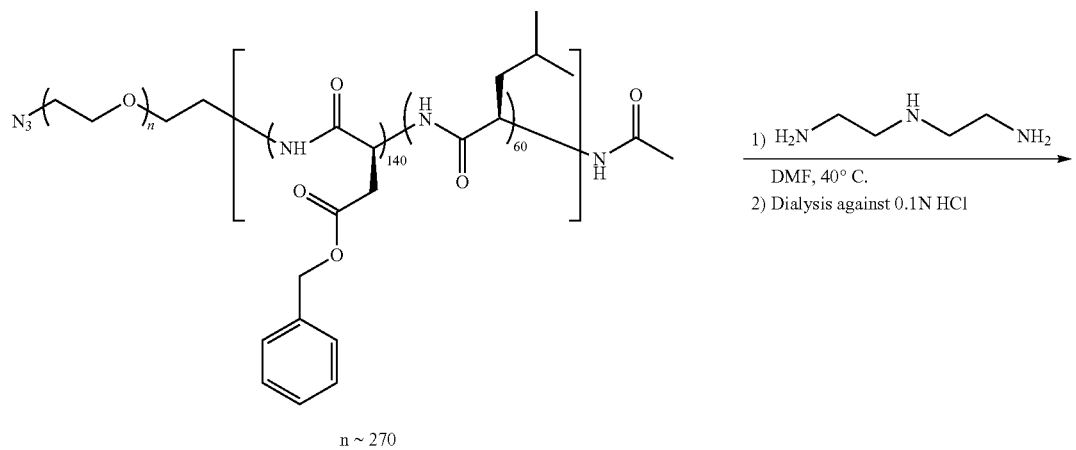
n ~ 270

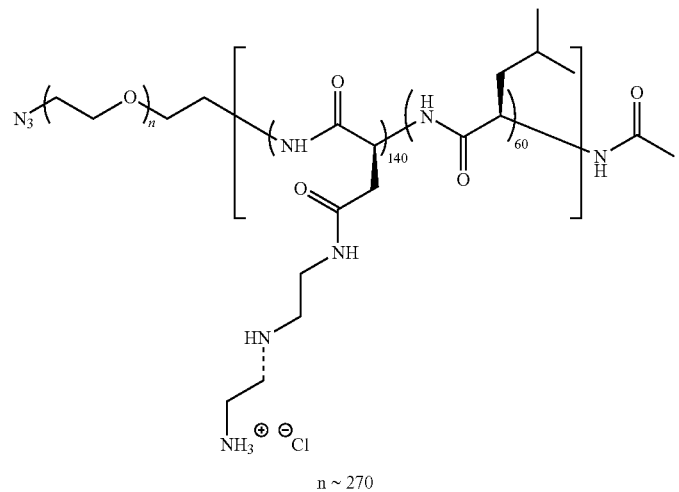
N$_3$-PEG12K-b-P(Asp(DET)$_{140}$-co-DLeu$_{60}$)—Ac was synthesized as described in Example 38 from N$_3$-PEG12K-b-P(Asp(OBzl)$_{140}$-co-DLeu$_{60}$)—Ac (1 g, 21.3 μmol), diethylenetriamine (DET, vacuum distilled from CaH$_2$, 5 mL, 46.5 mmol) and DMF (dry, 5 mL). A white fluffy powder was recovered. (0.5635 g, 51.5% yield) $^1$H NMR (D$_2$O) δ 4.40-4.16, 3.90-3.85, 3.85-3.43, 3.43-3.28, 3.28-3.11, 3.03-2.58, 1.74-1.39, 1.00-0.75 ppm
Example 59
Synthesis of N$_3$-PEG12K-b-P(Asp(DET)$_{100}$-co-DLeu$_{100}$)—Ac
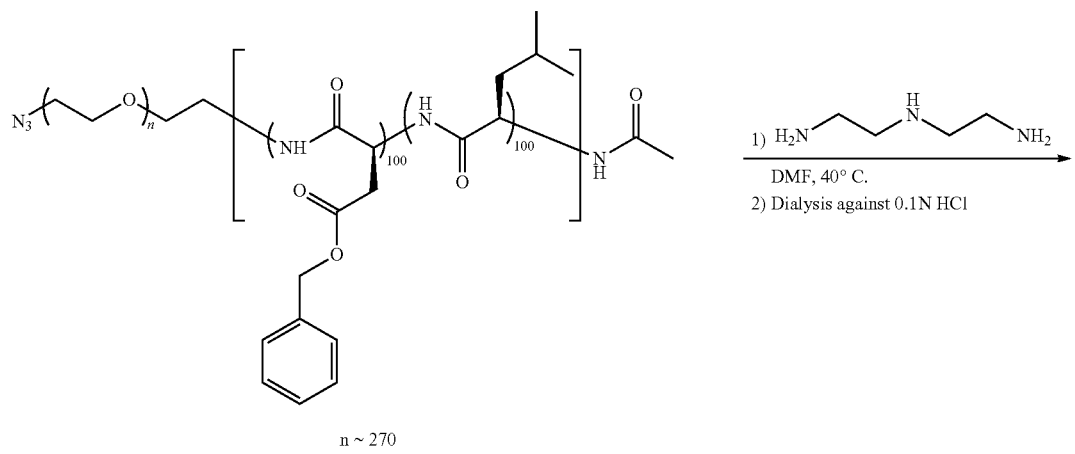

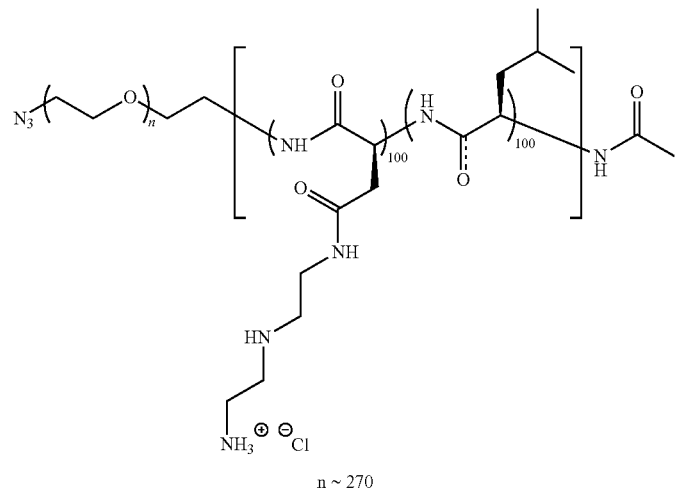
N$_3$-PEG12K-b-P(Asp(DET)$_{100}$-co-DLeu$_{100}$)—Ac was synthesized as described in Example 38 from N$_3$-PEG12K-b-P(Asp(OBzl)$_{100}$-co-DLeu$_{100}$)—Ac (1 g, 23.1 μmol), diethylenetriamine (DET, vacuum distilled from CaH$_2$, 5 mL, 46.5 mmol) and DMF (dry, 5 mL). A white fluffy powder was recovered. (0.8068 g, 75.1% yield) $^1$H NMR (D$_2$O) δ 4.40-4.16, 3.90-3.85, 3.85-3.43, 3.43-3.28, 3.28-3.11, 3.03-2.58, 1.74-1.39, 1.00-0.75 ppm
Example 60
Synthesis of N$_3$-PEG12K-b-P(Asp(DET)$_{190}$-co-DLeu$_{10}$)—Ac
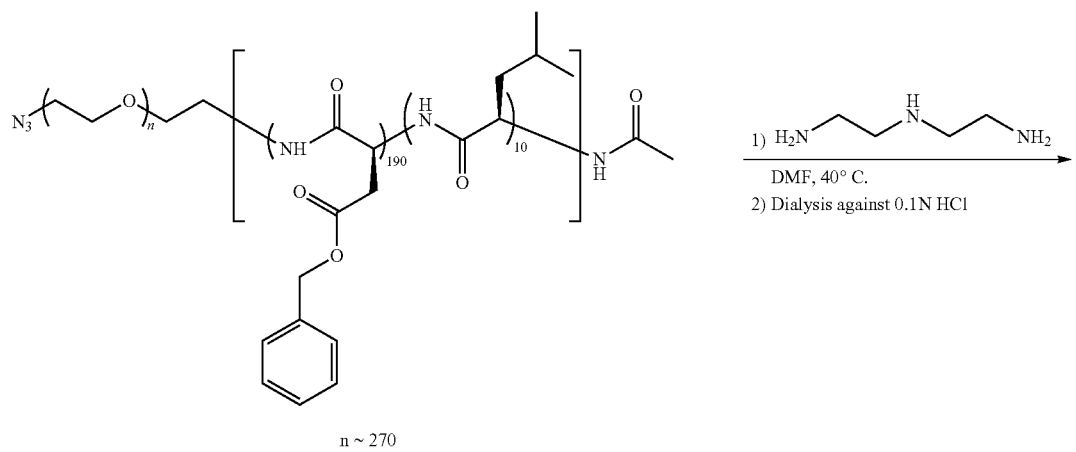

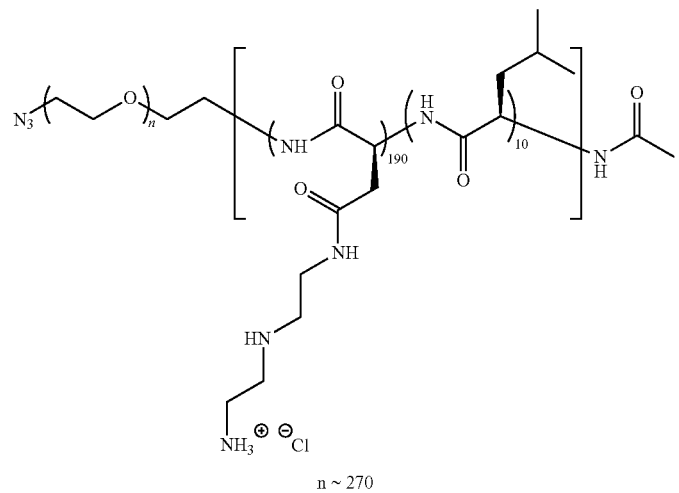
n ~ 270
N₃-PEG12K-b-P(Asp(DET)₁₉₀-co-DLeu₁₀)—Ac was synthesized as described in Example 38 from N₃-PEG12K-b-P(Asp(OBzl)₁₉₀-co-DLeu₁₀)—Ac (1 g, 19.4 μmol), diethylenetriamine (DET, vacuum distilled from CaH₂, 19.8 mL, 184 mmol) and DMF (dry, 10 mL). A white fluffy powder was recovered. (0.528 g, 47.3% yield) ¹H NMR (D₂O) δ 4.40- 4.16, 3.90-3.85, 3.85-3.43, 3.43-3.28, 3.28-3.11, 3.03-2.58, 1.74-1.39, 1.00-0.75 ppm
Example 61
Synthesis of N₃-PEG12K-b-P(Asp(DET)₁₇₀-co-DLeu₃₀)—Ac
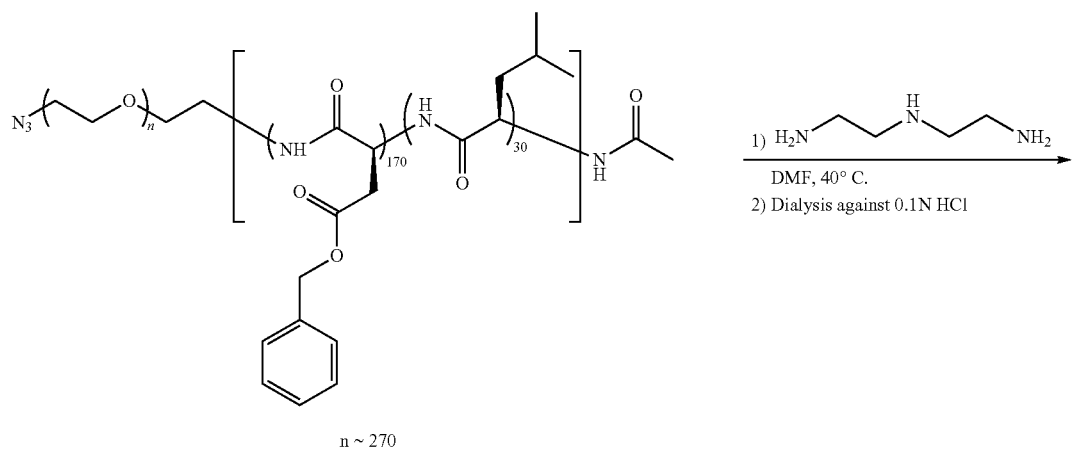
n ~ 270

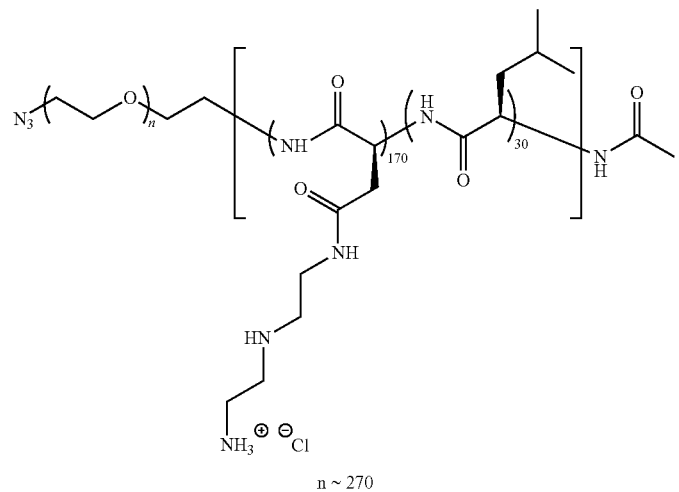
N₃-PEG12K-b-P(Asp(DET)₁₇₀-co-DLeu₃₀)—Ac was synthesized as described in Example 38 from N₃-PEG12K-b-P(Asp(OBzl)₁₇₀-co-DLeu₃₀)—Ac (0.998 g, 20.0 μmol), diethylenetriamine (DET, vacuum distilled from CaH₂, 18.3 mL, 170.3 mmol) and DMF (dry, 10 mL). A white fluffy powder was recovered. (0.501 g, 45.1% yield) ¹H NMR (D₂O) δ 4.40-4.16, 3.90-3.85, 3.85-3.43, 3.43-3.28, 3.28-3.11, 3.03-2.58, 1.74-1.39, 1.00-0.75 ppm
Example 62
Synthesis of N₃-PEG12K-b-P(Asp(DET)₁₆₀-co-DLeu₄₀)—Ac
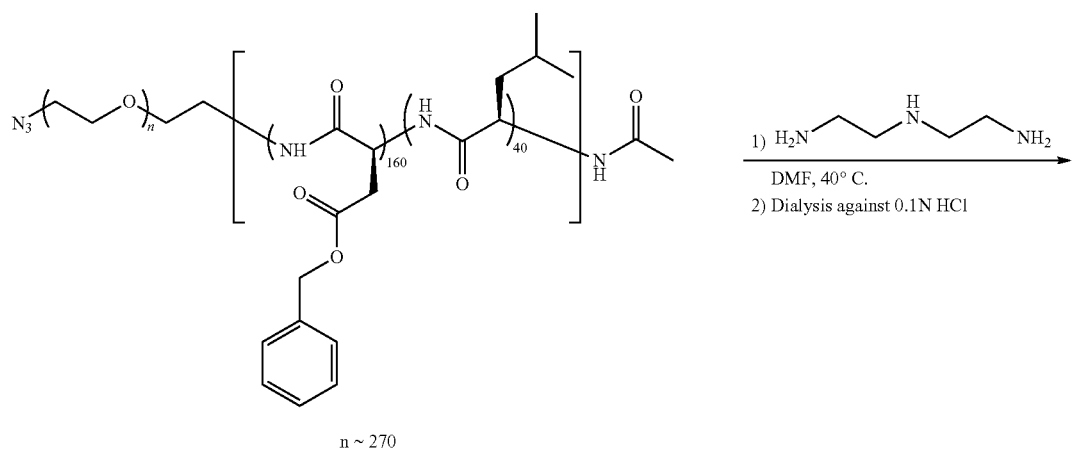

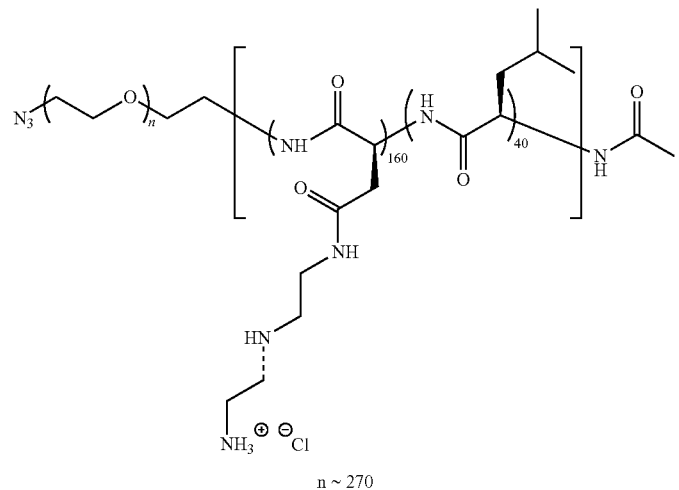
n ~ 270
N₃-PEG12K-b-P(Asp(DET)₁₆₀-co-DLeu₄₀)—Ac was synthesized as described in Example 38 from N₃-PEG12K-b-P(Asp(OBzl)₁₆₀-co-DLeu₄₀)—Ac (0.997 g, 20.4 μmol), diethylenetriamine (DET, vacuum distilled from CaH₂, 17.6 mL, 163.8 mmol) and DMF (dry, 10 mL). A white fluffy powder was recovered. (0.241 g, 21.9% yield) $^1$H NMR (D₂O) δ 4.40-4.16, 3.90-3.85, 3.85-3.43, 3.43-3.28, 3.28-3.11, 3.03-2.58, 1.74-1.39, 1.00-0.75 ppm
Example 63
Synthesis of N₃-PEG12K-b-P(Asp(DET)₁₅₀-co-DLeu₅₀)—Ac
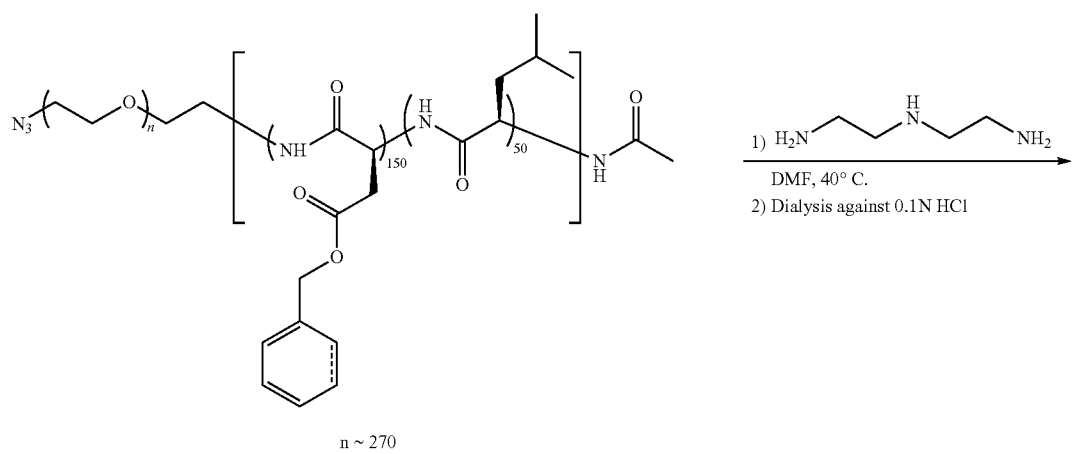
n ~ 270

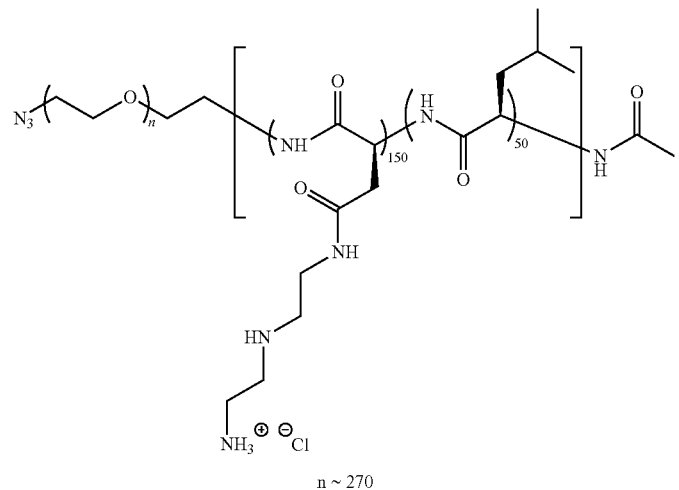
N$_3$-PEG12K-b-P(Asp(DET)$_{150}$-co-DLeu$_{50}$)—Ac was synthesized as described in Example 38 from N$_3$-PEG12K-b-P(Asp(OBzl)$_{150}$-co-DLeu$_{50}$)—Ac (0.996 g, 20.8 μmol), diethylenetriamine (DET, vacuum distilled from CaH$_2$, 16.8 mL, 156.3 mmol) and DMF (dry, 10 mL). A white fluffy powder was recovered. (0.600 g, 54.5% yield) $^1$H NMR (D$_2$O) δ 4.40-4.16, 3.90-3.85, 3.85-3.43, 3.43-3.28, 3.28-3.11, 3.03-2.58, 1.74-1.39, 1.00-0.75 ppm
Example 64
Synthesis of UPAR-PEG12K-b-P(Asp(OBzl)$_{90}$-co-DLeu$_{10}$)—Ac
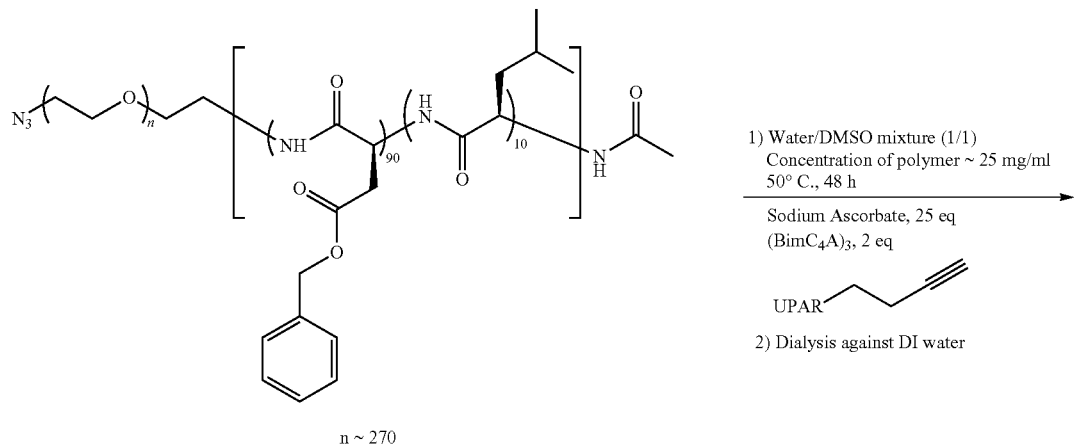

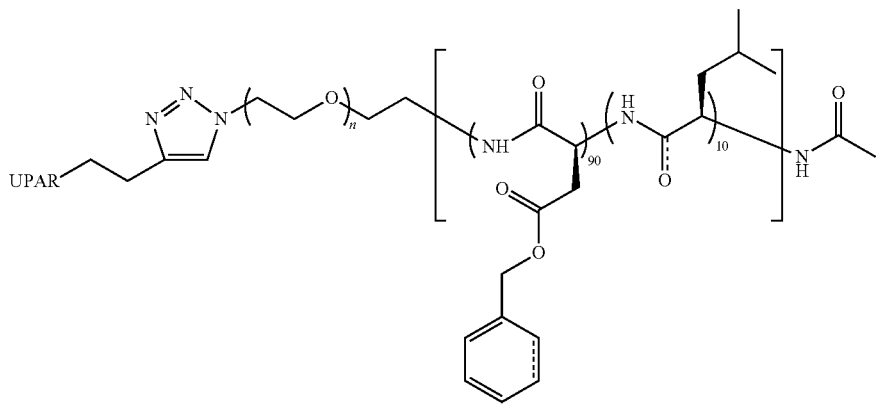

N$_3$-PEG12K-b-P(Asp(OBzl)$_{90}$-co-DLeu$_{10}$)—Ac (296.93 mg, 9.55 μmol), UPAR-Alkyne (12.27 mg, 12.9 μmol), sodium ascorbate (62.19 mg, 242 mmol), (BimC4A)$_3$ (18.9 mg, 19.3 μmol), CuSO$_4$.5H$_2$O (2.4 mg, 9.6 μmol), DMSO (6 mL) and water (6 mL) were added into a 20 mL vial, capped and stirred for 48 hr at 50° C. The light brown solution was dialyzed (3500 MWCO bag) 3 times against DI water with EDTA (15 g/L) and 2 times against DI water. The solution was freeze-dried and an off-white powder was obtained. (275.01 mg, 90% yield). $^1$H NMR (D$_2$O) δ 8.17, 7.84, 7.45-7.31, 4.61-4.23, 4.05-3.34, 2.98, 2.65, 2.46-2.26, 2.16-1.86, 1.86-1.50, 1.46-1.31, 0.96-0.78 ppm Example 65

Synthesis of UPAR-PEG12K-b-P(Asp(DET)$_{90}$-co-DLeu$_{10}$)—Ac

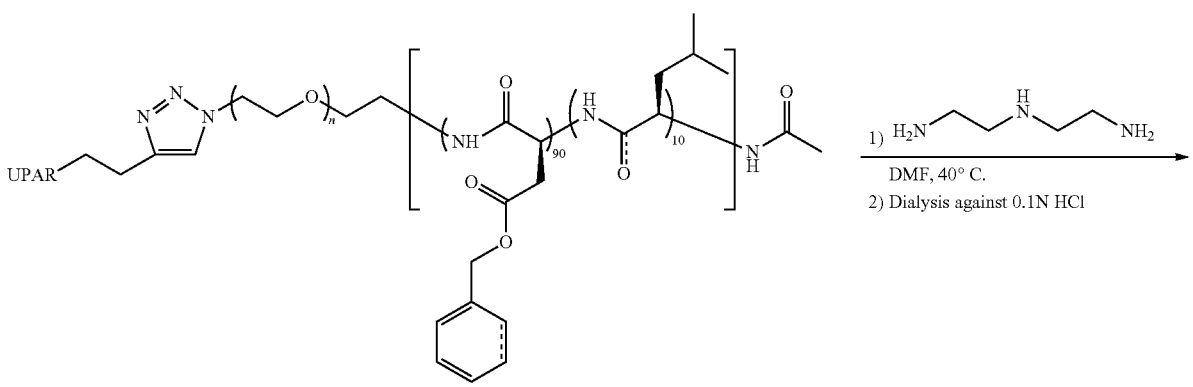

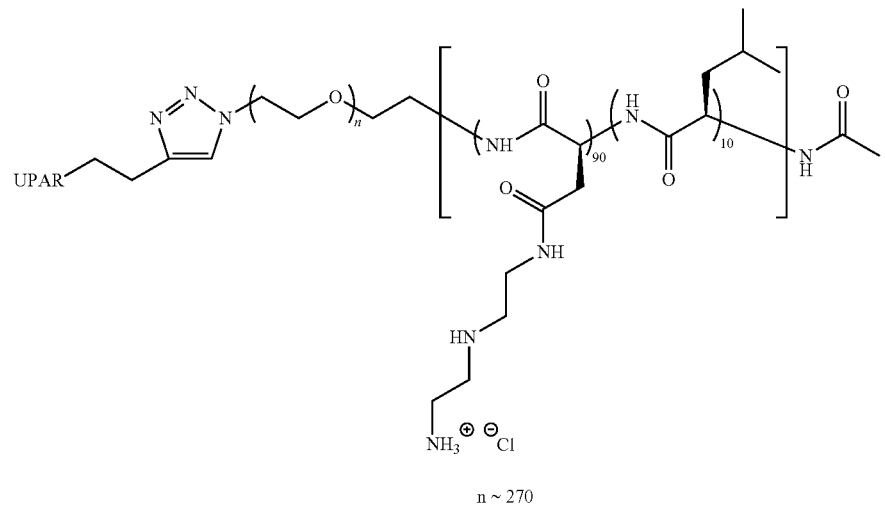
n ~ 270
UPAR-PEG12K-b-P(Asp(DET)$_{90}$-co-DLeu$_{10}$)—Ac was synthesized as described in Example 38 from N$_3$-PEG12K-b-P(OBzl)$_{90}$-co-DLeu$_{10}$)—Ac (0.2461 g, 7.7 μmol), diethylenetriamine (DET, vacuum distilled from CaH$_2$, 3.71 mL, 34.5 mmol) and DMF (dry, 3.7 mL). A white fluffy powder was recovered. (0.264 g, 98% yield) $^1$H NMR (D$_2$O) δ 8.42, 7.82, 4.58, 4.39-4.20, 4.01, 3.95-3.78, 3.78-3.66, 3.66-3.46, 3.46-3.31, 3.31-3.16, 3.09-2.56, 2.36-2.23, 2.10-1.86, 1.79-1.42, 0.95-0.79 ppm.
Example 66
Synthesis of UPAR-PEG12K-b-P(Asp(OBzl)$_{180}$-co-DLeu$_{20}$)—Ac
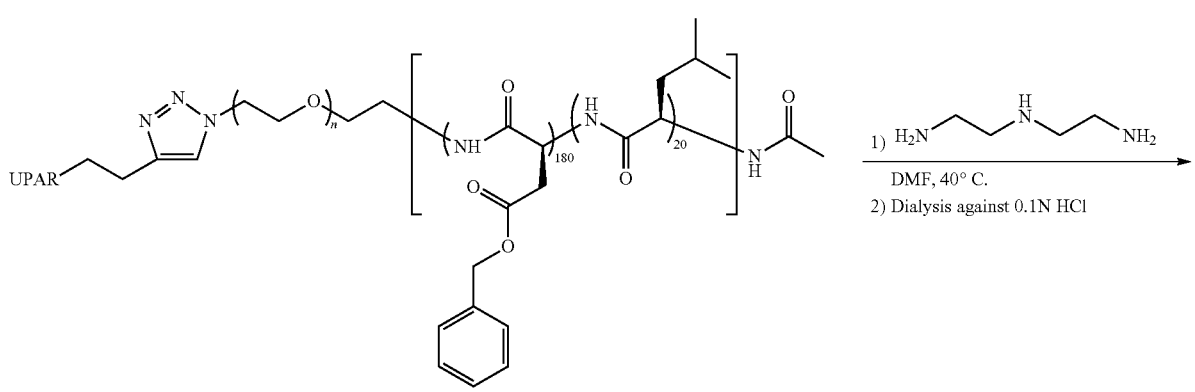
n ~ 270

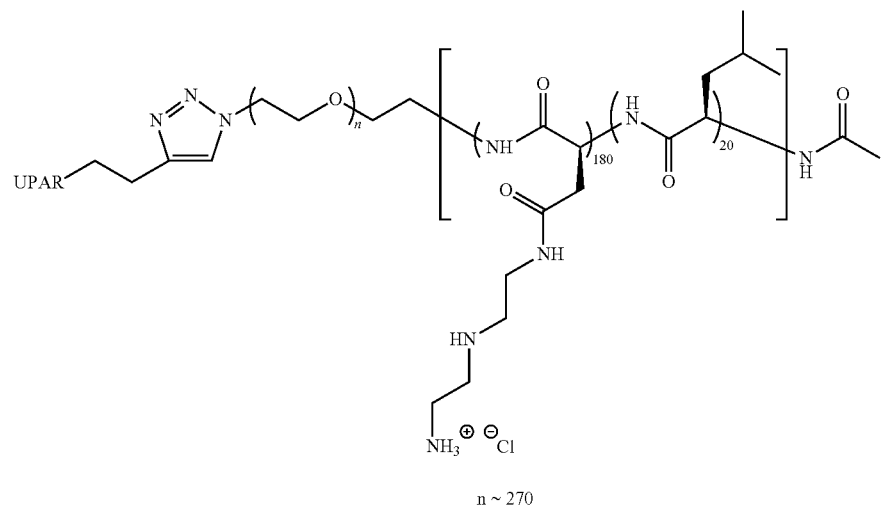

N$_3$-PEG12K-b-P(Asp(OBzl)$_{180}$-co-DLeu$_{20}$)—Ac (301.37 mg, 5.94 μmol), UPAR-Alkyne (7.93 mg, 8.3 μmol), sodium ascorbate (44.6 mg, 225 mmol), (BimC4A)$_3$ (9.72 mg, 13.7 μmol), CuSO$_4$.5H$_2$O (1.5 mg, 6 μmol), DMSO (6 mL) and water (6 mL) were added into a 20 mL vial, capped and stirred for 48 hr at 50° C. The light brown solution was dialyzed (3500 MWCO bag) 3 times against DI water with EDTA (15 g/L) and 2 times against DI water. The solution was freeze-dried and an off-white powder was obtained. (280.02 mg, 91.3% yield). $^1$H NMR (D$_2$O) δ 8.17, 7.84, 7.45-7.31, 4.61-4.23, 4.05-3.34, 2.98, 2.65, 2.46-2.26, 2.16-1.86, 1.86-1.50, 1.46-1.31, 0.96-0.78 ppm Example 67

Synthesis of UPAR-PEG12K-b-P(Asp(DET)$_{180}$-co-DLeu$_{20}$)—Ac

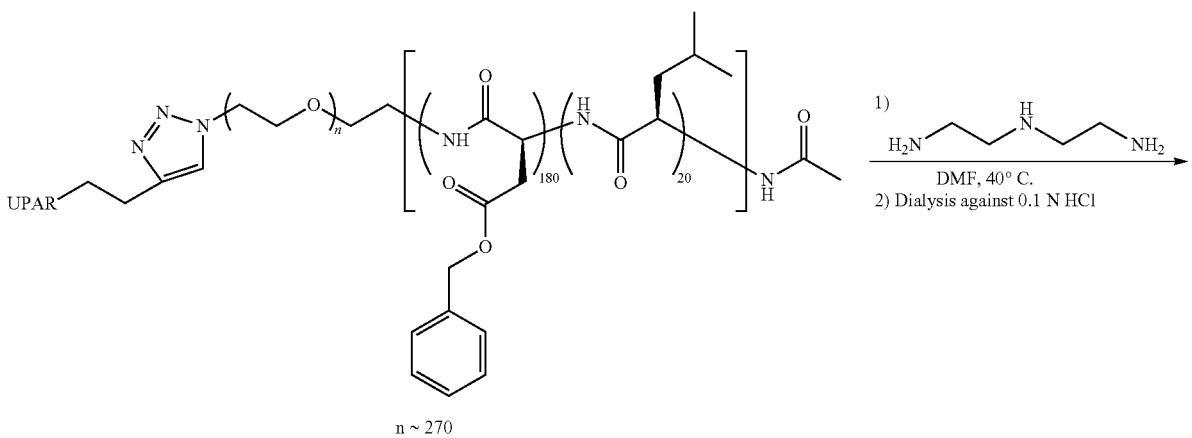

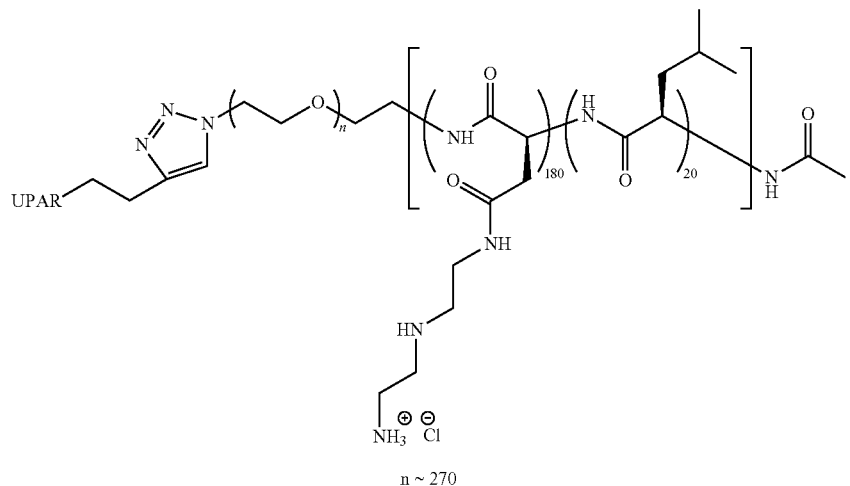
UPAR-PEG12K-b-P(Asp(DET)$_{180}$-co-DLeu$_{20}$)—Ac was synthesized as described in Example 38 from N$_3$-PEG12K-b-P(Asp(OBzl)$_{180}$-co-DLeu$_{20}$)—Ac (0.2529 g, 4.9 μmol), diethylenetriamine (DET, vacuum distilled from CaH$_2$, 4.7 mL, 43.7 mmol) and DMF (dry, 4.7 mL). A white fluffy powder was recovered. (0.253 g, 90% yield) $^1$H NMR (D$_2$O) δ 8.42, 7.82, 4.58, 4.39-4.20, 4.01, 3.95-3.78, 3.78-3.66, 3.66-3.46, 3.46-3.31, 3.31-3.16, 3.09-2.56, 2.36-2.23, 2.10-1.86, 1.79-1.42, 0.95-0.79 ppm.
Example 68
Synthesis of UPAR-PEG12K-b-P(Asp(OBzl)$_{140}$-co-DLeu$_{60}$)—Ac
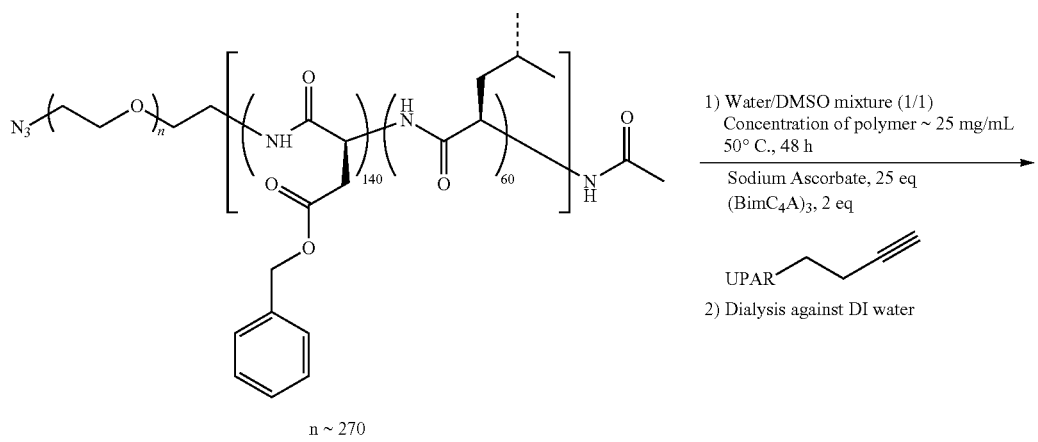

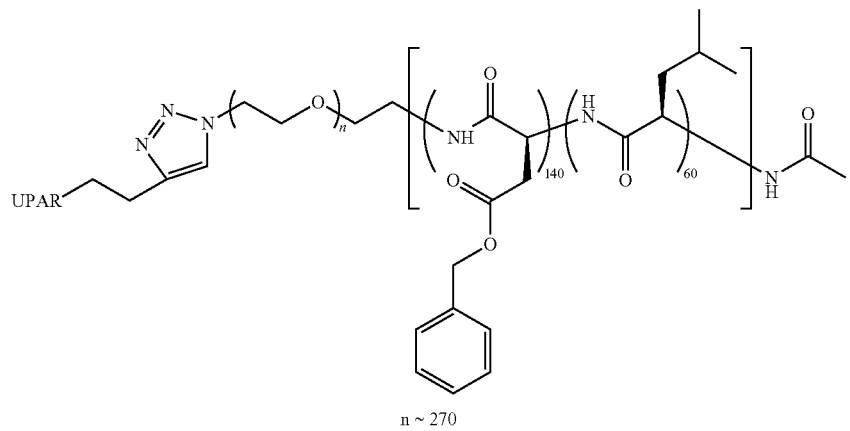

n ~ 270

$N_3$-PEG12K-b-P(Asp(OBzl)$_{140}$-co-DLeu$_{60}$)—Ac (289.57 mg, 6.2 μmol), UPAR-Alkyne (10.07 mg, 10.6 μmol), sodium ascorbate (37.99 mg, 192 mmol), (BimC4A)$_3$ (12.58 mg, 17.7 μmol), CuSO$_4$.5H$_2$O (1.6 mg, 6.4 μmol), DMSO (6 mL) and water (6 mL) were added into a 20 mL vial, capped and stirred for 48 hr at 50° C. The light brown solution was dialyzed (3500 MWCO bag) 3 times against DI water with EDTA (15 g/L) and 2 times against DI water. The solution was freeze-dried and an off-white powder was obtained. (278.43 mg, 94.2% yield). $^1$H NMR (D$_2$O) δ 8.17, 7.84, 7.45-7.31, 4.61-4.23, 4.05-3.34, 2.98, 2.65, 2.46-2.26, 2.16-1.86, 1.86-1.50, 1.46-1.31, 0.96-0.78 ppm Example 69

Synthesis of UPAR-PEG12K-b-P(Asp(DET)$_{140}$-co-DLeu$_{60}$)—Ac

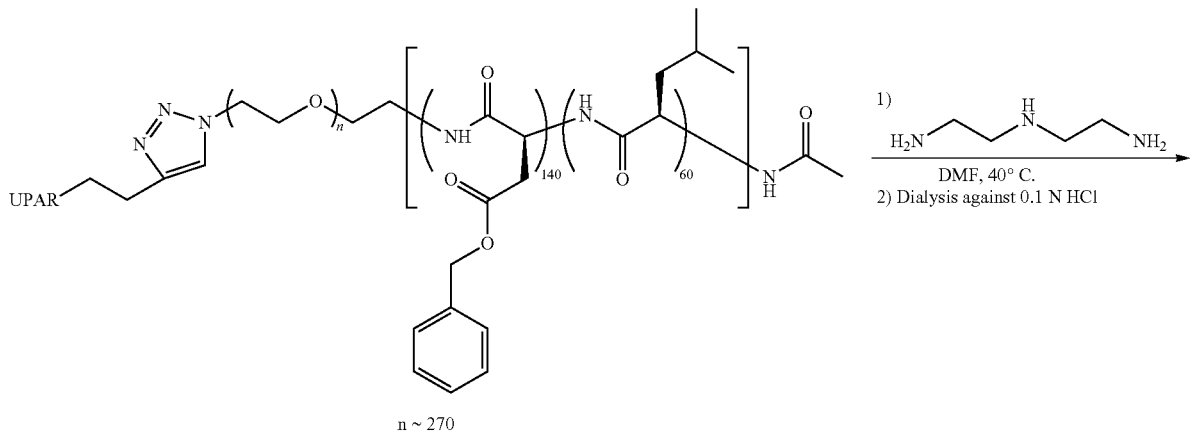

n ~ 270

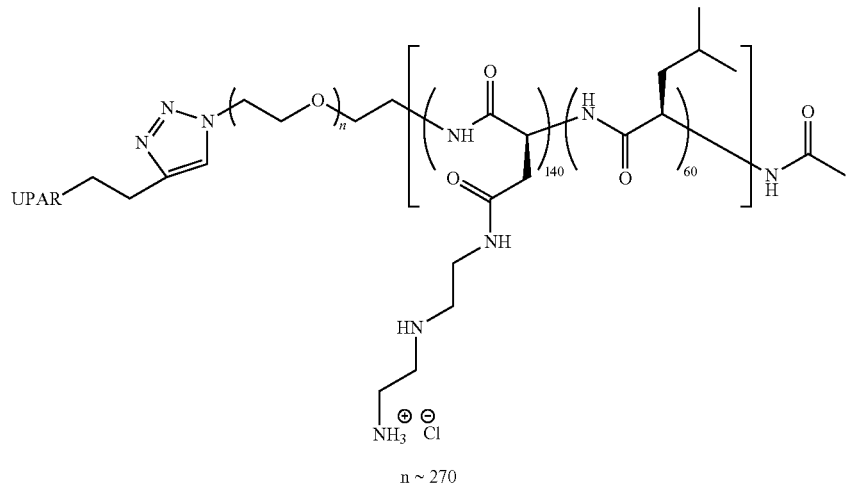
UPAR-PEG12K-b-P(Asp(DET)$_{140}$-co-DLeu$_{60}$)—Ac was synthesized as described in Example 38 from N$_3$-PEG12K-b-P(Asp(OBzl)$_{140}$-co-DLeu$_{60}$)—Ac (0.2767 g, 5.8 μmol), diethylenetriamine (DET, vacuum distilled from CaH$_2$, 4.3 mL, 40.0 mmol) and DMF (dry, 4.3 mL). A white fluffy powder was recovered. (0.265 g, 87.6% yield) $^1$H NMR (D$_2$O) δ 8.42, 7.82, 4.58, 4.39-4.20, 4.01, 3.95-3.78, 3.78-3.66, 3.66-3.46, 3.46-3.31, 3.31-3.16, 3.09-2.56, 2.36-2.23, 2.10-1.86, 1.79-1.42, 0.95-0.79 ppm
Example 70
Synthesis of N3-PEG12K-b-P(Asp(FITC)$_1$-co-Asp(DET)$_{89}$-co-DLeu$_{10}$)—Ac
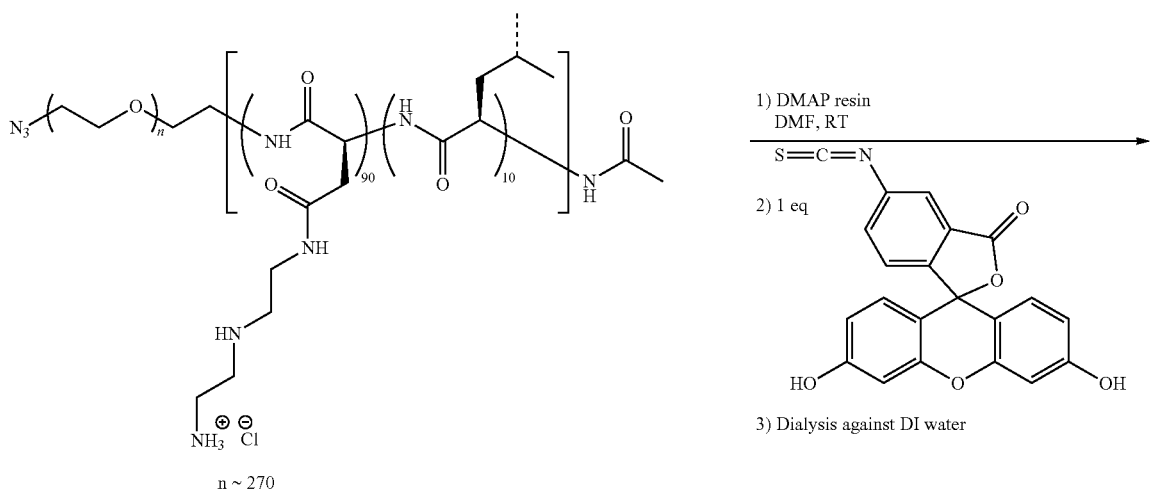

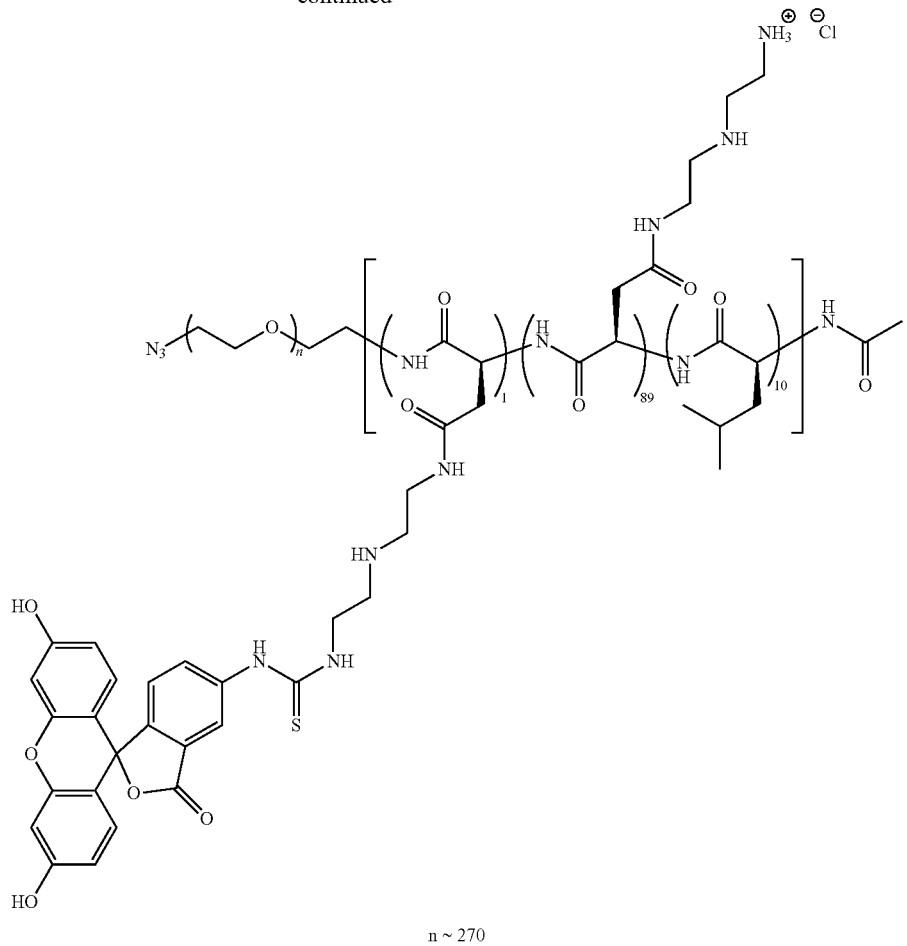

n ~ 270

$N_3$-PEG12K-b-P(Asp(DET)$_{90}$-co-DLeu$_{10}$)—Ac (100 mg, 2.95 μmol) was weighed into an oven-dried two neck round bottom flask and three vacuum/N2 cycles were applied. DMAP resin (1.47 mmol DMAP/g resin, 4 mg, 5.88 μmol), FITC (1.15 mg, 2.95 μmol) and DMSO (4 mL) were introduced into the reaction flask and were left reacting at room temperature overnight. The solution was then filtered through a Whatman filter paper #2, placed in a 3500 molecular weight cut-off dialysis bag, dialyzed 5 times against deionized water. The solution was filtered through a 0.45 μm filter and freeze dried. The polymer was recovered as a yellow fluffy powder (35 mg, 35% yield).

Example 71

Synthesis of N3-PEG12K-b-P(Asp(FITC)$_1$-co-Asp(DET)$_{179}$-co-DLeu$_{20}$)—Ac

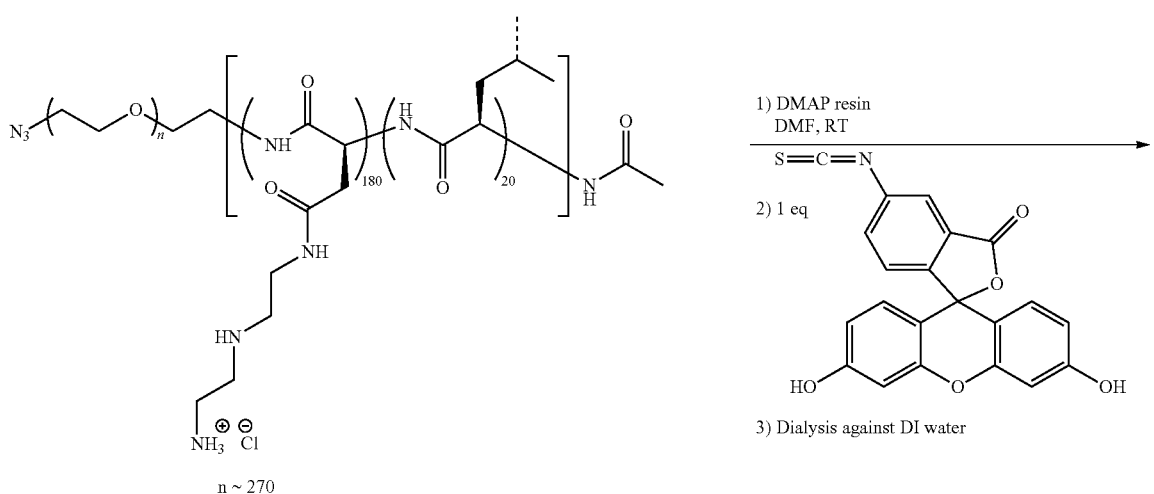

n ~ 270

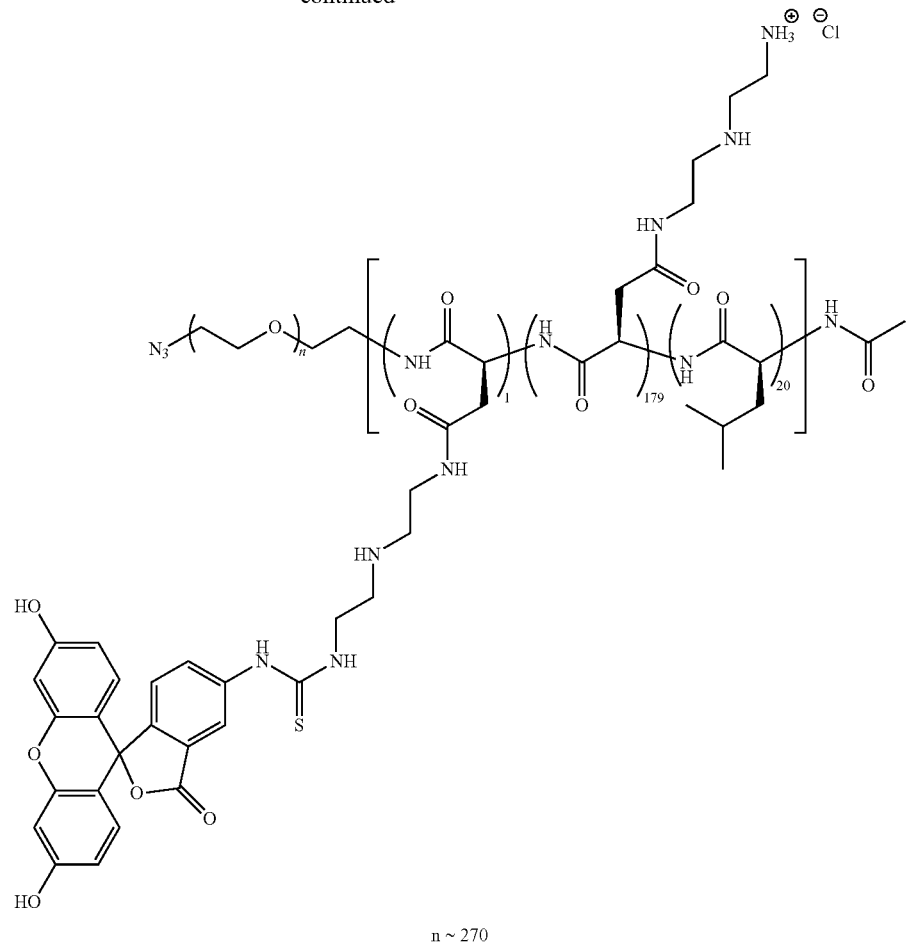
n ~ 270
$N_3$-PEG12K-b-P(Asp(FITC)$_1$-co-Asp(DET)$_{179}$-co-DLeu$_{20}$)—Ac was synthesized as described in Example 70 with N3-PEG12K-b-P(Asp(DET)$_{180}$-co-DLeu$_{10}$)—Ac (100 mg, 1.77 µmol), DMAP resin (1.47 mmol DMAP/g resin, 2.4 mg, 3.55 mmol), FITC (0.69 mg, 1.77 mmol) and DMSO (4 mL). The polymer was recovered as a yellow fluffy powder (25 mg, 25% yield).
Example 72
Synthesis of N3-PEG12K-b-P(Asp(FITC)$_1$-co-Asp(DET)$_{139}$-co-DLeu$_{60}$)—Ac
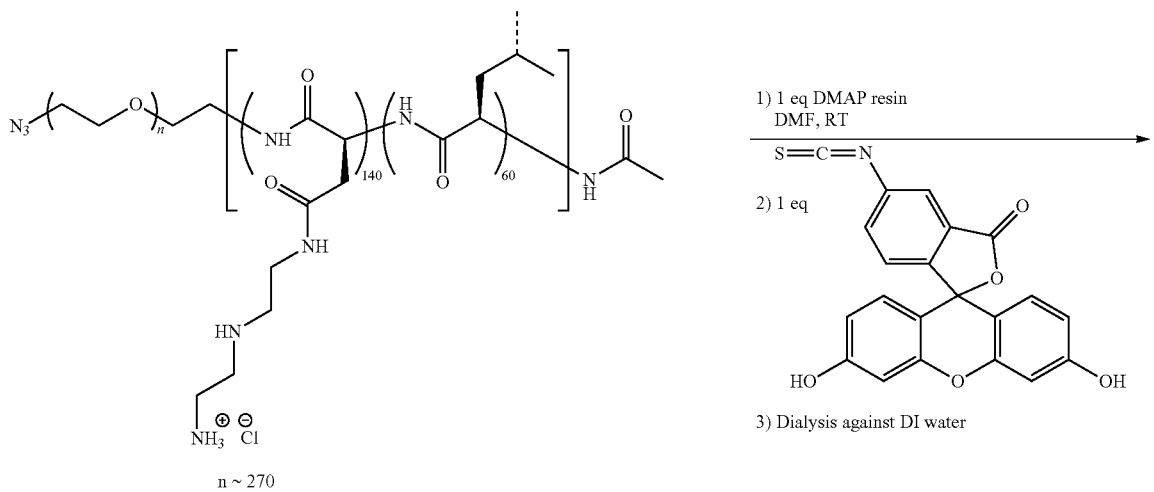
n ~ 270

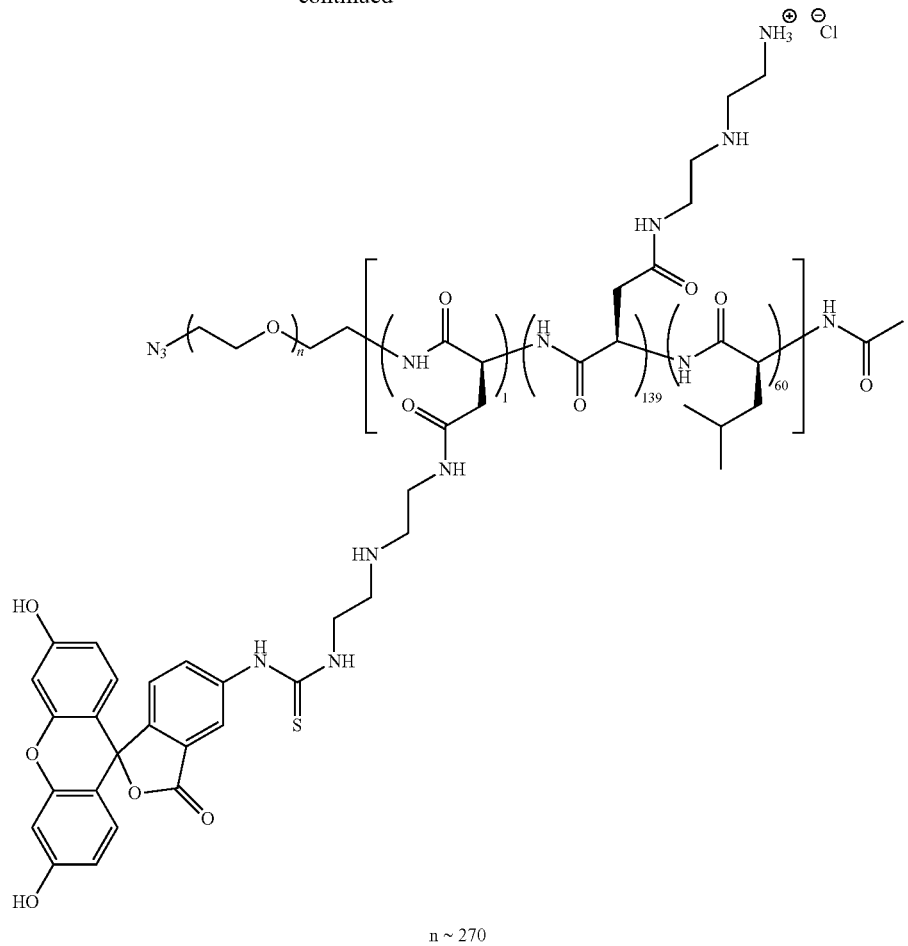
n ~ 270
N$_3$-PEG12K-b-P(Asp(FITC)$_1$-co-Asp(DET)$_{139}$-co-DLeu$_{60}$)—Ac was synthesized as described in Example 70 with N3-PEG12K-b-P(Asp(DET)$_{140}$-co-DLeu$_{60}$)—Ac (100 mg, 1.94 μmol), DMAP resin (1.47 mmol DMAP/g resin, 2.6 mg, 3.89 μmol), FITC (0.76 mg, 1.94 mmol) and DMSO (4 mL). The polymer was recovered as a yellow fluffy powder (50.6 mg, 56% yield).
Example 73
Synthesis of N$_3$-PEG12k-b-P(D-Leu$_{10}$-co-Phe$_{10}$)-b-P(Asp(OBzl)$_{50}$-co-D-Asp(OBzl)$_{50}$)—Ac
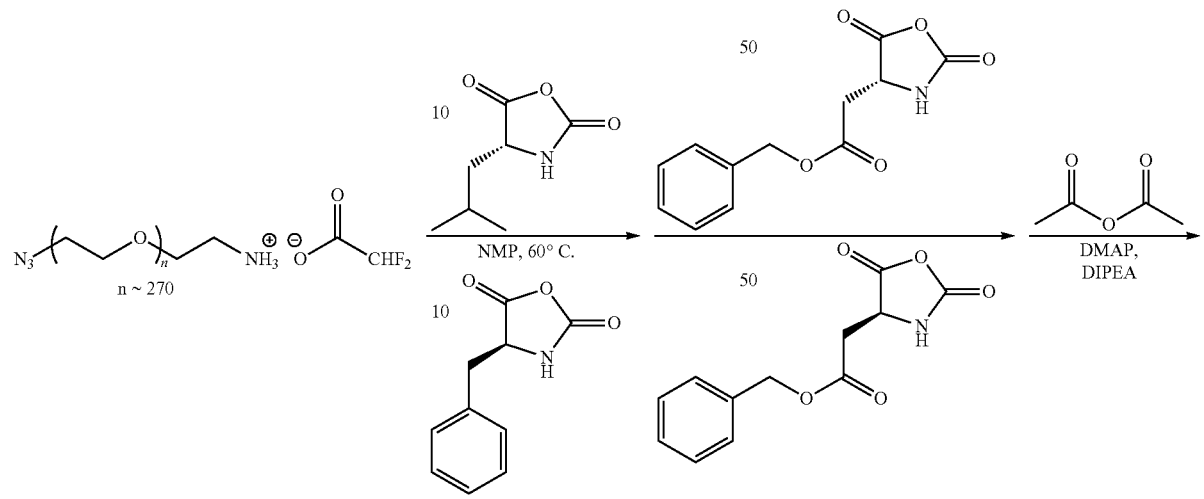

-continued
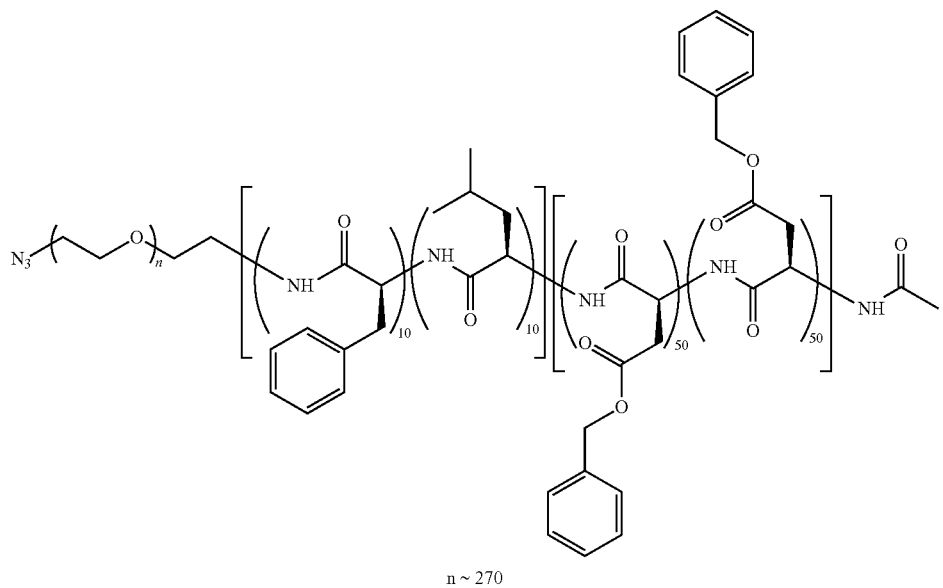
n ~ 270
Example 74
Synthesis of $N_3$-PEG12k-b-P(D-Leu$_{10}$-co-Phe$_{10}$)-b-P(Asp(DET)$_{50}$-co-D-Asp(DET)$_{50}$)—Ac
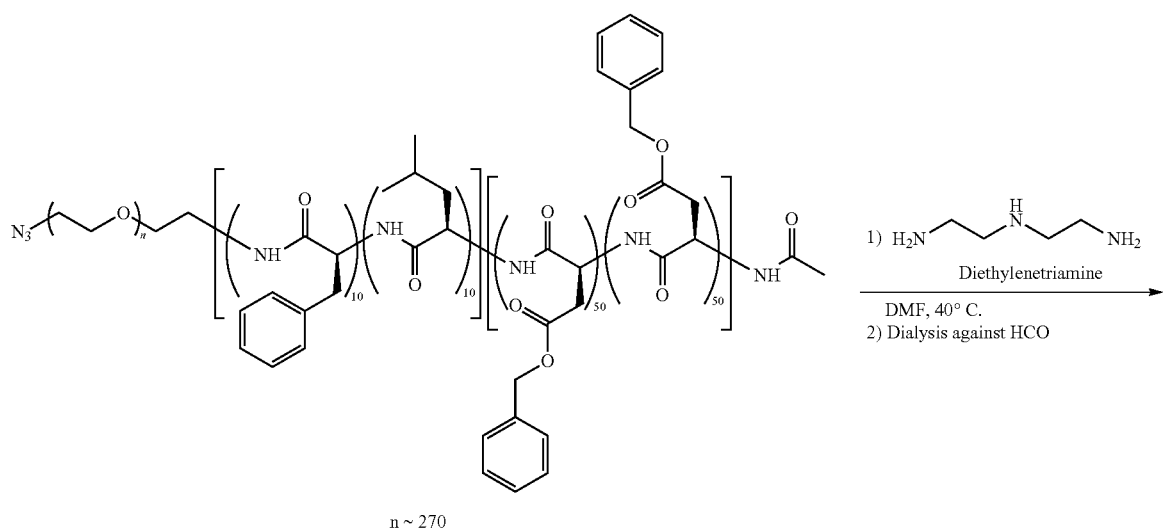
n ~ 270

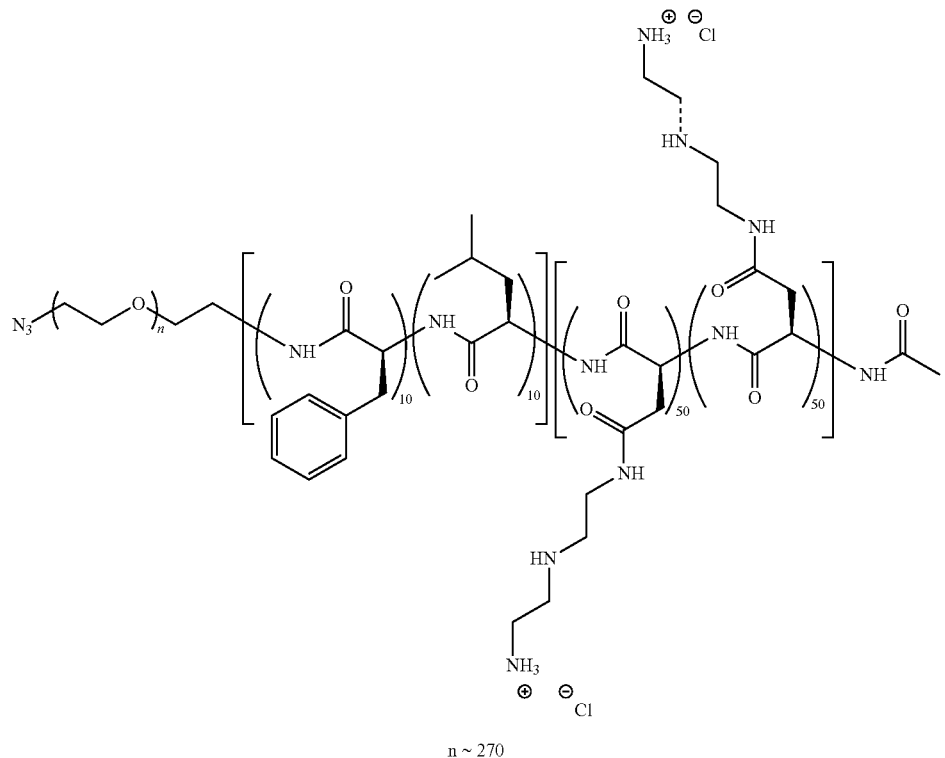
n ~ 270
Example 75
Synthesis of UPAR-PEG12k-b-P(D-Leu$_{10}$-co-Phe$_{10}$)-b-P(Asp(OBzl)$_{50}$-co-D-Asp(OBzl)$_{50}$)—Ac
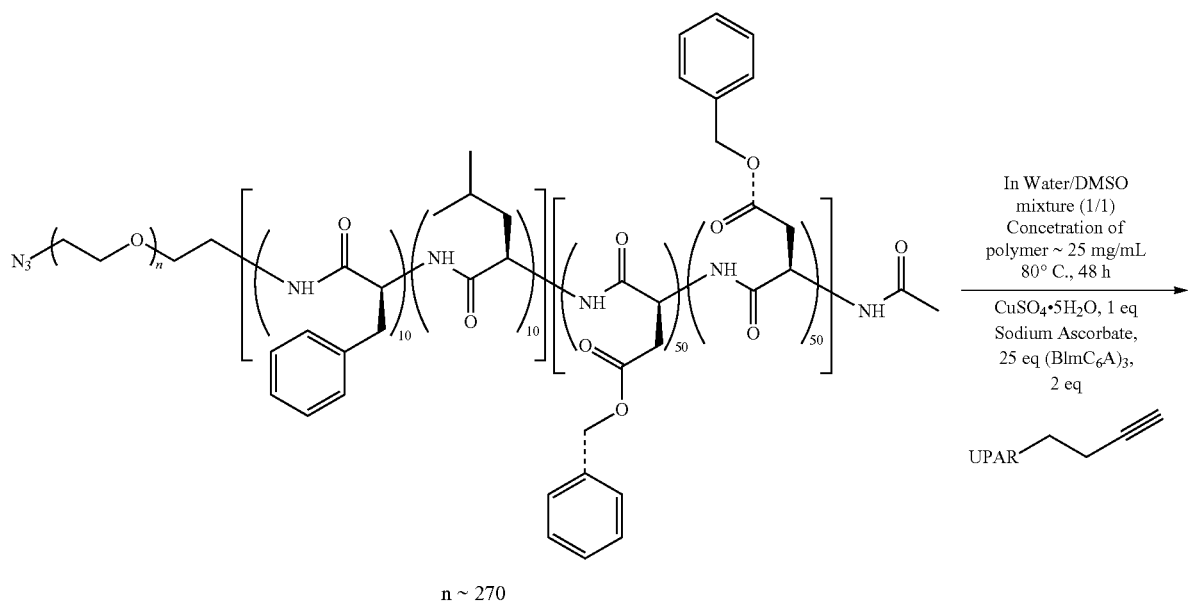
n ~ 270

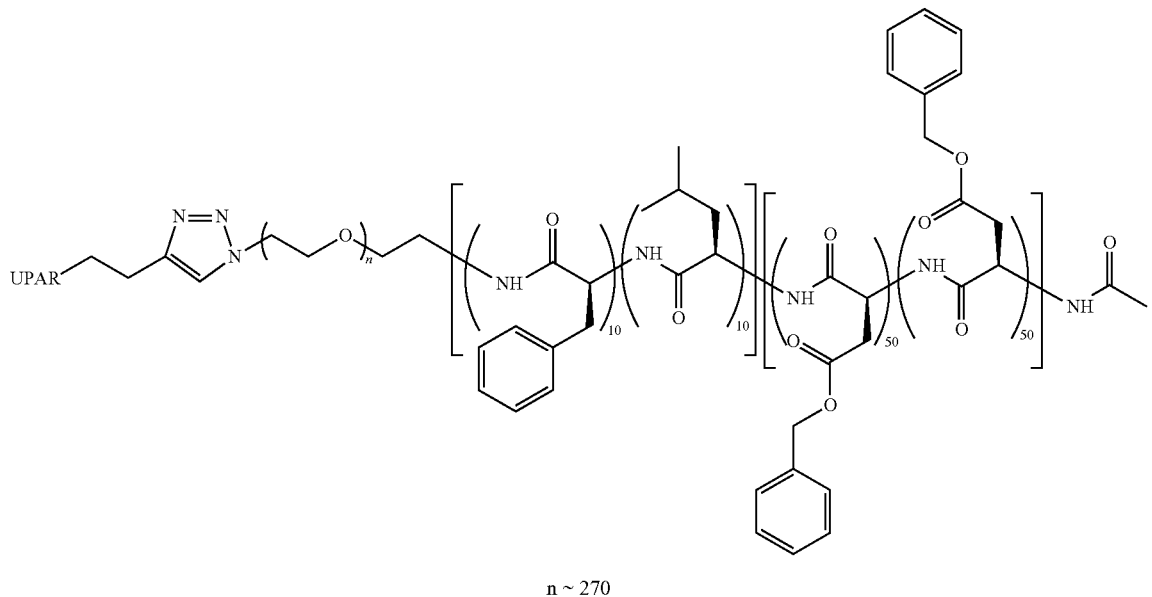
n ~ 270
Example 76
Synthesis of UPAR-PEG12k-b-P(D-Leu$_{10}$-co-Phe$_{10}$)-b-P(Asp(DET)$_{50}$-co-D-Asp(DET)$_{50}$)—Ac
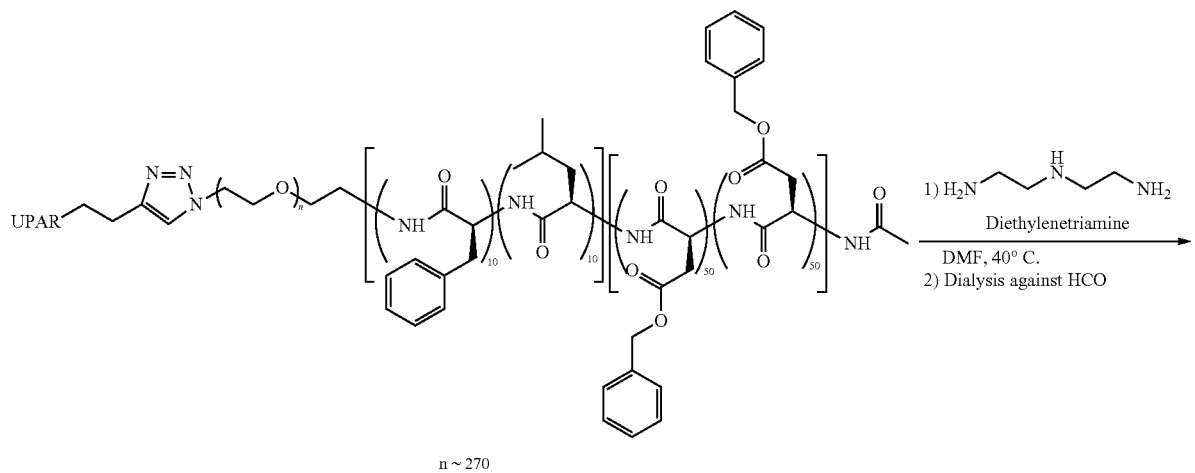
n ~ 270

-continued
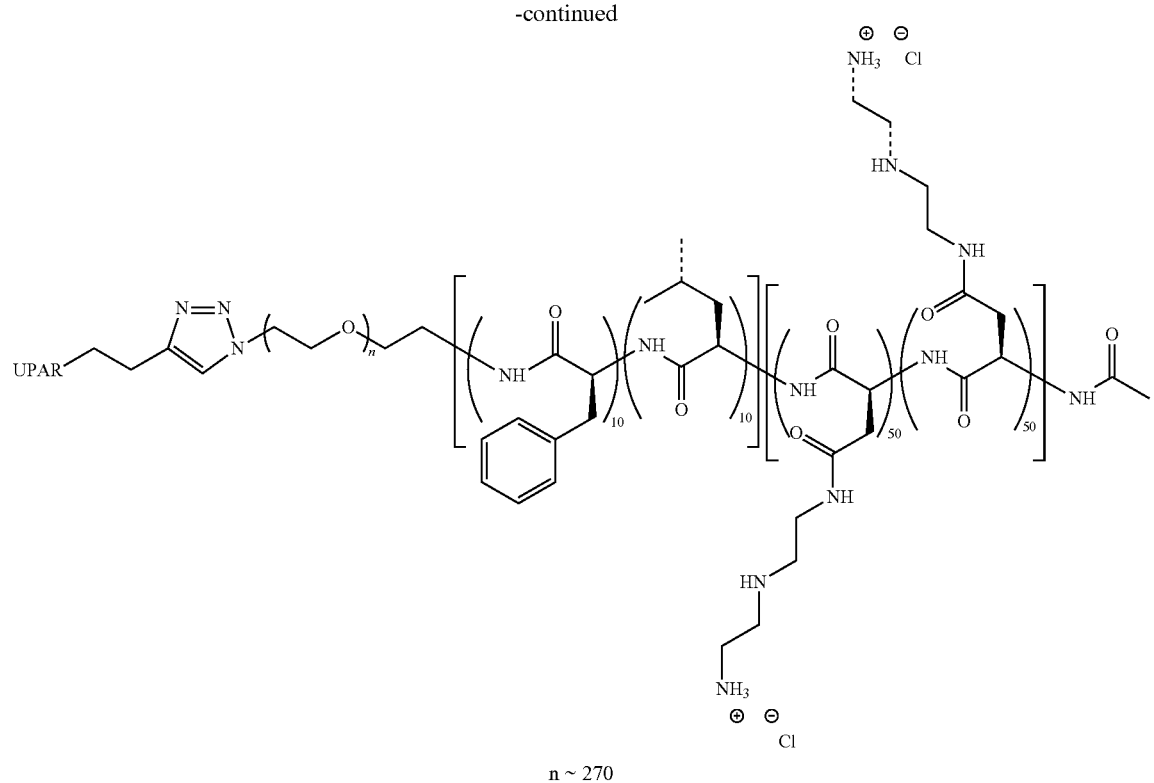
n ~ 270
Example 77
Synthesis of Alkyne-P(D-Leu₁₀-co-Phe₁₀)-b-P(Asp(OBzl)₅₀-co-D-Asp(OBzl)₅₀)-b-P(D-Leu₁₀-co-Phe₁₀)-alkyne
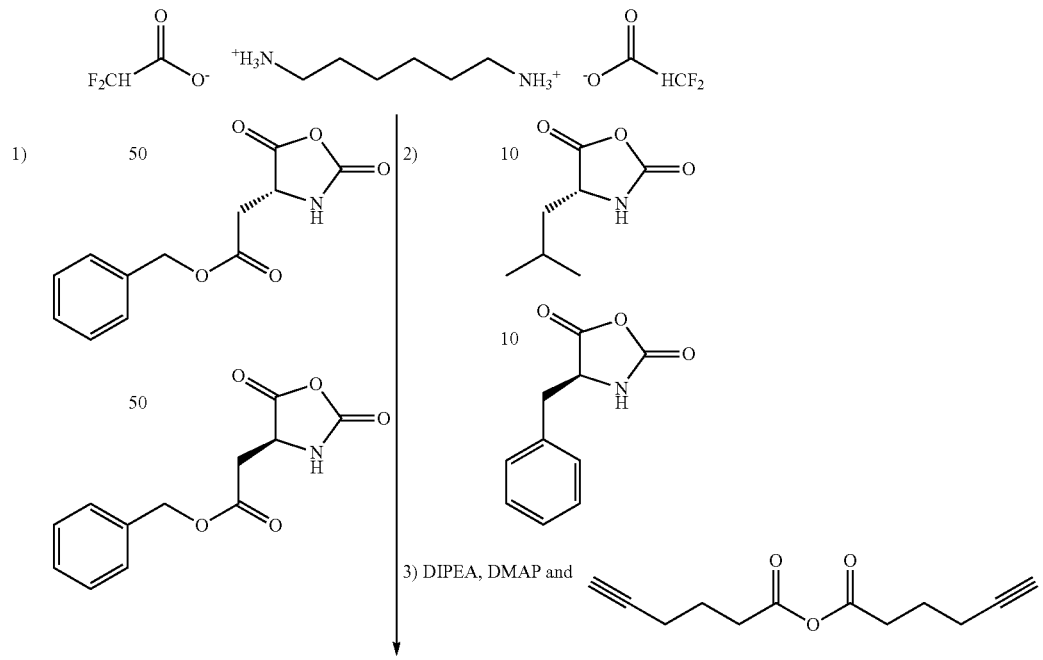

-continued
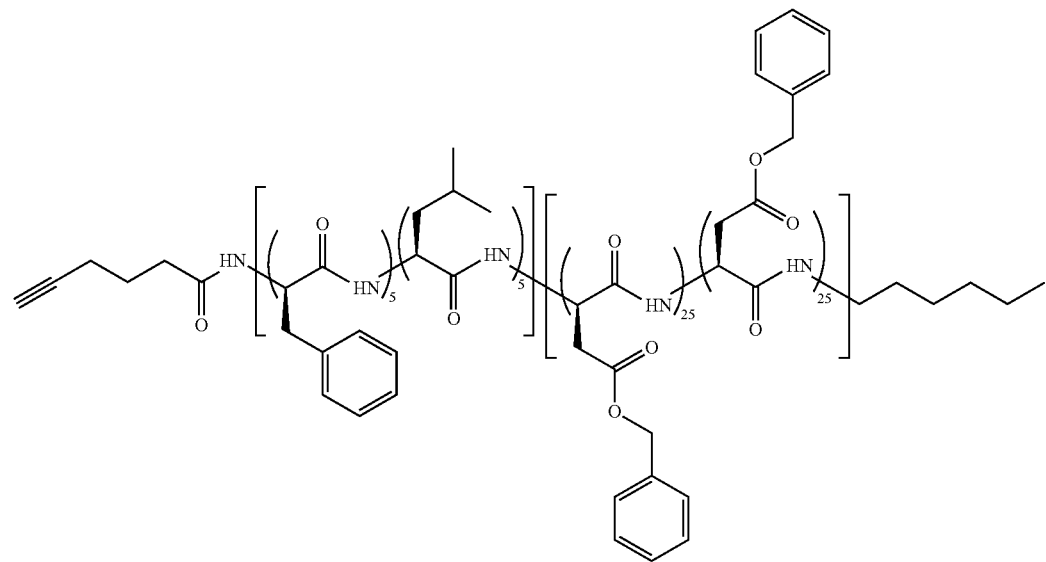
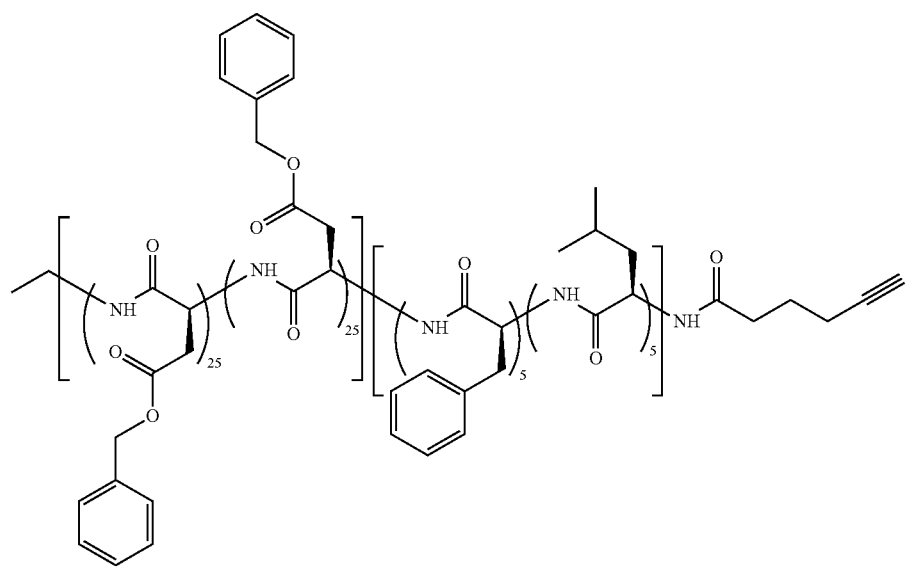

Example 78
Synthesis of N₃-PEG10k-b-P(D-Leu₁₀-co-Phe₁₀)-b-P(Asp(OBzl)₅₀-co-D-Asp(OBzl)₅₀)-b-P(D-Leu₁₀-co-Phe₁₀)-b-PEG10k-N3
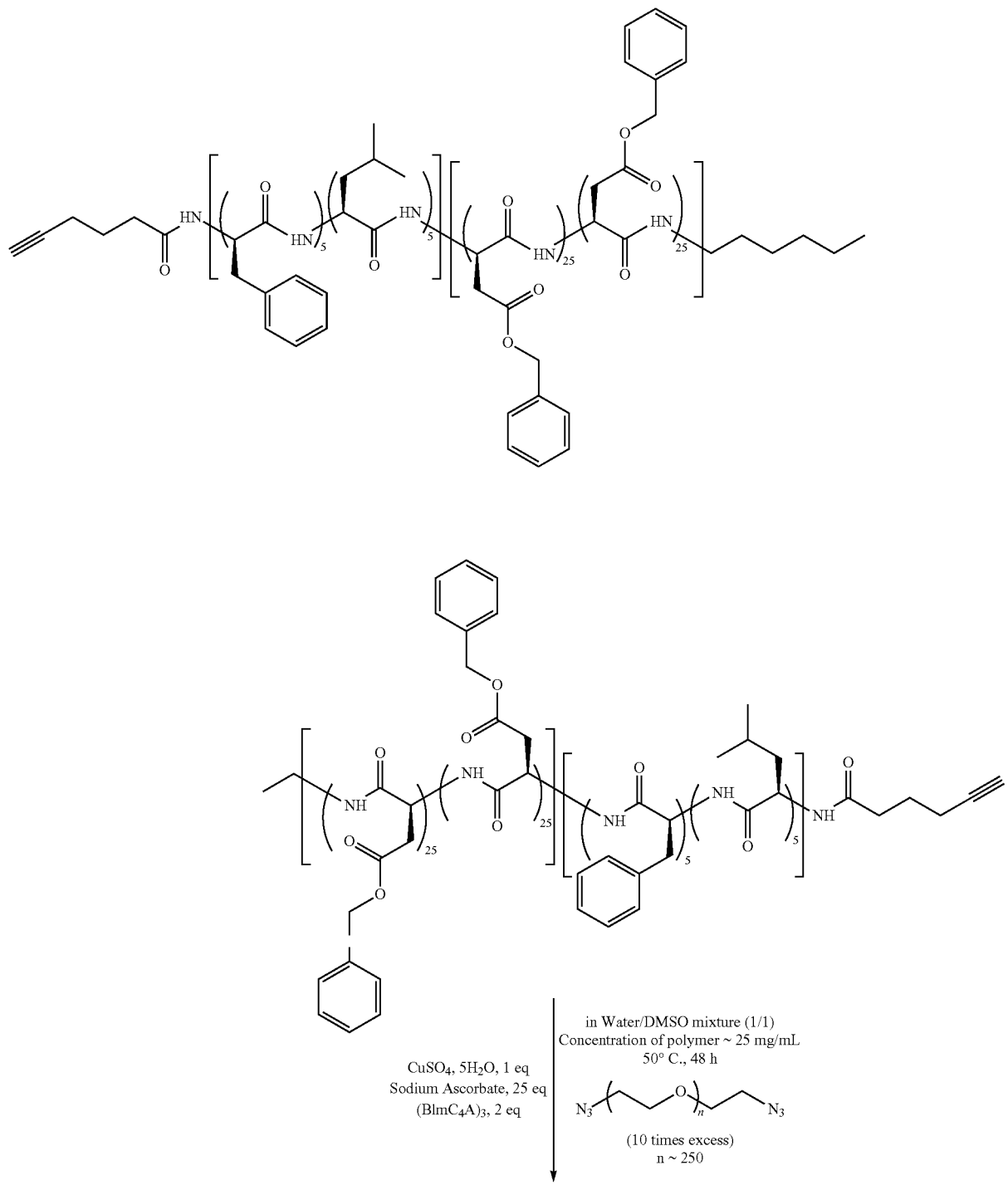

-continued
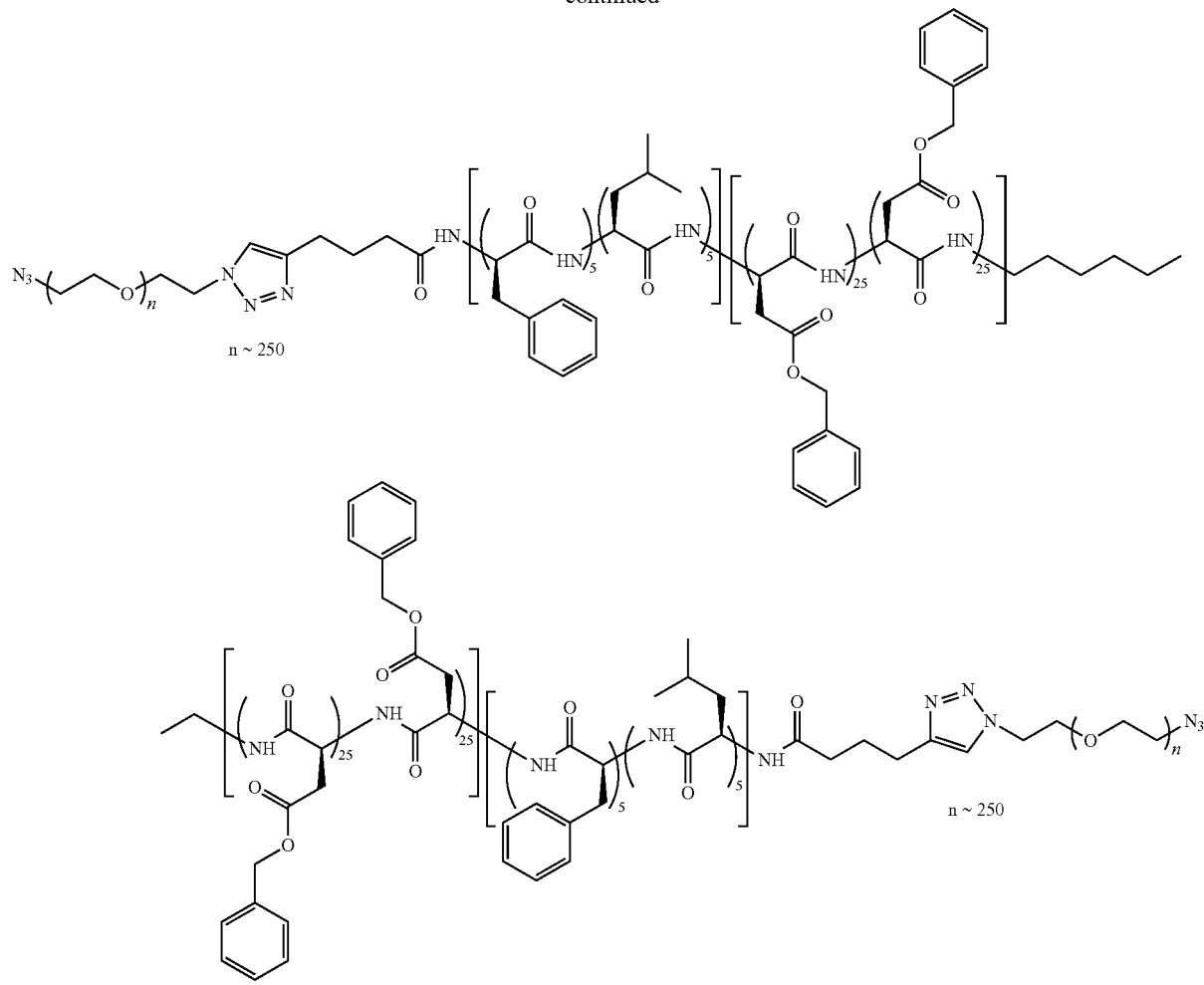
Example 79
N₃-PEG10k-b-P(D-Leu₁₀-co-Phe₁₀)-b-P(Asp(DET)₅₀-co-D-Asp(DET)₅₀)-b-P(D-Leu₁₀-co-Phe₁₀)-b-PEG10k-N3
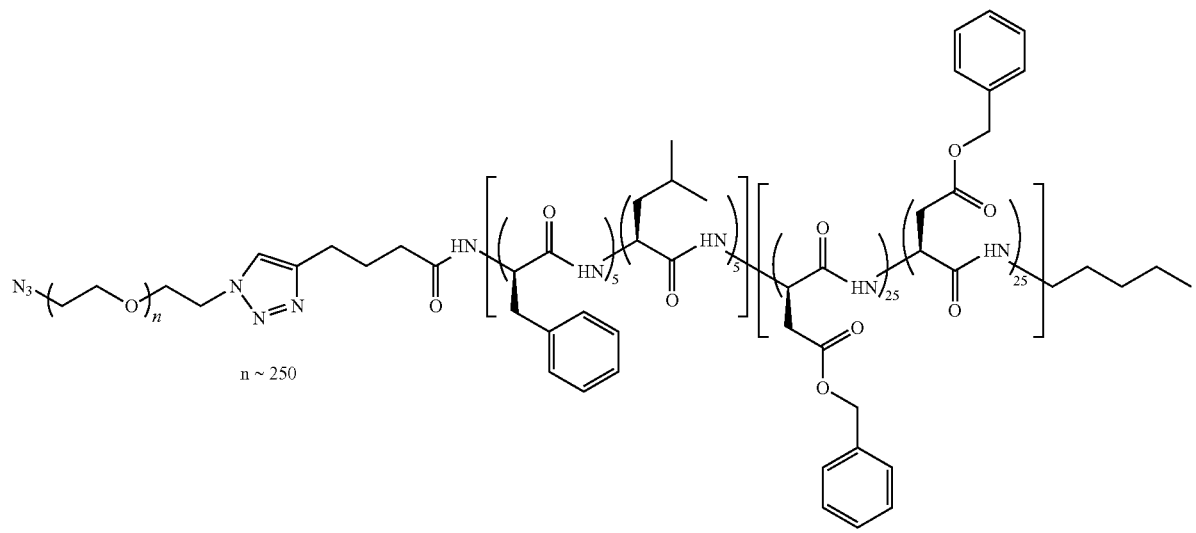

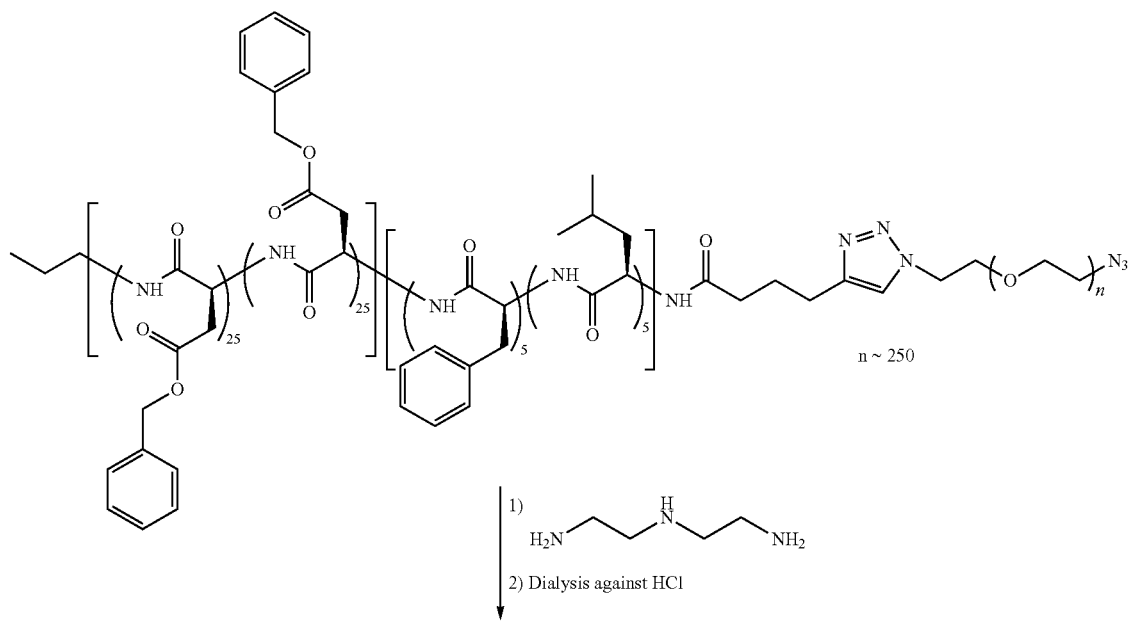
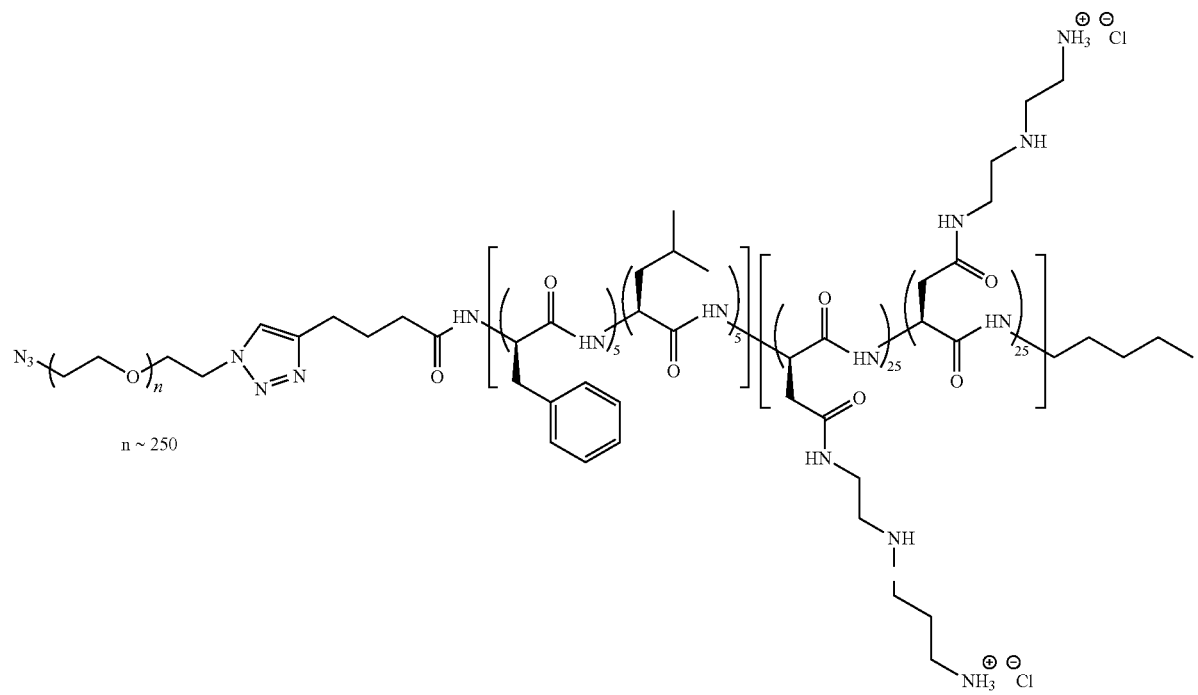

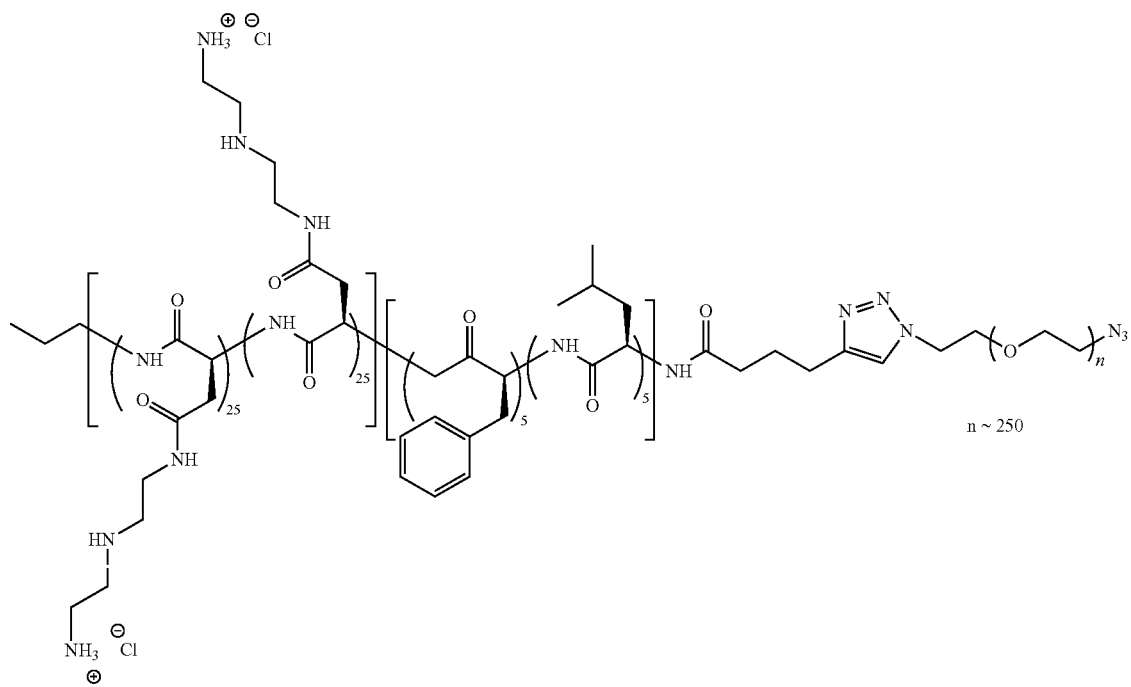
Example 80
Synthesis of UPAR-PEG10k-b-P(D-Leu$_{10}$-co-Phe$_{10}$)-b-P(Asp(OBzl)$_{50}$-co-D-Asp(OBzl)$_{50}$)-b-P(D-Leu$_{10}$-co-Phe$_{10}$)-b-PEG10k-UPAR
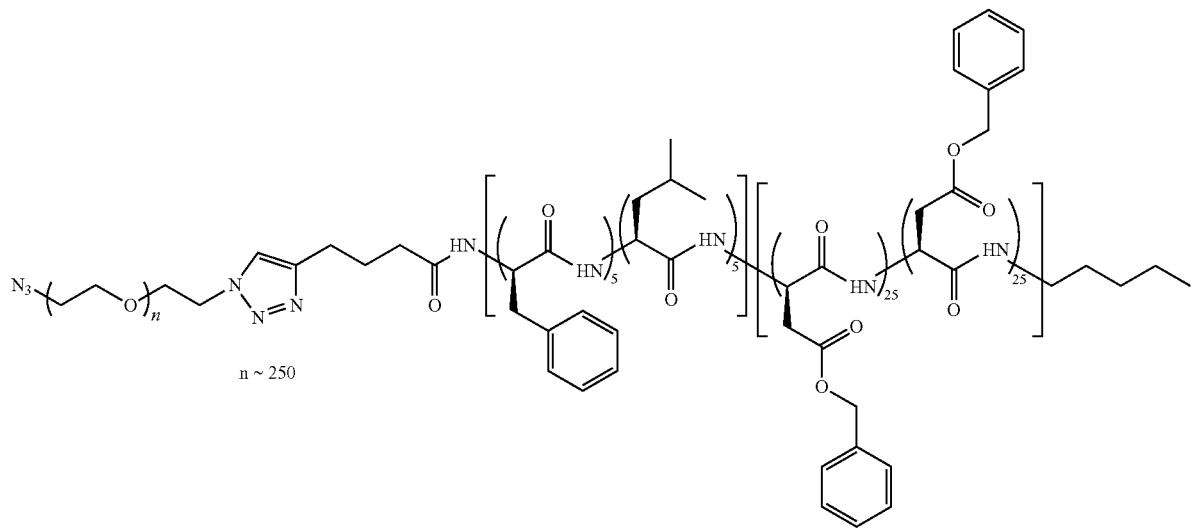

-continued
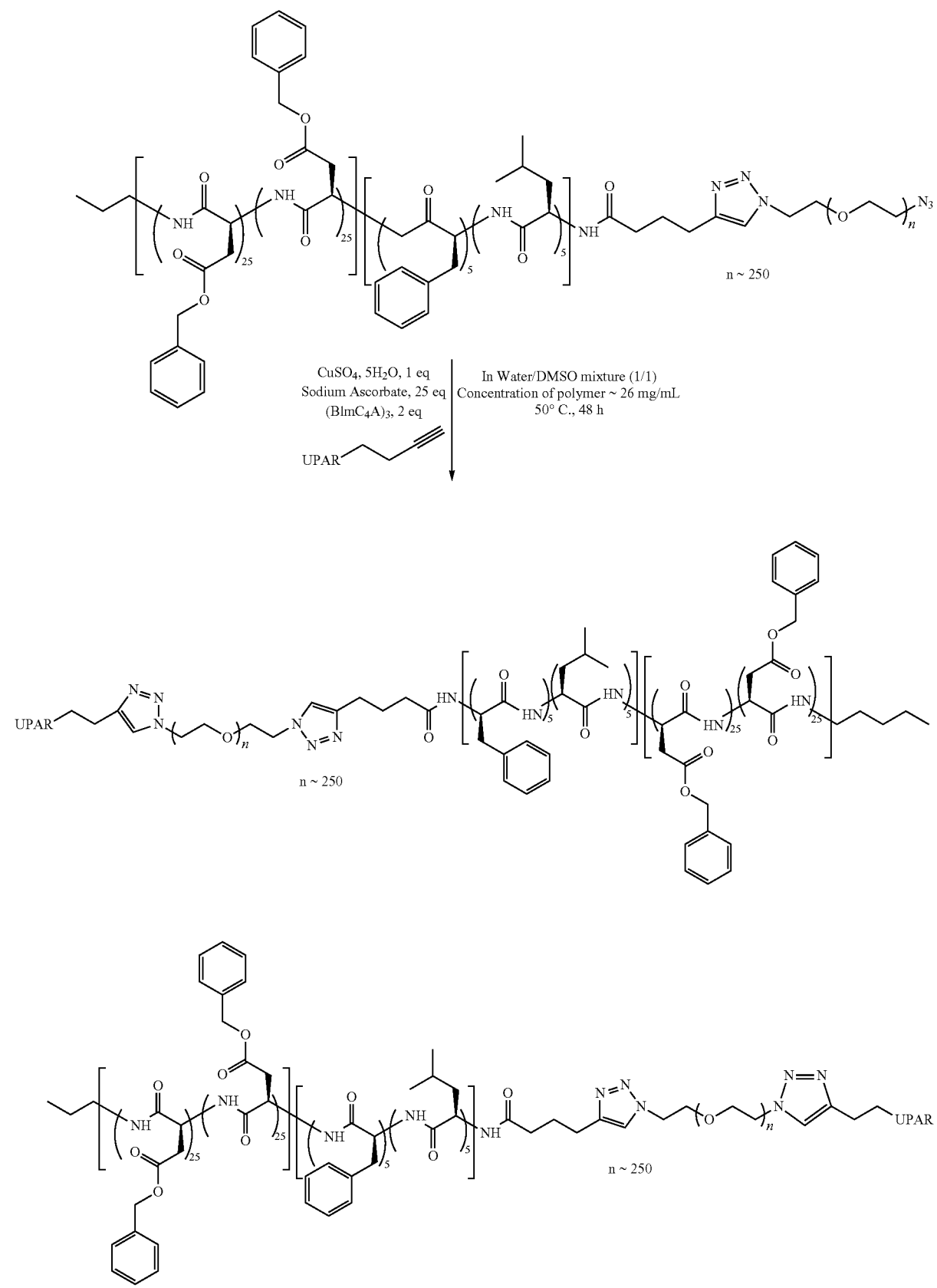

Example 81
Synthesis of UPAR-PEG10k-b-P(D-Leu$_{10}$-co-Phe$_{10}$)-b-P(Asp(DET)$_{50}$-co-D-Asp(DET)$_{50}$)-b-P(D-Leu$_{10}$-co-Phe$_{10}$)-b-PEG10k-UPAR
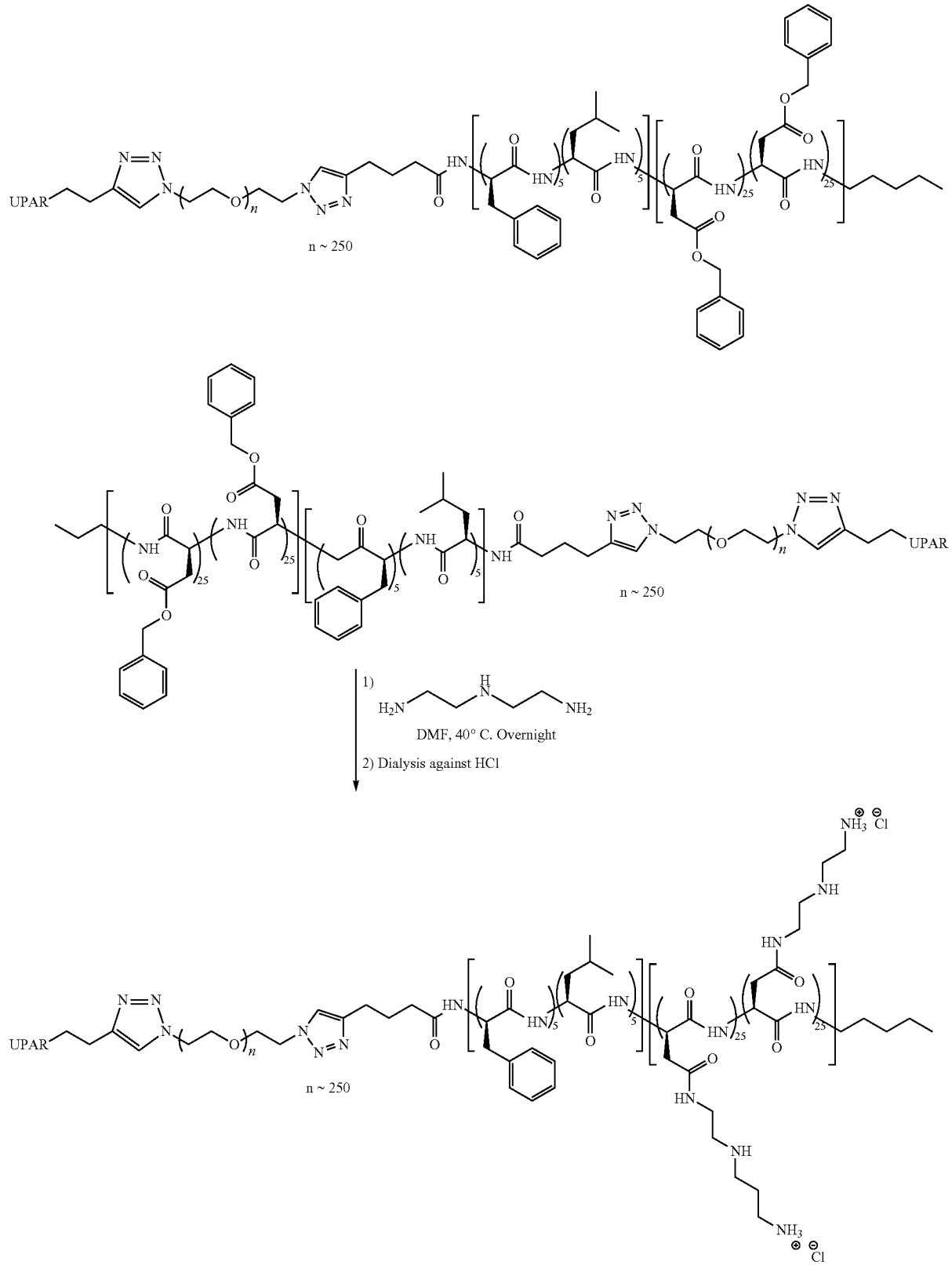

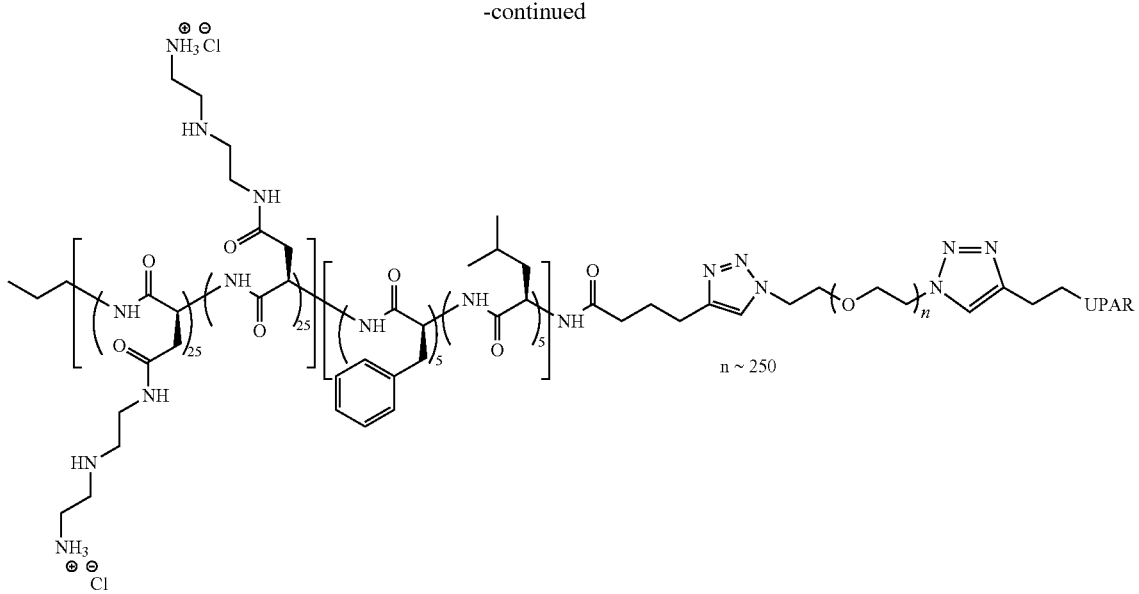

-continued

Example 82

Plasmid DNA Encapsulation and Transfection Using PEG-Containing Cationic Polymers HCT-116 colon cancer cells, obtained from ATCC, were maintained in McCoy's media supplemented with 10% FBS, 2 mM L-glutamine, and 100 units/mL penicillin/streptomycin. Twenty-five thousand HCT-116 cells, in a total volume of 100 µL McCoy's media, were seeded in each well of a 96-well format plate the day before transfection and incubated in 5% $CO_2$ at 37° C. On the day of transfection, polymers were prepared at N:P ratios between 20 and 600 in 10 mM Tris-HCl, pH7.4 based on a final amount of 0.25 µg plasmid DNA to be transfected per well. HCT-116 cells were transfected with either an EGFP plasmid (pZs-Green; Clontech, Mountain View, Calif.) or pGL4-luciferase plasmids, (Promega, Madison, Wis.). The polymers were diluted further to N:P ratios between 8 to 320 in 150 mM NaCl, and filter sterilized using a 0.22 µm PES filter. Polymers were complexed with plasmid DNA at N:P ratios between 1 and 320 for 1 hour at room temperature. The polymer-DNA complexes were diluted with Opti-MEM media (Invitrogen Corp, Carlsbad, Calif.) such that the final transfection volume was 60 µL per well. After removing media from the cells, the transfection complexes (60 µL) were added to the cells and incubated at 5% $CO_2$, 37° C. for four hours. One-hundred and twenty µL of fresh McCoy's media was added to transfection wells and cells were incubated at 37° C. After 24 hours incubation, the cells were visualized with an Olympus IX71 fluorescence inverted microscope equipped with an Olympus DP71 digital camera and relative cell viability was determined using the CellTiter-Glo® Luminescent Cell Viability Assay, according to the recommended commercial protocol (Promega). Luciferase activity was also determined using a standard luciferase assay kit (Promega). Protein quantiation was also determined using the Bradford Assay (Bio-Rad Labs, Hercules, Calif.). A BMG Labtech FLUOstar OPTIMA plate reader was used to obtain cell viability, luciferase and Bradord assay results. Experiments with the commercially available transfection reagents jetPEI (Polyplus Transfection Inc, New York, N.Y.) and Superfect (Qiagen, Valencia, Calif.) were performed using the manufacturers' recommended protocols. Furthermore, transfection experiments for each polymer and commercial transfection reagent was performed in triplicate, and the luciferase activity was normalized to the quantity of protein in each well. Colo205 colon cancer cells, A549 lung cancer cells and HeLa cervical cancer cells were obtained from ATCC, and cultured according to standard protocols. Transfection experiments were performed as described above. FIG. 1 demonstrates transfection efficiencies between 5 and 12 k PEG-b-P[(D/L)Asp(DET)] polymers. FIG. 2 compares the transfection efficiency between 5 k PEG-b-P[(D/L)Asp(DET)] and 12 k PEG-b-P[Asp(DET)-co-DLeu] polymers.

FIG. 1: GFP and Luciferase Expression of HCT-116 Cells Transiently Transfected with 5 and 12 k PEG D/L Asp-DET Polymers.

A) HCT-116 cells were transfected in triplicate in 96-well plates with various polymers that were complexed with a GFP expressing plasmid DNA pZs-Green, at the indicated N:P ratios at a final DNA concentration of 0.25 µg per well. Twenty-four hr after transfection, cells were imaged using phase contrast (top panel) and fluorescence for GFP expression (bottom panel). 5 k and 12 k PEG D/L Asp-DET polymers showed high levels of GFP expression and excellent cell viability 24 hr after transfection in colon cancer cells. ×10. B) GFP quantitation showed that cells transfected with 5 and 12 k PEG D/L Asp-DET polymers had higher levels of GFP expression than the commercial reagents (GC2-60 data represented by lefthand bars, GC2-67 data represented by righthand bars; in commercial data, JetPEI represented by lefthand bar and Superfect represented by righthand bar). C)HCT-116 cells were also transfected in triplicate in 96-well plates with various polymers that were complexed with firefly luciferase pGL4 plasmid DNA, at the indicated N:P ratios at a final DNA concentration of 0.25 µg per well. Commercial reagents were used according to the manufacturer's protocol. Twenty-four hr after transfection, luciferase activity for each sample was determined and was normalized to protein content. All results are representative of triplicate experiments. Luciferase activity for 5 k derivative was much higher than the 12 k derivative while both polymers exhibited excellent cell viability over a wide range of N:P ratios. D) 5 k and 12 k PEG Asp-DET polymers show varying degrees of transfection efficiencies and toxicities in various cell lines.

FIG. 2: GFP and Luciferase Expression of HCT-116 Cells Transiently Transfected with D/L Asp-DET or Asp-DET-D/Leu Polymers.

A) HCT-116 cells were transfected in triplicate in 96-well plates with various polymers that were complexed with a GFP expressing plasmid DNA pZs-Green, at the indicated N:P ratios at a final DNA concentration of 0.25 µg per well. Twenty-four hr after transfection, cells were imaged using phase contrast (top panel) and fluorescence for GFP expression (bottom panel). Both 5 k PEG D/L Asp-DET and 12 k PEG Asp-DET-D/Leu polymers showed high levels of GFP expression and excellent cell viability 24 hr after transfection in colon cancer cells. ×10. B) GFP quantitation showed that cells transfected with 5 k PEG D/L Asp-DET and 12 k PEG Asp-DET-D/Leu polymers had higher levels of GFP expression than the commercial reagents (GC2-112-4 data represented by lefthand bars, GC2-60 data represented by righthand bars; in commercial data, JetPEI represented by lefthand bar and Superfect represented by righthand bar). C)HCT-116 cells were also transfected in triplicate in 96-well plates with various polymers that were complexed with firefly luciferase pGL4 plasmid DNA, at the indicated N:P ratios at a final DNA concentration of 0.25 µg per well. Commercial reagents were used according to the manufacturer's protocol. Twenty-four hr after transfection, luciferase activity for each sample was determined and was normalized to protein content. All results are representative of triplicate experiments. Luciferase activity for 12 k PEG Asp-DET-D/Leu polymer was substantially greater than the 5 k PEG D/L Asp-DET polymer, while both polymers exhibited excellent cell viability over a wide range of N:P ratios.

Example 83

Polymer/DNA Complex Size Analysis

Polymers were prepared at a N:P ratio of 300 in 10 mM Tris-HCl, pH7.4 based on a final amount of 20 µg pGL4-luciferase plasmid DNA, (Promega, Madison, Wis.). The polymers were diluted further to a N:P of 120 in 150 mM NaCl, and filter sterilized using a 0.22 um PES filter. Polymers were complexed with plasmid DNA at N:P ratios between 40 and 80, in a final volume of 200 µL, for 1 hour at room temperature. Dynamic Light Scattering (DLS) was performed on Polymer/DNA complexes using a Wyatt DynaPro plate reader with a regularization fit and is represented in FIG. 3.

FIG. 3: Size Analysis of Polyplexes at Optimal N:P Ratios for DNA Transfection.

Dynamic light scattering (DLS) analysis for 5 k PEG D/L Asp-DET polymer complexed with 20 µg of pGL4-luciferase plasmid DNA. Polyplex sizes for the D/L polymer at optimal N:P ratios for DNA transfection ranged from ~100 to 150 nm.

Example 84

Gel Retardation Experiments

Polymers were prepared at a N:P ratio of 50 in 10 mM Tris-HCl, pH 7.4 based on a final amount of 0.5 µg EGFP plasmid DNA (pZs-Green; Clontech, Mountain View, Calif.). The polymers were diluted further to a N:P of 20 in 150 mM NaCl, and filter sterilized using a 0.22 µm PES filter. Polymers were complexed with plasmid DNA at N:P ratios between 1 and 20, in a final volume of 20 µL, for 1 hour at room temperature. Gel loading dye was added to each polymer/DNA complex and samples run on a 1% agarose/ethidium bromide gel in 1×TAE Buffer for 30 min at 200V, FIG. 4.

FIG. 4: Gel Retardation of DNA Complexed with Polymers.

Half a µg of pZs-Green plasmid DNA was complexed with GC2-60, GC2-112-4 and GC2-112-5 at N:P ratios between 1 and 10 for 1 hour at room temperature. Samples were then resolved on a 1% agarose/ethidium bromide gel. DNA retardation was observed in both DNA/polymers samples at N:P ratios of 2.5. Wells containing intact naked DNA served as controls. 1 kb; One kb DNA ladder.

Example 85

DNA Degradation Protection Assays

Polymers were prepared at a N:P ratio of 40 in 10 mM Tris-HCl, pH7.4 based on a final amount of 0.5 µg EGFP plasmid (pZs-Green; Clontech, Mountain View, Calif.) DNA. For DNA degradation experiments, polymers were complexed with plasmid DNA at N:P ratio of 40, in a final volume of 1 µL, for 1 hour at room temperature. Polymer-DNA complexes were incubated in 9 µL FBS (90% final conc) at 37° C. for up to 24 hours. At specific time points, samples were snap frozen in an ethanol/dry ice bath. Ten µL of 100 µg/µL Heparin (final concentration of 1000 ug/sample) was added to each sample and incubated at room temperature for 15 min. Gel loading dye was added to each sample and run on a 1% agarose/ethidium bromide gel in 1×TAE Buffer for 50 min at 150 V, FIG. 5.

FIG. 5: Polymers Protect DNA from Degradation in Serum.

Half a µg of naked pZs-Green plasmid DNA, or DNA complexed with GC2-67 at N:P ratio 40 was incubated with FBS for 0 to 24 hours at 37° C. At the indicated timepoints, samples were snap frozen and treated with Heparin at a final concentration of 1000 ug/sample for 15 minutes at room temperature. Samples were then resolved on a 1% agarose/ethidium bromide gel. Incubating naked DNA in 90% serum at 37° C. caused degradation within 30 min, with total degradation within 2 hr. In contrast, DNA complexed with PEG Asp-DET polymer form polyplexes that are extremely stable and protect DNA from degradation in 90% serum for at least 4 hr after incubation in serum. C; Control wells where Heparin was not added showing either intact naked DNA, or gel retarded DNA/polymer complexes. 1 kb; One kb DNA ladder.

Example 86

Cell Transfection and Plasmid Visualization Experiments

HeLa cells, obtained from ATCC, were maintained in minimum essential medium supplemented with 10% FBS, 2 mM L-glutamine, and 100 units/mL penicillin/streptomycin (MEM). Forty-thousand HeLa cells, in a total volume of 500 µL MEM media, were seeded in each well of a 24-well format plate the day before transfection. On the day of transfection, polymers were prepared at a N:P ratio of 600 in 10 mM Tris-HCl, pH 7.4 based on a final amount of 1.0 µg plasmid DNA to be transfected per well. EGFP plasmid (pZs-Green; Clontech, Mountain View, Calif.) was fluorescently labeled with 5-carboxy-X-rhodamine using the Label IT®Tracker™ Kit (Minis, Madison, Wis.). The polymers were diluted further to a N:P ratio of 320 in 150 mM NaCl, and filter sterilized using a 0.22 μm PES filter. Polymers were complexed with plasmid DNA at N:P ratios between 40 and 320 for 1 hour at room temperature. The polymer-DNA complexes were diluted with Opti-MEM media such that the final transfection volume was 600 μL per well. After removing media from cells, the transfection complexes (600 μL) were added to the cells and incubated at 37° C. for four hours. One thousand two hundred μL of fresh MEM was added to transfection wells and cells were incubated at 37° C. After 24 hours incubation, the media was changed. Forty-eight hours after transfection, cells were visualized with an Olympus IX71 microscope, FIG. 2. Experiments with the commercially available transfection reagent jetPEI were also performed using the manufacturer's recommended protocols.

Example 87

In Vivo Polymer/DNA Delivery Experiments

On the day of injection, polymers were prepared at a N:P ratio of 300 in 10 mM Tris-HCl, pH7.4 based on a final amount of 20 μg plasmid DNA to be injected per mouse. Athymic nude female mice, previously inoculated with HCT-116 and HT-29 Luc tumor cells, were injected with pGL4-luciferase plasmids, (Promega, Madison, Wis.). The polymers were diluted further to a N:P ratio of 120 in 150 mM NaCl, and filter sterilized using a 0.22 μm PES filter. Polymers were complexed with plasmid DNA at N:P ratios between 10 and 40 for 1 hour at room temperature. Twenty μg of pGL4-luciferase plasmid DNA was administered alone or as a PEG-b-P[Asp(DET)]D/L mix polymer complex by intratumoral (I.T.) or tail vein IV administration. Twenty four hours are DNA or Polymer/DNA administration, mice were injected intraperitoneally with 10 μL/g body weight of sterile d-luciferin substrate prepared in PBS at 15 mg/mL (resulting dose 150 μg/g body weight). After 5-10 minutes, mice were anesthetized with isoflurane and transferred to the thermoregulated, dark chamber of the In Vivo Imaging System (IVIS-200, Xenogen Corporation, CA). The system acquires and overlays photographic and luminescent images by measuring photons emitted from luciferase-expressing cells and transmitted through the tissue were acquired and analyzed with LivingImage software (included in Xenogen package). Mice were monitored for a period of up to seven days, FIG. 6.

FIG. 6: In Vivo Studies Using 5 and 12 k PEG D/L Asp-DET Polymers.

Twenty μg of pGL4 Luciferase plasmid DNA was administered alone or as a PEG-b-P[Asp(DET)]D/L mix polymer complex by intratumoral (I.T.) or IV administration to nude mice with subcutaneous HCT-116 and HT-29 Luc tumors. At specific time points, mice were injected intraperitoneally with d-luciferin, anesthetized and imaged for luminescence using the IVIS-200, Xenogen In Vivo Imaging System. A) I.T. injection of DNA only resulted in decreasing luciferase activity in HCT-116 cells compared to increasing activity with 5 k PEG-b-P[Asp(DET)]D/L mix polymer complexes. B) I.V. injection of 5 k PEG Polymer complexed Luciferase plasmid DNA resulted in non-specific luciferase activity within the tail and lymph node. C) I.V. injection of 12 k PEG-b-P[Asp (DET)]D/L mix polymer complexed Luciferase plasmid DNA again resulted in non-specific luciferase activity within the tail, however lymph nodes proximal to tumor showed intense luminescence.

Example 88

Polyplex Formation Using Copper Ions 30 uL of a 0.01 M $CuCl_2$ was added to 5 uL of a 0.1 M DNA solution and stirred for one hour. At that time, polymer (from Example 38) dissolved in Tris buffer at pH 7.4 was added such that the final N:P ratio was 2.5, 5, or 10. After incubating for an additional hour, the solutions were analyzed by optical microcopy (FIG. 7) and transmission electron microscopy (FIG. 8). FIG. 7 shows the optical micrographs of polyplexes formed with and without the copper chloride. FIG. 8 depicts the transmission electron micrographs of the polyplexes formed with copper chloride at N:P 10.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A micelle having a polynucleotide encapsulated therein, comprising a diblock copolymer of formula I-b:

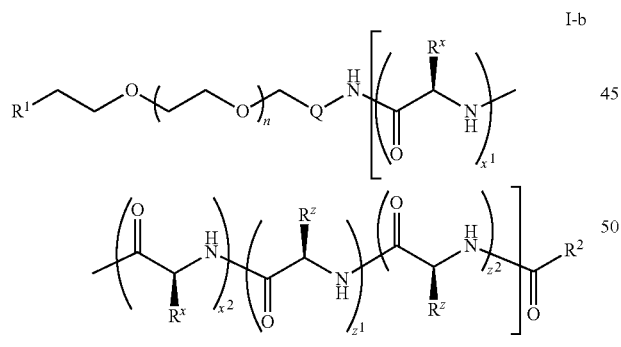

I-b wherein:
n is 50-2500;
$x^1$ is 0 to 250;
$x^2$ is 0 to 250;
$z^1$ is 0 to 250, provided that $x^1$ and $z^1$ are not simultaneously zero;
$z^2$ is 0 to 250, provided that $z^1$ and $z^2$ are not simultaneously zero;
$R^x$ is a natural or unnatural amino acid side-chain group that is hydrophobic;
$R^z$ is -L-$R^4$ wherein:

L is a bivalent, straight or branched, $C_{4\text{-}20}$ alkylene chain wherein at least one methylene unit of -L- is replaced by —C(O)NR— and 1-10 additional methylene units are independently replaced by —N(R)— or -Het-;
Het is a bivalent 5-6 membered saturated, partially unsaturated, or aromatic ring having at least one nitrogen and 0-3 additional heteroatoms independently selected from nitrogen, oxygen, or sulfur;
$R^4$ is R or $N(R)_2$;
each R is hydrogen or $C_{1\text{-}6}$ aliphatic, or two R on the same nitrogen are taken together with the nitrogen to form a 5-6 membered heterocyclic ring having 1-3 heteroatoms independently selected from nitrogen, oxygen, or sulfur;
$R^1$ is —Z(CH$_2$CH$_2$Y)$_p$(CH$_2$)$_t$R$^3$, wherein:
Z is a valence bond, a bivalent triazolyl moiety, —O—, —S—, —C≡C—, or —CH$_2$—;
each Y is independently —O— or —S—;
p is 0-10;
t is 0-10; and
$R^3$ is hydrogen, —N$_3$, —CN, a mono-protected amine, a di-protected amine, a protected aldehyde, a protected hydroxyl, a protected carboxylic acid, a protected thiol, a 9-30 membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety or a targeting group;

Q is a valence bond or a bivalent, saturated or unsaturated, straight or branched $C_{1-12}$ alkylene chain, wherein 0-6 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:

-Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;

$R^2$ is selected from an optionally substituted aliphatic group or a fusogenic peptide.

2. The micelle of claim 1, wherein the sum of $x^1$ and $x^2$ is about 25 and the sum of $z^1$ and $z^2$ is about 25.

3. The micelle of claim 1, wherein sum of $x^1$ and $x^2$ is about 50 and the sum of $z^1$ and $z^2$ is about 50.

4. The micelle of claim 1, wherein sum of $x^1$ and $x^2$ is about 100 and the sum of $z^1$ and $z^2$ is about 100.

5. The micelle of claim 1, wherein $R^x$ is an amino acid side-chain group corresponding to that of leucine, norleucine, or phenylalanine.

6. The micelle of claim 5, wherein $R^x$ is an amino acid side-chain group corresponding to that of leucine.

7. The micelle of claim 5, wherein $R^x$ is an amino acid side-chain group corresponding to that of norleucine.

8. The micelle of claim 5, wherein $R^x$ is an amino acid side-chain group corresponding to that of phenylalanine.

9. The micelle of claim 1, wherein $R^2$ is methyl.

10. The micelle of claim 1, wherein Q is —CH$_2$—.

11. The micelle of claim 1, wherein $R^1$ is N$_3$.

12. The micelle of claim 1, wherein $R^z$ is selected from the group consisting of:

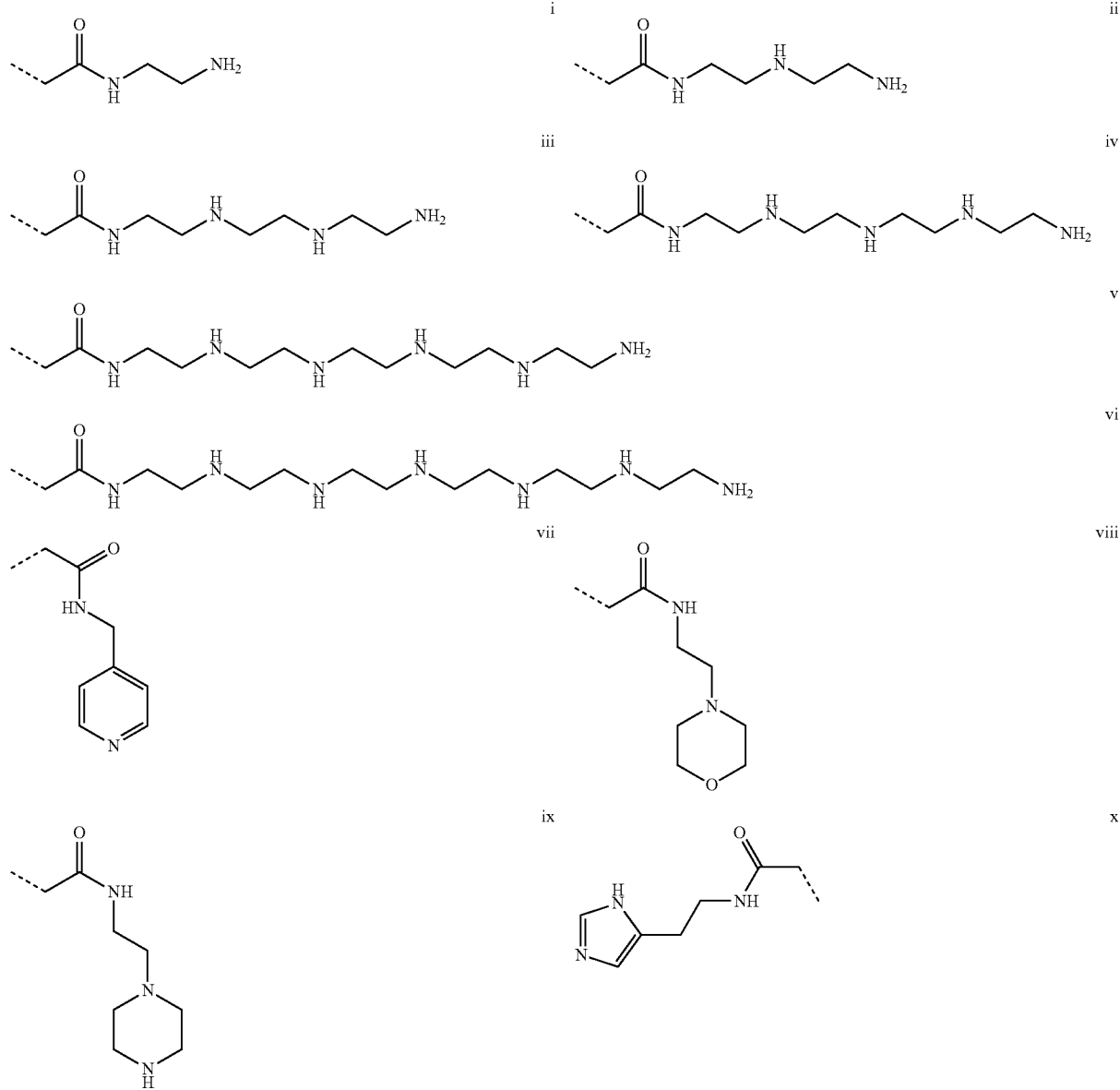

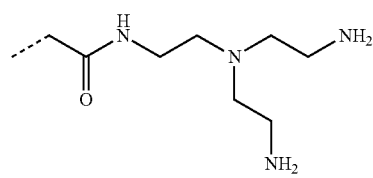 xi
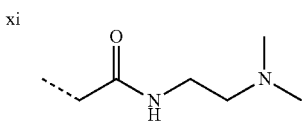 xii
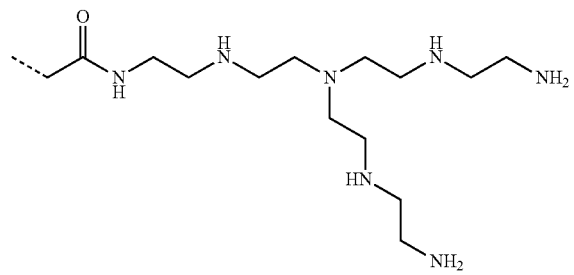 xiii
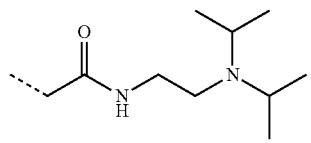 xiv
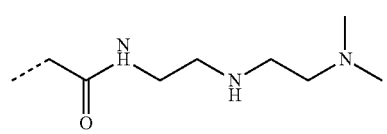 xv
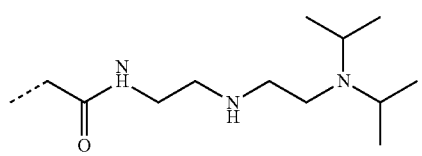 xvi
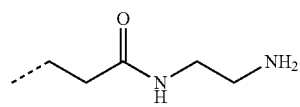 xvii
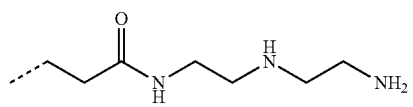 xviii
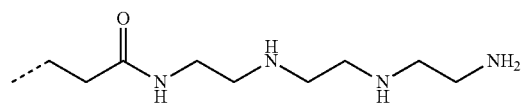 xix
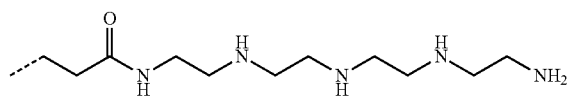 xx
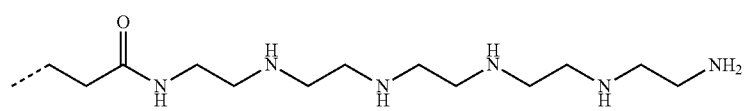 xxi
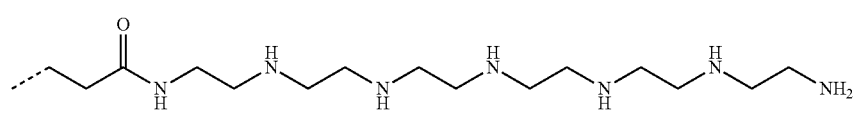 xxii
 xxiii
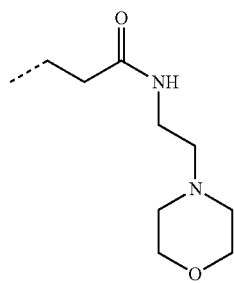 xxiv

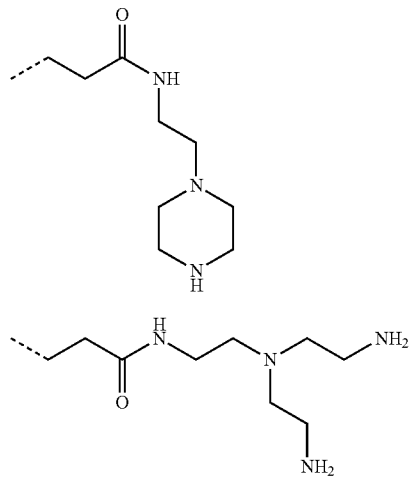

xxv

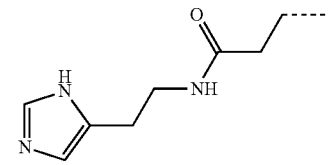

xxvi

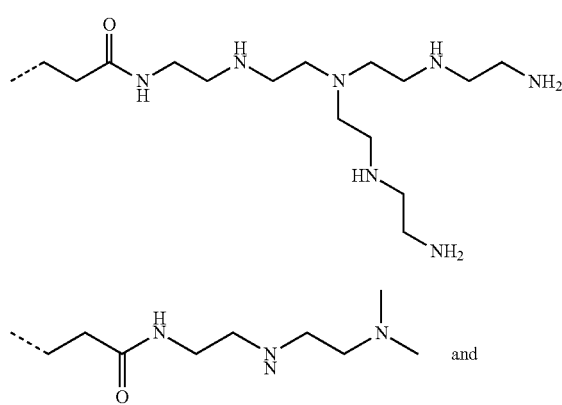

xxvii

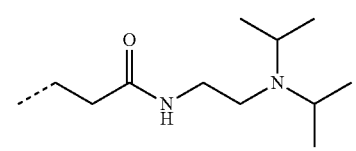

xxviii

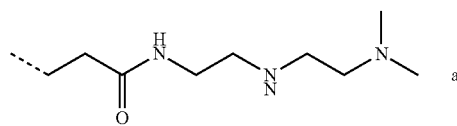

xxix

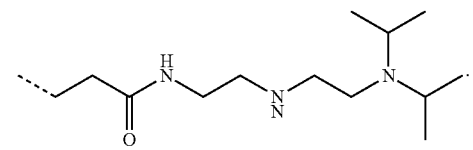

xxx xxxi xxxii and

13. The micelle of claim 1, wherein Z is a bivalent triazolyl moiety.
14. The micelle of claim 1, wherein Z is a valence bond.
15. The micelle of claim 1, wherein p is 0.
16. The micelle of claim 1, wherein p is 1-10.
17. The micelle of claim 1, wherein t is 0.
18. The micelle of claim 1, wherein t is 1-10.
19. The micelle of claim 1, wherein $R^3$ is —$N_3$.
20. The micelle of claim 1, wherein $R^3$ is a targeting group selected from the group consisting of folate, a Her-2 binding peptide, a urokinase-type plasminogen activator receptor (uPAR) antagonist, a CXCR4 chemokine receptor antagonist, a GRP78 peptide antagonist, an RGD peptide, an RGD cyclic peptide, a luteinizing hormone-releasing hormone (LHRH) antagonist peptide, an aminopeptidase targeting peptide, a brain homing peptide, a kidney homing peptide, a heart homing peptide, a gut homing peptide, an integrin homing peptide, an angiogencid tumor endothelium homing peptide, an ovary homing peptide, a uterus homing peptide, a sperm homing peptide, a microglia homing peptide, a synovium homing peptide, a urothelium homing peptide, a prostate homing peptide, a lung homing peptide, a skin homing peptide, a retina homing peptide, a pancreas homing peptide, a liver homing peptide, a lymph node homing peptide, an adrenal gland homing peptide, a thyroid homing peptide, a bladder homing peptide, a breast homing peptide, a neuroblastoma homing peptide, a lymphoma homing peptide, a muscle homing peptide, a wound vasculature homing peptide, an adipose tissue homing peptide, a virus binding peptide, and a fusogenic peptide.

21. The micelle of claim 1, wherein $R^3$ is an oligopeptide targeting group.
22. A micelle having a polynucleotide encapsulated therein, comprising a diblock copolymer of formula b:

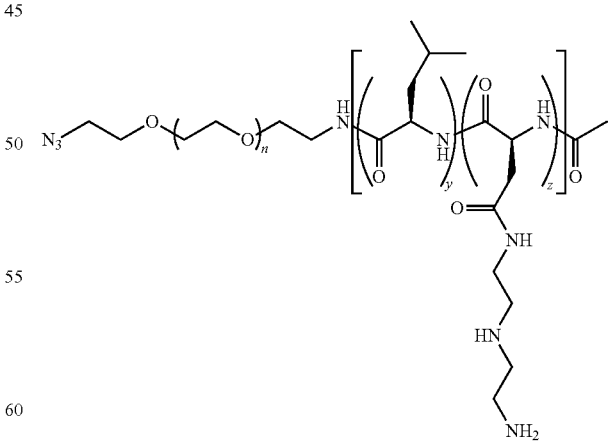

b wherein:
n is 50-2500;
y is 5 to 250; and
z is 5 to 250.

* * * * *

SEQUENCE LISTING

```
<160> NUMBER OF SEQ ID NOS: 13

<210> SEQ ID NO 1
<211> LENGTH: 23
<212> TYPE: PRT
<213> ORGANISM: Artificial Sequence
<220> FEATURE:
<223> OTHER INFORMATION: Synthetic peptide derived from Haemophilus
      Influenza Haemagglutinin-2

<400> SEQUENCE: 1

Gly Leu Phe Gly Ala Ile Ala Gly Phe Ile Glu Asn Gly Trp Glu Gly
1               5                   10                  15

Met Ile Asp Gly Gly Gly Cys
            20

<210> SEQ ID NO 2
<211> LENGTH: 30
<212> TYPE: PRT
<213> ORGANISM: Artificial Sequence
<220> FEATURE:
```

<223> OTHER INFORMATION: Synthetic amphipathic peptide

<400> SEQUENCE: 2

Trp Glu Ala Ala Leu Ala Glu Ala Leu Ala Glu Ala Leu Ala Glu His
1               5                   10                  15
Leu Ala Glu Ala Leu Ala Glu Ala Leu Glu Ala Leu Ala Ala
            20                  25                  30

<210> SEQ ID NO 3
<211> LENGTH: 30
<212> TYPE: PRT
<213> ORGANISM: Artificial Sequence
<220> FEATURE:
<223> OTHER INFORMATION: Synthetic amphipathic peptide

<400> SEQUENCE: 3

Trp Glu Ala Lys Leu Ala Lys Ala Leu Ala Lys Ala Leu Ala Lys His
1               5                   10                  15
Leu Ala Lys Ala Leu Ala Lys Ala Leu Lys Ala Cys Glu Ala
            20                  25                  30

<210> SEQ ID NO 4
<211> LENGTH: 10
<212> TYPE: PRT
<213> ORGANISM: Artificial sequence
<220> FEATURE:
<223> OTHER INFORMATION: Synthetic peptide derived from human
      immunodeficiency virus Tat protein

<400> SEQUENCE: 4

Gly Arg Lys Lys Arg Arg Gln Arg Arg Arg
1               5                   10

<210> SEQ ID NO 5
<211> LENGTH: 9
<212> TYPE: PRT
<213> ORGANISM: Artificial sequence
<220> FEATURE:
<223> OTHER INFORMATION: Synthetic peptide

<400> SEQUENCE: 5

Arg Arg Arg Arg Arg Arg Arg Arg Arg
1               5

<210> SEQ ID NO 6
<211> LENGTH: 5
<212> TYPE: PRT
<213> ORGANISM: Artificial sequence
<220> FEATURE:
<223> OTHER INFORMATION: Synthetic peptide

<400> SEQUENCE: 6

His His His His His
1               5

<210> SEQ ID NO 7
<211> LENGTH: 50
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(50)
<223> OTHER INFORMATION: Amino acid side chain modified with a benzyl
      group

<400> SEQUENCE: 7

Asp Asp Asp Asp Asp Asp Asp Asp Asp Asp Asp Asp Asp Asp Asp
1               5                   10                  15

Asp Asp Asp Asp Asp Asp Asp Asp Asp Asp Asp Asp Asp Asp Asp
            20                  25                  30

Asp Asp Asp Asp Asp Asp Asp Asp Asp Asp Asp Asp Asp Asp Asp
        35                  40                  45

Asp Asp
    50

<210> SEQ ID NO 8
<211> LENGTH: 75
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(75)
<223> OTHER INFORMATION: Amino acid side chain modified with a benzyl
      group

<400> SEQUENCE: 8

Asp Asp Asp Asp Asp Asp Asp Asp Asp Asp Asp Asp Asp Asp Asp
1               5                   10                  15

Asp Asp Asp Asp Asp Asp Asp Asp Asp Asp Asp Asp Asp Asp Asp
            20                  25                  30

Asp Asp Asp Asp Asp Asp Asp Asp Asp Asp Asp Asp Asp Asp Asp
        35                  40                  45

Asp Asp Asp Asp Asp Asp Asp Asp Asp Asp Asp Asp Asp Asp Asp
    50                  55                  60

Asp Asp Asp Asp Asp Asp Asp Asp Asp Asp Asp
65                  70                  75

<210> SEQ ID NO 9
<211> LENGTH: 100
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(100)
<223> OTHER INFORMATION: Amino acid side chain modified with a benzyl
      group

<400> SEQUENCE: 9

Asp Asp Asp Asp Asp Asp Asp Asp Asp Asp Asp Asp Asp Asp Asp
1               5                   10                  15

Asp Asp Asp Asp Asp Asp Asp Asp Asp Asp Asp Asp Asp Asp Asp
            20                  25                  30

Asp Asp Asp Asp Asp Asp Asp Asp Asp Asp Asp Asp Asp Asp Asp
        35                  40                  45

Asp Asp Asp Asp Asp Asp Asp Asp Asp Asp Asp Asp Asp Asp Asp
    50                  55                  60

Asp Asp Asp Asp Asp Asp Asp Asp Asp Asp Asp Asp Asp Asp Asp
65                  70                  75                  80

Asp Asp Asp Asp Asp Asp Asp Asp Asp Asp Asp Asp Asp Asp Asp
            85                  90                  95

Asp Asp Asp Asp
        100

```
<210> SEQ ID NO 10
<211> LENGTH: 50
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(50)
<223> OTHER INFORMATION: Ornithine benzyl carbamate

<400> SEQUENCE: 10

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa
    50

<210> SEQ ID NO 11
<211> LENGTH: 100
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(100)
<223> OTHER INFORMATION: Ornithine benzyl carbamate

<400> SEQUENCE: 11

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa
        100

<210> SEQ ID NO 12
<211> LENGTH: 50
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(50)
<223> OTHER INFORMATION: Ornithine

<400> SEQUENCE: 12

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30
```